US006100025A

United States Patent [19]
Wigler et al.

[11] Patent Number: 6,100,025
[45] Date of Patent: Aug. 8, 2000

[54] CLONING BY COMPLEMENTATION AND RELATED PROCESSES

[75] Inventors: Michael H. Wigler, Lloyd Harbor, N.Y.; John J. Colicelli, Los Angeles, Calif.

[73] Assignee: Cold Spring Harbor Laboratory, Cold Spring, N.Y.

[21] Appl. No.: 08/206,188

[22] Filed: Mar. 1, 1994

Related U.S. Application Data

[63] Continuation-in-part of application No. 07/688,352, Apr. 19, 1991, Pat. No. 5,527,896, which is a continuation-in-part of application No. 07/511,715, Apr. 20, 1990.

[51] Int. Cl.$^7$ .............................. C12Q 1/68; C12P 19/34; C07H 21/04; C07H 21/02
[52] U.S. Cl. ............................. 435/6; 435/91.2; 435/174; 435/320.1; 435/252.3; 536/23.1; 536/24.3; 536/24.33
[58] Field of Search ................................ 435/6, 91.2, 174, 435/320.1, 252.3; 536/23.1, 24.3, 24.33

[56] References Cited

U.S. PATENT DOCUMENTS 5,527,896   6/1996   Wigler et al. ........................... 536/23.5

OTHER PUBLICATIONS

Davis et al. PNAS 86:3604–3608, May 1989.
Ammerer, G., "Expression of Genes in Yeast Using the ADCI Promoter," *Meth. Enzymol.*, 101:192–201 (1983).
Barbacid, M., "ras Genes," *Ann. Rev. Biochem.*, 56:779–827 (1987).
Beavo, "Multiple Phosphodiesterase Isozymes Background, Nomenclature and Implications", In: *Cyclic Nucleotide Phosphodiesterases: Structure, Regulation and Drug Action*, Chapter 1, Beavo, J. and Houslay, M.D., (eds.), John Wiley & Sons, New York. pp. 3–15 (1990).
Beavo et al., "Primary Sequence of Cyclic Nucleotide Phosphodiesterase Isozymes and the Design of Selective Inhibitors," *TIPS (Reviews)*, 11:150–155 (1990).
Beavo, J.A., "Multiple Isozymes of Cyclic Nucleotide Phosphodiesterase," *Advances in Second Messenger and Phosphoprotein Research*, vol. II, Greengard et al., (eds.), Raven Press, New York, pp. 1–38 (1988).
Beckner et al., "The ras Oncogene Product p21 is not a Regulatory Component of Adenylate Cyclase," *Nature*, 317:71 (Sep. 5, 1985).
Bennetzen et al., "The Primary Structure of the *Saccharomyces cerevisiae* Gene for Alcohol Dehydrogenase I," *J. Biol. Chem.*, 257(6):3018–3025 (Mar. 25, 1982).
Biggin et al., "Buffer Gradient Gels and $^{35}$S Label as an Aid to Rapid DNA Sequence Determination," *Proc. Nat'l Acad. Sci., USA*, 80:3963–3965 (Jul. 1983).
Birchmeier et al., "RAS Proteins Can Induce Meiosis in Xeonopus Oocytes," *Cell*, 43:615–621 (Dec., 1985).
Bradford, M.M., "A Rapid and Sensitive Method for the Quantitation of Microgram Quantities of Protein Utilizing the Principle of Protein–Dye Binding," *Anal. Biochem.* 72:248–254 (1976).

Brugge et al., "Expression of Rous Sarcoma Virus Transforming Protein pp60$^{v-src}$ in *Saccharomyces cerevisiae* Cells," *Mol. & Cell. Biol.*, 7(6):2180–2187 (Jun., 1987).
Capon et al., "Activation of Ki–ras 2 Gene in Human Colon and Lung Carcinomas by Two Differnet Point Mutations," *Nature*, 304:507–513 (Aug., 1983).
Capon et al., "Complete Nucleotide Sequences of the T24 Human Bladder Carcinoma Oncogene and Its Normal Homologue," *Nature*, 302:33–37 (Mar. 3, 1983).
Charbonneau et al., "Identification of a Conserved Domain Among Cyclic Nucleotide Phosphodiesterases From Diverse Species," *Proc. Natl. Acad. Sci., USA*, 83:9308–9312 (Dec., 1986).
Chen et al., "Molecular Analysis of cDNA Clones and the Corresponding Genomic Coding Sequences of the Drosophila Dunce$^+$ Gene, The Structural Gene for cAMP Phosphodiesterase," *Proc. Nat'l Acad. Sci., USA*, 83:9313–9317 (Dec., 1986).
Chirgwin et al., "Isolation of Biologically Active Ribonucleic Acid from Sources Enriched in Ribonuclease," *Biochem.*, 18:5294–5299 (1979).
Colicelli et al., "Isolation and Characterization of Mammalian Gene Encoding a High–Affinity cAMP Phosphodiesterase," *Proc. Natl. Acad. Sci., USA*, 86:3599–3603 (May, 1989).
Davis, "Molecular Genetics of the Cyclic Nucleotide Phosphodiesterases", In: *Cyclic Nucleotide Phosphodiesterases: Structure, Regulation, and Drug Action*, Beavo, J. and Houslay, M.D., Eds.; John Wiley & Sons, New York, pp 227–241 (1990).
Davis et al., "A Partial Characterization of the Cyclic Nucleotide Phosphodiesterases of *Drosophila melanogaster*," *Arch. Biochem. & Biophys.* 203(1):412–421 (1980).
Davis et al., "A Simple Direct Assay of 3',5'–Cyclic Nucleotide Phosphodiesterase Activity Based on the Use of Polyacrylamide–Boronate Affinity Gel Chromatography," *J. of Cyclic Nucleotide Research*, 5(1):65–74 (1979).
Davis et al., "Cloning and Characterization of Mammalian Homologs of the Drosophila Dunce$^+$ Gene," *Proc. Nat'l. Acad. Sci., USA*, 86:3604–3608 (May, 1989).

(List continued on next page.)

*Primary Examiner*—W. Gary Jones
*Assistant Examiner*—Dianne Rees
*Attorney, Agent, or Firm*—Marshall, O'Toole, Gerstein, Murray & Borun

[57] ABSTRACT

Disclosed are methods for detecting mammalian genes encoding proteins which can function in microorganisms, particularly yeast, to modify, complement, or suppress a genetic defect associated with an identifiable phenotypic alteration or characteristic in the microorganism. Disclosed also are mammalian DNA sequences cloned by the above method, as well as polypeptide products of the expression of the DNA sequences in procaryotic or eucaryotic host cells and antibody substances which are specifically immunoreactive with said expression products. More specifically, the present invention relates to methods for cloning mammalian genes which encode products which modify, complement or suppress a genetic defect in a biochemical pathway in which cAMP participates or in a biochemical pathway which is controlled, directly or indirectly, by a RAS-related protein, to products (RNA, proteins) encoded by the mammalian genes cloned in this manner, and to antibodies which can bind the encoded proteins.

3 Claims, 34 Drawing Sheets

OTHER PUBLICATIONS

Davis et al., "Dunce Mutants of *Drosophila melanogaster*: Mutants Defective in the Cyclic AMP Phosphodiesterase Enzyme System," *J. Cell Biol.*, 90:101–107 (Jul., 1981).

De Vos et al., "Three–Dimensional Structure of an Oncogene Protein: Catalytic Domain of Human c–H–ras p21," *Science*, 239:888–893 (Feb., 1988).

DeFeo–Jones et al., "ras–Related Gene Sequences Identified and Isolated from *Saccharomyces cerevisiae*," *Nature*, 306:707–709 (Dec., 1983).

DeFeo–Jones et al., "Mammalian and Yeast ras Gene Products: Biological Function in Their Heterologous Systems," *Science*, 228:179–184 (Apr. 12, 1985).

Dhar et al., "Nucleotide Sequence of Two $ras^H$ Related–Genes Isolated from the Yeast *Saccharomyces cerevisiae*," *Nuc. Acids Res.*, 12:3611–3618 (1984).

Dudai, Y., "Neurogenetic Dissection of Learning and Short Term Memory in Drosophila," *Ann. Rev. Neurosci.*, 11:537–563 (1988).

Eckmann et al., "Rolipram Major Depression: Results of a Double Blind Comparative Study With Amitriptyline," *Current Therapeutic Research*, 43(2):291–295 (Feb., 1988).

Ellis et al., "The p21 src Genes of Harvey and Kristen sarcoma viruses Originate from Divergent Members of a Family of Normal Vertebrate Genes," *Nature*, 292:506–511 (1981).

Faure et al., "Disruption of *Dictyostelium discoideum* Morphogenesis by Overproduction of cAMP Phosphodiesterase," *Proc. Nat'l Acad. Sci., USA*, 85:8076–8080 (Nov., 1988).

Field et al., "Cloning and Characterization of CAP, the *S. cerevisiae* Gene Encoding the 70 kd Adenylyl Cyclase–Associated Protein," *Cell*, 61:319–327 (Apr. 20, 1990).

Field et al., "Mutations of the Adenylyl Cyclase Gene That Block RAS Function in *Saccharomyces cerevisiae*," *Science*, 247:464–467 (Jan., 1990).

Field et al., "Purification of a RAS–Responsive Adenylyl Cyclase Complex from *Saccharomyces cerevisiae* by Use of an Epitope Addition Method," *Mol. Cell. Biol.*, 8(5):2159–2165 (May, 1988).

Fukui et al., "Molecular Cloning and Sequence Analysis of a ras Gene from *Schizosaccharomyces pombe*," *EMBO J.*, 4:687–691 (1985).

Fukui et al., "Role of a ras Homolog in the Life cycle of *Schizosaccharomyces pombe*," *Cell*, 44:329–336 (Jan. 31, 1986).

Gerst et al., "CAP Is a Bifunctional Component of the *Saccharomyces cerevisiae* Adenylyl Cyclase Complex," *Mol. & Cell Biol.*, 11(3):1248–1257 (Mar., 1991).

Goldner et al., "Eine Neue Xanthin–Synthese," *Ann. Chem.* 691:142–158 (1966).

Hanahan, D., "Studies on Transformation of *Escherichia coli* with Plasmids," *J. Mol. Biol.*, 166:557–580 (1983).

Hancock et al., "All ras Proteins Are Polyiosprenylated but Only Some Are Palmitoylated," *Cell*, 57:1167–1177 (Jun., 1989).

Henikoff et al., "Isolation of a Gene from Drosophila by Complementation in Yeast," *Nature*, 289:33–37 (Jan., 1981).

Ito et al., "Transformation of Intact Yeast Cells Treated with Alkali Cations," *J. Bacteriol.*, 153:163–168 (Jan., 1983).

Kataoka et al., "DNA Sequence and Characterization of the *S. cerevisiae* Gene Encoding Adenylate Cyclase," *Cell*, 43:493–505 (Dec., 1985).

Kataoka et al., "Functional Homology of Mammalian and Yeast RAS Genes," *Cell*, 40:19–26 (Jan., 1985).

Kataoka et al., "Genetic Analysis of Yeast RAS1 and RAS2 Genes," *Cell*, 37:437–445 (Jun., 1984).

Kitayama et al., "A ras–Related Gene with Transformation Suppressor Activity," *Cell* 56:77–84 (Jan., 1989).

Le Trong et al., "Amino Acid Sequence of the Cyclic GMP Stimulated Cyclic Nucleotide Phosphodiesterase from Bovine Heart," *Biochemistry*, 29:10280–10288 (1990).

Lee & Nurse, "Complementation Used to Clone a Human Homologue of the Fission Yeast Cell Cycle Control Gene cdc2," *Nature*, 327:31–35 (1987).

Livi et al., "Cloning and Expression of cDNA for a Human Low–$K^m$, Rolipram–Sensitive Cyclic AMP Phosphodiesterase," *Mol. Cell Biol.*, 10(6):2678–2686 (Jun., 1990).

Lizardi, P.M., "Methods for the Preparation of Messenger RNA," *Methods Enzymol.*, 96:24–38 (1983).

Lugnier et al., "Substituted Carbostyrils as Inhibitors of Cyclic AMP Phosphodiesterase," *Eur. J. Med. Chem.–Chim. Ther.*, 20:121–125 (1985).

Lundberg et al., "High–fidelity Amplification Using a Thermostable DNA Polymerase Isolated from *Pyrococcus furiosus*," *Gene*, 108:1–16 (1991).

MacDonald et al., "Isolation of RNA Using Guanidinium Salts," *Meth. in Enzymol.* 152:219–227 (1983).

Mandel et al., "Calcium–dependent Bacteriophage DNA Infection." *J. Mol. Biol.*, 53:159–162 (1970).

Martins et al., "Purification and Characterization of a Cyclic GMP–Stimulated Cyclic Nucleotide Phosphodiesterase from Bovine Tissues," *J. Biol. Chem.* 255(4):1973–1979 (Feb., 1982).

McGrath et al., "Comparative Biochemical Properties of Normal and Activated Human ras p21 Protein," *Nature*, 310:644–649 (Aug., 1984).

McHale et al., "Expression of Human Recombinant cAMP Phosphodiesterase Isozyme IV Reverses Growth Arrest Phenotypes in Phosphodiesterase–Deficient Yeast," *Mol. Pharmacol.*, 39:109–113 (1991).

McKnight et al., "Identification and Molecular Analysis of a Third *Aspergillus nidulans* Alcohol Dehydrogenase Gene," *EMBO J.*, 4(8):2093–2099 (1985).

McLaughlin et al., "A Low–$K_m$, Rolipram–sensitive, cAMP–specific Phosphodiesterase from Human Brain," *J. Biol. Chem.*, 268(9):6470–6476 (Mar. 25, 1993).

McLeod et al., "The Product of the mei3+ Gene, Expressed Under Control of the Mating–Type Locus, Induces Meiosis and Sporulation in Fission Yeast," *EMBO J.*, 6(3):729–736 (1987).

Michaeli et al., "Isolation and Characterization of a Previously Undetected Human cAMP Phosphodiesterase by Complementation of cAMP Phosphodiesterase–deficient *Saccharomyces cerevisiae*," *J. Biol. Chem.*, 268(17):12925–12932 (1993).

Michaeli et al.,"Mutants of H–ras that Interfere with RAS Effector Function in *Saccharomyces cerevisiae*," *EMBO J.*, 8:3039–3044 (1989).

Mortimer et al., "Yeast Genetics," In: *The Yeast*, Chapter 8, Donner Laboratory, University of California, Berkley, California 94720, U.S.A., and Department of Genetics, University of Washington, Seattle, Washington 98105, U.S.A., pp. 386–460 (1969).

Neuman–Silberg et al., "The Drosophila ras Oncogenes: Structure and Nucleotide Sequence," *Cell*, 37:1027–1033 (Jul., 1984).

Nicholson et al., "Differential Modulation of Tissue Function and Therapeutic Potential of Selective Inhibitors of Cyclic Nucleotide Phosphodiesterase Isoenzymes," *Trends in Pharm. Sci.* 12:19–27 (Jan., 1991).

Nikawa et al., "Cloning and Characterization of the Low–Affinity Cyclic AMP Phosphodiesterase Gene of *Saccharomyces cerevisiae*," *Mol. Cell. Biol.*, 7(10):3629–3636 (Oct., 1987).

Ovchinnikov et al., "Cyclic GMP Phosphodiesterase from Bovine Retina: Amino Acid Sequence of the α–Subunit and Nucleotide Sequence of the Corresponding cDNA," *FEBS 05223*, 223:169–173 (Oct., 1987).

Papageorge et al., "Comparative Biochemical Properties of p21 ras Molecules Coded for by Viral and Cellular ras Genes," *J. Virol.*, 44(2):509–519 (Nov., 1982).

Powers et al., "Dominant Yeast and Mammalian RAS Mutants That Interfere with the CDC25–Dependent Activation of Wild–Type RAS in *Saccharomyces cerevisiae*," *Mol. Cell. Biol.*, 9(2):390–395 (Feb., 1989).

Powers et al, "Genes in *S. cerevisiae* Encoding Proteins with Domains Homologous to the Mammalian ras Proteins," *Cell*, 36:607–612 (Mar., 1984).

Powers et al., "RAM, A Gene of Yeast Required for a Functional Modification of RAS Proteins and for Production of Mating Pheromone a–Factor," *Cell*, 47:413–422 (Nov., 1986).

Qui et al., "Characterization of the Memory Gene Dunce of *Drosophila melanogaster*," *J. Mol. Biol.*, 222:553–565 (1991).

Reddy et al., "A Point Mutation is Responsible for the Acquisition of Transforming Properties by the T24 Human Bladder Carcinoma Oncogene," *Nature*, 300:149–152 (Nov., 1982).

Reymond et al., "Developmental Regulation of a Dictyostelium Gene Encoding a Protein Homologous to Mammalian ras Protein," *Cell*, 39:141–148 (Nov., 1984).

Saiki et al., "Primer–Directed Enzymatic Amplification of DNA with a Thermostable DNA Polymerase," *Science*, 239:487–491 (Jan., 1988).

Sanger et al., "DNA Sequencing with Chain–terminating Inhibitors," *Proc. Natl. Acad. Sci., USA*, 74:5463–5467 (Dec., 1977).

Sass et al., "Cloning and Characterization of the High–Affinity cAMP Phosphodiesterase of *Saccharomyces cerevisiae*," *Proc. Nat'l Acad. Sci., USA*, 83:9303–9307 (Dec., 1986).

Schacher et al., "Long–term Facilitation in Aplysia: Persistent Phosphorylation and Structural Changes," Cold Spring Harbor Symp. on Quant. Biol., LV:187:202 (1990).

Schuler et al., "A Workbench for Multiple Alignment Construction and Analysis," *Proteins: Struct. Funct. Genet.*, 9:180–190 (1991).

Shilo et al., "DNA Sequences Homologous to Vertebrate Oncogenes are Conserved in *Drosophila melanogaster*," *Proc. Nat'l Acad. Sci., USA*, 78:6789–6792 (Nov., 1981).

Shimizu et al., "Structure of the Ki–ras Gene of the Human Lung Carcinoma Cell Line Calu–1," *Nature*, 304:497–500 (Aug., 1983).

Shimizu et al., "Three Human Transforming Genes are Related to the Viral ras Oncogenes," *Proc. Natl. Acad. Sci.*, 80:2112–2116 (Apr., 1983).

Short et al., "Lambda ZAP: A Bacteriophage Lambda Expression Vector With In Vitro Excision Properties," *Nuc. Acids Res.*, 16(15):7583–7600 (Aug., 1988).

Swinnen et al., "Molecular Cloning of Rat Homologues of the *Drosophila melanogaster* Dunce cAMP Phosphodiesterase: Evidence for a Family of Genes," *Proc. Nat'l Acad. Sci., USA*, 86:5325–5329 (Jul., 1989).

Swinnen et al., "The mRNA Encoding a High–Affinity cAMP Phosphodiesterase if Regulated by Hormones and cAMP," *Proc. Nat'l Acad. Sci., USA*, 86:8197–8201 (Nov., 1989).

Tabin et al., "Mechanism of Activation of a Human Oncogene," *Nature*, 300:143–149 (Nov., 1982).

Taparowsky et al., "Activation of the T24 Bladder Carcinoma Transforming Gene is Linked to a Single Amino Acid Change," *Nature*, 300:762–765 (Dec., 1982).

Taparowsky et al., "Structure and Activation of the Human N–ras Gene," *Cell*, 34:581–586 (Sep., 1983).

Tempel et al., "Reward Learning in Normal and Mutant Drosophila," *Proc. Natl. Acad. Sci., USA*, 80:1482–1486 (Mar., 1983).

Thompson et al., "Identification of Type II (Cyclic GMP–Stimulatable) Cyclic Nucleotide Phosphodiesterase (CNPDE) mRNA in Rat Pheochromocytoma Cells (PC 12)," *FASEB J.*, 5(6):A1592 (Abstract 7092) (1991).

Toda et al., "Cloning and Characterization of BCY1, A Locus Encoding a Regulatory Subunit of the Cyclic AMP–Dependent Protein Kinase in *Saccharomyces cerevisiae*," *Mol. Cell. Biol.*, 7(4):1371–1377 (Apr., 1987).

Toda et al., "Exploring the Function of RAS Oncogenes by Studying the Yeast *Saccharomyces cerevisiae*," *Oncogenes and Cancer*, S.A. Aaronson et al., (Eds.), Japan Sci. Soc. Press., Tokyo/VNU Sci. Press, Utrecht, pp. 253–260 (1987).

Toda et al., "In Yeast, RAS Proteins Are Controlling Elements of Adenylate Cyclase," *Cell*, 40:27–36 (Jan., 1985).

Torphy et al., "Coexpression of Human cAMP–Specific Phosphodiesterase Activity and High Affinity Rolipram Binding in Yeast," *J. Biol. Chem.*, 267(3):1798–1804 (Jan., 25, 1992).

Trahey et al., "A Cytoplasmic Protein Stimulates Normal N–ras p21 GTPase, but Does Not Affect Oncogenic Mutants," *Science*, 238:542–545 (Oct., 1987).

Uno et al., "Characterization of Cyclic AMP–Requiring Yeast Mutants Altered in the Regulatory Subunit of Protein Kinase," *J. Biol. Chem.*, 257(23):14110–14115 (Dec., 1981).

Viera et al., "Production of Single–Stranded Plasmid DNA," *Methods in Enzymology*, 153:3–11 (1987).

Walter et al., "The Dunce Gene of Drosophila: Roles of $Ca^{2+}$ and Calmodulin in Adenosine 3':5'–Cyclic Monophosphate–specific Phosphodiesterase Activity," *J. Neurosci.*, 4(2):494–501 (Feb., 1984).

Watson et al., "An Alternative Procedure for the Synthesis of double–stranded cDNA for Cloning in Phage and plasmid Vectors," In: *DNA Cloning, A Practical Approach*, IRL Press, Oxford, pp. 79–88 (1984).

Wigler et al., "Studies of RAS Function in the Yeast *Saccharomyces cerevisiae*," *Cold Spring Harbor Symposium on Quant. Biol.*, LIII:649–655 (1988).

Willingham et al., "Localization of the src Gene Product of the Harvey Strain of MSV to Plasma Membrane of Transformed Cells by Electron Microscopic Immunocytochemistry," *Cell*, 19:1005–1014 (Apr., 1980).

Wilson et al., "SRA5 Encodes the Low–$K_m$ Cyclic AMP Phosphodiesterase of *Saccharomyces cerevisiae*," *Mol. & Cell. Biol.*, 8(1):505–510 (Jan., 1988).

Zhong et al., "Altered Synaptic Plasticity in Drosophila Memory Mutants with a Defective Cyclic AMP Cascade," *Science*, 251:198–201 (Jan. 11, 1991).

FIG. 1(A)

```
Jc44x  10  GCCGCGGCGGCCTAGGCCCGGCATCCCGGAGCTGCAACTGGTGTGGCCCTTCCCGGTGGCGGTG
                ||||||||||||||||||||||||||||||||||||||||||||||||||||||||||||
TM3-    1  gcggCCGCGGCGGCCTAGGCCCGGCATCCCGGAGCTGCAACTGGTGTGGCCCTTCCCGGTGGCGGTG Jc44x  68  GCGGCTGAGGACGAGGGCGTTCCTGCCCGAGCCCCTGGCCCCGCGCCCCGC
               ||||||||||||||||||||||||||||||||||||||||||||||||||||
TM3-   62  GCGGCTGAGGACGAGGGCGTTCCTGCCCGAGCCCCTGGCCCCGCGCCCCGC Jc44x 129  GTTCGCCGCCCTCCTGCCGTCTTCTTCGCCCAGCCCGTCCCCAACTTTCGCAGACGCCT
               ||||||||||||||||||||||||||||||||||||||||||||||||||||||||||
TM3-  123  GTTCGCCGCCCTCCTGCCGTCTTCTTCGCCCAGCCCGTCCCCAACTTTCGCAGACGCCT Jc44x 190  TCGGCTTCTCCGCAGCTGCCAGGATTTGGGCCGCCAGGGTTGGGCTGGCTTCGAG
               ||||||||||||||||||||||||||||||||||||||||||||||||||||||
TM3-  184  TCGGCTTCTCCGCAGCTGCCAGGATTTGGGCCGCCAGGGTTGGGCTGGCTTCGAG Jc44x 251  GCAGAGAATGGGCCGACACCATCTCCTGGCCCTGGACTCGCAGGCGAGCCCAG
               ||||||||||||||||||||||||||||||||||||||||||||||||||||
TM3-  245  GCAGAGAATGGGCCGACACCATCTCCTGGCCCTGGACTCGCAGGCGAGCCCAG Jc44x 312  GACTCGTGCTGCACGCCCAGCCGCCACCAGCCAGGGAGTCCTTCCTGTACCGCTC
               ||||||||||||||||||||||||||||||||||||||||||||||||||||||
TM3-  306  GACTCGTGCTGCACGCCCAGCCGCCACCAGCCAGGGAGTCCTTCCTGTACCGCTC
```

Fig. 1(B)

```
jc44x  373  AGACAGGCGACTATGACACATGTCACCCAAGACCATGTCCCGGAACTCATCGGTCACCAGCGAG
TM3-   366  AGACAGGCGACTATGACACATGTCACCCAAGACCATGTCCCGGAACTCATCGGTCACCAGCGAG jc44x  434             GC                              GCACGCTGAA
TM3-   427  GCacagtTGCTCTCTGCGGACCCCTGACCCTGTCCTCAATCACAGGCACGCTGAA jc44x  446  GACCTCATCGTAACACCATTTGCTCAGGTGCTGGCCCAGCCTCCGGAGCGTCCGTAGCAACT
TM3-   488  GACCTCATCGTAACACCATTTGCTCAGGTGCTGGCCCAGCCTCCGGAGCGTCCGTAGCAACT jc44x  507  TCTCACTCCTGACCAATGTGCCCTTCCCAGTAACAAGGCGGTCCCcgTGGGGGGCCCCA
TM3-   549  TCTCACTCCTGACCAATGTGCCCGTTCCCAGTAACAAGGCGGTCCC   GCTGGGGGGCCCCA jc44x  568  CCCCTGTCTGCAAGGCCACGCTGTC
TM3-   608  CCCCTGTCTGCAAGGCCACGCTGTCAGACCTTCTCAGTCACTACCCTGGCTGCCCCTTCCT jc44x  593  AGAAGAAACGTGTCAGCAGTTGGCCCGGGAGACTCTGGAGGAGCTGGACTGGTGTCTGGA
TM3-   669  TAGAAGAAACGTGTCAGCAGTTGGCCCGGGAGACTCTGGAGGAGCTGGACTGGTGTCTGGA
```

FIG. 1(C)

```
Jc44x  653  GCAGCTGGAGAGACCATGCAGAGACCTATCGCTGTCTGTCAGCGGAGATGGCCTCGCACAAGTTCAAA
            |||||||||||||||||||||||||||||||||||||||||||||||||||||||||||||||||||
TM3-   730  GCAGCTGGAGAGACCATGCAGAGACCTATCGCTGTCTGTCAGCGGAGATGGCCTCGCACAAGTTCAAA

Jc44x  714  AGGATGTTGAACCGTGAGCTCACACACCTGTCAGAAATGAGCAGGTCCGGAAACCAGGTCT
            ||||||||||||||||||||||||||||||||||||||||||||||||||||||||||||
TM3-   791  AGGATGTTGAACCGTGAGCTCACACACCTGTCAGAAATGAGCAGGTCCGGAAACCAGGTCT

Jc44x  775  CAGAGTACATTTCCACAACATTCCTGGACAAACAGAATGAAGTGGAGATCCCATCACCCAC
            ||||||||||||||||||||||||||||||||||||||||||||||||||||||||||||
TM3-   852  CAGAGTACATTTCCACAACATTCCTGGACAAACAGAATGAAGTGGAGATCCCATCACCCAC

Jc44x  836  GATGAAGGAACGAGAGAAAACAGCAAGCCGCGACCAAGACCCTCCCAGCCGCCCCCGCCC
            |||||||||||||||||||||||||||||||||||||||||||||||||||||||||||
TM3-   913  GATGAAGGAACGAGAGAAAACAGCAAGCCGCGACCAAGACCCTCCCAGCCGCCCCCGCCC

Jc44x  897  CCTGTACCACACTTACAGCCCATGTCCCAAATCACAGGGTTGAAAAAGTTGATGCATAGTA
            ||||||||||||||||||||||||||||||||||||||||||||||||||||||||||||
TM3-   974  CCTGTACCACACTTACAGCCCATGTCCCAAATCACAGGGTTGAAAAAGTTGATGCATAGTA

GB14     8                                AACATTCCCCGATTTGGGGTGAAGACCGATCAAGAAGAGCTCCT
                                          |||||||||||||||||||||||||||||||||||||||||||
Jc44x  958  ACAGCCTGAACAACTCTAACATTCCCCGATTTGGGGTGAAGACCGATCAAGAAGAGCTCCT
            ||||||||||||||||||||||||||||||||||||||||||||||||||||||||||||
TM3-  1035  ACAGCCTGAACAACTCTAACATTCCCCGATTTGGGGTGAAGACCGATCAAGAAGAGCTCCT
```

FIG. 1(D)

```
GB14    52  GGCCCAAGAACTGGAGAACCTGAACAAGTGGGGCCTGAACATCTTTTGCGTGTCGGATTAC
jc44x 1019  GGCCCAAGAACTGGAGAACCTGAACAAGTGGGGCCTGAACATCTTTTGCGTGTCGGATTAC
TM3-  1096  GGCCCAAGAACTGGAGAACCTGAACAAGTGGGGCCTGAACATCTTTTGCGTGTCGGATTAC

GB14   113  GCTGGAGGCCGCTCACTCACCTGCATCATGTACACGATGGTGACACGATGGTGACACGATGCTGACGCTGGAGAGGATCACTA
jc44x 1080  GCTGGAGGCCGCTCACTCACCTGCATCATGTACACGATGGTGACACGATGCTGACGCTGGAGAGGATCACTA
TM3-  1157  GCTGGAGGCCGCTCACTCACCTGCATCATGTACACGATGGTGACACGATGCTGACGCTGGAGAGGATCACTA

GB14   174  AGAAATTCCGCATCCCTGTGGACACGATGGTGACACAGCCTGCACGTGACGCTGACGCTGCAGTCCACCCAC
jc44x 1141  AGAAATTCCGCATCCCTGTGGACACGATGGTGACACAGCCTGCACGTGACGCTGCAGTCCACCCAC
TM3-  1218  AGAAATTCCGCATCCCTGTGGACACGATGGTGACACAGCCTGCACGTGACGCTGCAGTCCACCCAC

GB14   235  CCACGCTGACGTGGCCTACCATAACAGCCTGCACGTGACGCTGCAGTCCACCCAC
jc44x 1202  CCACGCTGACGTGGCCTACCATAACAGCCTGCACGTGACGCTGCAGTCCACCCAC
TM3-  1279  CCACGCTGACGTGGCCTACCATAACAGCCTGCACGTGACGCTGCAGTCCACCCAC
```

FIG. 1(E)

```
GB14   296  GTACTGCTGGCCACGCCT           GCACTAGATGCAGTGTTCACGGACCTGGAGATTC
JC44x 1263  GTACTGCTGGCCACGCCTTGGCCAACCCTTAAGGAATGCAGTGTTCACGGACCTGGAGATT
TM3-  1340  GTACTGCTGGCCACGCCT           GCACTAGATGCAGTGTTCACGGACCTGGAGATT

GB14   348  TCGCCGGCCCTCTTCGGCGGCCATCCACGATGTGGATCACCCTGGGGTCTCCAACCAGTT
JC44x 1324  TCGCCGGCCCTCTTCGGCGGCCATCCACGATGTGGATCACCCTGGGGTCTCCAACCAGT
TM3-  1392  TCGCCGGCCCTCTTCGGCGGCCATCCACGATGTGGATCACCCTGGGGTCTCCAACCAGT

GB14   409  CCTCATCAACACCAATTCGGAGCTCATGTACAACGATGAGTCGGTGCTCGAGAAT
JC44x 1385  CCTCATCAACACCAATTCGGAGCTCATGTACAACGATGAGTCGGTGCTCGAGAAT
TM3-  1453  CCTCATCAACACCAATTCGGAGCTCATGTACAACGATGAGTCGGTGCTCGAGAAT

GB14   470  CACCACCTGGCCCGTGGGCTTCAAGCTGCTGCAGGAGGACAACTGCGACATCTTCCAGAACC
JC44x 1446  CACCACCTGGCCCGTGGGCTTCAAGCTGCTGCAGGAGGACAACTGCGACATCTTCCAGAACC
TM3-  1514  CACCACCTGGCCCGTGGGCTTCAAGCTGCTGCAGGAGGACAACTGCGACATCTTCCAGAACC
```

FIG. 1(F)

```
GB14    531  TCAGCAAGCGGCCAGAGC TACGCAAGATGGTCATCG
JC44x  1507  TCAGCAAGCGGCCAGAGCCTACGCAAGATGGTCATCGACATGGTGCTGGCCACGGA
TM3-   1575            GCAGAGCCTACGCAAGATCATCGACATGGTGCTGGCCACGGA

JC44x  1568  CATGTCCAAGCACATGACCCTCCTGGCTGACCTGAAGACCATGGTGGAGACCAAGAAAGTG
TM3-   1635  CATGTCCAAGCACATGACCCTCCTGGCTGACCTGAAGACCATGGTGGAGACCAAGAAAGTG

JC44x  1629  ACCAGCTCAGGGGTCCTCCTGTCTAGATAACTACTCCGACCGCATCCAGGTCCTCCGGAACA
TM3-   1696  ACCAGCTCAGGGGTCCTCCTGTCTAGATAACTACTCCGACCGCATCCAGGTCCTCCGGAACA
GB18ARR   1                                                      ACA

JC44x  1690  TGGTGCACTGTGCCGACCTCAGCAACCCCACCAAGCCGCTGGAGCTGTACCGCCAGTGGAC
TM3-   1757  TGGTGCACTGTGCCGACCTCAGCAACCCCACCAAGCCGCTGGAGCTGTACCGCCAGTGGAC
GB18ARR   4  TGGTGCACTGTGCCGACCTCAGCAACCCCACCAAGCCGCTGGAGCTGTACCGCCAGTGGAC
```

FIG. 1(G)

```
jc44x    1751  AGACCGGCATCATGGCCGAGTTCTTCCAGCAGGGTGACCGAGAGGCGAGCGTGGAA
TM3-     1818  AGACCGGCATCATGGCCGAGTTCTTCCAGCAGGGTGACCGAGAGGCGAGCGTGGAA
GB18ARR    65  AGACCGGCATCATGGCCGAGTTCTTCCAGCAGGGTGACCGAGAGGCGAGCGTGGAA jc44x    1812  ATCAGCCCCATGTGTGACAAGCACACTGCCTCCGTGGAGAAGTCTCAGGTGGTTTATTG
TM3-     1879  ATCAGCCCCATGTGTGACAAGCACACTGCCTCCGTGGAGAAGTCTCAGGTGGTTTATTG
GB18ARR   126  ATCAGCCCCATGTGTGACAAGCACACTGCCTCCGTGGAGAAGTCTCAGGTGGTTTATTG jc44x    1873  ACTACATTGTGCACCCATTGTGGGAGGACCTGGGCGGGACCTTGTCCACCAGATGCCCAGGA
TM3-     1940  ACTACATTGTGCACCCATTGTGGGAGGACCTGGGCGGGACCTTGTCCACCAGATGCCCAGGA
GB18ARR   187  ACTACATTGTGCACCCATTGTGGGAGGACCTGGGCGGGACCTTGTCCACCAGATGCCCAGGA jc44x    1934  GATCTTGGACACTTTGGAGGACAACCGGGACTGGTACTACAGGCCATCCGGCAGAGCCCA
TM3-     2001  GATCTTGGACACTTTGGAGGACAACCGGGACTGGTACTACAGGCCATCCGGCAGAGCCCA
GB18ARR   248  GATCTTGGACACTTTGGAGGACAACCGGGACTGGTACTACAGGCCATCCGGCAGAGCCCA
```

FIG. 1(H)

```
jc44x   1995  TCTCCGCCACCCGAGGAGGAGTCAAGGGGGCCAGGCCACCCCTGCCTGACAAGTTCC
TM3-    2062  TCTCCGCCACCCGAGGAGGAGTCAAGGGGGCCAGGCCCACCCCTGCCTGACAAGTTCC
GB18ARR  309  TCTCCGCCACCCGAGGAGGAGTCAAGGGGGCCAGGCCCACCCCTGCCTGACAAGTTCC jc44x   2056  AGTTTGAGCTGACGCTGGAGGAGGAAGAGGAAGAAATATCAATGGCCCAGATACCGTG
TM3-    2123  AGTTTGAGCTGACGCTGGAGGAGGAAGAGGAAGAAATATCAATGGCCCAGATACCGTG
GB18ARR  370  AGTTTGAcgTGACGCTGGAGGAGGAAGAGGAAGAAATATCAATGGCCCAGATACCGTG jc44x   2117  CACAGCCCAAGAGGCATTGACTGAGCAGGAGTCGAGGAAGCTCTGGATGCA
TM3-    2184  CACAGCCCAAGAGGCATTGACTGAGCAGGAGTCGAGGAAGCTCTGGATGCA
GB18ARR  431  CACAGCCCAAGAGGCATTGAcTGcGCAGGAGTCGAGGAAGCTCTGGATGCA jc44x   2178  ACCATAGCCTGGGAGGCATCCCCGGCCCCCAGGAGTCGTTGGAAGTTATGGCACAGGAAGCAT
TM3-    2245  ACCATAGCCTGGGAGGCATCCCCGGCCCCCAGGAGTCGTTGGAAGTTATGGCACAGGAAGCAT
GB18ARR  492  ACCATAGCCTGGGAGGCATCCCCGGCCCCCAGGAGTCGTTGGAAGTTATGGCACAGGAAGCAT
```

FIG. 1(I)

```
Jc44x   2239  CCCTGGAGGCCGAGCTGGGAGGCAGTGTATTTGACACAGCAGGCACAGTCCACAGGCAGTGC
TM3-    2306  CCCTGGAGGCCGAGCTGGGAGGCAGTGTATTTGACACAGCAGGCACAGTCCACAGGCAGTGC
GB18ARR  553  CCCTGGAGGCCGAGCTGGGAGGCAGNGTATTTGACACAGCAGGCACAGTCCACAGGCAGTGC

Jc44x   2300  ACCTGTGGCTCCGGATGAGTTCTCGTCCCGGGAGGAATTCGTGGTTGCTGTAAGCCACAGC
TM3-    2367  ACCTGTGGCTCCGGATGAGTTCTCGTCCCGGGAGGAATTCGTGGTTGCTGTAAGCCACAGC
GB18ARR  614  ACCTGTGGCTCCGGATGAGTTCTCGTCCCGGGAGGAATTCGTGGTTGCTGTAAGCCACAGC

Jc44x   2361  AGCCCCTCTGCCCTGGCTCTTCAAAGCCCTTCCCTGCTTGGAGGACCCTGTCTGTTT
TM3-    2428  AGCCCCTCTGCCCTGGCTCTTCAAAGCCCTTCCCTGCTTGGAGGACCCTGTCTGTTT
GB18ARR  675  AGCCCCTCTGCCCTGGCTCTTCAAAGCCCTTCCCTGCTTGGAGGACCCTGTCTGTTT

Jc44x   2422  CAGAGCATGCCC  GGCCTCCCGGCCTCCCGGGCCTCCCACGGGCCGAGGTGGAGGCCCAACG
TM3-    2489  CAGAGCATGCCCcGGCCTCCCGGCCTCCCGGGCCTCCCACGGGCCGAGGTGGAGGCCCAACG
GB18ARR  736  CAGAGCATGCCCCGGCCTCCCGG  CCTCCCGGGCCTCCCACGGGCCCTAGGTGG    AACG
```

FIG. 1(J)

```
Jc44x  2481  AGAGCACCAGGCTGCCAAGAGGGCTTGCAGTGCCTGCGCAGGGACATTTGGGGAGGACACA
TM3-   2550  AGAGCACCAGGCTGCCAAGAGAGGCTTGCAGTGCCTGCGCAGGGACATTTGGGGAGGACACA
GB18ARR 790  AGAGCACCAGGCTGCCAAGAGAGGCTTGCAGTGCCTGCGCAGGGACATTTGGGGAGGACACA

Jc44x  2542  TCCGCACTCCCAGCTCCTGGTGGGCGGGGGGTCAGGTGGAGACCCTACCTGATCCCCAGACC
TM3-   2611  TCCGCACTCCCAGCTCCTGGTGGGCGGGGGGTCAGGTGGAGACCCTACCTGATCCCCAGACC
GB18ARR 851  TCCGCACTCCCAGCTCCTGGTGGGCGGGGGGTCAGGTGGAGACCCTACCTGATCCCCAGACC

Jc44x  2603  TCTGTCCCTGTTCCCCTCCCCTCCACTCCCCTGCTCCCCGACCACTCCTCCT
TM3-   2672  TCTGTCCCTGTTCCCCTCCCCTCCACTCCCCTGCTCCCCGACCACTCCTCCT
GB18ARR 912  TCTGTCCCTGTTCCCCTCCCCTCCACTCCCCTGCTCCCCGACCACTCCTCCT

Jc44x  2664  CTGCCCTCAAAGACTCTTGTCCTCTTGTCC
TM3-   2733  CTGCCCTCAAAGACTCTTGTCCTCTTGTCCCTCCCTGAGATTTTTTTTTTTTTTT
GB18ARR 973  CTGCCCTCAAAGACTCTTGTCCTCTTGTCCCTCCCTGAGA
```

FIG. 2(A)

```
PDE2RR    1                                              GAATTCcTTCTGACGTGGCATATCACAACA
                                                         |||||| ||||||||||||||||||||||
TM72   1300  TTTATAACCTACATGATGACTTTAGAAGACCATTACCATTCTGACGTGGCATATCACAACA

PDE2RR   31  GCCTGCACTGCTGCTGATGTAGCCCCAGTCGACCCCATGTNCTCC TTCTACNCCAGCATTAG
             ||||||||| ||||| |||||||||||||||||||||||||| |||||| ||||||||||
TM72   1361  GCCTGCACT GCTGCT GATGTAGCCCCAGTCGACCCCATGTTCTCCTTTCTACACCAGCATTAG

PDE2RR   91  ACGCTGTCTTCACAGATTTGGAAATCCTGGCTGCCATTTTGCAGCTGCCATCCATGACGT
             |||||||||||||||| |||||||||||||||||||||||||||||||||||||||||||
TM72   1422  ACGCTGTCTTCACAGATTTGGAGATCCTGGCTGCCATTTTGCAGCTGCCATCCATGACGT

PDE2RR  152  TGATCATCCTGGAGTCTCCAATCAGTTTCTCATCAACACAAATTCAGAACTGCTTTGATG
             ||||||||||||||||||||||||||||||||||||||||||||||||||||| |||||
TM72   1483  TGATCATCCTGGAGTCTCCAATCAGTTTCTCATCAACACAAATTCAGAAACTGCTTTGATG

PDE2RR  213  TATAATGATGAATCTGTGTTGGAAAATCATCACCCTTGCTGTGGGTTTCAAACTGCTGCAAG
             ||||||||||||||||||||||||||||||||||||||||||||||||||||||| |||
TM72   1544  TATAATGATGAATCTGTGTTGGAAAATCATCACCCTTGCTGTGGGTTTCAAACTGCTGCAAG

PDE2RR  274  AAGAACACTGTGACATCTTCATGAATCTCACCAAGAAGCAGACGTCAGACACTCAGGAAGAT
             |||||||||| ||||||| ||||||||| |||||||||||||||||||||||||||||||
TM72   1605  AAGAACACTGTGACATCTTCATGAATCTCACCAAGAAGCAGACAGCAGACACTCAGGAAGAT
```

FIG. 2(B)

```
PDE2RR  335   GGTTATTGACATGGTGTTAGCAACTGATATGTCTAAACATATGAGCCTGCTGGCAGACCTG
TM72    1666  GGTTATTGACATGGTGTTAGCAACTGATATGTCTAAACATATGAGCCTGCTGGCAGACCTG

PDE2RR  396   AAGACAATGGTAGAGAACGAAGAAAGTTACAAGTTCAGGGCGTTCTTCTCCTAGACAACTATA
TM72    1727  AAGACAATGGTAGAGAACGAAGAAAGTTACAAGTTCAGGGCGTTCTTCTCCTAGACAACTATA

PDE2RR  457   CCGATCGCATTCAGGTCCTTCGCAACATGTGTACACTGTGCAGACCTGAGCAACCCCACCAA
TM72    1788  CCGATCGCATTCAGGTCCTTCGCAACATGTGTACACTGTGCAGACCTGAGCAACCCCACCAA

PDE2RR  518   GTCCTTGGAATTGTATCGGCAATGGACACAGACCGCATCATGGAGGAATTTTTCCAGCAGGGA
TM72    1849  GTCCTTGGAATTGTATCGGCAATGGACACAGACCGCATCATGGAGGAATTTTTCCAGCAGGGA

PDE2RR  579   GACAAAGAGCGGGAGAGGGGAATGGAAATTAGCCCAATGTGTGATAAACACACAGCTTCTG
TM72    1910  GACAAAGAGCGGGAGAGGGGAATGGAAATTAGCCCAATGTGTGATAAACACACAGCTTCTG

PDE2RR  640   TGGAAAAATCCCAGGTTGGTTTCATCGACTACACATTGTCCATCCATTGTGGGAGACATGGGC
TM72    1971  TGGAAAAATCCCAGGTTGGTTTCATCGACTACACATTGTCCATCCATTGTGGGAGACATGGGC
```

FIG. 2(C)

```
PDE2RR   701  AGATTTGGTACAGCCTGATGCTCAGGACATTCTCGATACCTTAGAAGATAACAGGAACTGG
TM72    2032  AGATTTGGTACAGCCTGATGCTCAGGACATTCTCGATACCTTAGAAGATAACAGGAACTGG

PDE2RR   762  TATCAGAGCATGATATACCTCAAAGTCCCTCACCACTGGACCAGAGAACAGGACTGCC
TM72    2093  TATCAGAGCATGATATACCTCAAAGTCCCTCACCACTGGACCAGAGAACAGGACTGCC

PDE2RR   823  AGGGTCTGATGGAGAAGTTTCAGTTTGAACTGACTCTCGATGAGGAAGATTCTGAAGGACC
TM72    2154  AGGGTCTGATGGAGAAGTTTCAGTTTGAACTGACTCTCGATGAGGAAGATTCTGAAGGACC

PDE2RR   884  TGAGAAGGAGGGAGAGGGACACAGCTATTTCAGCAGCAGACATTGCAACAGAAGACAAGTCCC
TM72    2215  TGAGAAGGAGGGAGAGGGACACAGCTATTTCAGCAGCAGACATTGCAACAGAAGACAAGTCCC

PDE2RR   945  CCAGAAAACAGAGAGATTCCCTGGGAGAGACTGACATAGACATAGACATTCTATCCTTGATGAGCATGC
TM72    2276  CCAGAAAACAGAGAGATTCCCTGGGAGAGACTGACATAGACATAGACATTCTATCCTTGATGAGCATGC

PDE2RR  1006  CCGTGGATACATAATCCCCTGTGGGAGATGAACATTCTATCCTTGATGAGCATGC
TM72    2337  CCGTGGATACATAATCCCCTGTGGGAGATGAACATTCTATCCTTGATGAGCATGC
```

FIG. 2(D)

```
PDE2RR    1067  CAGCTATGTGGTAGGGCCAGCCCACCATGGGGGCCAAGACCTGCACAGGACAAGGCCACC
TM72      2337  CAGCTATGTGGTAGGGCCAGCCCACCATGGGGGCCAAGACCTGCACAGGACAAGGCCACC
PDE7        20                          CCCACCATGGGGGCCAAGACCTGCACAGGACAAGGCCACC
PDE10X-INV   7                          CCCACCATGGGGGCCAAGACCTGCACAGGACAA GGCCACC

PDE2RR    1128  TGGCCTTTCAGTTACTTGAGTTTGGAGTCAGAAAGCAAGACCAGGAAGCAAATAGCAGTC
TM72      2398  TGGCCTTTCAGTTACTTGAGTTTGGAGTCAGAAAGCAAGACCAGGAAGCAAATAGCAGTC
PDE7        62  TGGCCTTTCAGTTACTTGAGTTTGGAGTCAGAAAGCAAGACCAGGAAGCAAATAGCAGTC
PDE10X-INV  48  TGGCCTTTCAGTTACTTGAGTTTGGAGTCAGAAAGCAAGACCAGGAAGCAAATAGCAGTC

PDE2RR    1189  AGGAAATCCCACGGTTGACTTGCCTTGATGGCAAGCTTGGTGGAGAGGGCTGAAGCTGTTG
TM72      2459  AGGAAATCCCACGGTTGACTTGCCTTGATGGCAAGCTTGGTGGAGAGGGCTGAAGCTGTGG
PDE7       123  AGGAAATCCCACGGTTGACTTGCCTTGATGGCAAGCTTGGTGGAGAGGGCTGAAGCTGTTG
PDE10X-INV 109  AGGAAATCCCACGGTTGACTTGCCTTGATGGCAAGCTTGGTGGAGAGGGCTGAAGCTGTTG
```

FIG. 2(E)

```
PDE2RR    1250  CTGGGGCCGATTCTGATCAAGACACATGGCTTGAAAATGGAAGACACAAAACCGAGAGAT
TM72      2520  CTGGGGCCGATTCTGATCAAGACACATGGCTTGAAAATGGAAGACACAAAACTGAGAGAT
PDE7       184  CTGGGGCCGATTCTGATCAAGACACATGGCTTGAAAATGGAAGACACAAAACTGAGAGAT
PDE10X-INV 170  CTGGGGCCGNTTCTGATCAAGACACATGGCTTGAAAATGGAAGACACAAAACTGAGAGAT

PDE2RR    1311  CATTCTGCACTAAGTTTCGGGAACTTATCCCCGACAGTGACTGAACTCACTGACTAATAAC
TM72      2581  CATTCTGCACTAAGTTTCGGGAACTTATCCCCGACAGTGACTGAACTCACTGACTAATAAC
PDE7       245  CATTCTGCACTAAGTTTCGGGAACTTATCCCCGACAGTGACTGAACTCACTGACTAATAAC
PDE10X-INV 231  CATTCTGCACTAAGTTTCGGGAACTTATCCCCGACAGTGACTGAACTCACTGACTAATAAC

PDE2RR    1372  TTCATTTATGAATCTTCTCCCTTGTCTGCCAACCTGTGTGCCTTTTTGTAAA
TM72      2642  TTCATTTATGAATCTTCTCACTTGTCTGCCAACCTGTGTGCCTTTTTGTAAA
PDE7       306  TTCATTTATGAATCTTCTCCCTTGTCTGCCAACCTGTGTGCCTTTTTGTAAA
PDE10X-INV 292  TTCATTTATGAATCTTCTCCCTTGTCTGCCAACCTGTGTGCCTTTTTGTAAA
```

FIG. 2(F)

```
PDE2RR    1433  ACATTTTCATGTCTCTTAAAATGCCTGTTGAATACCTGGAGTTAGTATCAACTTCTACACA
TM72      2703  ACATTTTCATGTCTCTTAAAATGCCTGTTGAATACCTGGAGTTAGTATCAACTTCTACACA
PDE7       367  ACATTTTCATGTCTCTTAAAATGCCTGTTGAATACCTGGAGTTAGTATCAACTTCTACACA
PDE10X-INV 353  ACATNTTCANGTCTCTTAAAATGCCTGTTGAATACCTGGAGTT     AGATCAACTTCTACACA

PDE2RR    1494  GATAAGCTTTCAAAGTTGACAAACTTTTTGACTCTTTTGACTCTTTCTGGAAAAGGGAAAGAAAATAGT
TM72      2764  GATAAGCTTTCAAAGTTGACAAACTTTTTGACTCTTTTGACTCTTTCTGGAAAAGGGAAAGAAAATAGT
PDE7       428  GATAAGCTTTCAAAGTTGACAAACTTTTTGACTCTTTTGACTCTTTCTGGAAAAGGGAAAGAAAATAGT
PDE10X-INV 412  GATAAGCTTTCAAAGTTGACAAACTTTTTGACTCTT  CTGGAAAAGGGAAAGAAAATAGT

PDE2RR    1555  CTTCCTTCTTTCTTGGGCAATATCCTTCACTTTACTACAGTACTTTTGCAAACAGACAGA
TM72      2825  CTTCCTTCTTTCTTGGGCAATATCCTTCACTTTACTACAGTACTTTTGCAAACAGACAGA
PDE7       488  CTTCCTTCTTTCTTGGGCAATATCCTTCACTTTACTACAGTACTTTTGCAAACAGACAGA
PDE10X-INV 471  CTTCCTTCTTTCTTGGGCAATATCCTTCACTTTACTACAGTACTTTTGCAAACAGACAGA
```

FIG. 2(G)

```
PDE2RR     1616  AAGGATACACTTCTAACCACATTTAC
TM72       2886  AAGGATACACTTCTAACCACACATTTAC TCCTTCCCTGTTGTCCAGTCCAACTCCACAGT
PDE7        549  AAGGATACACTTCTAACCACACATTTACTTCCCTGTTGTCCAGTCCAACTCCACAGT
PDE10X-INV  532  AAGGATACACTTCTAACCACACATTTACTTCCCTGTTGTCCAGTCCAACTCCACAGT

TM72       2947                                            ACTTTAACTTTTT
PDE7        610  CACTCTTAAAACTTCTCTGTTGCCTGCCTCCAACAGT    ACTTTAACTTTTT
PDE10X-INV  593  CACTCTTAAAACTTCTCTCTGTTGCCTGCCTCCAACAGTACTTTAACTTTTT

TM72        662  GCTGTAAACAGAATAAAATTGAACAAATTAGGGGTAGAAAGGAGCAGTGGTGTCGTTCAC
PDE7        664  GCTGTAAACAGAATAAAATTGAACAAATTAGGGGTAGAAAGGAGCAGTGGTGTCGTTCAC
PDE10X-INV  654  GCTGTAAACAGAATAAAATTGAACAAATTAGGGGTAGAAAGGAGCAGTGGTGTCGTTCAC

TM72        723  CGTGAGAGTCTGCATAGAACTCAGCAGTGTGCCCTGCTCCTGTGTCTTGGACCCCTGC
PDE7        725  CGTGAGAGTCTGCATAGAACTCAGCAGTGTGCCCTGCTCCTGTGTCTTGGACCCTGCCCCCAC
PDE10X-IND  715  CGTGAGAGTCTGCATAGAACTCAGCAGTGTGCCCTGCTCCTGTGTCTTGGACCCTGCCCCCAC
```

Fig. 2(H)

| | | |
|---|---|---|
| PDE7 | 786 | AGGAGTTGTACAGTCCCTGGCCCTGTTCCCTACCTCCTCTTCACCCGTTAGGCTGTTT |
| PDE10X-INV | 776 | AGGAGTTGTACAGTCCCTGGCCCTGTTCCCTACCTCCTCTTCACCCGTTAGGCTGTTT |
| PDE7 | 847 | TCAATGTAATGCTGCCGTCCTTCTCTTGCACTGCCTTCTGCCTAACACCTCCATTCCTGT |
| PDE10X-INV | 837 | TCAATGTAATGCTGCCGTCCTTCTCTTGCACTGCCTTCTGCCTAACACCTCCATTCCTGT |
| PDE7 | 908 | TTATAACCGTGTATTATTACTTAATGTATATAATGTTTGTAAGTTATTAATTA |
| PDE10X-INV | 898 | TTATAACCGTGTATTATTACTTAATGTATATAATGTTTGTAAGTTATTAATTA |
| PDE7 | 969 | TATATCTAACATTGCCTGCCAATGGTGGTGTTAAATTTGTGTAGAAAACTCTGCCTAAGAG |
| PDE10X-INV | 959 | TATATCTAACATTGCCTGCCAATGGTGGTGTTAAATTTGTGTAGAAAACTCTGCCTAAGAG |
| PDE7 | 1030 | TTACGACTTTTTCTTGTAATGTTTTGTATTGTGTATTATATAACCCAAACGTCACTTAGTA |
| PDE10X-INV | 1020 | TTACGACTTTTTCTTGTAATGTTTTGTATTGTGTATTATATAACCCAAACGTCACTTAGTA |
| PDE7 | 1091 | GAGACATATGGCCCCCTTGGCAGAGAGGACAGGGGTGGGCTTTGTTCAAAGGGTCTGCCC |
| PDE10X-INV | 1081 | GAGACATATGGCCCCCTTGGCAGAGAGGACAGGGGTGGGCTTTGTTCAAAGGGTCTGCCC |

FIG. 2(I)

```
PDE7        1152  TTTCCCTGCCTGAGTTGCTACTTCTGCACAACCCCTTTATGAACCAGTTTTGGAAACAATA
                  ||||||||||||||||||||||||||||||||||||||||||||||||||||||||||||
PDE10X-INV  1142  TTTCCCTGCCTGAGTTGCTACTTCTGCACAACCCCTTTATGAACCAGTTTTGGAAACAATA

PDE7        1213  TTCTCACATTAGATACTAAATGGTTTATACTGAGCTTTACTTTTGTATAGCTTGATAGGG
                  ||||||||||||||||||||||||||||||||||||||||||||||||||||||||||||
PDE10X-INV  1203  TTCTCACATTAGATACTAAATGGTTTATACTGAGCTTTACTTTTGTATAGCTTGATAGGG

PDE7        1274  GCAGGGGGCAATGGGATGTAGTTTTACCCAGGTTCTATCCAAATCTATGTGGGCATGAGT
                  ||||||||||||||||||||||||||||||||||||||||||||||||||||||||||||
PDE10X-INV  1264  GCAGGGGGCAATGGGATGTAGTTTTACCCAGGTTCTATCCAAATCTATGTGGGCATGAGT

PDE7        1335  TGGGTTATAACTGGATCCTACTATCATTGTGGCTTTGGTTCAAAAGGAAACACTACATTTG
                  ||||||||||||||||||||||||||||||||||||||||||||||||||||||||||||
PDE10X-INV  1325  TGGGTTATAACTGGATCCTACTATCATTGTGGCTTTGGTTCAAAAGGAAACACTACATTTG

PDE7        1396  CTCACAGATGATTCTTCTGAATGCTCCCGAACTACTGACTTTGAAGAGGTAGCCTCCTGCC
                  ||||||||||||||||||||||||||||||||||||||||||||||||||||||||||||
PDE10X-INV  1386  CTCACAGATGATTCTTCTGAATGCTCCCGAACTACTGACTTTGAAGAGGTAGCCTCCTGCC

PDE7        1457  TGCCATTAAGCAGGAATGTCATGTTCCAGTTCATTACAAAAGAAACAATAAAACAATGTG
                  ||||||||||||||||||||||||||||||||||||||||||||||||||||||||||||
PDE10X-INV  1447  TGCCATTAAGCAGGAATGTCATGTTCCAGTTCATTACAAAAGAAACAATAAAACAATGTG
```

Fig. 2(J)

```
PDE7      1518  AATTTTTATAATAAAATGTGAACTGATGTAGCAAATTACGCAAATGTGAAGCCTCTTCTGA
                ||||||||||||||||||||||||||||||||||||||||||||||||||||||||||||
PDE10X-INV 1508 AATTTTTATAATAAAATGTGAACTGATGTAGCAAATTACGCAAATGTGAAGCCTCTTCTGA

PDE7      1579  TAACACTTGTTAGGCCCTCTTACTGATGTCAGTTTCAGTTTGTAAATATGTTTCATGCTTT
                ||||||||||||||||||||||||||||||||||||||||||||||||||||||||||||
PDE10X-INV 1569 TAACACTTGTTAGGCCCTCTTACTGATGTCAGTTTCAGTTTGTAAATATGTTTCATGCTTT

PDE7      1640  CAGTTCAGTCATTGTGACTCAGTAATTACAGAAAATGGCACAAATGTGCATGACCAATGGGT
                ||||||||||||||||||||||||||||||||||||
PDE10X-INV 1630 CAGTTCAGTCATTGTGACTCAGTAATTACAGAAAA
```

FIG. 3(A)

```
PDE18    1  GAATTCCT       TTGTTCA              CATCTTCTAGTT
            ||||||||       |||||||              ||||||||||||
GB25     1  GAATTCCTctgactaaTTCAagtatcccaaggtttggagtTAAAACTGAACAAGAAGATGT PDE18   28  CCTTGGCAAGGA                         CATCTTCATGTTTTCAGAATAGCAGAG
            ||||||||||||                         |||||||||||||||||||||||||
GB25    62  CCTTGGCAAGGAactagaagatgtgaacaaatgggGTCTTCATGTTTTCAGAATAGCAGAG PDE18   67  TTGTCTGGTAACCGGCCCTTGACTGTTATCATGCACACCATTTTTCAGGAACGGGATTTAT
            ||||||||||||||||||||||||||||||||||||||||||||||||||||||||||||
GB25   123  TTGTCTGGTAACCGGCCCTTGACTGTTATCATGCACACCATTTTCAGGAACGGGATTTAT PDE18  128  TAAAAACATTTAAAATTCCAGTAGATACTTAATTACATATCTTATGACTCTCGAAGACCA
            ||||||||||||||||||||||||||||||||||||||||||||||||||||||||||||
GB25   184  TAAAAACATTTAAAATTCCAGTAGATACTTAATTACATATCTTATGACTCTCGAAGACCA PDE18  189  TTACCATGCTGATGTGGCCTATCACAACAATATCCATGCTGCAGATGTTGTCCAGTCTACT
            ||||||||||||||||||||||||||||||||||||||||||||||||||||||||||||
GB25   245  TTACCATGCTGATGTGGCCTATCACAACAATATCCATGCTGCAGATGTTGTCCAGTCTACT PDE18  250  CATGTGCTATTATCTACACCTGCTTTGGGAGGCTGTGTTACAGATTTGGAGATTCTTGCAG
            ||||||||||||||||||||||||||||||||||||||||||||||||||||||||||||
GB25   306  CATGTGCTATTATCTACACCTGCTTTGGGAGGCTGTGTTACAGATTTGGAGATTCTTGCAG
```

FIG. 3(B)

```
PDE18  311  CAATTTTGCCAGTGCAATACATGATGTAGATCATCCTGGTGTGTCCAATCAATTCTGAT
GB25   367  CAATTTTGCCAGTGCAATACATGATGTAGATCATCCTGGTGTGTCCAATCAATTCTGAT

PDE18  372  CAATACAAACTCTGAACTTGCCTTGATGTGTACAATGATTCCTCAGTCTTAGAGAACCATCAT
GB25   428  CAATACAAACTCTGAACTTGCCTTGATGTGTACAATGATTCCTCAGTCTTAGAGAACCATCAT

PDE18  433  TTGGCTGTGGGCTTTAAATTGCTTCAGGAGAAAACTGTGACATTTCCAGAATTTGACCA
GB25   489  TTGGCTGTGGGCTTTAAATTGCTTCAGGAGAAAACTGTGACATTTCCAGAATTTGACCA

PDE18  494  AAAAACAAAGACAATCTTTAAGGAAAATGGTCATTGACACTGTACTTGCAACAGATATGTC
GB25   550  AAAAACAAAGACAATCTTTAAGGAAAATGGTCATTGACACTGTACTTGCAACAGATATGTC

PDE18  555  AAAAACACATGATGAATCTACTGGCTGATTTGAAGACTATGGTTGAAACTAAGAAAGTGACAAGC
GB25   611  AAAAACACATGATGAATCTACTGGCTGATTTGAAGACTATGGTTGAAACTAAGAAAGTGACAAGC

PDE18  616  TCTGGAGTTCTTCTTCTTGATAATTATTCCGATAGGATTCAGGTTCTTCAGAATATGGTGC
GB25   672  TCTGGAGTTCTTCTTCTTGATAATTATTCCGATAGGATTCAGGTTCTTCAGAATATGGTGC

PDE19  677  ACTGTGCAGATCTGAGCAACCCAACAAAGCCTCTCCAGCTGTACCGCCAGTGGACGGACCG
GB25   733  ACTGTGCAGATCTGAGCAACCCAACAAAGCCTCTCCAGCTGTACCGCCAGTGGACGGAC
```

FIG. 4(A)

```
TM72    212                                                                          SLRsVRNNFTiLTNL
RATDPD    1                                                                          SLRiVRNNFTlLTNL

TM72    219  HGtSNKRSPAASQpPVsRVnPQEESYQKLAMETLEELDWCLDQLETIQTYRSVSEMASNKF
RATDPD    8  HGaPNKRSPAASQaPVTRVSLQEESYQKLAMETLEELDWCLDQLETIQTYRSVSEMAShKF
JC44X    25                           EETCQqLARETLEELDWCLEQLETMQTYYSVSEMAShKF

TM72    287  KRMLNRELTHLSEMSRSGNQVSEYISNTFLDKQNDVEIPSPTQKDREK
RATDPD   72  KRMLNRELTHLSEMSRSGNQVSEYISNTFLDKQNDVEIPSPTQKDREK
JC44X    59  KRMLNRELTHLSEMSRSGNQVSEYISTFLDKQNeVEIPSPTmKeREKqQaPRPRPSQPPP

TM72    335  KKKQQLMTQISGVKKLMHSSSLNNTSISRFGVNTENEDHLAKELEDLNKWGLNIFNVAG
RATDPD  124  KKKQQLMTQISGVKKLMHSSSLNNTSISRFGVNTENEDHLAKELEDLNKWGLNIFNVAG
JC44X   123  PPVPHLQPMSQiTGLKKLMHSnSLNNsnIPRFGVKTQqEELLAQELEnLNKWGLNIFCVSD
```

FIG. 4(B)

```
PDE18   25  GNRPLTvIMhtIFQERDLLKTFKIPvDTLITYLMTLEDHYHADVAYHNNIHAADVvQST
TM72   394  YSHNRPLTcIMYAIFQERDLLKTFRiSSDTFiTYMMTLEDHYHSDVAYHNSLHAADVAQST
RATDPD 183  YSHNRPLTCIMYAIFQERDLLKTFKiSSDTFVTYMMTLEDHYHSDVAYHNSLHAADVAQST
JC44X  184  YaggRsLTCIMYMIFQERDLLKkFRIPvDTMVTYMLTLEDHYHADVAYHNSLHAADVLQST PDE18   85  HVLLSTP    ALEAVFTDLEILAAIFAsAIHDVDHPGVSNQFLINTNSELALMYNDsSVLE
TM72   455  HVLLSTP    ALDAVFTDLEILAAIFAAAIHDVDHPGVSNQFLINTNSELALMYNDESVLE
RATDPD 244  HVLLSTP    ALDAVFTDLEILAAIFAAAIHDVDHPGVSNQFLINTNSELALMYNDESVLE
JC44X  245  HVLLATPwPTLRNAVFTDLEILAALFAAAIHDVDHPGVSNQFLINTNSELALMYNDESVLE PDE21   3   LAVGFKLLQAENCDIFQNLSAKQRLSLRRMVIDMVLATDMSKHMNLLADLKTMVETKK
PDE18  143  NHHLAVGFKLLQEENCDIFQNLTKKQRQSLRKMVIDiVLATDMSKHMNLLADLKTMVETKK
TM72   513  NHHLAVGFKLLQEEHCDIFMNLTKKQRQTLRKMVIDMVLATDMSKHMSLLADLKTMVETKK
RATDPD 302  NHHLAVGFKLLQEEHCDIFQNLTKKQRQTLRKMVIDMVLATDMSKHMSLLADLKTMVETKK
JC44X  306  NHHLAVGFKLLQEDnCDIFQNLSKrQRQSLRKMVIDMVLATDMSKHMTLLADLKTMVETKK
```

FIG. 4(C)

```
PDE21    61  VTSLGVLLLLDNYSDRIQVLQNLVHCADLSNPTKPLPLYRQWTDRIMAEFFQQGDREREESGL
PDE18   204  VTSSGVLLLLDNYSDRIQVLQNMVHCADLSNPTKPLQLYRQWTDRIMEEFFRQGDRERERGM
TM72    574  VTSSGVLLLLDNYTDRIQVLRNMVHCADLSNPTKSLELYRQWTDRIMEEFFQQGDKERERGM
RATDPD  363  VTSSGVLLLLDNYTDRIQVLRNMVHCADLSNPTKSLELYRQWTDRIMEEFFQQGDKERERGM
MC44X   367  VTSSGVLLLLDNYSDRIQVLRNMVHCADLSNPTKPLELYRQWTDRIMAEFFQQGDRERERGM

PDE21   122  DISPMCDKHTASVEKSQVGFIDYIAHPLWETWADLVHPDAQDLLDTLEDNREWYQSKIPRS
PDE18   265  EISPMCDKHNASVEKSQVGFIDYIVHPLWETWADLVHPDAQDILDTLEDNREWYQSTIPQS
TM72    635  EISPMCDKHTASVEKSQVGFIDYIVHPLWETWADLVQPDAQDILDTLEDNRNWYQSMIPQS
RATDPD  424  EISPMCDKHTASVEKSQVGFIDYIVHPLWETWADLVQPDAQDILDTLEDNRNWYQSMIPQS
JC44X   428  EISPMCDKHTASVEKSQVGFIDYIVHPLWETWADLVHPDAQEILDTLEDNRDWYYSAIRQS
```

FIG. 4(D)

```
PDE21  183  PS       DLTNPE    RDGPDRFQFELTLEE                                              AEEEDEEEEEGEETALAKE
PDE18  326           PSPAPD    dPEegRQGqTEKFQFELTLEEdgesdtEKosGSQvEEDtscSdsKTLCtQDSE
TM72   696           PSPPLDEqnR         DCQGLMEKFQFELTLDEEDSEGPEK          EGEGhSYFSSTKTLC
RATDPD 485           PSPPLDErSR         DCQGLMEKFQFELTLEEEDSEGPEK          EGEGPNYFSSTKTLC
JC44X  489           PSPPPEEESRGPGHPPLPDKFQFELTLEEEEEEEISMAQIPCTAQEALTEQGLSGVEEALD PDE21  225  ALELPDTELLSPEAGPDGDLPLDNQRT
PDE18  386  STEIPLDEQVEEEAVGEEEESQPEACVIDDRSPDT
TM72   743           VIDPENRDSLGE      TDIDIATEDKSPvDT
RATDPD 536           VIDPENRDSLEE      TDIDIATEDKSLIDT
JC44X  551  ATIAWEASPAQESLEVMAQEASLEAELEAVYLTQQ
```

```
PDE43 (DPDE3)   FDVDNGTSA---GRSPLDPMTSPGSGLILQANFVHS-QRRESFLYRSDSDYDLSPKSMSRN    57
PDE46 (DPDE2)   FEAENGPTPSPGRSPLDSQA--SPGLVLHAGAATS-QRRESFLYRSDSDYDMSPKTMSRN    57
TM72  (DPDE4)   FDVENGPSP--GRSPLDPQASSSAGLVLHATFPGHSQRRESFLYRSDSDYDLSPKAMSRN    58
Dnc             FDVENGQG---ARSPLEGGSP-SAGLVLQNLP----QRRESFLYRSDSDFEMSPKSMSRN    52
                                                        └─UCR1──────

PDE43           SSIASDIHGDDLIVTPFAQVLASLRTVRNNFAALTNLQDRAPSKRSPMCNQPSINKATIT  117
PDE46           SSVTSEAHAEDLIVTPFAQVLASLRSNFSLLTNVPVP-SNKRSPLGGPTVPCKATLS    116
TM72            SSLPSEQHGDDLIVTPFAQVLASLRSVRNNFTILTNLHGT-SNKRSPAASQPPVSRVNPQ 117
Dnc             SSIASESHGEDLIVTPFAQILASLRSVRNNLLSLTNVPA--SNKRRPNQSSSASRSGNPP 110

PDE43           ------EEAYQKLASETLEELDWCLDQLETLQTRHSVSEMASNKFKRMLNRELTHLSEM  170
PDE46           ------EETCQQLARETLEELDWCLEQLETMQTYRSVSEMASHKFKRMLNRELTHLSEM  169
TM72            ------EESYQKLAMETLEELDWCLDQLETIQTYRSVSEMASNKFKRMLNRELTHLSEM  170
Dnc             GAPLSQGEEAYTRLATDTIEELDWCLDQLETIQTHRSVSDMASLKFKRMLNKELSHFSES 170
                      └─UCR2──────
```

FIGURE 6A

```
PDE43  SRSGNQVSEFISNTFLDKQHEVEIPS-------PTQKEKEKKRP----------------  208
PDE46  SRSGNQVSEYISTTFLDKQNEVEIPS-------PTMKEREKQQAPRPRPSQPPPPPVPHLQP----  224
TM72   SRSGNQVSEYISNTFLDKQNDVEIPS-------PTQKDREKKKQQL-----------------  210
Dnc    SRSGNQISEYICSTFLDKQQEFDLPS LRVEDNPELVAANAAGQQSAGQYARSRSPRGPP  230

PDE43  MSQISGVK KLM -HSSSLTNSSIPRFGVKTEQEDVLAKELEDVNKWGLHVFRIAELSGNRP  267
PDE46  MSQITGLK KLM -HSNSLNNSNIPRFGVKTDQEELLAQELENLNKWGLNIFCVSDYAGGRS  283
TM72   MTQISGVK KLM -HSSSLNNTSISRFGVNTENEDHLAKELEDLNKWGLNIFNVAGYSHNRP  269
Dnc    MSQISGVK RPLS HTNSFTGERLPTFGVETPRENELGTLLGELDTWGIQIFSIGEFSVNRP  290

PDE43  LTVIMHTIFQERDLLKTFKIPVDTLITYLMTLEDHYHADVAYHNNIHAADVVQSTHVLLS  327
PDE46  LTCIMYMIFQERDLLKKFRIPVDTMVTYMLTLEDHYHADVAYHNSLHAADVLQSTHVLLA  343
TM72   LTCIMYAIFQERDLLKTFRISSDTFITYMMTLEDHYHSDVAYHNSLHAADVAQSTHVLLS  329
Dnc    LTCVAYTIFQSRELLTSLMIPPKTFLNFMSTLEDHYVKDNPFHNSLHAADVTQSTNVLLN  350

PDE21(DPDE1)                                                LAVG     4
PDE43  TPALEAVFTDLEILAAIFASAIHDVDHPGVSNQFLINTNSELALMYNDSSVLENHHLAVG  387
PDE46  TPALDAVFTDLEILAALFAAAIHDVDHPGVSNQFLINTNSELALMYNDESVLENHHLAVG  403
TM72   TPALDAVFTDLEILAAIFAAAIHDVDHPGVSNQFLINTNSELALMYNDESVLENHHLAVG  389
Dnc    TPALEGVFTPLEVGGALFAACIHDVDHPGLTNQFLVNSSSELALMYNDESVLENHHLAVA  410
```

FIGURE 6B

```
PDE21  FKLLQAENCDIFQNLSAKQRLSLRRMVIDMVLATDMSKHMNLLADLKTMVETKKVTSLGV  64
PDE43  FKLLQEENCDIFQNLTKKQRQSLRKMVIDIVLATDMSKHNNLLADLKTMVETKKVTSSGV  447
PDE46  FKLLQEDNCDIFQNLSKRQRQSLRKMVIDMVLATDMSKHMTLLADLKTMVETKKVTSSGV  463
TM72   FKLLQEEHCDIFMNLTKKQRQTLRKMVIDMVLATDMSKHMSLLADLKTMVETKKVTSSGV  449
DNC    FKLLQNQGCDIFCNMQKKQRQTLRKMVIDIVLSTDMSKHMSLLADLKTMVETKKVAGSGV  470

PDE21  LLLDNYSDRIQVLQNLVHCADLSNPTKPLPLYRQWTDRIMAEFFQQGDRERESGLDISPM  124
PDE43  LLLDNYSDRIQVLQNMVHCADLSNPTKPLPLQLYRQWTDRIMEEFFRQGDRERERGMEISPM  507
PDE46  LLLDNYSDRIQVLRNMVHCADLSNPTKPLELYRQWTDRIMAEFFQQGDRERERGMEISPM  523
TM72   LLLDNYTDRIQVLRNMVHCADLSNPTKSLEELYRQWTDRIMEEFFQQGDKERERGMEISPM  509
DNC    LLLDNYTDRIQVLENLVHCADLSNPTKPLPLYKRWVALLMEEFFLQGDKERESGMDISPM  530

PDE21  CDKHTASVEKSQVGFIDYIAHPLWETWADLVHPDAQDLLDTLEDNREWYQSKIPRSPSPDL  184
PDE43  CDKHNASVEKSQVGFIDYIVHPLWETWADLVHPDAQDILDTLEDNREWYQSTIPQSPSPA  567
PDE46  CDKHTASVEKSQVGFIDYIVHPLWETWADLVHPDAQEILDTLEDNRDWYYSAIRQSPSPP  583
TM72   CDKHTASVEKSQVGFIDYIVHPLWETWADLVQPDAQDILDTLEDNRNWYQSMIPQSPSPP  569
DNC    CDRHNATIEKSQVGFIDYIVHPLWETWASLVHPDAQDILDTLEENRDYYQSMIPPSPPPS  590

FIGURE 6C
```

```
PDE21  TNPERDGP-------DRFQFELTLEEAEEEEEEGEETALAKEALELPDTELLSPEAG  238
PDE43  PDDPEEGRQGQT---EKFQFELTLEEDGESDTEKDSGSQVEEDTSCSDSKTLCTQDSESTE  625
PDE46  PEEESRGPGHPPLPDKFQFELTLEEEEEEISMAQIPCTAQEALTAQGLSGVEEALDATI   643
TM72   LDEQNRDCQGLM---EKFQFELTLDEEDSEGPEKEGEGHSYFSSTKTLCVIDPENRDSLGE 627
Dnc    GVDENPQE-------DRIRFQVTLEESDQENLAELEEGDESGGETTTTGTTGTTAASALRA 644

PDE21  PDPGDLPLDNQRT-----------------------------------------------  251
PDE43  IPLDEQVEEEAVGEEEESQPEACVIDDRSPDT----------------------------  657
PDE46  AWEASPAQESLEVMAQEASLEAELEAVYLTQQAQSTGSAPVAPDEFSSREEFVVAVSHSS  703
TM72   TDIDIATEDKSPVDT---------------------------------------------  642
Dnc    GGGGGGGGGMAPRTGGCQNQPQHGGM----------------------------------  670

PDE21  ------------------------------------------------------------  251
PDE43  ------------------------------------------------------------  657
PDE46  PSALALQSPLLPAWRTLSVSEHAPGLPGLPSTAAEVEAQREHQAAKRACSACAGTFGEDT  763
TM72   ------------------------------------------------------------  642
Dnc    ------------------------------------------------------------  670

PDE21  ------------------------  251
PDE43  ------------------------  657
PDE46  SALPAPGGGGSGGDPT--------  779
TM72   ------------------------  642
Dnc    ------------------------  670
```

FIGURE 6D

```
TM3     1   GLGRIPELQLVAFPVAVAAEDEAFLPEPLAPR
       33   APRRPRSPPSSPVFFASPSPTFRRRLRLLRSCQDLGRQAWAGAGFEAENG--

PDE46   1   MEPPTVPSERSLS
       14   LSLPGPREGQATLKPPPQHLWRQPRTPIRIQQRGYSDSAERAEREROPHR
       64   PIERADAMDTSDRPGLRTTRMSWPSSFHGTGTGSGGAGGGSSRRFEAENG--

PDE39   1   MDRTSYAVETGHRPGLKKSRMSWPSSFQG.........LRRFDVDNG--

PDE43   1   MMHVNNFPFRRHSWICFDVDNG--

TM72    1   MKKSRSVMTVMADDNVKDYFECSLSKSYSSSSNTLGIDLWRGRRCCSGNL
       50   QLPPLSQRQSERARTPEGDGISRPTTLPLTTLPSIAITTVSQECFDVENG--

PDE32   1   MKEHGGTFSSTGISGGSGDSAMDSLQPLQPNYMPVCLFAEESYQK--
```

FIGURE 6E

CLONING BY COMPLEMENTATION AND RELATED PROCESSES

CROSS-REFERENCE TO RELATED PATENT APPLICATION

This application is a continuation-in-part of co-pending U.S. Ser. No. 07/688,352; filed on Apr. 19, 1991 now U.S. Pat. No. 5,527,896 which is a continuation-in-part of co-pending U.S. Ser. No. 07/511,715; filed Apr. 20, 1990.

FUNDING

This invention was made with government support under grant number 5R35 CA329829-10 awarded by the National Institutes of Health. Work described herein was supported by the National Cancer Institute of the National Institutes of Health.

BACKGROUND

The present invention relates generally to novel cloning methods, to the DNA sequences obtained using these methods, the corresponding expression products of the DNA sequences and antibodies thereto, as well as to novel screening methods for compounds affecting protein activity. More specifically, the present invention provides novel complementation screening methods particularly useful in the isolation of DNAs encoding cyclic nucleotide phosphodiesterase polypeptides (PDEs) and RAS-related proteins. These DNAs, in turn, provide valuable materials useful as hybridization probes for related DNAs and useful in obtaining polypeptide expression products when used to transform suitable host cells.

Of interest to the present invention are the following discussions relating to the cyclic nucleotide phosphodiesterases and RAS-related proteins.

The RAS genes were first discovered as the transforming principles of the Harvey and Kirsten murine sarcoma viruses [Ellis et al., Nature, 292:506 (1981)]. The cellular homologs of the oncogenes of Harvey and Kirsten murine sarcoma viruses (H-RAS and K-RAS) constitute two members of the RAS gene family [Shimizu et al., Proc. Natl. Acad. Sci., 80:2112 (1983)]. A third member is N-RAS [Shimizu et al., Proc. Natl. Acad. Sci., 80:2112 (1983)]. These genes are known as oncogenes since point mutations in RAS can result in genes capable of transforming non-cancerous cells into cancerous cells [Tabin et al., Nature, 300:143 (1982); Reddy et al., Nature, 300:149 (1982); Taparowsky et al., Nature, 300:762 (1982)]. Many tumor cells contain RAS genes with such mutations [Capon et al., Nature, 302:33 (1983); Capon et al., Nature, 304:507 (1983); Shimizu et al., Nature, 304:497 (1983); Taparowsky et al., Cell, 34:581 (1983); Taparowsky et al., Nature, 300:762 (1982); Barbacid, Ann. Rev. Biochem., 56:779 (1987)]. Kitayana et al., Cell 56:77 (1989), described another "ras-related" gene called "K-rev" which showed revertant inducing activity of Kirsten-sarcoma virus transformed cells.

Despite the importance of the RAS oncogenes to our understanding of cancer, a complete understanding of the function of RAS genes in mammals has not yet been achieved. The RAS proteins are small proteins (21,000 daltons in mammals) which bind GTP and GDP [Papageorge et al., J. Virol., 44:509 (1982)]. The RAS proteins hydrolyze GTP slowly; specific cellular proteins can accelerate this process [McGrath et al., Nature, 310:644 (1984); Trahey et al., Science, 238:542 (1987)]. RAS proteins bind to the inner surface of the plasma membrane [Willingham et al., Cell, 19:1005 (1980)] and undergo a complex covalent modification at their carboxy termini [Hancock et al., Cell, 57:1167 (1989)]. The crystal structure of H-RAS is known (De Vos et al., Science, 239:888 (1988)].

The yeast Saccharomyces cerevisiae contains two genes, RAS1 and RAS2, that have structural and functional homology with mammalian RAS oncogenes [Powers et al., Cell, 36:607 (1984); Kataoka et al., Cell, 40:19 (1985); Defeo-Jones et al., Science, 228:179 (1985); Dhar et al., Nucl. Acids Res., 12:3611 (1984)]. Both RAS1 and RAS2 have been cloned from yeast plasmid libraries and the complete nucleotide sequence of their coding regions has been determined [Powers et al., Cell, 36:607 (1984); DeFeo-Jones et al., Nature, 306:707 (1983)]. The two genes encode proteins with nearly 90% identity to the first 80 amino acid positions of the mammalian RAS proteins, and nearly 50% identity to the next 80 amino acid positions. Yeast RAS 1 and RAS2 proteins are more homologous to each other, with about 90% identity for the first 180 positions. After this, at nearly the same position that the mammalian RAS proteins begin to diverge from each other, the two yeast RAS proteins diverge radically. The yeast RAS proteins, like proteins encoded by the mammalian genes, terminate with the sequence cysAAX, where A is an aliphatic amino acid, and X is the terminal amino acid [Barbacid, Ann Rev. Biochem., 56:779 (1987)]. Monoclonal antibody directed against mammalian RAS proteins immunoprecipitates RAS proteins in yeast cells [Powers et al., Cell, 47:413 (1986)]. Thus, the yeast RAS proteins have the same overall structure and interrelationship as is found in the family of mammalian RAS proteins.

RAS genes have been detected in a wide variety of eukaryotic species, including *Schizosaccharomyces pombe, Dictyostelium discoidiem* and *Drosophila melanogaster* [Fukui et al., EMBO, 4:687 (1985); Reymond et al., Cell, 39:141 (1984); Shilo et al., Proc. Natl. Acad. Sci. (USA), 78:6789 (1981); Neuman-Silberberg, Cell, 37:1027 (1984)]. The widespread distribution of RAS genes in evolution indicates that studies of RAS in simple eukaryotic organisms may elucidate the normal cellular functions of RAS in mammals.

Extensive genetic analyses of the RAS 1 and RAS2 of *S. cerevisiae* have been performed. By constructing in vitro RAS genes disrupted by selectable biochemical markers and introducing these by gene replacement into the RAS chromosomal loci, it has been determined that neither RAS1 nor RAS2 is, by itself, an essential gene. However, doubly RAS deficient (ras1$^-$ ras2$^-$) spores of doubly heterozygous diploids are incapable of resuming vegetative growth. At least some RAS function is therefore required for viability of *S. cerevisiae* [Kataoka et al., Cell, 37:437 (1984)]. It has also been determined that RAS1 is located on chromosome XV, 7 centimorgans (cM) from ADE2 and 63 cM from HIS3; and that RAS2 is located on chromosome XIV, 2 cM from MET4 [Kataoka et al., Cell, 37:437 (1984)].

Mammalian RAS expressed in yeast can function to correct the phenotypic defects than otherwise would result from the loss of both RAS1 and RAS2 [Kataoka et al., Cell, 40:19 (1985)]. Conversely, yeast RAS1 is capable of functioning in vertebrate cells [De Feo-Jones et al., Science, 228:179 (1985)]. Thus, there has been sufficient conservation of structure between yeast and human RAS proteins to allow each to function in heterologous host cells.

The missense mutant, RAS2$^{val19}$, which encodes valine in place of glycine at the nineteenth amino acid position, has the same sort of mutation that is found in some oncogenic mutants of mammalian RAS genes [Tabin et al., Nature, 300:143 (1982); Reddy et. al., *Nature*, 300:149 (1982); Taparowsky et al., *Nature*, 300:762 (1982)]. Diploid yeast cells that contain this mutation are incapable of sporulating efficiently, even when they contain wild-type RAS alleles [Kataoka et al., *Cell*, 37:437 (1984)]. When an activated form of the RAS2 gene (e.g., RAS2$^{va119}$) is present in haploid cells, yeast cells fail to synthesize glycogen, are unable to arrest in G1, die rapidly upon nutrient starvation, and are acutely sensitive to heat shock [Toda et al., *Cell*, 40:27 (1985); Sass et al., *Proc. Natl. Acad. Sci.*, 83:9303 (1986)].

*S. cerevisiae* strains containing RAS2$^{va119}$ have growth and biochemical properties strikingly similar to yeast carrying the IAC or bcy1 mutations, which activate the cyclic AMP (cAMP) pathway in yeast [Uno et al., *J. Biol. Chem.*, 257:14110 (1981)]. Yeast strains carrying the IAC mutation have elevated levels of adenylyl cyclase activity which is responsible for catalyzing the conversion of ATP to cyclic-AMP. bcy1$^-$ cells lack the regulatory component of the cAMP dependent protein kinase [Uno et al., *J. Biol. Chem.*, 257:14110 (1982); Toda et al., *Mol. Cell. Biol.*, 7:1371 (1987)]. Yeast strains deficient in RAS function exhibit properties similar to adenylyl cyclase-deficient yeast [Toda et al., *Cell*, 40:27 (1985)]. The bcy1$^-$ mutation suppresses lethality in ras1$^-$ ras2$^-$ yeast. These results suggest that in the yeast *S. cerevisiae*, RAS proteins function in the cAMP signalling pathway.

Adenylyl cyclase has been shown to be controlled by RAS proteins [Toda et al., *Cell*, 40:27 (1985)]. RAS proteins, either from yeast or humans, can stimulate adenylyl cyclase up to fifty fold in in vitro biochemical assays. RAS proteins will stimulate adenylyl cyclase only when bound with GTP [Field et al., *Mol. Cell. Biol.*, 8:2159 (1988)]. The phenotypes resulting from the activation of RAS, including sensitivity to heat shock and starvation, are primarily the result of overexpression or uncontrolled activation of the cAMP effector pathway via adenylyl cyclase [Kataoka et al., *Cell*, 37:437 (1984); Kataoka et al., *Cell*, 43:493 (1985); Toda et al., *Cell*, 40:27 (1985); Field et al., *Mol. Cell. Biol.*, 8:2159 (1988)].

Cellular concentrations of cAMP are controlled not only by the rate of cAMP production by adenylyl cyclase but also by the rate of cAMP degradation by phosphodiesterases (PDEs). PDEs are the enzymes responsible for the degradation of cAMP to AMP and cGMP to GMP.

Two *S. cerevisiae* yeast genes, PDE1 and PDE2, which encode the low and high affinity cAMP phosphodiesterases, respectively, have been isolated [Sass et al., *Proc. Natl. Acad. Sci.*, 83:9303 (1986); Nikawa et al., *Mol. Cell. Biol.*, 7:3629 (1987)]. These genes were cloned from yeast genomic libraries by their ability to suppress the heat shock sensitivity in yeast cells harboring an activated RAS2$^{va119}$ gene. Cells lacking the PDE genes (i.e., pde1$^-$ pde2$^-$ yeast) are heat shock sensitive, are deficient in glycogen accumulation, fail to grow on an acetate carbon source, and in general have defects due to activation of the cAMP signaling pathway [Nikawa et al., *Mol. Cell. Biol.*, 7:3629 (1987)].

Genetic analysis clearly indicates that RAS proteins have other functions in *S. cerevisiae* in addition to stimulating adenylyl cyclase [Toda et al., *Japan Sci. Soc. Press., Tokyo/VNU Sci. Press*, pp. 253 (1987); Wigler et al., *Cold Spring Harbor Symposium*, LIII:649 (1988); Michaeli et al., *EMBO*, 8:3039 (1989)]. The precise biochemical nature of these functions is unknown. Experiments with other systems, such as *S. pombe* and *Xenopus laevis* oocytes, indicate that RAS stimulation of adenylyl cyclase is not widespread in evolution [Birchmeier et al., *Cell*, 43:615 (1985)]. It is unlikely that RAS stimulates adenylyl cyclase in mammals (Beckner et al., *Nature;* 317:1 (1985)).

While the cAMP effector pathway plays a role in heat shock and starvation in yeast, it plays other roles in higher organisms. For example, in mammals, cAMP is a "second messenger" that mediates the response of cells to a variety of hormones and neurotransmitters including calcitonin, chorionic gonadotropin, corticotropin, epinephrine, follicle-stimulating hormone, glucagon, luteinizing hormone, lipotropin, melanocyte-stimulating hormone, norepinephrine, parathyroid hormone, thyroid-stimulating hormone, and vasopressin.

In humans, cAMP has been implicated in a number of important physiological responses including smooth muscle relaxation, strength of cardiac contractility, release of histamine and other immunoreactive molecules, lymphocyte proliferation, and platelet aggregation [Robison et al., *Cyclic AMP, Academic Press, New York and London* (1971)].

Among its many functions cAMP has also been implicated in central nervous system function in both invertebrates and mammals. In particular, cAMP has been shown to play a role in learning and memory. For example, in Aplysia, the long term potentiation of neurons in the gill retraction reflex that occurs with learning is associated with alterations in activity of several components of the cAMP signaling pathway, particularly adenylyl cyclase and a cAMP dependent protein kinase [Schacher et al., *Cold Spring Harbor Symp. Quant. Biol.* LV: 187–202 (1990)].

In *Drosophila melanogaster* numerous learning associated genes have been isolated, mutations in which affect learning. One of these genes is the dunce gene (dnc) which codes a cAMP specific phosphodiesterase (PDE). [Dudai, Y., *Ann. Rev. Neurosci*, 11:537–563 (1988); Qie, et al., *J. Mol. Biol.*, 222:553–565 (1991)]. Electrophysiologic studies of neurons from dnc Drosophila have shown alterations in neuronal latency suggesting that the functional changes occurring in learning in wild-type flies may be similar to those seen in Aplysia [Zong, et al., *Science*, 251:198–201 (1991)].

Evidence for a functional role of dunce-like PDEs in the mammalian CNS comes from the use of cAMP specific PDE inhibitors, including the drug Rolipram which in addition to their ability to inhibit PDEs, have clinical activity as antidepressants [Eckmann, et al., *Curr. Therapeutic Res.*, 43:291–295 (1988)].

In rat at least 4 different genes encoding dnc homologs have been identified. However, only 2 cDNAs encoding a human dnc homolog have been cloned and expressed. Livi, et al., (*Mol. Cell Biol.*, 10:2678–2686 (1990)) have cloned and expressed a cDNA for a human, low $K_m$, Rolipram sensitive cAMP phosphodiesterase. McLaughlin, et al., *J. Biol. Chem.*, 265:6470–6476 (1993) have isolated a different cDNA encoding a low $K_m$ Rolipram sensitive cAMP phosphodiesterase.

Given the importance of cAMP in the regulation of a variety of metabolic and physiologic processes, considerable effort has been directed toward developing and evaluating cAMP analogues, as well as inhibitors of phosphodiesterases which may serve as pharmaceutical agents capable of altering cAMP levels which are associated with a variety of pathological conditions. As described above, one way to modulate cAMP levels in cells is through the modulation of cAMP phosphodiesterase activity. Certain drugs useful in treating heart failure, asthma, depression, and thrombosis, appear to work by inhibiting cAMP phosphodiesterases. However, the pharmaceutical industry has not been notably successful in finding suitably specific drugs which inhibit cAMP phosphodiesterases, in part because effective drug screens have not been available. In addition, most tissues contain so many different isoforms of phosphodiesterases that drug screening based on traditional methods involving inhibition of crude tissue extracts is unlikely to yield anything other than a broadly acting inhibitor of phosphodiesterases. Broadly acting inhibitors of cAMP phosphodiesterases, such as theophylline, have many deleterious side effects.

As noted above, PDE inhibitor research has as its goal the development of highly specific PDE inhibitors. This lack of PDE inhibitor specificity is in part attributable to the existence of several distinct molecular forms of PDE present within a single tissue type, indeed, present among the various cell types comprising a particular tissue type. These various forms can be distinguished according to substrate specificity (cAMP vs. cGMP), intracellular location (soluble vs. membrane bound), response to calmodulin and can, in certain instances, be selectively inhibited by various therapeutic agents. Developing agents that will selectively act upon PDEs is directed toward reproducing the desirable effects of cyclic nucleotides, e.g., bronchodilation, increased myocardial contractility, anti-inflammation, yet without causing the undesirable effects, e.g., increased heart rate or enhanced lipolysis.

One approach to screening agents for their potential utility as PDE inhibitors, e.g. drug screening, requires "kinetically pure" preparations of PDE enzymes. That is, the use of whole tissue homogenates or extracts is unlikely to identify inhibitors selective for an individual PDE isozyme because, as described above, most tissues are heterogeneous with respect to cell type and may contain multiple PDE isozymes.

At least five different families of PDEs have been described based on characteristics such as substrate specificity, kinetic properties, cellular regulatory control, size, and in some instances, modulation by selective inhibitors. [Beavo, Adv. in Second Mess. and Prot. Phosph. Res. 22:1–38 (1988)]. The five families include:

I $Ca^{2+}$/calmodulin-stimulated
II cGMP-stimulated
III cGMP-inhibited
IV cAMP-specific
V cGMP-specific Within each family there are multiple forms of closely related PDEs. See Beavo, "Multiple Phosphodiesterase Isozymes Background, Nomenclature and Implications", pp. 3–15 In: *Cyclic Nucleotide Phosphodiesterases: Structure, Regulation and Drug Action,* Beavo, J. and Houslay, M. D., Eds.; John Wiley & Sons, New York (1990). See, also, Beavo, *TIPS,* 11:150 (1990).

Of the many distinct PDE enzymes now recognized, for only certain of the cGMP specific PDEs is complete cDNA sequence information available. With the acquisition of complete structural information for all PDEs, it may be possible to identify and localize (cellular and subcellular distribution) each PDE isozyme and thereby design isozyme-selective PDE inhibitors as therapeutic agents for specific diseases thereby minimizing untoward side-effects. However, the heterogeneity, instability, and relatively low abundance of some of the PDE isozymes have presented major obstacles in purifying and characterizing these enzymes. Thus, it is clear that the cloning and characterization of genes coding for PDEs will facilitate the design of more specific and more effective PDE inhibitors.

Several methods are presently available for cloning mammalian genes. A standard approach to cloning mammalian genes requires obtaining purified protein, determining a partial amino acid sequence of the purified protein, using the partial amino acid sequence to produce degenerate oligonucleotide probes, and screening cDNA libraries with these probes to obtain cDNA encoding the protein. This method is time consuming and, because of the degeneracy of the probes used, may identify sequences other than those encoding the protein(s) of interest. Many mammalian genes have been cloned this way including, for example, the gene encoding the cGMP phosphodiesterase expressed in retina [Ovchinnikov et al., *FEBS,* 223:169 (1987)].

A second approach to cloning genes encoding a protein of interest is to use a known gene as a probe to find homologs. This approach is particularly useful when members of a gene family or families are sufficiently homologous. The *Drosophila melanogaster* dunce phosphodiesterase gene was used, for example to clone rat homologs. Davis et al., *Proc. Natl. Acad. Sci. (USA),* 86:3604 (1989); and Swinnen et al., *Proc. Natl.,Acad. Sci. (USA),* 86:5325 (1989). Although additional members of one family of phosphodiesterase genes might be cloned once a first member of that family has been cloned, it is never known in advance whether the nucleotide sequences of genes belonging to different phosphodiesterase gene families will exhibit sufficient homology to use probes derived from one family to identify members of another family.

Yet another approach to cloning genes is known as complementation. A number of researchers have reported the isolation of yeast genes by their ability to complement a mutation/defect in the corresponding gene in another yeast. See, for example: McKnight et al., *EMBO J.,* 4:2093 (1985)—*Aspergillus nidulans* gene encoding alcohol dehydrogenase isolated by its ability to complement an adh1 mutation in *S. cerevisiae;* Sass et al., *PNAS (USA),* 83:9303 (1986)—*S. cerevisiae* PDE2 gene isolated by its ability to complement a $RAS2^{va119}$ allele in *S. cerevisiae* strain TK161-R2V; Nikawa et al., *Mol. Cell. Biol.,* 7:3629 (1987)—*S. cerevisiae* PDE1 gene isolated by transforming *S. cerevisiae* strain TK161-R2V; and Wilson, *Molec. Cell. Biol.,* 8:505 (1988)—*S. cerevisiae* SRA5 gene isolated by virtue of its ability to rescue a $RAS^+$ sra5-5 *S. cerevisiae* strain RW60-12C.

Yeast have also been used to isolate non-yeast genes. For example, Henikoff et al., *Nature,* 289:33 (1981), reported the isolation of a *D. melanogaster* gene by complementation of yeast mutants and Lee et al., *Nature,* 327:31 (1987), reported the isolation of human gene by its ability to complement a mutation in the cdc2 gene in *S. pombe.* The expression vector employed included a viral (SV40) promoter.

More recently, complementation screening has been used by the applicants herein to detect and isolate mammalian cDNA clones encoding certain types of phosphodiesterases (PDEs). Colicelli et al., *PNAS (USA),* 86:3599 (1989) reports the construction of a rat brain cDNA library in a *Saccharomyces cerevisiae* expression vector and the isolation therefrom of genes having the capacity to function in yeast to suppress the phenotypic effects of $RAS2^{va119}$, a mutant form of, the RAS2 gene analogous to an oncogenic mutant of the human H-RAS gene. A rat species cDNA so cloned and designated DPD (dunce-like phosphodiesterase) has the capacity to complement the loss of growth control associated with an activated $RAS2^{va119}$ gene harbored in yeast strains TK161-R2V. The gene encodes a high-affinity cAMP specific phosphodiesterase that is highly homologous to the cAMP phosphodiesterase encoded by the dunce locus of *D. melanogaster.*

Relatively few PDE genes have been cloned to date. Of those cloned, most belong to the cAMP-specific family of phosphodiesterases (cAMP-PDEs). See Davis, "Molecular Genetics of the Cyclic Nucleotide Phosphodiesterases", pp. 227–241 in *Cyclic Nucleotide Phosphodiesterases: Structure, Regulation, and Drug Action,* Beavo, J. and Houslay, M. D., Eds.; John Wiley & Sons, New York; 1990. See also, e.g., Faure et al., *PNAS (USA),* 85:8076 (1988)—*D. discoideum:* Sass et al., supra—*S. cerevisiae,* PDE class IV, designated PDE2; Nikawa et al., supra—*S. cerevisiae,* designated PDE1; Wilson et al., supra—*S. cerevisiae,* designated SRA5; Chen et al., *PNAS (USA),* 83:9313 (1986)—*D. melanogaster,* designated dnc$^+$; Ovchinnikov, et al., supra—bovine retina, designated cGMP PDE; Davis et al., supra—rat liver, designated rat dnc-1; Colicelli, et al., supra—rat brain, designated DPD; Swinnen, et al., *PNAS (USA),* 86:5325 (1989)—rat testis, rat PDE1, PDE2, PDE3 and PDE4; and Livi, et al., *Mol. Cell. Biol.,* 10:2678 (1990)—human monocyte, designated hPDE1. See also, LeTrong et al., *Biochemistry,* 29:10280 (1990) reporting cloning of a DNA encoding a fragment of a bovine adrenal cGMP stimulated PDE and Thompson et al., *J. FASEB,* 5(6):A1592 (Abstract No. 7092, 1991) reporting the cloning of a "Type II PDE" from rat pheochromocytoma cells.

Thus, there continues to exist a need in the art for improved cloning procedures effective for isolating genes, both of known and unknown function, for expression products sufficiently kinetically pure so as to be suitable for use in drug testing, and for drug screening methods that do not require kinetically pure protein preparations, and for the production of expression products having improved immunological specificity.

BRIEF SUMMARY OF THE INVENTION

The present invention relates to methods for cloning mammalian genes encoding proteins which can function in microorganisms, particularly yeast, and can modify, complement, or suppress a genetic defect associated with an identifiable phenotypic alteration or characteristic in the microorganism. Provided by the invention are mammalian genes cloned according to the method, as well as products encoded by such genes, and antibodies immunologically reactive with the encoded proteins.

More specifically, the present invention relates to a method of detecting mammalian genes that encode products that modify, complement or suppress a genetic defect in a biochemical pathway in which cAMP participates, or in a biochemical pathway which is controlled, directly or indirectly, by a RAS protein (i.e. RAS-related protein); to the genes so cloned; to products (nucleic acids, proteins) encoded by the mammalian genes cloned including novel mammalian genes that encode, for example, cAMP phosphodiesterases, proteins that interact with RAS proteins, and other proteins affecting cell growth and maintenance.

The present method can be used to detect a mammalian gene of interest that functions in a microorganism that is genetically altered or defective in a defined manner (an altered microorganism) to correct the genetic alteration or defect and, as a result, modifies an identifiable phenotypic alteration or characteristic associated with the genetic alteration or defect (produces a phenotype more like that of normal or unaltered microorganism). Altered microorganisms illustrating those useful in practice of methods of the invention include *S. cerevisiae* strains TK161-R2V, 10DAB and SKN37 and *S. pombe* strain SP65.

The present invention thus provides novel methods for detecting, in a genetically altered microorganism (such as a mutant yeast or mammalian host cell), a mammalian gene that is capable of modifying a phenotypic alteration associated with a genetic alteration. The steps of the novel methods include: (a) providing mammalian cDNA in an expression vector capable of expressing the mammalian cDNA in the genetically altered microorganism (preferred vectors including an endogenous host cell promoter DNA sequence operatively associated with the cDNA); (b) introducing the expression vector into the genetically altered microorganism; (c) maintaining the genetically altered microorganisms containing the expression vector under conditions appropriate for growth; and (d) identifying genetically altered microorganisms in which the phenotypic alteration associated with the genetic alteration in the microorganism is modified. Optionally included is the step of isolating the cDNA inserted in microorganisms identified in step (d).

Although use of the present method to clone mammalian genes is described in detail with respect to cAMP phosphodiesterases and proteins that interact with RAS proteins, it can be used to clone and identify other mammalian genes that function in an appropriately selected altered microorganism to correct, complement or supplement the genetic alteration and, as a result, correct the associated phenotypic alteration. Phenotypic alterations of yeast cells which illustrate the invention include heat shock sensitivity, nitrogen starvation, failure to synthesize normal amounts of glycogen, failure to grow on acetate and failure to sporulate.

In presently preferred forms, the novel DNA sequences comprise cDNA sequences; however, alternate DNA forms such as genomic DNA, and DNA prepared by partial or total chemical synthesis from nucleotides, as well as DNA with deletions or mutations and degenerate codons, is also within the contemplation of the invention.

Association of DNA sequences provided by the invention with homologous or heterologous species expression control DNA sequences, such as promoters, operators, regulators and the like, allows for in vivo and in vitro transcription to form messenger RNA which, in turn, is susceptible to translation to provide the invention proteins, and related poly- and oligo-peptides in large quantities. Presently preferred vectors for use in practice of the invention include plasmids pADNS, pADANS, pAAUN and pAAUN-ATG.

Specifically provided by the invention are mammalian DNA sequences encoding cyclic nucleotide phosphodiesterases and fragments thereof as well as RAS protein-related DNA sequences which are present as mammalian DNA inserts in bacterial plasmids which are the subject of deposits made with the American Type Culture Collection, 12301 Parklawn Drive, Rockville, Md. 20852 in accordance with U.S. Patent and Trademark Office and Budapest Treaty requirements. Deposits were made on Apr. 15, 1991 unless otherwise indicated. Mammalian PDE DNAs made subject of the deposits include:

1. Plasmid pRATDPD in *E. coli* (A.T.C.C. accession No. 68586) containing a rat brain cDNA insert, encoding a dunce-like PDE;
2. Plasmid pJC44x in *E. coli* (A.T.C.C. accession No. 68603) containing a human glioblastoma cell cDNA insert encoding a cAMP specific PDE;
3. Plasmid pTM3 in *E. coli* (A.T.C.C. accession No. 68600) containing a human glioblastoma cell cDNA insert encoding a cAMP specific PDE;
4. Plasmid pTM72 in *E. coli* (A.T.C.C. accession No. 68602) containing a human glioblastoma cell cDNA insert encoding a cAMP specific PDE;
5. Plasmid pPDE21 in *E. coli* (A.T.C.C. accession No. 68595) containing a human temporal cortical cell cDNA insert encoding a cAMP specific PDE;

6. Plasmid pGB18ARR in *E. coli* (A.T.C.C. accession No. 68596) containing a human temporal cortical cell cDNA insert encoding a cAMP specific PDE;
7. Plasmid pGB25 in *E. coli* (A.T.C.C. accession No. 68594) containing a human temporal cortical cell cDNA insert encoding a cAMP specific PDE;
8. Plasmid pTM22 in *E. coli* (A.T.C.C. accession No. 68601) containing a human glioblastoma cell cDNA insert encoding a PDE of unclassifiable family designation.
9. Plasmid pPDE32 in *E. coli* (deposited Feb. 4, 1994, A.T.C.C. accession No. 69549) containing a cDNA insert derived from human frontal cortex encoding a cAMP specific PDE;
10. Plasmid pPDE39 in *E. coli* (deposited Feb. 4, 1994, A.T.C.C. accession No. 69550) containing a cDNA insert derived from human fetal brain and encoding a cAMP specific PDE;
11. Plasmid pPDE43 in *E. coli* (deposited Feb. 4, 1994, A.T.C.C. accession No. 69551) containing a cDNA insert derived from human fetal brain and encoding a cAMP specific PDE; and
12. Plasmid pPDE46 in *E. coli* (deposited Feb. 4, 1994, A.T.C.C. accession No. 69552) containing a cDNA insert derived from human fetal brain and encoding a cAMP specific PDE.

Mammalian RAS-related DNAs made the subject of deposits include:
13. Plasmid pJC99 in *E. coli* (A.T.C.C. accession No. 68599) containing a human glioblastoma cell cDNA insert encoding a RAS-related polypeptide;
14. Plasmid pJC265 in *E. coli* (A.T.C.C. accession No. 68598) containing a human glioblastoma cell cDNA insert encoding a RAS-related polypeptide;
15. Plasmid pJC310 in *E. coli* (A.T.C.C. accession No. 68597) containing a human glioblastoma cell cDNA insert encoding a RAS-related polypeptide;
16. Plasmid pML5 in *E. coli* (A.T.C.C. accession No. 68593) containing a human glioblastoma cell cDNA insert encoding a RAS-related polypeptide;
17. Plasmid pATG16 in *E. coli* (A.T.C.C. accession No. 68592) containing a human glioblastoma cell cDNA insert encoding a RAS-related polypeptide; and
18. Plasmid pATG29 in *E. coli* (A.T.C.C. accession No. 68591) containing a human glioblastoma cell cDNA insert encoding a RAS-related polypeptide.

Yeast expression plasmids deposited in connection with the present invention include:
19. Plasmid pAAUN in *E. coli* (A.T.C.C. accession No. 68590);
20. Plasmid pAAUN-ATG in *E. coli* (A.T.C.C. accession No. 68589);
21. Plasmid pADANS in *E. coli* (A.T.C.C. accession No. 68587); and,
22. Plasmid pADNS in *E. coli* (A.T.C.C. accession, No. 68588).

Yeast host cells made the subject of deposit in connection with the present invention include:
23. *S. pombe* SP565 (A.T.C.C. accession No. 74047);
24. *S. cerevisiae* SKN37 (A.T.C.C. accession No. 74048);
25. *S. cerevisiae* 10DAB (A.T.C.C. accession No. 74049); and,
26. *S. cerevisiae* TK161-R2V (A.T.C.C. accession No. 74050).

Novel protein products of the invention include polypeptides having the primary structural conformation (i.e., amino acid sequence) of phosphodiesterase proteins as well as those having the primary structural conformation of non-phosphodiesterase proteins, including peptide fragments thereof and synthetic peptides assembled to be duplicative of amino acid sequences thereof. Proteins, protein fragments, and synthetic peptides of the invention are projected to have numerous uses including therapeutic, diagnostic and prognostic uses and will provide the basis for preparation of monoclonal and polyclonal antibodies specifically immunoreactive with these proteins. Preferred protein fragments and synthetic peptides include those duplicating regions of the proteins which are not involved in substrate binding functions and the most preferred are those which share at least one antigenic epitope with the proteins of the invention.

Use of mammalian host cells for expression of DNAs of the invention is expected to provide for such post-translational modifications (e.g., truncation, lipidation, glycosylation, and tyrosine, serine or threonine phosphorylation) as may be needed to confer optimal biological activity on recombinant expression products of the invention.

Also provided by the present invention are antibody substances (including polyclonal and monoclonal antibodies, chimeric antibodies and single chain antibodies) characterized by their ability to bind with high immunospecificity to the proteins and to their fragments and peptides, recognizing unique epitopes which are not common to other proteins, especially phosphodiesterases.

Also provided by the present invention are novel procedures for the detection and/or quantification of normal, abnormal, or mutated forms of the proteins as well as nucleic acids (e.g., DNA and mRNA) associated therewith. Illustratively, antibodies of the invention may be employed in known immunological procedures for quantitative detection of the proteins in fluid and tissue samples, of DNA sequences of the invention that may be suitably labelled and employed for quantitative detection of mRNA encoding these proteins.

Among the multiple aspects of the present invention, therefore, is the provision of (a) novel nucleic acid sequences encoding cyclic nucleotide phosphodiesterase polypeptides and RAS-related proteins as hereinafter described, and (b) DNA sequences which hybridize thereto under hybridization conditions of the stringency equal to or greater than the conditions described herein and employed in the initial isolation of certain cDNAs of the invention, as well as (c) DNA sequences encoding the same, or allelic variant, or analog polypeptides through use of, at least in part, degenerate codons. Correspondingly provided are viral vectors or circular plasmid DNA vectors incorporating such DNA sequences and procaryotic and eucaryotic host cells transformed or transfected with such DNA sequences and vectors as well as novel methods for the recombinant production of proteins encoded by the DNA sequences through cultured growth of such hosts and isolation of these proteins from the hosts or their culture media.

The present invention further relates to a method of identifying agents that modify or alter (i.e., reduce or stimulate) the activity of the protein products of such mammalian genes expressed in microorganisms, such as yeast. Identification of such agents can be carried out using two types of screening procedures: one based on biochemical assays of mammalian proteins of known enzymatic function and one based on phenotypic assays for proteins of determined or as yet undetermined function. In the former case, if the encoded proteins are phosphodiesterases, for example, pharmacological screens include assays for chemical agents that alter (i.e., reduce or stimulate) phosphodiesterase activity. In the latter case, if the encoded proteins interact with RAS proteins, for example, pharmacological screens include the assay for agents that reduce or stimulate interactions with RAS proteins. These screening methods can be used with either whole cell preparations or cell extracts and do not require enzyme purification.

Other aspects and advantages of the present invention will be apparent upon consideration of the following detailed description thereof which includes numerous illustrative examples of the practice of the invention, reference being made to the drawings wherein:

BRIEF DESCRIPTION OF THE DRAWINGS

FIG. 1A–1D are a comparative alignment of the nucleotide sequences of the human cDNA inserts of plasmids pJC44X, pTM3, pGB14 and pGB18ARR, wherein lower case letters designate lack of homology and gaps indicate absence of corresponding base positions;

FIG. 2(A)–2(D) are a comparative alignment of the nucleotide sequences of the human cDNA inserts of plasmids pPDE2RR, pTM72, pPDE7 and pPDE 10x-INV, with lower case letters designating lack of homology and gaps indicating the absence of corresponding base positions;

FIG. 3 is a comparative alignment of the nucleotide sequences of the human cDNA inserts of plasmids pPDE18 and pGB25, with lower case letters designating lack of homology and gaps indicating the absence of corresponding base positions; and FIG. 4 is a comparative alignment of deduced amino acid sequences of plasmids pTM72 (TM72), pRATDPD, pJC44X, pPDE18 and pPDE21, wherein lower case letters designate non-homologous residues and gaps indicate lack of any residue at the aligned position.

FIG. 6A and 6B show the deduced amino acid sequences encoded by the four human dunce genes.

DETAILED DESCRIPTION

Figure 5:
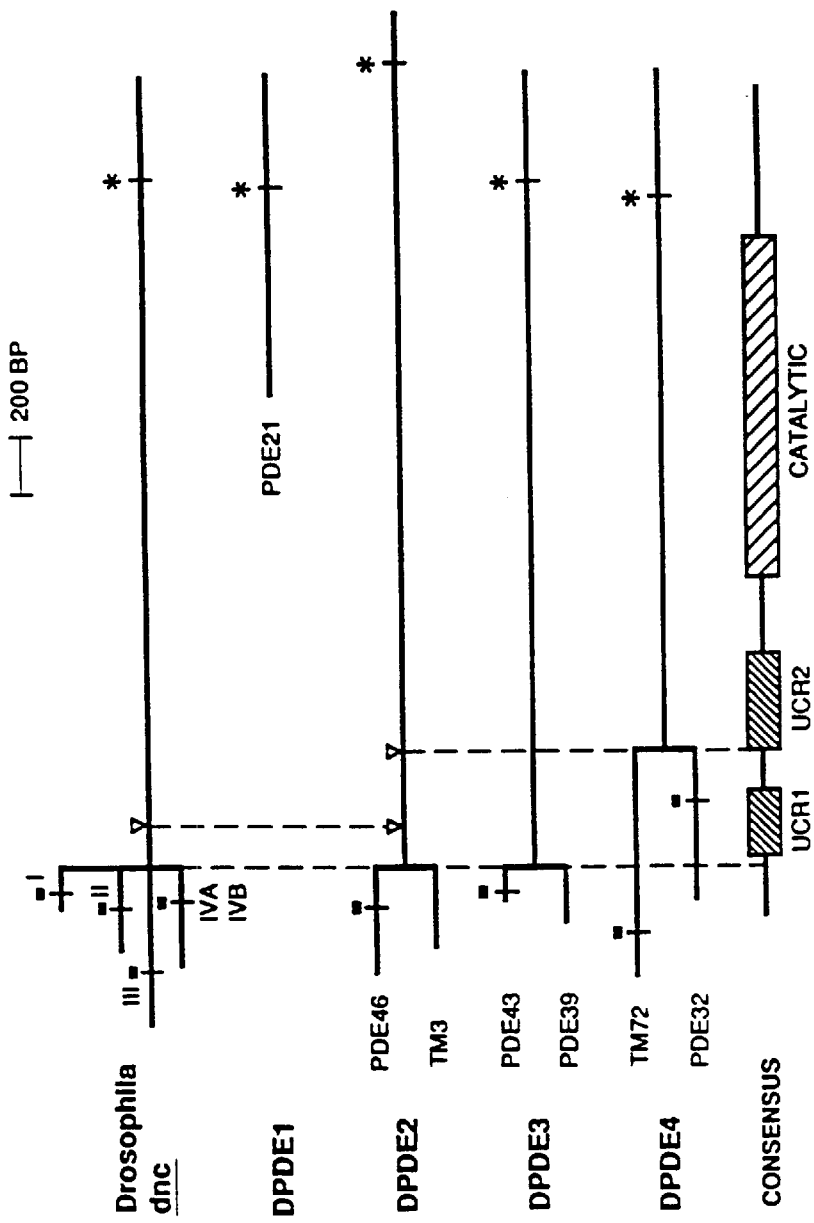
FIG. 5 is an alignment of cDNAs from four human dunce loci with those from the Drosophila dnc locus.

The following examples illustrate practice of the invention.

Example 1 relates to cloning and identification of mammalian genes by complementation in yeast. Example 2 relates to, cloning and identification of mammalian genes by hybridization with mammalian genes cloned by complementation. Example 3 relates to characterization of cloned genes by complementation capacity. Example 4 relates to further characterization of cloned genes by nucleotide sequence analysis. Example 5 relates to screening and identification of agents which alter phosphodiesterase enzymatic activity. Example 6 relates to the cloning of human dunce-like cDNAs. Example 7 relates to putative alternative splicing variants and other variants of DPDE 2, 3 and 4 transcripts. Example 8 relates to the alignment of Drosophila and human dunce sequences. Example 9 relates to the enumeration of human dunce-like genes. Example 10 relates to the expression of human dunce-like genes in the human central nervous system. Example 11 relates to the biochemical and pharmacologic properties of the expression products of the human dunce-like genes. Example 12 relates to the effects of phosphodiesterase inhibitors on dunce-encoded PDEs.

EXAMPLE 1

Cloning of Mammalian Genes By Complementation in Yeast

In its most general form, the methods of the present invention are as follows.

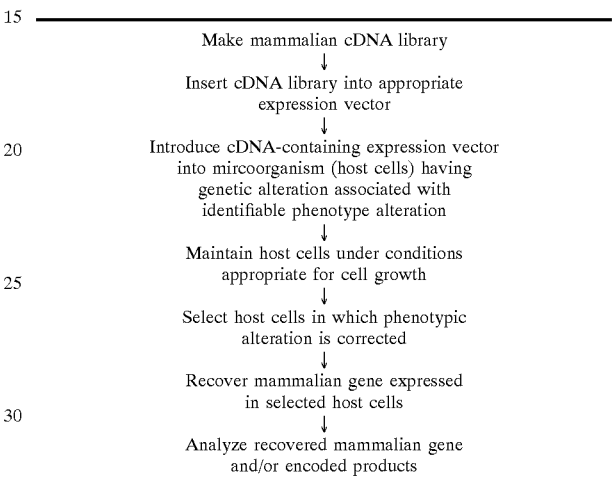

First, a cDNA library of mammalian mRNAs is produced using known techniques. This library can be made by cloning double stranded cDNA into an expression vector. The cDNA can be prepared from a pre-existing cDNA library, or it can be prepared by the reverse transcription of mRNA purified from a tissue or cell line of choice, using standard procedures. Watson et al., In: *DNA Cloning, a Practical Approach*, IRL Press Oxford (1984)).

The cDNA so obtained is cloned into an expression vector capable of expressing mammalian, cDNA inserts as mRNA which in turn can be translated into protein in a host cell of choice, e.g., altered yeast such as *S. pombe* SP565 (ras1::Leu2/ras1::Leu2) (A.T.C.C. 74047), *S. cerevisiae* 5KN37 (cap::H1S3) (A.T.C.C. 74048), *S. cerevisiae*—10DAB (pde1⁻, pde2⁻) (A.T.C.C. 74049); and *S. cerevisiae* TK161-R2V (RAS2$^{val19}$) (A.T.C.C. 74050). Expression vectors which have been used for this purpose are described in the examples which follow and include pAAUN (A.T.C.C. 68590), pAAUNATG (A.T.C.C. 68589), pADNS (A.T.C.C. 68587), and pADANS (A.T.C.C. 68588).

Preferred expression vectors contain a transcriptional promoter specific for the host into which the vector is introduced, e.g., promoters specific for expression in *S. cerevisiae*. The transcribed mRNA may utilize the ATG of the cDNA insert as the "start" codon or may express the cDNA product as a fusion product.

The cDNA library (present as cDNA inserts in a selected expression vector) is introduced into a suitable host cell. This host cell contains genetic alterations which cause the host cell to have an identifiable phenotypic alteration or abnormality associated with the genetic alteration. The host cell may be a eukaryotic microorganism, such as the yeast *S. cerevisiae* or a mammalian cell.

Known methods, such as lithium acetate-induced transformation, are used to introduce the cDNA-containing expression vector. In the examples that follow, transformation of yeast cells was performed with lithium acetate. Yeast cells were grown in either rich medium (YPD) or synthetic medium with appropriate auxotrophic supplements (SC). Mortimer et al., *In: The Yeast*, 1:385 (1969). Ito et al., *J. Bacteriol.*, 153:163 (1983).

The genetic alterations of the selected host cell, may for example, lead to defects in the metabolic pathways controlled by the RAS proteins and the associated readily discernible phenotype may be sensitivity to heat shock or nitrogen starvation, failure to synthesize normal amounts of glycogen, failure to grow on certain carbon sources, failure to sporulate, failure to mate, or other properties associated with defects in the pathways controlled by or controlling RAS proteins. For example, the genetic alteration can be the presence of the RAS2$^{val19}$ gene. Yeast containing such an alteration exhibit heat shock sensitivity, which can be overcome by expression of an appropriate mammalian gene. In the examples that follow, heat shock experiments were performed by replica plating onto preheated SC plates which were maintained at 55° C. for 10 minutes, allowed to cool, and incubated at 30° C. for 24–48 hrs.

Other host cells with genetic alterations can be chosen, such as disruptions of the PDE1 and PDE2 genes in *S. cerevisiae* or disruptions of, or the presence of an activated allele of RAS1 in *S. pombe*. Other genetic alterations in a host cell may be correctable by different subsets of mammalian cDNAs.

After introduction of the cDNA insert-containing expression vector, host cells are maintained under conditions appropriate for host cell growth. Those host cells which have been corrected for their phenotypic alteration are selected or otherwise identified and the mammalian gene which they express can be recovered e.g., by transformation of *E. coli* with DNA isolated from the host cell. Segregation analysis in the examples that follow was performed by growing yeast transformants in YPD for 2–3 days, plating onto YPD plates, and replica plating onto YPD, SC-leucine (plasmid selection), and YPD heat shock plates. *E. coli* strain HB101 was used for plasmid propagation and isolation, and strain SCS1 (Stratagene, LaJolla, Calif.) was used for transformation and maintenance of the cDNA library. Mandel et al., *Mol. Biol.*, 53:159 (1970); Hanahan *J. Mol. Biol.*, 166:557 (1983).

If desired, the mammalian gene can be isolated and sequenced; alternatively, the protein encoded by the gene can be identified and expressed in cultured cells for use in further processes.

Parts A, B, and C below describe the isolation of mammalian genes by complementation in yeast and their subsequent biochemical characterization.

A. Isolation and Biochemical Characterization of a Rat Brain cDNA Encoding a Phosphodiesterase A rat brain cDNA library was produced and cloned into the yeast expression vector, pADNS. RNA was purified from Sprague-Dawley rat brains by published procedures. Chirgwin et al., *Biochem.*, 18:5294 (1979); Lizardi, *Methods Enzymol.*, 96:24 (1983); Watson et al., *In: DNA cloning, a practical approach*, IRL, Press Oxford (1984). pADNS consists of a 2.2kbp BglII to HpaII fragment containing the *S. cerevisiae* LEU2 gene from YEp213 [Sherman et al., *Laboratory Manual for Methods in Yeast Genetics*, Sherman, F., Fink, G. R. and Hicks, J. B., eds., Cold Spring Harbor Laboratory, Cold Spring Harbor, NY (1986)], a 1.6kbp HpaI to HindIII fragment of the *S. cerevisiae* 2 µ plasmid containing the origin of replication, and a 2.1 kbp SspI to EcoRI fragment containing the ampicillin resistance gene from the plasmid pUC18. It also contains a 1.5kbp BamHI to HindIII fragment of the modified *S. cerevisiae* alcohol dehydrogenase (ADH1) promoter [Bennetzen et al., *J. Biol. Chem.*, 257:3018 (1982); Ammerer, *Meth. Enzymol* 101:192 (1983)] and a 0.6kbp HindIII to BamHI fragment containing the ADH1 terminator sequences. The promoter and terminator sequences are separated by a polylinker that contains the restriction endonuclease sites NotI, SacI, and SfiI between the existing HindIII and SacI sites.

Double stranded cDNAs were prepared and ligated to NotI linkers, cleaved with NotI restriction enzyme, and cloned into pADNS at the NotI site situated between the alcohol dehydrogenase promoter and termination sequences of the vector. The use of the rare cutting NotI obviated the need for restriction site methylases commonly used in cDNA cloning. cDNAs were ligated to the NotI linker oligonucleotides:

SEQ ID NO: 1 5'-AAGCGGCCGC, and
SEQ ID NO: 2 5'-GCGGCCGCTT

Approximately 1.5×10$^5$ independent cDNA inserts were contained in the library, with an average insert size of 1.5kbp. DNA prepared from the cDNA expression library was used to transform the RAS2$^{val19}$ yeast strain TK161-R2V. The 50,000 Leu$^+$ transformants obtained were subsequently tested for heat shock sensitivity. Only one transformant displayed heat shock resistance which was conditional upon retention of the expression plasmid. The plasmid, designated pRATDPD, was isolated from this transformant and the 2.17 kb NotI insert was analyzed by restriction site mapping and nucleotide sequencing. SEQ ID NO: 3 and SEQ ID NO: 4 provide the nucleotide sequence of the insert and the corresponding deduced amino acid sequence. Sequencing was performed using the dideoxy chain termination method. Sanger et al., *Proc. Natl. Acad. Sci. (USA)*, 74:5463 (1977); Biggin, et al., *Proc. Natl. Acad. Sci. (USA)*, 80:3963 (1983)). GENALIGN was used to align the DPD and dunce sequences (GENALIGN is a copyrighted software product of IntelliGenetics, Inc., developed by Dr. Hugo Martinez).

A large open reading frame of 562 codons was found. The first ATG appears at codon 46 and a protein which initiates at this codon would have a predicted molecular weight of approximately 60 kDa. This rat gene is designated RAT-DPD. A search for similar sequences was performed by computer analysis of sequence data banks, and the *Drosophila melanogaster* dunce gene was found. The two genes would encode proteins with an 80% amino acid identity, without the introduction of gaps, over a 252 amino acid region located in the center of the rat DPD cDNA. The dunce gene has been shown to encode a high affinity cAMP phosphodiesterase. Chen et al., *Proc. Natl. Acad. Sci. (USA)*, 83:9313 (1986); Davis et al., *J. Cell Biol.*, 90:101 (1981); Walter et al., *J. Neurosci.*, 4:494 (1984)).

To demonstrate that the sequences upstream and downstream of the large sequence identity region were in fact contiguous with that region in the mRNA, rather than artifacts of the method for cDNA cloning, the structure of the cloned cDNA was compared with the structure of DPD cDNAs contained in an independently prepared, first strand cDNA population obtained by reverse transcribing total rat brain poly(A)$^+$ RNA with an oligo dT primer. Oligonucleotide primers complementary to sequences located within the identity region, and to sequences near the 5' or 3' ends of the coding strand, were made. Using either the cloned pRATDPD DNA or the total first strand cDNA material as template, polymerase chain reactions (PCR) were carried out using four different primer sets and the reaction products were analyzed by polyacrylamide gel electrophoresis.

Polymerase chain reactions (PCRs) were carried out in thermocycler (Perkin Elmer, Cetus) using a modification of published procedures. Saiki et al., *Science*, 239:487 (1988). Reaction mixtures contained template DNA (1ng of cloned DNA, or 1 µg of total first strand cDNA), 25 pmoles of oligonucleotide primers, 200 µM deoxyribonucleotide triphosphates, 10 mM Tris HCl (pH 8.4), 50 mM KCl, 3mM MgCl$_2$, and 0.01% (w/v) gelatin. The oligonucleotide primers used were:

SEQ ID NO: 5 A,5'-CACCCTGCTGACAAACCT$^{44}$;
SEQ ID NO: 6 B,5'-ATGGAGACGCTGGAGGAA$^{153}$;
SEQ ID NO: 7 C,5'-ATACGCCACATCAGAATG$^{676}$;
SEQ ID NO: 8 D,5'-TACCAGAGTATGATTCCC$^{1449}$;
SEQ ID NO: 9 E,5'-GTGTCGATCAGAGACTTG$^{1668}$;
SEQ ID NO: 10 F,5'-GCACACAGGTTGGCAGAC$^{2048}$.

The superscript numbers indicate position coordinates in pRATDPD SEQ ID NO: 3. Primers C, E and F are non-coding strand sequences. Thirty cycles (1.5 min at 94° C., 3 min at 55° C., and 7 min at 72° C.) were performed and the reaction products were analyzed by polyacrylamide gel electrophoresis.

In each case, a fragment of the predicted length was obtained using either of the template DNAs. The band assignments were confirmed by cleavage with restriction endonucleases having recognition sites within the amplified DNA, product. Again, in each case, the primary PCR product obtained using either source of template yielded cleavage products of the predicted sizes. The results indicate that the sequence arrangement in the cloned cDNA faithfully reflects the structure of the rat mRNA.

To analyze the biochemical properties of the pRATDPD gene product, crude cell extracts were prepared from one liter cultures of 10DAB yeast cells which had been transformed with either pADNS or pRATDPD.

Yeast strain 10DAB cells are pde1$^-$ and pde2$^-$ and do not have a measurable level of endogenous cyclic nucleotide phosphodiesterase activity.

Phosphodiesterase activity assays were performed using cAMP as substrate as follows. Yeast cells were grown at 30° C. for 36 hours in one liter cultures of synthetic media (SC-leucine). Cells were harvested and washed with buffer C (20 mM MES (pH 6.2), 0.1 mM MgCl$_2$, 0.1 mM EGTA, 1 mM β-mercaptoethanol), were resuspended in 30 ml buffer C with 50 µl 1M PMSF, and were disrupted with a French press. The extracts were centrifuged at 1,600×g for 10 min and the supernatants were spun at 18,000×g for 90 min (4° C.). The supernatant was assayed for phosphodiesterase activity as in Collicelli et al., supra. All the reactions contained Tris-HCl (pH7.5) (100 mM), cell extract (50 µg protein/ml), 5'-nucleotidase (Sigma, 20ng/ml) and 10 mM Mg$^{2+}$ (unless otherwise stated) and the indicated cyclic nucleotide concentrations. Assays for the cGMP hydrolysis used 1.5 µM cGMP. Inhibition studies employed 5 µM cAMP in the presence of varying amounts of cGMP up to 500 µM. [$^3$H]cAMP and [$^3$H]cGMP were obtained from NEN (New England Nuclear). Reactions were incubated for 10 min at 30° C. and stopped with 5X stop solution (250 mM EDTA, 25 mM AMP, 100 mM cAMP).

Control extracts (10 DAB with pADNS) showed no cAMP phosphodiesterase activity. Results with the controls were unchanged when performed at 0° C. or in the absence of Mg$^{2+}$ and were comparable to results obtained when no extract was added. These results indicate that there is no detectable background phosphodiesterase activity in the non-transformed control strain 10 DAB.

In contrast, considerable cAMP phosphodiesterase activity was seen in the 10 AB yeast strain transformed with pRATDPD. The rate of cAMP hydrolysis in the resulting transformants was measured as a function of cAMP concentration. The deduced $K_m$ for cAMP is 3.5 µM and the calculated $V_{max}$ is 1.1 nmol/min/mg.

The assay conditions were varied to ascertain the cation preferences of the enzyme and to determine the ability of calcium and calmodulin to stimulate its activity. In these assays, Mn$^{2+}$ can be utilized as well as Mg$^{2+}$, and either cation in 1 mM final concentration was sufficient. Calcium/calmodulin was unable to stimulate the measured phosphodiesterase activity in the extract. A parallel assay using beef heart phosphodiesterase (Boehringer Mannheim) yielded a 6.5 fold stimulation with the addition of calcium/calmodulin. Finally, no cGMP phosphodiesterase activity was detected in these assays. Beef heart phosphodiesterase was again used as a positive control. In addition, cGMP present in amounts 100 fold over substrate concentrations did not inhibit cAMP phosphodiesterase activity.

Biochemical characterization of the pRATDPD cDNA product expressed in yeast indicates that it is a high affinity cAMP specific phosphodiesterase, as is dunce. Davis et al., *J. Cell. Biol.*, 90:101 (1981); Walter et al., *J. Neurosci.*, 4 (1984). In addition, the phosphodiesterase activity is not stimulated by the presence of calcium/calmodulin. This property is shared with dunce and is distinct from some other phosphodiesterases. Beavo, *In Advances in Second Messenger and Phosphoprotein Research*, Greengard et al., eds., Raven Press (1988). The two proteins encoded by RATDPD and dunce respectively, thus appear to have similar biochemical characteristics. However, it should also be noted that RATDPD encodes a protein product which shows much less significant homology (35%) to dunce beyond the previously described highly conserved core region. These non-conserved sequences could result in an altered or refined function for this mammalian dunce homolog.

The pRATDPD nucleotide sequence as set forth in SEQ ID NO: 3 encodes a methionine codon at position 46 and the established reading frame remains open through to position 563, resulting in a protein with a predicted molecular weight of 60 kDa. The same reading frame, however, is open beyond the 5' end of the coding strand. At present, it is not known if the methionine codon at position 46 is the initiating codon for the DPD protein. The coding sequence is interrupted by three closely spaced terminator codons. However, the established reading frame then remains open for an additional 116 codons, followed by more terminator codons, a polyadenylylation consensus signal and a polyadenine stretch. This 3' open reading frame could possibly be incorporated into another dunce-like phosphodiesterase through alternate splicing.

B. Cloning of Human Glioblastoma Cell cDNAs By Complementation

A cDNA library was constructed in λZAP using NotI linkers. In this example, the cDNA derived from mRNA was purified from the human glioblastoma cell line U118MG. Inserts from the λ vector were transferred into two yeast expression vectors pADNS and pADANS. Plasmid pADANS differs from pADNS in that the mRNA transcribed will direct the synthesis of a fusion protein including an N-terminal portion derived from the alcohol dehydrogenase protein and the remainder from the mammalian cDNA insert.

The two mammalian cDNA expression libraries so constructed were screened, as in the previous example, for cDNAs capable of correcting the heat shock sensitivity of the S. cerevisiae host TK161-R2V. Several cDNAs were isolated and analyzed by sequencing. Four different cDNAs, contained as inserts in plasmids pJC44x, pJC99, pJC265, and pJC310, were thereby discovered, and their DNA and deduced amino acid sequences are provided in SEQ ID NOs: 11 and 12; 13 and 14; 15 and 16; and 17 and 18; respectively.

The insert of pJC44x was shown by computer analysis to be homologous to the rat RATDPD gene and biochemical analysis of cellular lysates demonstrated that it encodes a cAMP phosphodiesterase. The inserts in pJC99, pJC265, and pJC310, show no significant homology to previously isolated genes.

C. Cloning of Human Glioblastoma Cell Phosphodiesterase cDNAs By Complementation The human glioblastoma cDNA expression library previously described was screened for cDNAs capable of correcting the heat shock sensitivity of the phosphodiesterase deficient yeast strain 10DAB. Several cDNAs were so isolated and analyzed by nucleotide and restriction endonuclease sequencing mapping. The cDNA insert in pTM22 encodes a novel human gene. Its nucleotide sequence and deduced amino acid sequence are shown in SEQ ID NOs: 19 and 20.

Based on a computer analysis of the nucleotide sequence of the pTM22 insert, the insert putatively encodes a protein homologous to various cAMP phosphodiesterases, such as the bovine $Ca^{2+}$/calmodulin dependent cAMP phosphodiesterase and the rat DPD phosphodiesterase described in Example 1A. Biochemical analysis has proven that the isolated DNA encodes a novel cAMP phosphodiesterase.

Sequences related to the pTM22 insert were found to be expressed in the human heart as well, and splicing variants of TM22 were isolated from a human heart cDNA library using pTM22 insert sequences as a nucleic acid hybridization probe.

Plasmid pTM22 was unable to correct the heat shock sensitivity of $RAS2^{val19}$ yeast strains, i.e., of TK161-R2V. It thus appears that the pde1$^-$ pde2$^-$ yeast strain 10 DAB is more sensitive to phenotypic reversion by mammalian cAMP phosphodiesterase clones than is the $RAS2^{val19}$ yeast strain.

Several other human glioblastoma cDNAs, isolated as inserts in the plasmids designated pTM3 and pTM72, were similarly characterized. These two different cAMP phosphodiesterase cDNAs were found to be very closely related to, but distinct from, the pRATDPD cDNA insert and the pJC44x cDNA insert. Their nucleotide sequences and deduced amino acid sequences are shown in SEQ ID NOs: 21 and 22 (pTM3); and 23 and 24 (pTM72), respectively.

Biochemical analysis of cell lysates has established that the cDNAs of pTM3 and pTM72, pJC44x and pRATDPD encode Rolipram sensitive cAMP phosphodiesterases.

D. Kinetic Analysis of pPDE cDNA Expression Products

Samples containing approximately $10^{10}$ transformed S. cerevisiae 10 DAB cells expressing the human cDNAs inserted in pJC44x, pTM3, a pTM22-like plasmid (designated L22 Met and including a 1.7 kb fragment insert derived from pTM22 and encoding the PDE activity) and pAD72 (a TM72-like clone) were resuspended in 2.5 ml phosphate-buffered saline (PBS) and disrupted by vortexing in the presence of glass beads at 4° C.

The supernatant fraction following centrifugation for 5 min at 12,000×g was the source for enzyme in these studies.

Phosphodiesterase activity was determined as described, with minor modifications, in Davis et al., J. Nuc. Res., 5:65–74 (1979). Incubation mixtures contained 40 mM Tris pH 8.0, 1 mM EGTA, 5 mM $MgCl_2$, 0.1 mg/ml BSA, diluted yeast extract, [$^3$H]cAMP, and varying amounts of unlabeled cyclic nucleotides to a final volume of 0.25 ml. Reactions were terminated by the addition of 0.25 ml stop buffer containing 0.5 M carbonate pH 9.3, 0.5 M NaCl and 0.1% SDS. Nucleotide products and unreacted substrates were separated on 8 X 33 mm boronate columns (BioRad Affigel 601 boronic acid gel). The products were eluted from the boronate columns with sorbitol into scintillation vials for tritium analysis. All kinetic data represent measurements of initial reaction rates determined by incubations for multiple time intervals at suitable dilutions of enzyme.

Analysis of kinetic data by the Lineweaver-Burk transformation of the Michaelis-Menten kinetic model demonstrates a linear double reciprocal plot indicative of a simple kinetic model for each enzyme tested. Cyclic nucleotide concentrations varied from $3 \times 10_{-8}$ to $1 \times 10^{-4}$ M cAMP. The results obtained are shown in Table 1, below.

TABLE 1

Preliminary Kinetic Analysis of Human Cyclic Nucleotide Phosphodiesterase Derived by Yeast Complementation

| Clone Name | $K_m^1$ | $V_{max}^2$ |
|---|---|---|
| pJC44x | 3.0 µM | 830 |
| pAD72 | 1.3 µM | 670 |
| pTM3 | 4.5 µM | 16 |
| pL22Met | 0.1 µM | 240 |

$^1$expressed as µM cAMP
$^2$expressed as nmol/min/$10^{12}$ cells

E. Cloning of Human Glioblastoma Cell RAS-related cDNAs By Complementation in Yeast In this example, four human glioblastoma cell cDNAs were isolated which do not encode PDEs. They were obtained by complementation of two genetically altered S. cerevisiae and S. pombe yeast strains.

Clone S46 was selected by complementation in S. cerevisiae strain RS60.15B. This strain contains a mutant allele of RAS2, $RAS2^{val19, ala}15$, which renders cells unable to grow at 36° C. [Powers et al., Mol. Cell Biol., 9:390–395 (1989)], because such cells are defective in RAS function at elevated temperatures. Human cDNAs from a human glioblastoma cell library were selected that could complement this defect. One cDNA found this way was designated S46. Its nucleotide and deduced amino acid sequences are provided in SEQ ID NOs: 25 and 26. The deduced amino acid sequence is homologous to a Xenopus laevis gene that encodes a known protein kinase, the S6 protein kinase.

Plasmid pML5 was selected by complementation in another S. cerevisiae strain, SKN37. This particular strain contains a disrupted allele of CAP, c::HIS3. CAP encodes an adenylyl cyclase associated protein of undetermined function. [Field et al., Cell, 61:319–327 (1990)]. As a consequence of this gene disruption, SKN37 fails to grow in medium rich in amino acids [Gerst et al., Mol. Cell Biol., 11:1248–1257 (1991)]. Human cDNAs were selected that could complement this defect. One cDNA insert found this way is present in pML5. Its nucleotide and deduced amino acid sequences are provided in SEQ ID NOs: 27 and 28. Its coding capacity is not yet certain.

Plasmids pATG16 and pATG29 were selected by complementation in the S. pombe diploid strain SP565. This strain is homozygous for disruptions of ras1 (ras1::LEU2). As a consequence, this strain fails to sporulate [Fukui et al., Cell, 44:329–336 (1986)] and human cDNAs were selected that could complement this defect. DNA sequence information for the inserts of pATG16 and pATG29 is set forth in SEQ ID NOs: 29 and 30; 31 and 32; respectively. These genes have unknown function. The vector used for screening in S. pombe differs from the vector used for screening in S. cerevisiae. This vector, pAAUN-ATG, utilizes an S. pombe specific promoter, the adh promoter, and was constructed as follows. The cloning vector pAAUN was derived from plasmid pART1 (McLeod et al., EMBO J., 6:729–736 (1987) by replacing the S. cerevisiae LEU2 gene with a 1.8 kbp HindIII ura4 fragment from S. pombe and adding NotI linkers at the SmaI site of the polylinker (PL) derived from Viera et al., Methods in Enzymology, 153:3–11 (1987). pAAUN contains the S. pombe adh promoter for gene expression and an ARS region for DNA replication. Plasmid pAAUN-ATG, was derived from plasmid pART8, obtained from David Beach, at Cold Spring Harbor Laboratory, and from pAAUN. The fragment of BamHI-EcoRV in pAAUN was replaced with the fragment of BamHI and EcoRV in pART8 which had a ATG start codon supplied by NdeI site in the polylinker.

EXAMPLE 2

Cloning and Identification of Mammalian Genes By Hybridization With Mammalian Genes Cloned By Complementation This example relates to the cloning and identification of additional mammalian genes by hybridization to probes having sequences derived from the genes described in Example 1, i.e., those genes cloned via complementation in yeast.

Low and high stringency hybridizations were done under the same conditions for 12 to 16 hours at 65° C. in an aqueous solution consisting of 6 times the normal concentration of sodium chloride-sodium citrate (SSC) (see below), 5 times the normal concentration of Denhardt's solution, 0.5% sodium dodecyl sulfate (SDS), 0.05 mg/ml of denatured salmon sperm DNA and probe. After hybridization, nitrocellulose filters were incubated for five minutes in 2×SSC, 0.5% SDS, at room temperature, and for twenty minutes in fresh 2×SSC, 0.5% SDS, at 60° C.

For high stringency hybridizations only, a third wash is performed for twenty minutes at 60° C. in 0.1×SSC, 0.1% SDS. The normal concentration of SSC is 0.15M sodium citrate and 0.15M sodium chloride, and the normal concentration of Denhardt's solution is 0.2 g/l Ficoll, 0.2 g/l polyvinyl-pyrrolidone, and 0.2 g/l bovine serum albumin:

Plasmids pPDE7, pPDE10X inv, and pPDE2RR were isolated by low stringency hybridization screens of a human temporal lobe cDNA library using the pRATDPD insert as probe. Nucleotide sequence (SEQ ID NOs: 33, 34 and 35, respectively) comparisons indicate that the inserts are representatives of the same genetic locus as the insert in pTM72. SEQ ID NO. 36 sets out the deduced amino acid sequence of the insert of pPDE2RR.

Plasmids pGB14 and pGB18ARR were obtained in the same manner. DNA sequence analysis (SEQ ID Nos: 37 and 39, respectively) revealed that they are representatives of the same genetic locus as the inserts in pTM3 and pJC44x. The deduced amino acid sequences of the inserts are set out in SEQ ID NOs. 38 and 40, respectively.

Plasmid pGB25 was also obtained by low stringency hybridization using the pRATDPD insert as a probe. Judged by its nucleotide and deduced amino acid sequence as set out in SEQ ID NOs: 41 and 42 it represents a novel member of PDE family IV.

The cDNA insert of pGB25 was used as a probe to obtain pPDE18 and pPDE21. The cDNA of pPDE18 (SEQ ID NO: 43) represents the same locus as that of pGB25 (SEQ ID NO: 41) and contains more sequence information than the pGB25 cDNA. The pPDE21 insert represents a fourth member of PDE family IV. Its DNA and deduced amino acid sequences are set out in SEQ ID NOs.: 45 and 46.

No biochemical data on expression products of these clones has yet been obtained. Their assignment to class IV is made solely based on sequence relationships.

EXAMPLE 3

Characterization of Cloned Genes By Complementation Capacity

This example relates to the further characterization of the genes cloned in Example 1 by their capacity to complement phenotypic defects in yeast strains other than the yeast strain originally used to clone the gene.

For example, 10DAB cells (pde1$^-$, pde2$^-$) were transformed with the DPD expression plasmid, pRATDPD, and assayed for heat shock sensitivity. Expression of the rat DPD gene indeed rendered this host resistant to heat shock. Similarly, pJC44x was able to correct the phenotypic defects of this pde1$^-$ pde2$^-$ yeast strain.

In contrast, pJC99, pJC265, and pJC310 were unable to do so. This suggests that the cDNAs of the latter inserts do not encode cAMP phosphodiesterases. Rather, these genes encode proteins of undetermined function which appear to be able to correct phenotypic defects in yeast with activated RAS proteins as reflected by their capacity to complement yeast strain TK161-R2V.

The procedures described below operate to establish that cDNAs need not be cloned by complementation (or by hybridization to DNAs cloned by complementation) in order to be functional in a genetically altered host. Put another way, the following procedures demonstrate that chemical agent screening methodologies according to the present invention need not involve initial direct or indirect cloning of pertinent DNAs by mean of complementation.

A. Yeast Phenotype Complementation by Expression of a cDNA Encoding Bovine Brain CaM-PDE Plasmid pCAM-40 (in E. coli, A.T.C.C. accession No. 68576) includes a bovine brain cDNA insert encoding a 61 kDa $Ca^{2+}$/calmodulin stimulated cyclic nucleotide phosphodiesterase.

A 2.2 kb cDNA fragment, adapted for insertion into yeast expression plasmids pADNS and pADANS was derived from the plasmid pCAM-40 by polymerase chain reaction. Briefly, the following PCR amplification was employed to alter the pCAM-40 DNA insert to align it appropriately with the ADH1 promoter in the vectors.

One oligonucleotide primer (Oligo A) used in the PCR reaction

SEQ ID NO: 47
5'-TACGAAGCTTTGATGGGGTCTACTGCTAC-3'
anneals to the pCaM-40 cDNA clone at base pair positions 100–116 and includes a HinDIII site before the initial methionine codon. A second oligonucleotide primer (Oligo B)

SEQ ID NO: 48
5'-TACGAAGCTTTGATGGTTGGCTTGGCATATC-3'
was designed to anneal at positions 520–538 and also includes a HinDIII site two bases before a methionine codon. The third oligonucleotide SEQ ID NO: 49 5'-ATTACCCCTCATAAAG-3'
annealed to a position in the plasmid that was 3' of the insert. For one reaction, Oligo A and Oligo C were used as primers with pCAM-40 as the template. The nucleic acid product of this reaction included the entire open reading frame. A second reaction used Oligo B and Oligo C as primers on the template pCAM-40 and yielded a nucleic acid product that lacked the portion of the cDNA sequence encoding the calmodulin binding domain. These amplified products were digested with HinDIII and NotI and ligated to HinDIII/NotI-digested yeast expression vectors pADNS and pADANS. Plasmid clones containing inserts were selected and transformed into *S. cerevisiae* strain 10DAB by lithium acetate transformation.

Transformed yeast were streaked in patches on agar plates containing synthetic medium lacking the amino acid leucine (SC-leucine agar) and grown for 3 days at 30° C. Replicas of this agar plate were made with three types of agar plates: one replica on SC-leucine agar, one replica on room temperature YPD agar, and three replicas on YPD agar plates that had been warmed to 56° C. The three warmed plates were maintained at 56° C. for 10, 20, or 30 minutes. These replicas were then allowed to cool to room temperature and then all of the plates were placed at 30° C. Yeast transformed with plasmids constructed to express the CaM-PDE were resistant to the thermal pulse. More specifically, both the construct designed to express the complete open reading frame and that designed to express the truncated protein (including the catalytic region but not the calmodulin binding domain), in either pADNS or pADANS, complemented the heat shock sensitivity phenotype of the 10DAB host cells, i.e., rendered them resistant to the 56° C. temperature pulse.

B. Biochemical Assay of Expression Products

The CaM-PDE expression product was also evaluated by preparing cell-free extracts from the yeast and measuring the extracts' biochemical phosphodiesterase activity. For this purpose, 200 ml cultures of transformed yeast were grown in liquid SC- leucine to a density of about 6 million cells per ml. The cells were collected by centrifugation and the cell pellets were frozen. Extracts were prepared by thawing the frozen cells on ice, mixing the cells with 1 ml of PBS and an equal volume of glass beads, vortexing them to disrupt the yeast cells, and centrifuging the disrupted cells at approximately 12,000×g for 5 min to remove insoluble debris. The supernatant was assayed for phosphodiesterase activity.

Extracts of yeast cells, up to 50 $\mu$l, were assayed for phosphodiesterase activity in 50 mM Tris (pH 8.0), 1.0 mM EGTA, 0.01 mg/ml BSA (bovine serum albumin), [$^3$H]-cyclic nucleotide (4–10,000 cpm/pmol), and 5 mM $MgCl_2$ in a final volume of 250 $\mu$l at 30° C. in 10×75 mm glass test tubes. The incubations were terminated by adding 250 $\mu$l of 0.5 M sodium carbonate (pH 9.3), 1M NaCl, and 0.1% SDS. The products of the phosphodiesterase reaction were separated from the cyclic nucleotide by chromatography on 8×33 mm columns of BioRad Affi-Gel 601 boronic acid gel. The columns were equilibrated with 0.25 M sodium bicarbonate (pH 9.3) and 0.5 M NaCl. The reactions were applied to the columns. The assay tubes were rinsed with 0.25 M sodium bicarbonate (pH 9.3), and 0.5M NaCl and this rinse was applied to the columns. The boronate columns were washed twice with 3.75 ml of 0.25M sodium bicarbonate (pH 9.3) and 0.5 M NaCl followed by 0.5 ml of 50 mM sodium acetate (pH 4.5). The product was eluted with 2.5 ml of 50 mM sodium acetate (pH 4.5) containing 0.1 M sorbitol and collected in scintillation vials. The eluate was mixed with 4.5 ml Ecolite Scintillation Cocktail and the radioactivity measured by liquid scintillation spectrometry.

Both the construct designed to express the complete open reading frame and that designed to express a truncated protein, in either pADNS or pADANS, expressed active protein as determined by biochemical assay of phosphodiesterase activity in cell extracts using a cAMP substrate.

C. Yeast Phenotype Complementation by Expression of a cDNA Encoding a Bovine Adrenal cGS-PDE The plasmid p3CGS-5 (A.T.C.C. 68579) which contains a 4.2-kb DNA fragment encoding the bovine cGMP stimulated cyclic nucleotide phosphodiesterase (cGS-PDE), was adapted for cloning into pADNS and pADANS by replacing the first 147 bases of the cDNA with a restriction site suitable for use in the insertion into the plasmids. The oligonucleotide BS1, having the sequence:

SEQ ID NO: 50
5'-TACGAAGCTTTGATGCGCCGACAGCCTGC-3'
encodes a HinDIII site and anneals to positions 148–165 of the cDNA insert. An oligonucleotide designated BS3
SEQ ID NO: 51 5'-GGTCTCCTGTTGCAGATATTG-3'
anneals to positions 835–855 just 3' of a unique NsiI site. The resulting PCR-generated fragment was digested with HinDIII and NsiI was then ligated to HinDIII- and NsiI-digested p3CGS-5 thereby replacing the original 5' end of the bovine cDNA. A plasmid derived from this ligation was digested with HinDIII and NotI to release the modified cDNA insert. The insert was cloned into pADNS and pADANS at their HinDIII and NotI sites. These plasmids were then transformed into the yeast strain 10DAB by the lithium acetate method and the transformed cells were grown and subjected to elevated temperatures as in Section A, above. Both transformations resulted in complementation of the heat shock sensitivity phenotype of the 10DAB host cells.

D. Biochemical Assay of Expression Product

The expression of the cGS-PDE was also evaluated by preparing cell-free extracts from the yeast and measuring the extracts' biochemical phosphodiesterase activity. For this purpose, 50 ml cultures of transformed yeast were grown in liquid SC-leucine to a density of about 10 million cells per ml. Sherman et al., *Methods in Yeast Genetics,* Cold Spring Harbor Laboratory, Cold Spring Harbor, New York (1986). The cells were collected by centrifugation, the cell pellets were washed once with water, and the final cell pellets were frozen. To prepare an extract, the frozen cells were thawed on ice, mixed with 1 ml of PBS and an equal volume of glass beads, vortexed to disrupt the yeast cells, and centrifuged to remove debris. The supernatant was then assayed for phosphodiesterase activity as in Section B, above.

Constructs in either pADNS or pADANS expressed active protein as determined by biochemical phosphodiesterase assay of cell extracts using cGMP.

EXAMPLE 4

Further Characterization of Cloned Genes By Nucleotide Sequence Analysis

This example describes the family-relatedness of the various human PDE clones described in the preceding examples. These clones include both those obtained by complementation and those obtained by hybridization. Clones pPDE32, pPDE39, pPDE43, and pPDE46 are described in detail in Example 6.

| COMPLEMENTATION | HYBRIDIZATION |
| --- | --- |
| pJC44x | pPDB7 |
| pTM22 | pPDE10 X inv |
| pTM3 | pPE2RR |

-continued

| COMPLEMENTATION | HYBRIDIZATION |
|---|---|
| pTM72 | pGB14 |
| | pGB18ARR |
| | pGB25 |
| | pPDB21 |
| | pPDE18 |
| | pPDB32 |
| | pPDE39 |
| | pPDEA3 |
| | pPDEA6 |

The uniqueness of its DNA sequence indicates that the pPDE21 cDNA derives from a locus herein designated PDE Class IV1.

Plasmid pTM3, pJC44x, pGB18ARR and pGB14, pPDE46 (see Example 6) cDNA all derive from the same genetic locus, herein designated PDE Class IV2. Evidence for this relation is shown in FIG. 1 demonstrating virtual sequence identity between pTM3, pJC44x, pGB18ARR and pGB14. The sequence of the cDNA insert in pPDE46 as set out in Example 6 also indicates that it is also derived from class IV2.

Likewise pTM72, pPDE7, pPDE10Xinv, pPDE2RR, and pPDE32 (See Example 6) cDNAs all derive from a genetic locus, herein designated PDE Class IV4. Evidence for this relation is shown in FIG. 2 demonstrating virtual sequence identity between pTM72, pPDE7, pPDE10Xinv, pPDE2RR. The sequence of pPDE32 as set out in Example 6 also indicates that it is derived from class IV4.

The cDNAs of pGB25, pPDE18, pPDE39 (Example 6), and pPDE43 (Example 6) derive from yet another genetic locus, herein designated PDE class IV3. Evidence of this relation is shown in FIG. 3 which demonstrates virtual sequence identity between the cDNA inserts in pGB25 and pPDE18. The cDNA insert in pPDE39 and in pPDE 43 as set out in Example 6 also indicate that they are derived from class IV3.

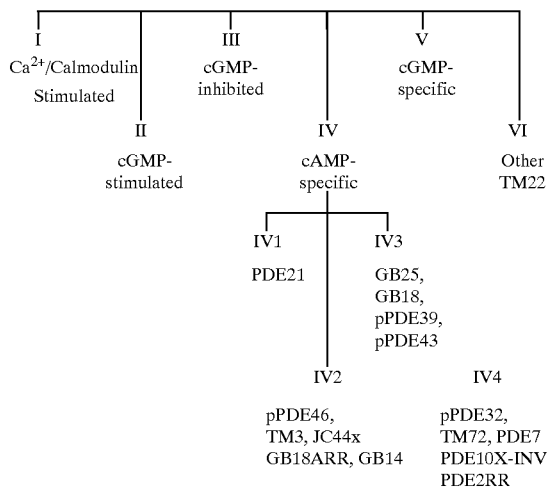

The sequences derived from any given locus are not identical. These sequence deviations can derive from a number of different sources including, sequencing errors, true polymorphisms in human populations, cloning artifacts, and differences in splicing patterns. Differences in splicing patterns perhaps account for the major differences in the pTM3 and pJC44x inserts. The pJC44x insert cDNA also may contain some cloning artifacts.

Sequence errors, not only for the clones described above, but also for published PDE sequences may have occurred. Naturally occurring sequence variations, or polymorphisms, may also account for the observed results. This introduces some uncertainty into the deduced amino acid sequence of the product of a given locus. Accordingly, it is to be appreciated that the nucleotide sequences claimed encompass not only the specific sequences claimed but also DNA sequences which are substantially the same as those provided herein for cloned cDNAs of interest.

The PDE family IV classes 1–4 comprise a gene family that is related to the rat DPD. The evidence for this is based on the similarity of the encoded amino acid sequences of representatives of this family.

Ostensibly, there are just four members of PDE family IV. In the description that follows, the term "human dunce PDEs" refers to all members of family IV, i.e., the genes that show nucleotide sequence homology to the Drosophila dnc PDE nucleotide sequences.

Only a subset of the members of a gene family may be expressed in any given tissue. Attempts to quantitate a gene family by studying cDNAs cloned from one, or only a few, tissues may therefore underestimate the total number of members of the family. However, analysis of genomic DNA avoids this problem. Human genomic DNA was used as a substrate in PCR reactions performed in parallel, each containing one of a number of different pairs of oligonucleotides corresponding to various regions of the family IV PDEs. The regions chosen were those strongly conserved in evolution and/or present in all the known members of this human gene family. The oligonucleotides were comprised of mixtures representing the full degeneracy of codons specifying the desired amino acid sequence. The vast majority of the oligonucleotide pairs tested produced several different PCR products which were heterogenous in length but always equal to or longer than those produced from the corresponding cDNA. However, two pairs produced only products identical in length to the cDNA. The longer heterogenous populations of products resulted from the priming of oligonucleotide pairs located on two separate exons. The two oligonucleotide pairs that produced identical length products primed off the same exon.

To confirm that the heterogenous fragment populations truly represented priming from separate exons, human family IV PDE genomic DNA clones were used as substrates in control PCR reactions. In these experiments, each of these clones produced a single PCR product, which was always equal in length to one of the heterogenous products obtained from genomic DNA.

The products from one of the reactions using oligonucleotides pairs that primed from one exon were cloned and sequenced. The oligonucleotides used were:
SEQ ID NO: 52 5'TTYAARTCTNYTNCARGRNGA, and
SEQ ID NO: 53 5'ACNATRTCTRATNACCATYTT
wherein: N is any of the four nucleotides; Y is C or T; and R is G or A. This corresponds to the fully degenerate codons specifying four potential amino acid sequences
FKLLQ(E/G)EN represented by SEQ ID NOs: 54 and 55, and
DMVID(M/I)V represented by SEQ ID NOs: 56 and 57 respectively, the two conserved domains boxed in FIG. 4. Using these primers, four different PCR clones were obtained, each corresponding in nucleotide sequence to one of the members of the known human family IV PDEs. The numbers of clones falling into each category were as follows:

| TYPE | TOTALS |
|---|---|
| TM72 type (Class IV4): | 16 |
| JC44 type (Class IV2): | 29 |
| PDE18 type (Class IV3): | 25 |
| PDE21 type (Class IV1): | 9 |
| Total: | 79 |

Assuming that the human genes each exist as single copies (which is consistent with this analysis of the available genomic clones), the four PCR products should be obtained ideally at equal frequency. The slightly skewed distribution obtained here probably reflects differing efficiencies in the production of these products in a PCR reaction due to mismatches with the PCR oligonucleotides. However, all four previously known genes were represented in the final PCR product, and no new sequences were identified. Therefore, the human PDE family IV most likely consists of a total of four members. Had this method identified a novel member of the family, the PCR clone could have been used as a probe to isolate cDNA clones. It is possible, however, that this family IV family has other members which have diverged at the codons specifying the amino acids sequences boxed in FIG. 4.

The cDNA insert pTM22 represents a genetic locus that is not a member of family IV. The evidence for this is that while the deduced amino acid sequence of the pTM22 insert has the general features expected of a cAMP phosphodiesterase, this sequence is not particularly closely related to the sequences of members of the family IV or the family I, the $Ca^{2+}$/calmodulin sensitive PDEs, or of the other known PDE families.

EXAMPLE 5

Screening and Identification of Agents Which Alter Enzymatic Activity

In their most general form, the pharmacological screening methods of the invention permit screening for agents that reduce or stimulate the activity of any mammalian protein whose presence or expression in an altered microbial host cell in which a genetic alterations associated with an identifiable phenotypic alteration results in correction of the phenotypic alteration. Two general types of screens are possible. Both methods are applicable to either living cells, or cell preparations, or cell extracts.

A. Identification of Agents That Affect Proteins of Known Activity

The first type of pharmacological screen is applicable when the mammalian gene encodes a protein of known and assayable biochemical function. The mammalian gene is first expressed in a microbial host by utilizing an appropriate host expression vector of the type already described. Either whole cells or extracts of host cells can be used. Extracts are prepared, using known techniques, i.e., the cells are disrupted and their cellular constituents released. Crude cellular extract of purified mammalian protein is assayed for the known biochemical function in the presence of agents, the effects of which on the protein are to be assessed. In this manner, agents which inhibit or stimulate the activity of the mammalian protein can be identified.

This type of procedure can be carried out to analyze the effects of selected agents on mammalian cAMP phosphodiesterases. For example, a yeast strain lacking both endogenous PDE1 and PDE2 genes can be used as the host cell, into which cDNA encoding mammalian cAMP phosphodiesterase is introduced in an appropriate expression vector and expressed. Such a host cell is particularly useful because there is no endogenous (background) cAMP phosphodiesterase activity. [Colicelli et al., Proc. Natl. Acad. Sci. (USA), 86:3599 (1989)]. Hence, activity of the mammalian enzyme can be cleanly assayed even in crude cell extracts. This procedure is illustrated below, in which it is demonstrated that the enzymatic activity of the rat DPD gene product is readily inhibited by the pharmacological agents Rolipram and R020 1724, but not as readily by the pharmacological agent theophylline.

The genes and cells described in the preceding examples can be used to identify chemical compounds which inhibit the activity of a known enzyme, the rat DPD phosphodiesterase. To test the efficiency of known inhibitory compounds, cell free extracts were made. Yeast cells deficient in endogenous phosphodiesterase (10DAB), and expressing the rat DPD or yeast PDE2 genes from the described expression vector, were used. One liter cultures were harvested, washed in buffer C (20 mM MES(pH 6.2)/0.1 mM $MgCl_2$/0.1 mM EGTA/1 mM 2-mercaptoethanol), resuspended in buffer C containing 1.5 mM phenylmethylsulfonyl fluoride (PMSF), and disrupted in a French press at 4° C. Cell extracts were clarified at 100×g for 10 minutes and at 18000×g for 90 minutes. PDE activities were assayed as published (Charbonneau et al., Proc. Natl. Acad. Sci. (USA), 83:9308–9312 (1986); Tempel et al., Proc. Natl. Acad. Sci. (USA), 80:1482–1486 (1983)) in a reaction mix containing 50 μg of cell protein/ml, 100 mM Tris (pH 7.5), 10 mM $Mg^{2+}$, 5 μM cAMP, 5'-nucleotidase and [3H] cAMP. AMP was separated from cAMP using AG1-X8 resin from Bio Rad. About $10^4$ cpm were obtained for 10 min reactions and backgrounds (phosphodiesterase deficient-yeast or no extract) were about 300 cpm. The cytosolic fraction was assayed in the presence or absence of inhibitory compounds. These assays measure the amount of adenosine 5' monophosphate (AMP) produced by phosphodiesterase-catalyzed hydrolysis of adenosine 3', 5'-cyclic adenosine monophosphate (cAMP). For each extract the percent inhibition for various concentrations of known inhibitors is given in Table 2. The percent inhibition represents the decrease in phosphodiesterase activity relative to measurements made in the absence of inhibitors. Rolipram, and the related compound R020 1724, were the most effective inhibitors of DPD activity.

TABLE 2

Inhibition of Phosphodiesterases by Chemicals

| Phosphodiesterase | Agent | Concentration (μM) | Inhibition % |
|---|---|---|---|
| PDE2 | Theophylline | 250 | 0.0 |
|  | IBMX | 250 | 0.0 |
|  | R020 1724 | 100 | 3.0 |
|  | Rolipram | 100 | 0.0 |
| rat DPD | Theophylline | 250 | 42.0 |
|  | IBMX | 250 | 87.0 |
|  | R020 1724 | 0.1 | 35.0 |
|  |  | 1.0 | 52.0 |
|  |  | 10.0 | 79.0 |
|  |  | 100.0 | 92.0 |
|  | Rolipram | 0.1 | 50.0 |
|  |  | 1.0 | 72.0 |
|  |  | 10.0 | 92.0 |

TABLE 2-continued

Inhibition of Phosphodiesterases by Chemicals

| Phosphodiesterase | Agent | Concentration ($\mu M$) | Inhibition % |
|---|---|---|---|
| | | 100.0 | 95.0 |

This analysis can, of course, be extended to test new or related chemical compounds for their ability to inhibit PDE activity, or the activity of another phosphodiesterase expressed in this system. Clearly, this form of analysis can also be extended to other genes cloned and expressed in a similar manner for which there is an assayable enzymatic activity.

Phosphodiesterase activity was determined as described in the previous table using 0.04 and 1.0 $\mu M$ cAMP for pL22 Met and pJC44x, respectively. These concentrations of cAMP were specifically chosen to be below the $K_m$ for their respective enzymes. Thus, the $EC_{50}$ closely approximates the inhibitor constant or $K_i$ of each enzyme. All kinetic data represent initial velocities of enzyme catalysis.

TABLE 3

Inhibitor Sensitivities of Human Cyclic AMP
Phosphodiesterases Derived by Yeast Complementation

| Agent | $EC_{50}$[1] pJC44x | pL22 Met |
|---|---|---|
| cAMP | 3 | 0.2 |
| cGMP | >300 | >300 |
| Rolipram | 0.4 | >300 |
| RO 20-1724 | 3 | >300 |
| Milrinone | 30 | 30 |
| Theophylline | 300 | >300 |

[1]$EC_{50}$ = Inhibitor concentration at 50% enzyme velocity, concentration expressed in $\mu M$ The following procedure was applied to the screening of whole transformed host cells. The yeast strain 10DAB was transformed with the expression vector pAD72, which expresses a human family IV phosphodiesterase, i.e., a cAMP specific PDE. This transformed strain was grown in SC-leucine medium for three days at 30° C. These cultures achieved a cell density of about 50 million cells per ml. Aliquots of this culture (300 $\mu l$) were taken and mixed with 4.8 $\mu l$ 10% DMSO or 10% DMSO containing an appropriate concentration of phosphodiesterase inhibitor. The treated cultures were then incubated for two hours at 30° C., after which two 3 $\mu l$ aliquots were removed and transferred to an SC-leucine agar plate. Then, a 100 $\mu l$ aliquot was removed from the treated cultures and transferred to a glass 12×75 mm test tube and the test tubes were incubated at 50° C. in a mineral oil-containing hot block for 30 min. The test tubes were removed from the hot block and placed at room temperature. Two 3 $\mu l$ aliquots were removed and transferred to an SC-leucine plate. The agar plates were then incubated at 30° C. and examined at various times to evaluate growth.

Yeast treated with 10% DMSO alone showed a slight decrease in the number of viable cells following the 50° C. heat treatment. Treatment of cells with Rolipram reduced the number of viable cells, such that at 100 $\mu M$ Rolipram, less than 10 out of approximately 150,000 cells remained viable. Milrinone concentrations up to 100 $\mu M$, had no observable effect on the culture.

B. Identification of Agents Which Affect Proteins of Unspecified Function

This example illustrates the use of the genes and methods described above for use in identifying chemical compounds which affect the function of the encoded mammalian proteins expressed in yeast, even when the function of that protein has not yet been determined.

10DAB cells, which are phosphodiesterase deficient, are sensitive to heat shock. As already discussed, when these cells acquire the capacity to express the cDNA of pRATDPD, they become resistant to heat shock. 10DAB cells expressing the cDNA of pRATDPD were maintained in rich medium (YPD) for three days at stationary phase. These cultures were then treated with Rolipram, a known phosphodiesterase inhibitor, for 40 minutes at a final concentration of 100 $\mu M$. Control cultures were not treated with any inhibitor. These cultures were then heat shocked in glass tubes at 50° C. 9 for 30 minutes. One microliter of each culture was plated. Cultures treated with Rolipram were much more sensitive to heat shock, reflecting an inhibition of enzymatic function.

The second type of pharmacological screen is applicable even when the mammalian gene encodes a protein of undetermined function, and, thus, cannot be assayed by a biochemical activity. In this method, agents to be tested are applied or introduced directly to the genetically altered microbial host expressing the mammalian protein. Agents capable of inhibiting the mammalian gene or gene product are identified by their ability to reverse the phenotype originally corrected by expression of the mammalian protein in the altered host.

This procedure has been used for mammalian cDNAs encoding cyclic nucleotide phosphodiesterases and a yeast containing $RAS2^{va119}$ as the host strain. When the rat DPD gene is introduced into the heat shock sensitive host and expressed, the host strain becomes heat shock resistant. When the now-resistant cells are incubated in Rolipram, they become heat shock sensitive again, indicating that Rolipram inhibits the activity of the rat DPD gene product. This pharmacological screen does not require that the function of the DPD gene product be known. This same approach can be applied to assess other genes.

In addition, any other phenotype that is dependent on DPD phosphodiesterase activity should be affected by the presence of the inhibitory drug. The effect of a drug or agent can be assessed as described. Finally, in the most generalized case, inhibitory chemicals for proteins of unknown function, expressed from mammalian cDNAs in yeast can be discovered in a similar way. This approach depends only on the phenotype consequent to expression of the protein and not on knowledge of its function.

For example, tyrosine kinases comprise a very large and diverse superfamily of proteins. They are important in regulation of cell growth. Certain tyrosine kinases are expressed ubiquitously in cells. Other tyrosine kinases display tissue specific distribution. Truly specific inhibitors of such tyrosine kinases could thus be expected to have specific and desirable therapeutic effects without unwanted side effects. For example, specific inhibitors of the PDGF receptor-tyrosine kinase could be expected to retard the growth of atherosclerotic plaques or retard scar formation; specific inhibitors of the lck tyrosine kinase, which mediates signals from the CD4 and CDB T-cell receptors, could be expected to be anti-inflammatory without being cytotoxic.

It is probable that yeast can be used to screen pharmacological agents for inhibition of specific tyrosine kinases. Brugge et al., *Mol. Cell. Biol.*, 7:2180–2187 (1987) demonstrated that expression of the avian v-src gene in the yeast *S. cerevisiae* inhibits growth. This viral gene encodes a tyrosine specific protein kinase that closely resembles the cellular src genes that are expressed ubiquitously in mammalian and avian cells. If this is a general property of active mammalian tyrosine kinases expressed in yeast, then the following design for a pharmacological screen would be expected to be effective.

A specific mammalian tyrosine kinase cDNA gene can thus be inserted in a yeast shuttle vector such that it is under the control of an inducible yeast promoter, such as the GAL10 promoter which is inducible in the presence of galactose and in the absence of glucose. Introduction of this vector into a yeast cell can be anticipated to render that cell unable to grow in induction medium (containing galactose in the absence of glucose), since under such conditions the mammalian tyrosine kinase would be expressed to the detriment of the cell. In the presence of an inhibitor of the tyrosine kinase, such cells would thrive on induction medium. This provides a simple screen for pharmacological agents that inhibit mammalian tyrosine kinases. False positive would include agents that blocked induction of the expression of kinase. Such false positive could be distinguished by the failure of the mammalian kinase to be induced, which can be determined by quantitation with specific antibodies.

EXAMPLE 6

Cloning of Human Dunce-like PDE cDNAs

As suggested in Example 4, it appears that there are only four members of human PDE Family IV (human dunce PDEs). In an effort to confirm this observation, additional attempts were made to clone cDNAs for all homologs of dunce in the human genome. To this end, three independent methods were utilized. The first approach used PCR to amplify human cDNA with homology to sequences present in both Drosophila dnc and rat DPD. This approach was used to analyze cDNA from several regions of human brain, and four different sequences, each highly homologous to dnc, were obtained. The second approach used low stringency hybridization using the DPD cDNA as a probe, to probe cDNA libraries from human brain and is described in more detail in Example 2. This approach yielded cDNA clones which collectively contained the same four sequences obtained by PCR. These cDNA clones are described in more detail below. The third approach was to isolate cDNAs that could suppress the heat shock sensitive phenotype of strains of S. cerevisiae with mutations in the RAS/cAMP pathway. Activating mutations of this pathway produce at least a portion of their phenotype by raising intracellular cAMP levels, and introduction of an exogenous PDE into these cells can lower cAMP levels sufficiently to revert this phenotype. Two different screens, both previously reported (Lundberg et al., Gene 108:1–6 (1991); and McHale et al., Mol. Pharmacol. 39:109–113 (1991)), were performed on a cDNA library from a human glioblastoma cell line. One of these screens isolated suppressors of the S. cerevisiae RAS2$^{val119}$ mutation, while the other yielded suppressors of a S. cerevisiae strain (10DAB) with disruptions of both endogenous PDE genes. Both these screens generated cDNAs encoded by several different human genes. Only some of these clones were homologous to dnc, and only these are described here.

These approaches confirm that there are only 4 different human loci, hereinafter referred to as DPDE1, DPDE2, DPDE3, and DPDE4 which encode cDNAs strongly homologous to that of dnc. These loci correspond to PDE classes IV 1–4 as described in Example 4. The longest and most complete of the cDNAs from each of these loci are presented in FIG. 5. The clones pPDE21, pPDE24, pPDE32, pPDE39, pPDEA43, and pPDE46 were all obtained from the low-stringency screen described above and have the following DNA sequence number and deduced amino acid sequences, respectively: pPDE21; (SEQ ID NOS. 45 and 46); pPDE32, (SEQ ID NOS. 58 and 59); pPDE39, (SEQ ID NOS. 60 and 61); pPDE43, (SEQ ID NOS. 62 and 63); and pPDE46, (SEQ ID NOS. 64 and 65). Clones pTM3 and pTM72 clones were isolated from the S. cerevisiae genetic screens and are described in more detail in Examples 2 and 4.

A. Hybridization Screening of cDNA and Genomic Libraries

The complete insert from the pRATDPD (SEQ ID NO. 3) cDNA clone described in Example 1 was used to screen a human temporal cortex cDNA library at low stringency (6×SSC, 0.5% SDS, 50° C., final wash: 0.2×SSC, 0.1% SDS, 50° C.). All cDNAs were cloned into the EcoRI site of λZAP and were obtained from Stratagene (LaJolla, Calif.). Incomplete cDNA clones from 3 different loci (DPDEs 2, 3, and 4) were isolated from this low stringency screening. These incomplete clones include clones corresponding to pGB25, pPDE7, pPDE 10x-inv, pPDE2RR, pGB18ARR and pGB14, and pPDE9. The clone pPDE9 is very unusual in that it contains numerous insertions.

The incomplete clones were then used in high stringency hybridization screening (as described above, but with final wash 0.1×SSC, 0.1% SDS, 68° C.) in an attempt to isolate longer clones.

High stringency hybridization using a portion of the cDNA insert is pGB25 corresponding to nucleotides 1–288 (SEQ ID NO. 66) yielded pPDE39. Similarly, high stringency hybridization using the complete sequence of pGB25 yielded a clone corresponding to pPDE21. A high stringency hybridization using the pPDE21 gave rise to pPDE43. A portion of pPDE9 was used in high stringency hybridization screening which gave rise to a clone pPDE24, which in turn was used as a probe in a high stringency screening that gave rise to the clone pPDE32. Finally, a fragment of the cDNA insert in pJC44x corresponding to nucleotides 1–604 (SEQ ID NO. 68) was used in a high stringency hybridization which gave rise to pPDEA6.

Genomic clones were isolated from a human placental DNA library by high stringency hybridization using cloned pTM72, pPDE46, pPDE43 (or clones corresponding to various regions thereof), and the complete insert of pPDE21 as probes and were cloned into λFIX II (Stratagene).

B. Cloning of Human Dunce-Like Sequences By Degenerate Primer PCR

Polymerase chain reactions were carried out in a Perkin-Elmer Thermocycler (Perkin-Elmer Cetus) according to a modification of the method described in (Saiki et al., Science, 239:487–491 1988) using as template, DNA isolated from cDNA libraries described above. To reduce background in the PCR reaction from the λZAP vector arms, the plasmid pBluescript, containing the cDNA insert, was excised in vivo, using a mass scale-up of the procedure previously described (Short et al., Nucl. Acids Res., 16:7583–7600 [1988]). 200 ng of this DNA was used in PCR reactions, with Taq polymerase. PCR reaction conditions consisted of 40 cycles of 94° C. for 1.5 min, 55° C. for 3 min., and 72° C. for 5 min. The oligonucleotide primers used in these reactions pairs HDUN3 (SEQ ID NO: 69) and HDUN5 (SEQ ID NO: 71), HDUN4 (SEQ ID NO: 70) and 11 (SEQ ID NO: 73), and HDUN4 (SEQ ID NO: 70) and HDUN6 (SEQ ID NO: 72), respectively, (and set forth in Table 4) represent the degenerate coding sequence (or its complement) of regions conserved between the rat DPD gene and dnc.

clones with regions of variant sequence. FIG. 5 illustrates full-length cDNAs from three of the four human dunce loci, aligned with those from the Drosophila dnc locus.

TABLE 4

| PCR Primers | | Translation | Location[+] | SEQ ID NO |
|---|---|---|---|---|
| HDUN3 | 5' GAGGTACCACYTTYTTNGTYTCNACCAT 3' | MVETKKV[*] | 459 | 69 |
| HDUN4 | 5' CTAGCAGTGCGGTACCGCCCANGTYTCCCANARNGG 3' | PLWETWA[*] | 552 | 70 |
| HDUN5 | 5' GAATTCATHCAYGTNGAYCAYCC 3' | IHDVDHP | 372 | 71 |
| HDUN6 | 5' CGATGCTACGGAATTCGAYATGWSNAARCAYATG 3' | DMSKHM | 445 | 72 |
| HDUN11 | 5' CGATGCTACGGAATTCAARATGGTNATHGAYATNGT 3' | KMVID(I/M)V | 435 | 73 |
| HDUN20 | 5' CTAGCAGTGCGTTACCACNATRTCDATNACCATYTT 3' | KMVID(I/M)V[*] | 435 | 74 |
| HDUN24 | 5' CGATGCTACGGAATTCTTYAARYTNYTNCARGRNGA 3' | FKLLQ(E/A)E | 411 | 75 |

The abbreviations for positions containing degeneracies are: H; A or C or T, N; A or C or G or T, R; A or G, S; C or G, or T, R; A or G, S; C or G, W; A or T, Y; C or T; (*; Primes off the non-coding strand. +; Location on the dnc sequence (Fig. 6A)).

PCR was also performed, as described above, on first-strand cDNA, which was synthesized from polyadenylated RNA isolated from human temporal cortex (obtained from patients undergoing surgery for epilepsy, but grossly normal in appearance). RNA was isolated by the guanidine thiocyanate -cesium chloride method (McDonald et al., *Meth. Enzymol.* 152:219–227 [1983]), and first strand cDNA was prepared with oligo-dT priming and AMV reverse transcriptase [Sambrook et al., *Molecular Cloning a Laboratory Manual, Cold Spring Harbor Press* (1989)]. Approximately 200 ng of cDNA was used in PCR reactions as described above. PCR was also performed on genomic DNA, with either 10 ng of DNA from genomic clones (see below), or 200 ng of human placental DNA, in reactions otherwise identical to those described above.

PCR products were analyzed as follows: the reaction mixture was purified by agarose gel electrophoresis, the DNA cleaved at the restriction sites in the PCR primers, and the resulting fragments were cloned into pUC19 (Sambrook et al.). The inserts of approximately 80 recombinant clones from each PCR reaction were then individually sequenced as described below. For this purpose, single-strand template was prepared by PCR reactions as described above, but with primers recognizing sequences on the pUC19 plasmid, added to the PCR reaction in a 1:0.005 molar ratio, respectively. The primers had the following sequences (5' to 3'): AACAGCTATGACCATGATTA (SEQ ID NO: 76), and AGGGTTTTCCCAGTCACGAC (SEQ ID NO: 77). This template was then used in sequencing reactions with Sequenase, in a modification of the procedures outlined by the manufacturer (United States Biochemical, Cleveland, OH). The changes from the standard protocol were: (a) as a sequencing primer, an oligomer (M13–20 primer, New England Biolabs) was labelled with $^{32}$P by kinasing; (b) the $^{35}$S-dATP, and the initial elongation step, were both omitted; and (c) manganese was used in all reactions. This approach yielded cDNA clones which collectively contained the same four sequences obtained by hybridization screening.

EXAMPLE 7

Putative Alternative Splicing and Other Variants of the DPDE2, 3 and 4 Transcripts Comparison of the sequences of different cDNAs from the DPDE2, 3 and 4 genes revealed that each locus produced In FIG. 5, regions of variant sequence in the clones from each locus are shown by alternate lines. Areas of common sequence are shown by merged lines. Vertical dashed lines indicate homologous divergence points that occur in clones from different loci. The positions of putative initiation and termination codons are marked by a small box and a star, respectively. Regions of strong sequence conservation are shown in the areas defined by cross-hatched boxes. The UCR1 consensus is not found in pPDE32. Roman numerals indicate the various alternatively spliced isoforms from the dnc locus. The small triangle above the dnc cDNA indicates the location of the alternatively spliced exon 4 seen in some of these isoforms (Types I, II, and IVA). Exon 3 of dnc is found between these two points of alternative splicing. The small triangles above the DPDE2 cDNAs indicate the positions of the insertions in pTM3.

FIGS. 6A and B illustrate the deduced amino acid sequences of the cDNAs of the four human dunce genes, respectively. FIG. 6A illustrates the alignment of the homologous portions of pTM72, pPDE46, pPDE43 and the type IVB splicing product of dnc (exons 3 to 13, excluding exon 4) (Qiu et al., *J. Mol. Biol.* 222:553–565 (1991)). The available sequence from pPDE21 is also shown. Alignments were performed with the MACAW program (Schuler et al., *Proteins: Struct. Funct., Genet.* 9:180–190 (1991)). The two upstream conserved regions, UCR1 and UCR2, are delineated with heavy horizontal lines. The small triangles above the alignments indicate the positions of the insertions in pTM3.

FIG. 6B shows the deduced amino acid sequences of the amino-terminal regions of the cDNA clones. Sequence that overlaps with the alignment in (A) is underlined. Capital letters and vertical lines (or colons) show the area of sequence conservation between pPDE39 and pPDEA6. Dots indicate gaps which facilitate this alignment. The most common variations were seen in the DPDE2 and DPDE3 loci, and consisted of substitutions of blocks of sequences 5' to the phenylalanine codon which marks the start of homology between the human and Drosophila cDNA clones (FIGS. 5 and 6A). This location is homologous to the beginning of dnc exon 3, where considerable alternative splicing occurs. Qiu et al.,*J. Mol. Biol.* 222:553–565 (1991).

Two cDNA clones pPDE32 and pTM72 from the DPDE4 locus also contained alternative coding sequences at their 5' end (FIGS. 5 and 6A). The point of divergence is not known to be an alternative splice site in dnc, but does correspond to one of the insertions in pTM3. The deduced amino acid sequences of the alternative amino-terminal regions showed no obvious homology to each other, but the sequences of both were strongly homologous (76% and 74% exact amino acid homology, respectively) to alternative transcripts from the corresponding locus in the rat.

One clone, pTM3, contained two insertions of blocks of sequence, which disrupt its open reading frame (ORF). These blocks are not seen in pPDE46, nor in any other cDNA clone we have isolated from this locus, and have no sequence homology to any human or Drosophila gene. Splice consensus sequences are apparent at three of the four ends of these blocks. We believe these blocks to be improperly spliced introns, and that pTM3 is unlikely to encode a protein normally found in human cells, but one that can function genetically in yeast (possibly by initiating translation 3' to the insertions). The insertions occur at points of alternative splicing in the dnc or human loci (FIG. 5), suggesting that at least some of the genomic structure of the dunce genes is conserved in evolution.

EXAMPLE 8

The Alignment of Drosophila dnc and Human Dunce-Like Sequences

Sequence analysis of the 7 human dunce-like cDNA clones illustrated schematically in FIG. 5 showed that four of them pPDE46, pPDE43, pPDE32, and pTM72 contain complete ORFs, with stop codons in all three reading frames upstream of the putative initiation ATG. The ORF of pPDE39 is open at its 5' end, and a possible initiation ATG is shown in FIG. 6A, although the ORF may continue amino-terminal to this point. pPDE39 also ends at amino acid 419 of pPDE43, before the termination codon of DPDE3 transcripts is reached. The ORFs of pTM3 and pPDE21 are open at their 5' end, but continue to their respective termination codons. The termination codons of dnc and the cDNAs for the DPDE1, DPDE3, and DPDE4 loci are all within 20 codons of each other (FIG. 6A), whereas that of pPDE46 is located about 100 codons 3' to this region. The sequence of pPDE46 in this region is identical that of pTM3 and other clones we have isolated for this locus.

Figure 7:
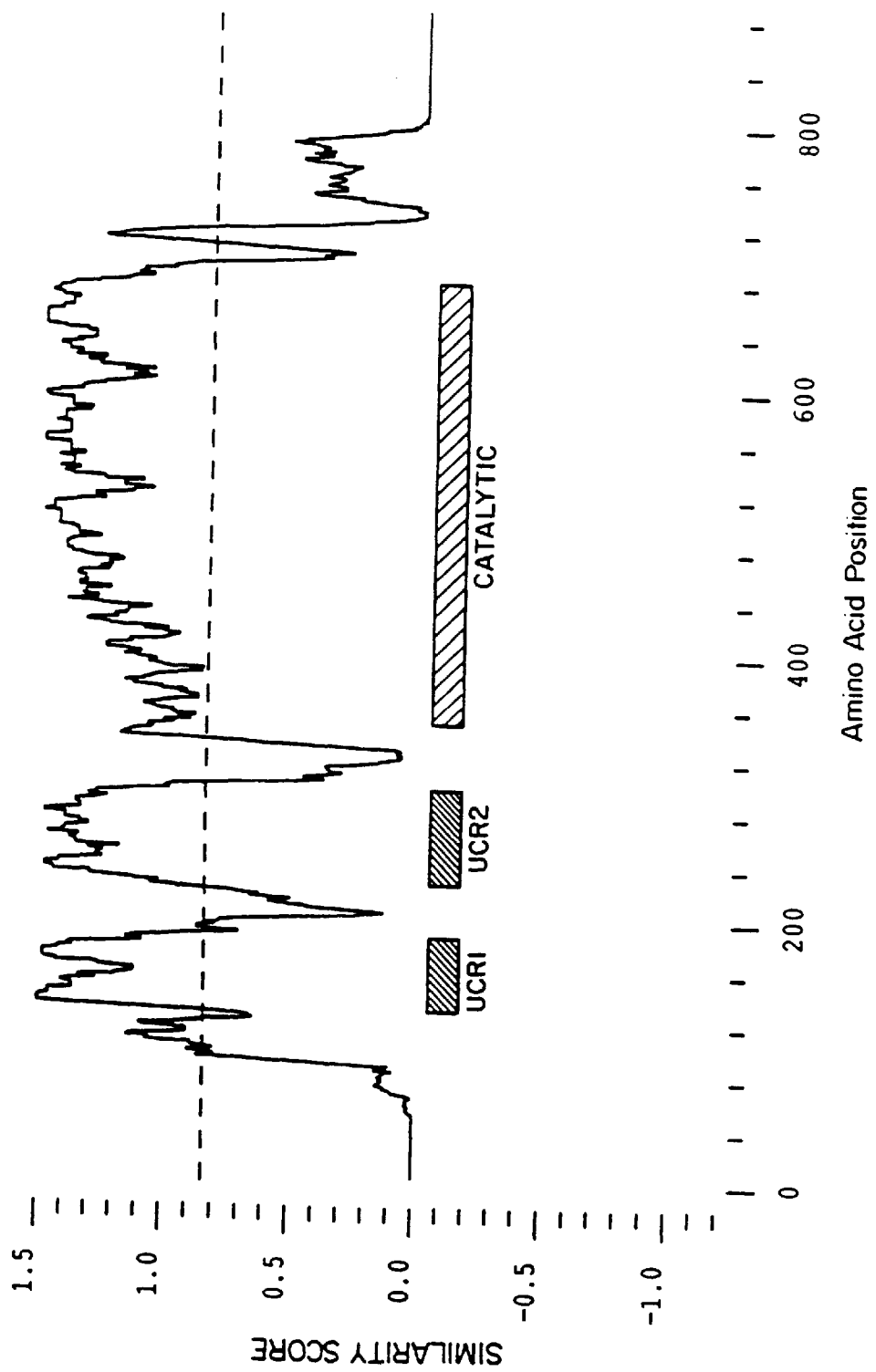
FIG. 7 shows a quantitative assessment of the homology between the full-length cDNA clones for dnc, pPDE46, pPDE43, and pTM72 as measured by the PLOTSIMILARITY program.

The alignment of the deduced amino acid sequences of these clones showed impressive homology to dnc (FIGS. 6 and 7). Alternative mRNA splice variants of dnc that did not contain exon 4 required the fewest gaps for alignment (FIGS. 6A). The homology begins at the phenylalanine corresponding to the beginning of dnc exon 3, and then becomes very striking in two regions of homology, neither of which has been previously recognized, that we call upstream conserved regions (UCR1 and UCR2). UCR1 and UCR2 are separated from each other, and from the catalytic region closer to the carboxyl terminus, by regions of lower homology in which there is also heterogeneity in length. The beginning of UCR2 also corresponds to the point of putative alternative splicing in the DPDE4 locus, i.e., pTM72 contains UCR1 but pPDE32 does not. In contrast, the N-terminal alternate regions of the genes were strongly divergent. Neither Drosophila nor humans showed any homology in these regions, with the exception of a single block of conserved amino acids (12 of 15 identical) in the pPDE46 and pPDE39 clones (FIG. 6A).

Comparison of the dunce PDE sequences to other families of cyclic nucleotide PDEs shows both conserved and novel features. The dunce catalytic region shares weak but significant homology (approximately 30% amino acid identity) with the catalytic regions of other PDE classes (Davis et al., Proc. Nat'l. Acad. Sci. USA 86:3604–3608 [1989]; Swinnen et al., Proc. Nat'l. Acad. Sci. USA 86:5325–5329 [1989]; and Livi et al. Mol. Cell. Biol. 10:2678–2686 [1990]). The UCR1 and UCR2 regions, however, share no apparent homology with the sequence of any non-dunce PDE, nor with any other genes in the EMBL, Genbank, or Swiss Protein databases. The strong evolutionary conservation of the UCR1 and UCR2 regions among the dunce PDEs suggests that they are important in dunce PDE function.

Livi et al., have isolated a dunce-like PDE cDNA from a human blood monocyte line which corresponds to our pPDEA6, but which is truncated at its amino terminus. The DNA sequence of that clone also contains a number of single nucleotide changes which alters the open reading frame 5' from the proline at position 103 of pPDE46. The deduced amino acid sequence upstream from this point of pPDE46 is probably correct because it is conserved in the homologous regions of the Drosophila, DPDE3, and DPDE4 genes. The data of Livi et al., may reflect sequencing or cloning errors in this region, although the presence of polymorphisms cannot be rigorously excluded. More recently, McLaughlin et al. J. Biol. Chem. 265:6970–6976 (1993) have isolated a clone whose deduced amino acid sequence is identical to that of our pPDE32.

EXAMPLE 9

Enumeration of the Human Dune-Like Genes

To ensure that the four dunce-like PDEs cDNAs isolated above represent all of the dunce-like genes in the human genome, the PCR approach used in the analysis of cDNA described above was extended to genomic DNA. Genomic DNA was studied because, as discussed in Example 4, not necessarily all dunce-like PDE loci were expressed in the tissues from which mRNA was derived for the libraries studied previously. PCR primers were prepared corresponding to the fully degenerate codons of 9 different regions of amino acids that were conserved between the Drosophila, human and rat dunce genes. Pairs of these primers (a total of 19 pairs), and either human genomic DNA, human dunce cDNA clones, or human dunce genomic clones were used in PCR reactions as described in Example 4. When genomic DNA was used as template, the majority of these primer pairs each produced several PCR products as was the case in Example 4. These were of different sizes, all larger than those produced by that pair with cDNA.

When genomic clones were used as templates, they each produced single bands, identical in size to one of those seen with genomic DNA as template suggesting that each of the bands seen with genomic DNA was produced from a different gene by priming off sequences separated by an intron. The products were of different sizes because the lengths of these introns presumably vary among the dunce genes. However, two of the PCR primer pairs each produced a single band from genomic DNA which was identical in size with those from the genomic clones and to that from cDNA suggesting that these single bands were produced by priming off sequences located on a single exon. The PCR products produced from genomic DNA by one of these primer pairs (HDUN24 and HDUN20, Table 4) were cloned, and sequences from 79 individual clones were analyzed. Four different sequences were obtained: 9 from DPDE1, 29 from DPDE2, 25 from DPDE3, and 16 from DPDE4. No other PCR products homologous to dnc were found, and therefore it is likely that there are only four dnc homologs in humans, although it is possible albeit unlikely that a homolog exists that by chance, failed to anneal to these primers.

Southern blotting and gene mapping have demonstrated that each human dnc homolog occurs as a single copy. Therefore, it is likely that the differing abundances of the PCR products obtained in this experiment were due to varying efficiencies of PCR priming.

Based on the results of the experiments set out in Examples 4 and 6–9, it is very likely that there are only 4 human dunce-like loci. Grouping the class IV clones from Example 4 with the clones derived in Example 6 under their respective loci, the following relationship between the various PDE loci and their expression products emerges and is set out is Table 5.

TABLE 5

The Human Dunce-like Loci

| DPDE1 | DPDE2 | DPDE3 | DPDE4 |
| --- | --- | --- | --- |
| pPDE21 | pPDE46 | pPDE39 | pPDE32 |
|  | pTM3 | pPDE43 | pTM72 |
|  | pJC44x | pGB25 | pPDE7 |
|  | pGB18ARR | pPDE18 | pPDE10x-inv. |
|  | pGB14 |  | pPDE2RR |

The clones shown in bold type represent what are most likely full-length expression products of their respective loci. Other than pPDE21 (which does not appear to represent a complete DPDE1 transcript), no other expression products of the DPDE1 locus have been isolated.

Of the clones derived from the DPDE2 locus, pJC44x has a number of unusual structural features which may represent cloning artifacts, although this has not been proven. However, pJC44x has shown biological activity when expressed in yeast. Clones pGB18ARR and pGB14 appear to be fragments of pPDE46. Clones pPDE46 and pTM3 appear to be full-length expression products of the DPDE2 locus.

Clones pPDE39 and pPDE43 are most likely full-length expression products of the DPDE3 locus. pGB25 and pPDE18 appear to represent fragments of the mRNAs corresponding to pPDE39 and/or pPDE43. pPDE18 also contains an unusual 42-nucleotide sequence at the 5' end of its open reading frame which is consistent with a cloning artifact.

Full-length expression products of the DPDE4 locus include pPDE32 and pTM72 while pPDE7, pPDE10x-inv. and pPDE2RR appear to be derived from fragments of mRNA from the region of sequence that is common to the full-length clones or from regions of these mRNAs that are 3 ' to the regions included in the full-length clones.

A total of four homologs of dnc have also been isolated from the rat (Davis et al., *Proc. Nat'l. Acad. Sci. USA* 86:3604–3608 [1989]; Swinnen et al., *Proc. Nat'l. Acad. Sci. USA* 86:5325–5329 [1989]; Swinnen et al., *Proc. Nat'l Acad. Sci. USA* 86:8197–8201 [1989]; and Colicelli et al., *Proc. Nat'l. Acad. Sci. USA* 86:3599–3608 [1989]). Evidence also suggests that the rat genes have a 1:1 correspondence with their human counterparts. This pairwise relationship is apparent only upon comparison of coding sequences that lie outside of the putative catalytic regions, and which were not included among the rat cDNA sequences that were previously published.

EXAMPLE 10

Tissue and Cell Specific Expression of the Human Dunce-Like Genes

A. Northern Blotting and RNAase Protection Analysis

Northern blotting and RNA protection analysis were performed to examine the cell and tissue distribution of expression of the human dunce-like genes. Northern blotting was performed on polyadenylated RNA from human temporal cortex (see Example 2) by electrophoresis through formaldehyde-agarose gels and transfer to nitrocellulose filters (Sambrook et al.). Filters were hybridized to $^{32}$P-dCTP labelled probes generated by random priming. The probe for pTM72 corresponded to nucleotides (NT) 2422 to 3181 (SEQ ID NO. 78) For pPDE46, pPDE43, and pPDE21, they corresponded from nucleotide 693 to nucleotide 2733 in the 3' non-coding region of pPDE46 (SEQ ID NO. 79), 611 to nucleotide 2788 in the 3' non-coding regions of pPDE43 (SEQ ID NO. 80), and from codon 222 to nucleotide 1155 in the 3' non-coding regions of pPDE21 (SEQ ID NO. 81). respectively. Washing was performed at high stringency (final wash, 0.1×SSC, 0.5% SDS, 68° C.). Blots were exposed to x-ray film for 7 days at −70° C., with intensifying screens.

For RNAase protection analysis, total RNA was isolated from human tumor cell lines by the guanidine thiocyanate—cesium chloride method (MacDonald et al. *Meth. Enzymol.* 152:219:221). All the cell lines used are available from the American Type Culture Collection (Rockville, Md.). Total RNA was also similarly isolated from testes removed from patients undergoing therapy for carcinoma of the prostate. Single-stranded antisense RNA probes were generated from appropriate regions of the four cDNAs, cloned under the control of the SP6 promoter in pGEM3Zf or pGEM4Zf, (Promega, Madison, Wis.). The probes were designed to hybridize to the divergent carboxyl-termini of the cDNAs, the probes were located in non-coding DNA 3. to the termination codon, i.e., for pTM72, NT 2828 to 3181 (SEQ ID NO. 82); pPDE43, NT 2628 to 2788 (SEQ ID NO. 83); and pPDE21, NT 786 to 1155 (SEQ ID NO. 84). RNAase protection assays were performed as described by Sambrook et al. RNAase digestion was done with 20 µg of RNA per assay, and ribonucleases A and T1 (Worthington) for one hour at 30° C. Autoradiograms of the gels were exposed for 5 days at −70° C.

Figure 8:
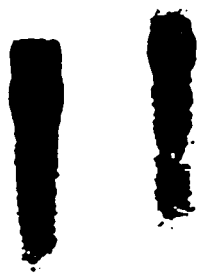
FIG. 8 shows a photograph of a Northern blot of human brain polyadenylated RNA with human dunce cDNA probes.

The expression of the human dunce-like genes in the central nervous system (CNS) tissue was studied by Northern blotting as illustrated in FIG. 8. Each lane contains approximately 5 µg of RNA from human temporal cortex and each lane was hybridized individually with the appropriate probes. The probes in this study were specific to each of the four genes, and recognized sequences 3' to the consensus sequence QFELTLEE, which greatly differ among the 4 genes (FIG. 6B). Lanes 1–4 represent hybridization with probes from pPDE46, pTM72, pPDE43, and pPDE21, respectively. Using a probe for pTM72, bands of sizes 4.6 kb and 4.0 kb were seen in polyadenylated RNA from normal human temporal cortex which was surgically removed. A band of 4.5 kb was seen with a pPDE46 probe, and the pPDE43 and pPDE21 probes produced no clearly detectable signal.

The 4.5 kb band detected by the pPDE46 probe in brain is similar to that observed in a variety of human tissues outside of the CNS using a similar probe. (Livi et al., *Mol. Cell. Biol.* 10:2678–2686 [1990]). The two bands detected by pTM72 are similar to those observed in a variety of human tissues by others using a similar probe. (McLaughlin et al., *J. Biol. Chem.* 268:6470–6476 [1993]). Since pPDE43 and pPDE21 were derived from a cDNA library derived from the same region of human brain (temporal cortex) as the mRNA used in the Northern blots described above. Thus, despite the lack of a readily detectable signal, it is likely that these genes are expressed at very low levels in the temporal cortex.

The expression of the human dunce-like genes was also studied by RNAase protection and is summarized in Table 6. Antisense RNA probes specific to each of the 4 genes were prepared, which, as in the Northern analysis, recognized sequences 3' to the sequence QFELTLEE. RNAse protection assays were performed on RNAs from the glioblastoma line U118 RNA; retinoblastoma line Y79; the neuroblastoma line SK-N-SH; the lung small cell carcinoma line Calu 3; the testicular embryonal carcinoma line Cates 1B; the T-lymphoblast line Molt 3; and from normal human testis RNA. Controls included RNAse protection analysis of transfer RNA and probe clone with no RNAse treatment. Size markers are MspI digested pBR322. The predicted size of the pPDE43 probe was 160NT, and such a band was detected by autoradiography. Table 6 represents a summary of the data.

TABLE 6

RNAase Protection Analysis

| Probe | U118 | Y29 | Sk-N-SH | Calu 3 | Cates 1B | Molt 3 | Testes |
|---|---|---|---|---|---|---|---|
| TM72 | ++ | − | ++ | − | − | − | − |
| PDE46 | +++ | +++ | + | + | ++ | + | − |
| PDE21 | − | + | + | − | − | − | − |
| PDE43 | + | − | ++ | ++ | + | ++ | − |

The signal produced by each RNA source as determined visually from the autoradiograms, is presented relative to that of other samples using the same probe. Analysis of total RNA from various cell lines and tissues with these probes demonstrated significant differences in the expression among the 4 genes. Among the cell lines tested, transcripts from the DPDE1 locus appeared to be restricted to those of neuronal origin (the retinoblastoma line Y79 and the neuroblastoma line SK-N-SH). In contrast, transcripts from the DPDE2 locus were expressed in almost all the cell lines, although at varying levels. Transcripts from the DPDE3 and DPDE4 loci were each present in distinctive patterns. Although these data are obtained from cell lines derived from tumors, they demonstrate that each of the DPDE loci can be expressed in a distinctive cell-specific pattern.

EXAMPLE 11

Biochemical and Pharmacologic Properties of the Expression Products of the Human Dunce-Like Genes The biochemical and pharmacologic properties of the protein expression products of the human dunce-like genes were analyzed in order to allow their assessment as potential targets for screening pharmacologic agents as described in Example 5.
A. Construction of Clones for Biochemical and Pharmacological Assays To examine the biochemical and pharmacologic properties of the dunce PDEs, cDNA clones for dnc and fragments of pTM72, pPDE46, pPDE43, representing three of the human loci (DPDEs 2, 3, and 4) were cloned into the NotI site of pADANS and expressed in the *S. cerevisiae* strain 10DAB, in which both endogenous PDE genes have been genetically disrupted (Colicelli et al., *Proc. Nat'l. Acad. Sci. USA* 86:3599–3603 [1989]). To ensure that any biochemical differences observed between the dunce genes reflected variations in their homologous coding regions, rather than potential differences in 5' alternative splicing (see above), slightly truncated constructs of cDNAs from dnc (Type II splice variant) and the 3 human loci were prepared, all of which started at the phenylalanine codon homologous to that at the beginning of dnc exon 3 (FIG. 5). Full-length constructs of the dnc Type II and pTM72 cDNA clones were also analyzed. All the resulting constructs produced a transcript generated off the *S. cerevisiae* alcohol dehydrogenase (ADH) promoter, and contained 13 amino acids at their amino termini derived from the ADH gene product, in frame with the open reading from (ORF) of the human cDNA. The inserts were generated by PCR, using Pfu polymerase, as described in Lundberg et al., *Gene* 108:1–16 (1991). PCR reactions were performed with 20 cycles of 94° C. for 1 min. 30 sec., 65° C. for 2 min., and 72° C. for 5 min. Not I sites were incorporated into the PCR primers to aid in subsequent cloning.
B. Phosphodiesterase Activity Assay Cells used in biochemical and pharmacologic studies were isolated at mid-log phase of growth at 30° C. on selective media (SC-leucine). Pellets containing approximately $1 \times 10^{10}$ cells, (1 g wet weight), were resuspended in 20 mM Tris-Cl pH8.0, 5mM EDTA, 5mM EGTA, 1 mM O-phenanthroline, 0.1 mM 4-(2-aminoethyl)-benzenesulfonylflouride, 1 mM benzamidine, 10 µg/ml leupeptin, 10 µg/ml pepstatin, 10 µg/ml aprotinin, and 10 µg/ml of both calpain inhibitors I and II. Cells were lysed by rapid mixing with glass beads and centrifuged at 10,000×g for 10 min to remove cell debris. Aliquots of the supernatant were assayed for PDE activity immediately, or stored at −80° C. for later analysis. Protein was measured by the method of Bradford (Branford, *Anal. Biochem.* 72:248–254 (1976)) using a kit (Pierce, Rockford, Ill.).

Cyclic nucleotide phosphodiesterase activity was assayed as described in Martins et al. *J. Biol. Chem.* 255:1973–1979 (1982); and Michaeli, et al., *J. Biol. Chem.* 268:12925–12932 (1993) with modifications. Assays were performed in vinyl microtiter plates at 30° C. Incubation mixtures contained 40 mM Tris-Cl pH 8.0, 1 mM EGTA, 5mM magnesium chloride, 0.1 mg/ml bovine serum albumin, diluted enzyme, $^3$H-cAMP (1.3–7.5 µCi/ml, New England Nuclear Inc., Boston, Mass.), $^{14}$C-AMP (0.11 µCi/ml, New England Nuclear Inc.), and varying amounts of unlabelled cyclic nucleotides in a total volume of 100 µl. Assays were performed for 15 min. Three minutes prior to termination of the reaction, 5 µl of *Crotalus atrox* snake venom 5' nucleotidase (15 mg/ml) (Sigma, St. Louis, Mo.) was added. The assays were terminated by adding 50 µl of 20 mM Tris-Cl pH 7.5, 100 mM EDTA and 0.15% cetylpyridinium chloride. The nucleoside products were separated from the unreacted cyclic nucleotides by anion exchange chromatography on Sephadex A25 columns (8–30 mm) (Pharmacia, Piscataway, N.J.). After sample application, the columns were washed with 0.25 ml of 25 mM Tris-Cl pH 7.5, and then eluted with 3 applications (0.5 ml) of the same buffer. The eluate was mixed with EcoLume (ICN Biochemicals, Irvine, Calif.) and analyzed for $^3$H and $^{14}$C content by dual channel liquid scintillation spectroscopy. The recovery of $^3$H-nucleotide reaction products were corrected for the recovery of $^{14}$C-AMP.

For estimation of kinetic parameters, the PDE assays utilized a constant specific activity of 0.03µCi/nmol of $^3$H-cAMP. Initial rates of hydrolysis were determined from 5 duplicate 4-fold dilutions of the initial extract stock with cAMP concentrations ranging from 0.1 to 300 μM. The kinetic data were fit to a Michaelis-Menten model using TableCurve (Jandel Scientific, San Rafael, Calif.) to obtain estimates of the apparent $K_m$, $V_{max}$ (enzymatic specific activity), and associated errors. The model used the following equation: y=(ax)(b+x) where y is velocity, x is [cAMP], a is $V_{max}$, and b is $K_m$.

Inhibitor analysis was performed using 1 μM cAMP as substrate. Milrinone, and IBMX were from Sigma (St. Louis, Mo.); Rolipram and RO 20-1724 were from BIO-MOL Research Laboratories (Plymouth Meeting, Pa.); 8-Methoxy-IBMX was obtained from Jack Wells, Vanderbilt University; and zaprinast was obtained from Paul Feldman, Glaxo Inc. Research Institute (Research Triangle Park, N.C.). Denbufylline and cilostamide (OPC 3689) were synthesized as described in Lugnier et al., *Eur. J. Med. Chem.— Chim. Ther.* 20:121–125 (1985); and Goldner et al., *Ann. Chem.* 691:142–158 (1966). Inhibitory compound stocks were initially made up in 100% dimethylsulfoxide (DMSO) (Aldrich, Milwaukee, Wisconsin) and final DMSO concentrations in the PDE assay never exceeded 1%(v/v). Data were normalized to protein concentration and represent estimates of initial rates, determined by incubations at multiple enzyme dilutions.

Dose response inhibitory curves were fitted using a 4 parameter logistic dose response model described by the following equation: $y=a+b/(1+(x/c)^d)$ were y is % total PDE activity, a is the minimum activity level, b is the maximal activity level, c the inhibitor concentration at 50% maximal activity ($IC_{50}$), x is the inhibitor concentration, and d is a parameter that determines the slope of the curve at the $IC_{50}$. The four-parameter model was used for fitting the inhibitor data because the inhibitory curves frequently spanned a broader range of inhibitor concentration than would be fit accurately by a simpler model. The ability to adjust the slope inherent in the four-parameter logistic curve permitted a better fit to these data. However, for certain data sets, a two-parameter model was used to provide an estimate of the $IC_{50}$, described by the following equation: $y =b/(1+(x/c))$, where y is % total PDE activity, b is the maximal activity level, c is the $IC^{50}$, and x is the inhibitor concentration. This model assumes a baseline of zero activity and does not permit variation in the slope at the $IC_{50}$. It was used for two categories of data sets: (1) when activity could not be reduced to baseline, even at high inhibitor concentrations (i.e., $IC_{50}$ greater than 500 μM), or (2) when data sets were too variable to estimate the baseline.

Phosphodiesterase assays were performed as described above. Because the pPDE21 clones encoded only a portion of the predicted protein, it was not tested in these assays.

Table 7 shows a summary of the kinetic analysis of the dunce-like PDE clones.

TABLE 7

Summary of Kinetic Analysis for Dunce-Like PDE Clones

| Locus | Plasmid | $K_m$ (S.D.) μM | Specific Activity (nmol/min-mg) |
|---|---|---|---|
| DPDE2* | pADH46R | 18 (5.9) | 21 to 64 |
| DPDE3* | pADH43 | 8 (2.2) | 54 to 138 |
| DPDE4* | pADH72 | 7.2 (2) | 29 to 50 |
| dnc* | pADDROSF | 27 (16) | 0.8 to 5.6 |
| dnc | pADDROSC | 32 (9.5) | 0.6 to 2.5 |

(*cDNAs truncated at amino-terminal end, S.D.: Standard Deviation).

Kinetic parameters were obtained for the hydrolysis of $^3$H cAMP (0.1–300 μM) from supernatants of yeast extracts, derived form cells harboring the indicated plasmids. Values were determined in duplicate from three separate cell pellets. Each value for the $K_m$ represents the average of six determinations, with the standard deviation shown in parentheses. The specific activity at $V_{max}$ is reported as the range of determinations for the six experiments. The data show that the slightly truncated constructs all show PDE activity.

There was no detectable difference in PDE activity between the truncated form of dnc and its full-length construct (Table 7). Neither was there any difference in PDE activity between the full-length pTM72 clone and its truncated construct. The $K_m$ for cAMP for the 3 human clones was in the range previously reported for mammalian cAMP-specific PDEs analyzed in partially purified extracts ($7\times10^6$ to $1.8\times10^5$ M). The $K_m$ for cAMP for the full length and truncated forms of dnc was approximately $3\times10^5$ M, and about three-fold higher than previously reported for crude preparations of cAMP-specific PDE activity from extracts of Drosophila (Davis et al., *Arch. Biochem. Biophys.* 203:412–421 [1980]).

EXAMPLE 12

Inhibition of Phosphodiesterase Activity

In order to more fully characterize and compare PDEs encoded by the human and Drosophila genes described above, the effect of a number of PDE inhibitors on the activity was examined and the results summarized in Table 8.

TABLE 8

$IC_{50}$ values for Inhibition of Dunce-Like PDE Clones

| Locus Name: | DPDE2+ | DPDE4+ | DPDE4 | DPDE3+ | dnc+ | dnc |
|---|---|---|---|---|---|---|
| Plasmid: | pADH46R | pADH72 | pADH72C | pADH43 | pADDROSF | pDDROS |
| Inhibitor | | | | | | |
| cAMP | 9.7 (2.8) | 10 (1) | 8.5 (0.9) | 8.2 (1) | 54 (12) | 73 (63) |
| cGMP | >1000* | >1000* | >1000* | >1000* | >1000* | >1000* |
| Denbufylline | 0.22 (0.15) | 0.2 (0.2) | 0.19 (0.03) | 0.1 (0.01) | 1.5 (1.7) | 3 (0.5) |
| Rolipram | 0.5 (0.3) | 0.4 (0.02) | 0.3 (0.01) | 0.18 (0.04) | >1000* | >740* |
| IBMX | 9.3 (0.7) | 15 (4) | 11 (2) | 10 (2) | 11 (0.4) | 12 (0.3) |
| 8-Methoxy IBMX | 220 (48) | 220 (7) | 190 (74) | 160 (13) | 120 (69) | 170 (17) |
| Milrinone | 59 (9) | 59 (70) | 23 (2) | 16 (7) | >1000* | >1000* |
| Cilostamide | 140* | 55 (13) | ND | 90* | >1000* | >1000* |
| Zaprinast | 120 (38) | 90 (8) | ND | 88 (20) | 130 (20) | 58 (2) |

(+: cDNA truncated at 5' end, as described in Example 11. Numbers in parentheses represent the standard deviation. *: Data sets analyzed with the two-parameter model. ND: Not Determined).

IC$_{50}$ values ($\mu$M) shown in Table 8 were obtained for the hydrolysis of 1$\mu$M $^3$H cAMP from yeast extracts, derived from cells harboring the indicated plasmids. The IC$_{50}$ was determined by fitting the data to either a four-parameter model, or a two-parameter model, as described above. Wherever possible, the four-parameter model was used, because it could provide an accurate fit to inhibitor curves that spanned a wide range of concentrations. Data sets that could not be fitted to the four-parameter model were fitted to the two-parameter model. Each value represents the mean from 2 to 5 experiments. The values in parentheses represent the standard deviation of the mean for each experiment.

The ability of these compounds to inhibit the human dunce-like PDEs displayed a pattern of potency expected for a cAMP-specific PDE. All were inhibited by IBMX, a non-specific cyclic nucleotide PDE inhibitor, with no detectable difference in the concentration needed to produce a 50% inhibition (IC$_{50}$). Inhibitors specific to other classes of PDEs, such as milrinone or cilostamide (inhibitors of cGMP-inhibited PDEs), 8-Methoxy IBMX (an inhibitor of calcium/calmodulin-dependent PDEs), or zaprinast (an inhibitor of cGMP-specific PDEs) produced some inhibition, but at IC$_{50s}$10 to 1000-fold higher than for their specific PDE classes (Beavo et al., *Trends Pharm. Sci.* 11:150–155 [1990]; and Nichobon et al., *Trends in Pharm. Sci.* 12:19–27 [1991]). All the three human clones were markedly inhibited by the antidepressant drug Rolipram, an inhibitor of the cAMP-specific PDEs, with IC$_{50s}$ of 0.2 to 0.5 $\mu$M. The human dnc homologs were also inhibited by denbufylline and RO 20–1724 (IC$_{50s}$ in the range of 1 to 10 $\mu$M), two additional specific inhibitors of cAMP-specific PDEs. Dose-response curves for Rolipram (not shown), RO 20-1724, and denbufylline inhibition of the human clones were relatively flat and spread over three logs of inhibitor concentration. This property is consistent with the complex inhibitory kinetics previously reported for the human dnc homologs cloned by Levi et al., *Mol. Cell. Biol.* 10:2678–2686 (1990); McLaughlin et al., *J. Biol. Chem.* 265:6470–6476 (1993); and Torphy et al., *J. Biol. Chem.* 267:1798–1804 (1992).

The three human PDEs shared similar biochemical and pharmacologic properties. In fact, there was no more than a 6-fold difference in the K$_m$ for cAMP, and less than a 3-fold difference in the IC$_{50s}$ for denbufylline or Rolipram, among the PDEs encoded by these clones. For some of the cAMP-specific inhibitors, the pharmacologic properties of the human PDEs differed from those of dnc. The dnc gene product was not inhibited by Rolipram nor by RO 20-1724 (IC$_{50}$1000 $\mu$M). Denbufylline exhibited substantial inhibitory activity against the Drosophila dnc encoded PDEs (IC$_{50}$=1–3 $\mu$M), although this activity is still approximately 10-fold lower than that for the human enzymes. Thus, while the human and Drosophila cAMP-specific PDEs share some characteristics, they are readily distinguishable by their response to specific PDE inhibitors.

While the present invention has been described in terms of specific illustrative methods and materials, it is understood that modifications and variations thereof will occur to those skilled in the art upon consideration of the above detailed description. Consequently only such limitations as appear in the appended claims should be placed thereon.

The deposit of plasmids (and the DNA contained therein), referred to in the claims have been made in accordance with the Budapest Treaty. Should the microorganisms mutate, become non-viable or be inadvertently destroyed, the Applicants will replace such microorganisms for at least thirty (30) years from the date of the original deposit, or for at least five (5) years from the date of the most recent request for release of a sample, or for the enforceable life of any patent issued on the above-mentioned application, whichever period is longest.

---

We claim:

1. A purified and isolated DNA said DNA comprising a DNA encoding a mammalian cyclic nucleotide phosphodiesterase and selected from the group consisting of the mammalian DNA inserts present in plasmids pPDE46 (ATCC No. 69552), pPDE43 (ATCC No 69551), and pPDE339 (ATCC No. 69550).

2. A purified and isolated DNA comprising a DNA encoding a mammalian cyclic nucleotide phosphodiesterase which DNA hybridizes under stringent conditions to a DNA selected from the group consisting of DNA according to claim 1 and SEQ ID NOS.: 60, 62, and 64.

3. A purified and isolated DNA said DNA comprising a DNA which encodes a polypeptide encoded by a DNA according to claim 1 or 2 by means of degenerate codons.

* * * * *

UNITED STATES PATENT AND TRADEMARK OFFICE
CERTIFICATE OF CORRECTION

PATENT NO. : 6,100,025
DATED : August 8, 2000
INVENTOR(S) : Wigler et al.

It is certified that error appears in the above-identified patent and that said Letters Patent is hereby corrected as shown below:

Column 1,
Lines 14-16, replace "Work described herein was supported by the National Cancer Institute of the National Institutes of Health." with -- The United States government may own certain rights in the invention --.

Column 11,
Line 17, replace "FIG. 1A-1D" with -- FIGS. 1A-1J --.
Line 22, replace "FIG. 2(A)-2(D)" with -- FIGS. 2A-2J --.
Line 27, replace "FIG. 3" with -- FIGS. 3A-3B --.
Line 33, replace "FIG. 4" with -- FIGS. 4A-4D --.
Line 40, replace "FIG. 6A and 6B" with -- FIGS. 6A-6E --.

Column 18,
Line 51, replace "CAP, c::H1S3" with -- CAP, cap::H1S3 --.

Column 22,
Line 64, replace "pPDB7" with -- pPDE7 --.

Column 23,
Line 8, replace "pPDB21" with -- pPDE21 --.
Line 9, replace "pPDB32" with -- pPDE32 --.
Line 11, replace "pPDEA3" with -- pPDE43 --.
Line 12, replace "pPDEA6" with -- pPDE46 --.

Column 26,
Line 35, replace "[3H]" with -- [$^{3}$H] --.

Column 34,
Line 15, replace "pPDEA6" with -- pPDE46 --.

Column 36,
Line 36, replace "3." with -- 3' --.

UNITED STATES PATENT AND TRADEMARK OFFICE
CERTIFICATE OF CORRECTION

PATENT NO. : 6,100,025
DATED : August 8, 2000
INVENTOR(S) : Wigler et al.

It is certified that error appears in the above-identified patent and that said Letters Patent is hereby corrected as shown below:

Column 40,
Line 14, replace "(*cDNAs" with -- (*:cDNAs --.
Lines 32-33, replace "($7 \times 10^6$ to $1.8 \times 10^5$m)" with -- ($7 \times 10^{-6}$ to $1.8 \times 10^{-5}$m) --.
Line 34, replace "$3 \times 10^5$m" with -- $3 \times 10^{-5}$m --.
Table 8, line 4, replace "pDDROS" with -- pADDROSC --.

Column 215,
Line 23, replace "ATCC No 69551" with -- ATCC No. 69551 --.

Signed and Sealed this

Twelfth Day of February, 2002

Attest:

JAMES E. ROGAN
*Attesting Officer*  *Director of the United States Patent and Trademark Office*

UNITED STATES PATENT AND TRADEMARK OFFICE
CERTIFICATE OF CORRECTION

PATENT NO. : 6,100,025 Page 1 of 1
APPLICATION NO. : 08/206188
DATED : August 8, 2000
INVENTOR(S) : Michael H. Wigler et al.

It is certified that error appears in the above-identified patent and that said Letters Patent is hereby corrected as shown below:

Column 1, line 13, replace "5R35 CA329829-10 with -- CA39829 --.

Signed and Sealed this

First Day of April, 2008

JON W. DUDAS
*Director of the United States Patent and Trademark Office*

SEQUENCE LISTING (1) GENERAL INFORMATION:

(iii) NUMBER OF SEQUENCES: 84

(2) INFORMATION FOR SEQ ID NO:1:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (xi) SEQUENCE DESCRIPTION: SEQ ID NO:1:

AAGCGGCCGC                                                          10

(2) INFORMATION FOR SEQ ID NO:2:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (xi) SEQUENCE DESCRIPTION: SEQ ID NO:2:

GCGGCCGCTT                                                          10

(2) INFORMATION FOR SEQ ID NO:3:

(i) SEQUENCE CHARACTERISTICS:
        (A) LENGTH: 2158 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1688

(xi) SEQUENCE DESCRIPTION: SEQ ID NO:3:

```
AGC TTG CGA ATC GTA AGA AAC AAT TTC ACC CTG CTG ACA AAC CTT CAC        48
Ser Leu Arg Ile Val Arg Asn Asn Phe Thr Leu Leu Thr Asn Leu His
 1               5                  10                  15

GGA GCA CCG AAC AAG AGG TCG CCA GCG GCT AGT CAG GCT CCA GTC ACC        96
Gly Ala Pro Asn Lys Arg Ser Pro Ala Ala Ser Gln Ala Pro Val Thr
             20                  25                  30

AGA GTC AGC CTG CAA GAA GAA TCA TAT CAG AAA CTA GCA ATG GAG ACG       144
Arg Val Ser Leu Gln Glu Glu Ser Tyr Gln Lys Leu Ala Met Glu Thr
         35                  40                  45

CTG GAG GAA CTA GAC TGG TGC CTA GAC CAG CTA GAG ACC ATC CAG ACC       192
Leu Glu Glu Leu Asp Trp Cys Leu Asp Gln Leu Glu Thr Ile Gln Thr
     50                  55                  60

TAC CGC TCT GTC AGC GAG ATG GCT TCA AAC AAG TTC AAA AGG ATG CTG       240
Tyr Arg Ser Val Ser Glu Met Ala Ser Asn Lys Phe Lys Arg Met Leu
 65                  70                  75                  80

AAC CGG GAG CTG ACA CAC CTC TCA GAG ATG AGC AGA TCA GGG AAC CAA       288
Asn Arg Glu Leu Thr His Leu Ser Glu Met Ser Arg Ser Gly Asn Gln
                 85                  90                  95

GTG TCT GAA TAC ATT TCG AAC ACG TTC TTA GAC AAG CAG AAC GAT GTG       336
Val Ser Glu Tyr Ile Ser Asn Thr Phe Leu Asp Lys Gln Asn Asp Val
            100                 105                 110

GAA ATC CCA TCT CCC ACC CAG AAG GAC AGG GAG AAG AAG AAG AAG CAG       384
Glu Ile Pro Ser Pro Thr Gln Lys Asp Arg Glu Lys Lys Lys Lys Gln
        115                 120                 125

CAG CTC ATG ACC CAG ATA AGT GGA GTG AAG AAA CTG ATG CAC AGC TCA       432
Gln Leu Met Thr Gln Ile Ser Gly Val Lys Lys Leu Met His Ser Ser
    130                 135                 140

AGC CTG AAC AAC ACA AGC ATC TCA CGC TTT GGA GTC AAC ACG GAA AAT       480
Ser Leu Asn Asn Thr Ser Ile Ser Arg Phe Gly Val Asn Thr Glu Asn
145                 150                 155                 160

GAG GAT CAT CTA GCC AAG GAG CTG GAA GAC CTG AAC AAA TGG GGC CTT       528
Glu Asp His Leu Ala Lys Glu Leu Glu Asp Leu Asn Lys Trp Gly Leu
                165                 170                 175

AAC ATC TTC AAC GTG GCT GGG TAC TCC CAT AAT CGG CCC CTC ACA TGC       576
Asn Ile Phe Asn Val Ala Gly Tyr Ser His Asn Arg Pro Leu Thr Cys
            180                 185                 190

ATC ATG TAC GCC ATT TTC CAG GAA AGA GAC CTT CTA AAG ACG TTT AAA       624
Ile Met Tyr Ala Ile Phe Gln Glu Arg Asp Leu Leu Lys Thr Phe Lys
        195                 200                 205

ATC TCC TCC GAC ACC TTC GTA ACC TAC ATG ATG ACT TTA GAA GAC CAT       672
Ile Ser Ser Asp Thr Phe Val Thr Tyr Met Met Thr Leu Glu Asp His
    210                 215                 220

TAC CAT TCT GAT GTG GCG TAT CAC AAC AGC CTG CAC GCT GCT GAC GTG       720
Tyr His Ser Asp Val Ala Tyr His Asn Ser Leu His Ala Ala Asp Val
225                 230                 235                 240

GCC CAG TCA ACG CAC GTT CTC CTC TCT ACG CCA GCA CTG GAT GCT GTC       768
Ala Gln Ser Thr His Val Leu Leu Ser Thr Pro Ala Leu Asp Ala Val
```

-continued

```
              245                 250                 255
TTC ACA GAC CTG GAA ATC CTG GCT GCC ATT TTT GCA GCT GCC ATC CAT      816
Phe Thr Asp Leu Glu Ile Leu Ala Ala Ile Phe Ala Ala Ala Ile His
            260                 265                 270

GAT GTT GAT CAT CCT GGA GTC TCC AAT CAG TTT CTC ATC AAT ACA AAT      864
Asp Val Asp His Pro Gly Val Ser Asn Gln Phe Leu Ile Asn Thr Asn
            275                 280                 285

TCC GAA CTT GCT TTG ATG TAT AAT GAC GAA TCT GTG CTG GAA AAC CAT      912
Ser Glu Leu Ala Leu Met Tyr Asn Asp Glu Ser Val Leu Glu Asn His
            290                 295                 300

CAC CTC GCT GTG GGA TTC AAG CTC CTT CAA GAG GAA CAT TGC GAC ATC      960
His Leu Ala Val Gly Phe Lys Leu Leu Gln Glu Glu His Cys Asp Ile
305                 310                 315                 320

TTT CAG AAT CTT ACC AAG AAG CAA CGC CAG ACA CTC AGG AAA ATG GTG     1008
Phe Gln Asn Leu Thr Lys Lys Gln Arg Gln Thr Leu Arg Lys Met Val
                325                 330                 335

ATT GAC ATG GTG TTA GCA ACT GAT ATG TCC AAG CAC ATG AGC CTC CTG     1056
Ile Asp Met Val Leu Ala Thr Asp Met Ser Lys His Met Ser Leu Leu
                340                 345                 350

GCT GAC CTT AAA ACG ATG GTA GAA ACC AAA AAG GTG ACG AGC TCC GGT     1104
Ala Asp Leu Lys Thr Met Val Glu Thr Lys Lys Val Thr Ser Ser Gly
            355                 360                 365

GTT CTC CTC CTG GAC AAC TAT ACT GAC CGG ATA CAG GTT CTT CGC AAC     1152
Val Leu Leu Leu Asp Asn Tyr Thr Asp Arg Ile Gln Val Leu Arg Asn
        370                 375                 380

ATG GTA CAT TGT GCA GAC CTG AGC AAC CCT ACC AAG TCC TTG GAG TTG     1200
Met Val His Cys Ala Asp Leu Ser Asn Pro Thr Lys Ser Leu Glu Leu
385                 390                 395                 400

TAT CGG CAA TGG ACT GAT CGC ATC ATG GAG GAG TTT TTC CAA CAG GGA     1248
Tyr Arg Gln Trp Thr Asp Arg Ile Met Glu Glu Phe Phe Gln Gln Gly
                405                 410                 415

GAC AAA GAA CGG GAG AGG GGA ATG GAG ATT AGC CCA ATG TGT GAT AAA     1296
Asp Lys Glu Arg Glu Arg Gly Met Glu Ile Ser Pro Met Cys Asp Lys
                420                 425                 430

CAC ACA GCT TCT GTG GAA AAG TCC CAG GTT GGT TTC ATT GAC TAC ATT     1344
His Thr Ala Ser Val Glu Lys Ser Gln Val Gly Phe Ile Asp Tyr Ile
            435                 440                 445

GTC CAT CCA TTG TGG GAG ACC TGG GCA GAC CTG GTT CAG CCT GAT GCT     1392
Val His Pro Leu Trp Glu Thr Trp Ala Asp Leu Val Gln Pro Asp Ala
        450                 455                 460

CAA GAC ATT TTG GAC ACA CTA GAA GAT AAC AGG AAC TGG TAC CAG AGT     1440
Gln Asp Ile Leu Asp Thr Leu Glu Asp Asn Arg Asn Trp Tyr Gln Ser
465                 470                 475                 480

ATG ATT CCC CAG AGC CCC TCT CCA CCA CTG GAC GAG AGG AGC AGG GAC     1488
Met Ile Pro Gln Ser Pro Ser Pro Pro Leu Asp Glu Arg Ser Arg Asp
                485                 490                 495

TGC CAA GGC CTT ATG GAG AAG TTT CAG TTC GAA CTG ACC CTT GAA GAA     1536
Cys Gln Gly Leu Met Glu Lys Phe Gln Phe Glu Leu Thr Leu Glu Glu
                500                 505                 510

GAG GAT TCT GAA GGA CCG GAA AAG GAG GGA GAA GGC CCC AAC TAT TTC     1584
Glu Asp Ser Glu Gly Pro Glu Lys Glu Gly Glu Gly Pro Asn Tyr Phe
            515                 520                 525

AGC AGC ACA AAG ACA CTT TGT GTG ATC GAT CCA GAG AAC AGG GAT TCT     1632
Ser Ser Thr Lys Thr Leu Cys Val Ile Asp Pro Glu Asn Arg Asp Ser
        530                 535                 540

CTG GAA GAG ACT GAC ATA GAC ATT GCC ACA GAA GAC AAG TCT CTG ATC     1680
Leu Glu Glu Thr Asp Ile Asp Ile Ala Thr Glu Asp Lys Ser Leu Ile
545                 550                 555                 560

GAC ACA TA ATCTCCCTCT GTGTGGAGGT GAACATTCTA TCCTTGACGA GCATGCCAGC   1738
Asp Thr
```

Asp Thr

```
TGAGTGGTAG GGCCCACCTA CCAGAGCCAA GGCCTGCACA AAACAAAGGC CACCTGGCTT    1798

TGCAGTTACT TGAGTTTGGA GCCAGAATGC AAGGCCGTGA AGCAAATAGC AGTTCCGTGC    1858

TGCCTTGCCT TGCCGGCGAG CTTGGCGAGA CCCGCAGCTG TAGTAGAAGC CAGTTCCCAG    1918

CACAGCTAAA TGGCTTGAAA ACAGAGGACA GAAAGCTGAG AGATTGCTCT GCAATAGGTG    1978

TTGAGGGGCT GTCCCGACAG GTGACTGAAC TCACTAACAA CTTCATCTAT AAATCTCACC    2038

CATCCTGTTG TCTGCCAACC TGTGTGCCTT TTTTGTAAAA TGTTTTCGTG TCTTTGAAAT    2098

GCCTGTTGAA TATCTAGAGT TTAGTACCTC CTTCTACAAA CTTTTTTGAG TCTTTCTGGG    2158
```

(2) INFORMATION FOR SEQ ID NO:4:

(i) SEQUENCE CHARACTERISTICS:
        (A) LENGTH: 562 amino acids
        (B) TYPE: amino acid
        (D) TOPOLOGY: linear (ii) MOLECULE TYPE: protein (xi) SEQUENCE DESCRIPTION: SEQ ID NO:4:

```
Ser Leu Arg Ile Val Arg Asn Asn Phe Thr Leu Leu Thr Asn Leu His
 1               5                  10                  15

Gly Ala Pro Asn Lys Arg Ser Pro Ala Ala Ser Gln Ala Pro Val Thr
                20                  25                  30

Arg Val Ser Leu Gln Glu Glu Ser Tyr Gln Lys Leu Ala Met Glu Thr
            35                  40                  45

Leu Glu Glu Leu Asp Trp Cys Leu Asp Gln Leu Glu Thr Ile Gln Thr
        50                  55                  60

Tyr Arg Ser Val Ser Glu Met Ala Ser Asn Lys Phe Lys Arg Met Leu
65                  70                  75                  80

Asn Arg Glu Leu Thr His Leu Ser Glu Met Ser Arg Ser Gly Asn Gln
                85                  90                  95

Val Ser Glu Tyr Ile Ser Asn Thr Phe Leu Asp Lys Gln Asn Asp Val
            100                 105                 110

Glu Ile Pro Ser Pro Thr Gln Lys Asp Arg Glu Lys Lys Lys Lys Gln
        115                 120                 125

Gln Leu Met Thr Gln Ile Ser Gly Val Lys Lys Leu Met His Ser Ser
    130                 135                 140

Ser Leu Asn Asn Thr Ser Ile Ser Arg Phe Gly Val Asn Thr Glu Asn
145                 150                 155                 160

Glu Asp His Leu Ala Lys Glu Leu Glu Asp Leu Asn Lys Trp Gly Leu
                165                 170                 175

Asn Ile Phe Asn Val Ala Gly Tyr Ser His Asn Arg Pro Leu Thr Cys
            180                 185                 190

Ile Met Tyr Ala Ile Phe Gln Glu Arg Asp Leu Leu Lys Thr Phe Lys
        195                 200                 205

Ile Ser Ser Asp Thr Phe Val Thr Tyr Met Met Thr Leu Glu Asp His
    210                 215                 220

Tyr His Ser Asp Val Ala Tyr His Asn Ser Leu His Ala Ala Asp Val
225                 230                 235                 240

Ala Gln Ser Thr His Val Leu Leu Ser Thr Pro Ala Leu Asp Ala Val
                245                 250                 255

Phe Thr Asp Leu Glu Ile Leu Ala Ala Ile Phe Ala Ala Ala Ile His
            260                 265                 270
```

-continued

```
Asp Val Asp His Pro Gly Val Ser Asn Gln Phe Leu Ile Asn Thr Asn
        275                 280                 285

Ser Glu Leu Ala Leu Met Tyr Asn Asp Glu Ser Val Leu Glu Asn His
    290                 295                 300

His Leu Ala Val Gly Phe Lys Leu Leu Gln Glu His Cys Asp Ile
305                 310                 315                 320

Phe Gln Asn Leu Thr Lys Lys Gln Arg Gln Thr Leu Arg Lys Met Val
                325                 330                 335

Ile Asp Met Val Leu Ala Thr Asp Met Ser Lys His Met Ser Leu Leu
            340                 345                 350

Ala Asp Leu Lys Thr Met Val Glu Thr Lys Lys Val Thr Ser Ser Gly
        355                 360                 365

Val Leu Leu Leu Asp Asn Tyr Thr Asp Arg Ile Gln Val Leu Arg Asn
370                 375                 380

Met Val His Cys Ala Asp Leu Ser Asn Pro Thr Lys Ser Leu Glu Leu
385                 390                 395                 400

Tyr Arg Gln Trp Thr Asp Arg Ile Met Glu Glu Phe Phe Gln Gln Gly
                405                 410                 415

Asp Lys Glu Arg Glu Arg Gly Met Glu Ile Ser Pro Met Cys Asp Lys
            420                 425                 430

His Thr Ala Ser Val Glu Lys Ser Gln Val Gly Phe Ile Asp Tyr Ile
        435                 440                 445

Val His Pro Leu Trp Glu Thr Trp Ala Asp Leu Val Gln Pro Asp Ala
450                 455                 460

Gln Asp Ile Leu Asp Thr Leu Glu Asp Asn Arg Asn Trp Tyr Gln Ser
465                 470                 475                 480

Met Ile Pro Gln Ser Pro Ser Pro Leu Asp Glu Arg Ser Arg Asp
                485                 490                 495

Cys Gln Gly Leu Met Glu Lys Phe Gln Phe Glu Leu Thr Leu Glu Glu
            500                 505                 510

Glu Asp Ser Glu Gly Pro Glu Lys Gly Glu Gly Pro Asn Tyr Phe
        515                 520                 525

Ser Ser Thr Lys Thr Leu Cys Val Ile Asp Pro Glu Asn Arg Asp Ser
530                 535                 540

Leu Glu Glu Thr Asp Ile Asp Ile Ala Thr Glu Asp Lys Ser Leu Ile
545                 550                 555                 560

Asp Thr
```

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:5:

CACCCTGCTG ACAAACCT                                                  18

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:6:

ATGGAGACGC TGGAGGAA                                                    18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:7:

ATACGCCACA TCAGAATG                                                    18

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:8:

TACCAGAGTA TGATTCCC                                                    18

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:9:

GTGTCGATCA GAGACTTG                                                    18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:10:

GCACACAGGT TGGCAGAC                                                    18

(2) INFORMATION FOR SEQ ID NO:11:

(i) SEQUENCE CHARACTERISTICS:
        (A) LENGTH: 2702 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 8..2701

(ix) FEATURE:
        (A) NAME/KEY: misc_feature
        (B) LOCATION: 2433

(D) OTHER INFORMATION: /note= "A shift in reading frame may occur at this nucleotide."

(xi) SEQUENCE DESCRIPTION: SEQ ID NO:11:

```
AAGCTTG CGG CCG CGC GGC CTA GGC CGC ATC CCG GAG CTG CAA CTG GTG        49
        Arg Pro Arg Gly Leu Gly Arg Ile Pro Glu Leu Gln Leu Val
         1               5                  10

GCC TTC CCG GTG GCG GTG GCG GCT GAG GAC GAG GCG TTC CTG CCC GAG        97
Ala Phe Pro Val Ala Val Ala Ala Glu Asp Glu Ala Phe Leu Pro Glu
 15              20                  25                  30

CCC CTG GCC CCG CGC GCG CCC CGC CGC CGC GTT CGC CGC CCT CCT CGC       145
Pro Leu Ala Pro Arg Ala Pro Arg Arg Arg Val Arg Arg Pro Pro Arg
                 35                  40                  45

CCG TCT TCT TCG CCA GCC CGT CCC CAA CTT TCC GCA GAC GCC TTC GGC       193
Pro Ser Ser Ser Pro Ala Arg Pro Gln Leu Ser Ala Asp Ala Phe Gly
                 50                  55                  60

TTC TCC GCA GCT GCC AGG ATT TGG GCC GCC AGG CTT GGG CTG GGG CTG       241
Phe Ser Ala Ala Ala Arg Ile Trp Ala Ala Arg Leu Gly Leu Gly Leu
             65                  70                  75

GCT TCG AGG CAG AGA ATG GGC CGA CAC CAT CTC CTG GCC GCA GCC CCT       289
Ala Ser Arg Gln Arg Met Gly Arg His His Leu Leu Ala Ala Ala Pro
         80                  85                  90

GGA CTG CAG GCG AGC CCA GGA CTC GTG CTG CAC GCC GGG GCG GCC ACC       337
Gly Leu Gln Ala Ser Pro Gly Leu Val Leu His Ala Gly Ala Ala Thr
 95                 100                 105                 110

AGC CAG CGC CGG GAG TCC TTC CTG TAC CGC TCA GAC AGC GAC TAT GAC       385
Ser Gln Arg Arg Glu Ser Phe Leu Tyr Arg Ser Asp Ser Asp Tyr Asp
                 115                 120                 125

ATG TCA CCC AAG ACC ATG TCC CGG AAC TCA TCG GTC ACC AGC GAG GCG       433
Met Ser Pro Lys Thr Met Ser Arg Asn Ser Ser Val Thr Ser Glu Ala
         130                 135                 140

CAC GCT GAA GAC CTC ATC GTA ACA CCA TTT GCT CAG GTG CTG GCC AGC       481
His Ala Glu Asp Leu Ile Val Thr Pro Phe Ala Gln Val Leu Ala Ser
     145                 150                 155

CTC CGG AGC GTC CGT AGC AAC TTC TCA CTC CTG ACC AAT GTG CCC GTT       529
Leu Arg Ser Val Arg Ser Asn Phe Ser Leu Leu Thr Asn Val Pro Val
 160                 165                 170

CCC AGT AAC AAG CGG TCC CCG CTG GGC GGC CCC ACC CCT GTC TGC AAG       577
Pro Ser Asn Lys Arg Ser Pro Leu Gly Gly Pro Thr Pro Val Cys Lys
175                 180                 185                 190

GCC ACG CTG TCA GAA GAA ACG TGT CAG CAG TTG GCC CGG GAG ACT CTG       625
Ala Thr Leu Ser Glu Glu Thr Cys Gln Gln Leu Ala Arg Glu Thr Leu
                 195                 200                 205

GAG GAG CTG GAC TGG TGT CTG GAG CAG CTG GAG ACC ATG CAG ACC TAT       673
Glu Glu Leu Asp Trp Cys Leu Glu Gln Leu Glu Thr Met Gln Thr Tyr
         210                 215                 220

CGC TCT GTC AGC GAG ATG GCC TCG CAC AAG TTC AAA AGG ATG TTG AAC       721
Arg Ser Val Ser Glu Met Ala Ser His Lys Phe Lys Arg Met Leu Asn
     225                 230                 235

CGT GAG CTC ACA CAC CTG TCA GAA ATG AGC AGG TCC GGA AAC CAG GTC       769
Arg Glu Leu Thr His Leu Ser Glu Met Ser Arg Ser Gly Asn Gln Val
 240                 245                 250

TCA GAG TAC ATT TCC ACA ACA TTC CTG GAC AAA CAG AAT GAA GTG GAG       817
Ser Glu Tyr Ile Ser Thr Thr Phe Leu Asp Lys Gln Asn Glu Val Glu
255                 260                 265                 270

ATC CCA TCA CCC ACG ATG AAG GAA CGA GAA AAA CAG CAA GCG CCG CGA       865
Ile Pro Ser Pro Thr Met Lys Glu Arg Glu Lys Gln Gln Ala Pro Arg
                 275                 280                 285

CCA AGA CCC TCC CAG CCG CCC CCG CCC CCT GTA CCA CAC TTA CAG CCC       913
Pro Arg Pro Ser Gln Pro Pro Pro Pro Pro Val Pro His Leu Gln Pro
```

```
                    290                 295                 300
ATG TCC CAA ATC ACA GGG TTG AAA AAG TTG ATG CAT AGT AAC AGC CTG    961
Met Ser Gln Ile Thr Gly Leu Lys Lys Leu Met His Ser Asn Ser Leu
        305                 310                 315

AAC AAC TCT AAC ATT CCC CGA TTT GGG GTG AAG ACC GAT CAA GAA GAG   1009
Asn Asn Ser Asn Ile Pro Arg Phe Gly Val Lys Thr Asp Gln Glu Glu
        320                 325                 330

CTC CTG GCC CAA GAA CTG GAG AAC CTG AAC AAG TGG GGC CTG AAC ATC   1057
Leu Leu Ala Gln Glu Leu Glu Asn Leu Asn Lys Trp Gly Leu Asn Ile
335                 340                 345                 350

TTT TGC GTG TCG GAT TAC GCT GGA GGC CGC TCA CTC ACC TGC ATC ATG   1105
Phe Cys Val Ser Asp Tyr Ala Gly Gly Arg Ser Leu Thr Cys Ile Met
                355                 360                 365

TAC ATG ATA TTC CAG GAG CGG GAC CTG CTG AAG AAA TTC CGC ATC CCT   1153
Tyr Met Ile Phe Gln Glu Arg Asp Leu Leu Lys Lys Phe Arg Ile Pro
            370                 375                 380

GTG GAC ACG ATG GTG ACA TAC ATG CTG ACG CTG GAG GAT CAC TAC CAC   1201
Val Asp Thr Met Val Thr Tyr Met Leu Thr Leu Glu Asp His Tyr His
        385                 390                 395

GCT GAC GTG GCC TAC CAT AAC AGC CTG CAC GCA GCT GAC GTG CTG CAG   1249
Ala Asp Val Ala Tyr His Asn Ser Leu His Ala Ala Asp Val Leu Gln
        400                 405                 410

TCC ACC CAC GTA CTG CTG GCC ACG CCT TGG CCA ACC TTA AGG AAT GCA   1297
Ser Thr His Val Leu Leu Ala Thr Pro Trp Pro Thr Leu Arg Asn Ala
415                 420                 425                 430

GTG TTC ACG GAC CTG GAG ATT CTC GCC GCC CTC TTC GCG GCT GCC ATC   1345
Val Phe Thr Asp Leu Glu Ile Leu Ala Ala Leu Phe Ala Ala Ala Ile
                435                 440                 445

CAC GAT GTG GAT CAC CCT GGG GTC TCC AAC CAG TTC CTC ATC AAC ACC   1393
His Asp Val Asp His Pro Gly Val Ser Asn Gln Phe Leu Ile Asn Thr
                450                 455                 460

AAT TCG GAG CTG GCG CTC ATG TAC AAC GAT GAG TCG GTG CTC GAG AAT   1441
Asn Ser Glu Leu Ala Leu Met Tyr Asn Asp Glu Ser Val Leu Glu Asn
            465                 470                 475

CAC CAC CTG GCC GTG GGC TTC AAG CTG CTG CAG GAG GAC AAC TGC GAC   1489
His His Leu Ala Val Gly Phe Lys Leu Leu Gln Glu Asp Asn Cys Asp
        480                 485                 490

ATC TTC CAG AAC CTC AGC AAG CGC CAG CGG CAG AGC CTA CGC AAG ATG   1537
Ile Phe Gln Asn Leu Ser Lys Arg Gln Arg Gln Ser Leu Arg Lys Met
495                 500                 505                 510

GTC ATC GAC ATG GTG CTG GCC ACG GAC ATG TCC AAG CAC ATG ACC CTC   1585
Val Ile Asp Met Val Leu Ala Thr Asp Met Ser Lys His Met Thr Leu
                515                 520                 525

CTG GCT GAC CTG AAG ACC ATG GTG GAG ACC AAG AAA GTG ACC AGC TCA   1633
Leu Ala Asp Leu Lys Thr Met Val Glu Thr Lys Lys Val Thr Ser Ser
            530                 535                 540

GGG GTC CTC CTG CTA GAT AAC TAC TCC GAC CGC ATC CAG GTC CTC CGG   1681
Gly Val Leu Leu Leu Asp Asn Tyr Ser Asp Arg Ile Gln Val Leu Arg
        545                 550                 555

AAC ATG GTG CAC TGT GCC GAC CTC AGC AAC CCC ACC AAG CCG CTG GAG   1729
Asn Met Val His Cys Ala Asp Leu Ser Asn Pro Thr Lys Pro Leu Glu
        560                 565                 570

CTG TAC CGC CAG TGG ACA GAC CGC ATC ATG GCC GAG TTC TTC CAG CAG   1777
Leu Tyr Arg Gln Trp Thr Asp Arg Ile Met Ala Glu Phe Phe Gln Gln
575                 580                 585                 590

GGT GAC CGA GAG CGC GAG CGT GGC ATG GAA ATC AGC CCC ATG TGT GAC   1825
Gly Asp Arg Glu Arg Glu Arg Gly Met Glu Ile Ser Pro Met Cys Asp
                595                 600                 605

AAG CAC ACT GCC TCC GTG GAG AAG TCT CAG GTG GGT TTT ATT GAC TAC   1873
```

```
           Lys His Thr Ala Ser Val Glu Lys Ser Gln Val Gly Phe Ile Asp Tyr
                       610                 615                 620

ATT GTG CAC CCA TTG TGG GAG ACC TGG GCG GAC CTT GTC CAC CCA GAT         1921
Ile Val His Pro Leu Trp Glu Thr Trp Ala Asp Leu Val His Pro Asp
            625                 630                 635

GCC CAG GAG ATC TTG GAC ACT TTG GAG GAC AAC CGG GAC TGG TAC TAC         1969
Ala Gln Glu Ile Leu Asp Thr Leu Glu Asp Asn Arg Asp Trp Tyr Tyr
640                 645                 650

AGC GCC ATC CGG CAG AGC CCA TCT CCG CCA CCC GAG GAG GAG TCA AGG         2017
Ser Ala Ile Arg Gln Ser Pro Ser Pro Pro Pro Glu Glu Glu Ser Arg
655                 660                 665                 670

GGG CCA GGC CAC CCA CCC CTG CCT GAC AAG TTC CAG TTT GAG CTG ACG         2065
Gly Pro Gly His Pro Pro Leu Pro Asp Lys Phe Gln Phe Glu Leu Thr
                675                 680                 685

CTG GAG GAG GAA GAG GAG GAA ATA TCA ATG GCC CAG ATA CCG TGC             2113
Leu Glu Glu Glu Glu Glu Glu Ile Ser Met Ala Gln Ile Pro Cys
            690                 695                 700

ACA GCC CAA GAG GCA TTG ACT GAG CAG GGA TTG TCA GGA GTC GAG GAA         2161
Thr Ala Gln Glu Ala Leu Thr Glu Gln Gly Leu Ser Gly Val Glu Glu
            705                 710                 715

GCT CTG GAT GCA ACC ATA GCC TGG GAG GCA TCC CCG GCC CAG GAG TCG         2209
Ala Leu Asp Ala Thr Ile Ala Trp Glu Ala Ser Pro Ala Gln Glu Ser
            720                 725                 730

TTG GAA GTT ATG GCA CAG GAA GCA TCC CTG GAG GCC GAG CTG GAG GCA         2257
Leu Glu Val Met Ala Gln Glu Ala Ser Leu Glu Ala Glu Leu Glu Ala
735                 740                 745                 750

GTG TAT TTG ACA CAG CAG GCA CAG TCC ACA GGC AGT GCA CCT GTG GCT         2305
Val Tyr Leu Thr Gln Gln Ala Gln Ser Thr Gly Ser Ala Pro Val Ala
                755                 760                 765

CCG GAT GAG TTC TCG TCC CGG GAG GAA TTC GTG GTT GCT GTA AGC CAC         2353
Pro Asp Glu Phe Ser Ser Arg Glu Glu Phe Val Val Ala Val Ser His
            770                 775                 780

AGC AGC CCC TCT GCC CTG GCT CTT CAA AGC CCC CTT CTC CCT GCT TGG         2401
Ser Ser Pro Ser Ala Leu Ala Leu Gln Ser Pro Leu Leu Pro Ala Trp
            785                 790                 795

AGG ACC CTG TCT GTT TCA GAG CAT GCC CGG CCT CCC GGG CCT CCC CTC         2449
Arg Thr Leu Ser Val Ser Glu His Ala Arg Pro Pro Gly Pro Pro Leu
            800                 805                 810

CAC GGC GGC CGA GGT GGA GGC CCA ACG AGA GCA CCA GGC TGC CAA GAG         2497
His Gly Gly Arg Gly Gly Gly Pro Thr Arg Ala Pro Gly Cys Gln Glu
815                 820                 825                 830

GGC TTG CAG TGC CTG CGC AGG GAC ATT TGG GGA GGA CAC ATC CGC ACT         2545
Gly Leu Gln Cys Leu Arg Arg Asp Ile Trp Gly Gly His Ile Arg Thr
                835                 840                 845

CCC AGC TCC TGG TGG CGG GGG GTC AGG TGG AGA CCC TAC CTG ATC CCC         2593
Pro Ser Ser Trp Trp Arg Gly Val Arg Trp Arg Pro Tyr Leu Ile Pro
            850                 855                 860

AGA CCT CTG TCC CTG TTC CCC TCC ACT CCT CCC CTC ACT CCC CTG CTC         2641
Arg Pro Leu Ser Leu Phe Pro Ser Thr Pro Pro Leu Thr Pro Leu Leu
            865                 870                 875

CCC CGA CCA CCT CCT CCT CTG CCT CAA AGA CTC TTG TCC TCT TGT CCG         2689
Pro Arg Pro Pro Pro Pro Leu Pro Gln Arg Leu Leu Ser Ser Cys Pro
            880                 885                 890

CGG CCG CAA GCT T                                                        2702
Arg Pro Gln Ala
895

(2) INFORMATION FOR SEQ ID NO:12:

(i) SEQUENCE CHARACTERISTICS:
```

(A) LENGTH: 898 amino acids
           (B) TYPE: amino acid
           (D) TOPOLOGY: linear (ii) MOLECULE TYPE: protein (xi) SEQUENCE DESCRIPTION: SEQ ID NO:12:

Arg Pro Arg Gly Leu Gly Arg Ile Pro Glu Leu Gln Leu Val Ala Phe
 1               5                  10                  15

Pro Val Ala Val Ala Ala Glu Asp Glu Ala Phe Leu Pro Glu Pro Leu
                20                  25                  30

Ala Pro Arg Ala Pro Arg Arg Val Arg Arg Pro Arg Pro Arg Pro Ser
            35                  40                  45

Ser Ser Pro Ala Arg Pro Gln Leu Ser Ala Asp Ala Phe Gly Phe Ser
 50                  55                  60

Ala Ala Ala Arg Ile Trp Ala Ala Arg Leu Gly Leu Gly Leu Ala Ser
 65                  70                  75                  80

Arg Gln Arg Met Gly Arg His His Leu Leu Ala Ala Pro Gly Leu
                85                  90                  95

Gln Ala Ser Pro Gly Leu Val Leu His Ala Gly Ala Ala Thr Ser Gln
                100                 105                 110

Arg Arg Glu Ser Phe Leu Tyr Arg Ser Asp Ser Asp Tyr Asp Met Ser
            115                 120                 125

Pro Lys Thr Met Ser Arg Asn Ser Ser Val Thr Ser Glu Ala His Ala
130                 135                 140

Glu Asp Leu Ile Val Thr Pro Phe Ala Gln Val Leu Ala Ser Leu Arg
145                 150                 155                 160

Ser Val Arg Ser Asn Phe Ser Leu Leu Thr Asn Val Pro Val Pro Ser
                165                 170                 175

Asn Lys Arg Ser Pro Leu Gly Gly Pro Thr Pro Val Cys Lys Ala Thr
            180                 185                 190

Leu Ser Glu Glu Thr Cys Gln Gln Leu Ala Arg Glu Thr Leu Glu Glu
            195                 200                 205

Leu Asp Trp Cys Leu Glu Gln Leu Glu Thr Met Gln Thr Tyr Arg Ser
210                 215                 220

Val Ser Glu Met Ala Ser His Lys Phe Lys Arg Met Leu Asn Arg Glu
225                 230                 235                 240

Leu Thr His Leu Ser Glu Met Ser Arg Ser Gly Asn Gln Val Ser Glu
                245                 250                 255

Tyr Ile Ser Thr Thr Phe Leu Asp Lys Gln Asn Glu Val Glu Ile Pro
            260                 265                 270

Ser Pro Thr Met Lys Glu Arg Glu Lys Gln Gln Ala Pro Arg Pro Arg
            275                 280                 285

Pro Ser Gln Pro Pro Pro Pro Val Pro His Leu Gln Pro Met Ser
290                 295                 300

Gln Ile Thr Gly Leu Lys Lys Leu Met His Ser Asn Ser Leu Asn Asn
305                 310                 315                 320

Ser Asn Ile Pro Arg Phe Gly Val Lys Thr Asp Gln Glu Glu Leu Leu
                325                 330                 335

Ala Gln Glu Leu Glu Asn Leu Asn Lys Trp Gly Leu Asn Ile Phe Cys
            340                 345                 350

Val Ser Asp Tyr Ala Gly Gly Arg Ser Leu Thr Cys Ile Met Tyr Met
            355                 360                 365

Ile Phe Gln Glu Arg Asp Leu Leu Lys Lys Phe Arg Ile Pro Val Asp
370                 375                 380

-continued

```
Thr Met Val Thr Tyr Met Leu Thr Leu Glu Asp His Tyr His Ala Asp
385                 390                 395                 400

Val Ala Tyr His Asn Ser Leu His Ala Ala Asp Val Leu Gln Ser Thr
            405                 410                 415

His Val Leu Leu Ala Thr Pro Trp Pro Thr Leu Arg Asn Ala Val Phe
        420                 425                 430

Thr Asp Leu Glu Ile Leu Ala Ala Leu Phe Ala Ala Ile His Asp
    435                 440                 445

Val Asp His Pro Gly Val Ser Asn Gln Phe Leu Ile Asn Thr Asn Ser
450                 455                 460

Glu Leu Ala Leu Met Tyr Asn Asp Glu Ser Val Leu Glu Asn His His
465                 470                 475                 480

Leu Ala Val Gly Phe Lys Leu Leu Gln Glu Asp Asn Cys Asp Ile Phe
                485                 490                 495

Gln Asn Leu Ser Lys Arg Gln Arg Gln Ser Leu Arg Lys Met Val Ile
            500                 505                 510

Asp Met Val Leu Ala Thr Asp Met Ser Lys His Met Thr Leu Leu Ala
        515                 520                 525

Asp Leu Lys Thr Met Val Glu Thr Lys Lys Val Thr Ser Ser Gly Val
    530                 535                 540

Leu Leu Leu Asp Asn Tyr Ser Asp Arg Ile Gln Val Leu Arg Asn Met
545                 550                 555                 560

Val His Cys Ala Asp Leu Ser Asn Pro Thr Lys Pro Leu Glu Leu Tyr
                565                 570                 575

Arg Gln Trp Thr Asp Arg Ile Met Ala Glu Phe Phe Gln Gln Gly Asp
            580                 585                 590

Arg Glu Arg Glu Arg Gly Met Glu Ile Ser Pro Met Cys Asp Lys His
        595                 600                 605

Thr Ala Ser Val Glu Lys Ser Gln Val Gly Phe Ile Asp Tyr Ile Val
    610                 615                 620

His Pro Leu Trp Glu Thr Trp Ala Asp Leu Val His Pro Asp Ala Gln
625                 630                 635                 640

Glu Ile Leu Asp Thr Leu Glu Asp Asn Arg Asp Trp Tyr Tyr Ser Ala
                645                 650                 655

Ile Arg Gln Ser Pro Ser Pro Pro Glu Glu Ser Arg Gly Pro
            660                 665                 670

Gly His Pro Pro Leu Pro Asp Lys Phe Gln Phe Glu Leu Thr Leu Glu
        675                 680                 685

Glu Glu Glu Glu Glu Glu Ile Ser Met Ala Gln Ile Pro Cys Thr Ala
    690                 695                 700

Gln Glu Ala Leu Thr Glu Gln Gly Leu Ser Gly Val Glu Glu Ala Leu
705                 710                 715                 720

Asp Ala Thr Ile Ala Trp Glu Ala Ser Pro Ala Gln Glu Ser Leu Glu
                725                 730                 735

Val Met Ala Gln Glu Ala Ser Leu Glu Ala Glu Leu Ala Val Tyr
            740                 745                 750

Leu Thr Gln Gln Ala Gln Ser Thr Gly Ser Ala Pro Val Ala Pro Asp
        755                 760                 765

Glu Phe Ser Ser Arg Glu Glu Phe Val Val Ala Val Ser His Ser Ser
    770                 775                 780

Pro Ser Ala Leu Ala Leu Gln Ser Pro Leu Leu Pro Ala Trp Arg Thr
785                 790                 795                 800
```

```
Leu Ser Val Ser Glu His Ala Arg Pro Pro Gly Pro Leu His Gly
                805                 810                 815

Gly Arg Gly Gly Gly Pro Thr Arg Ala Pro Gly Cys Gln Glu Gly Leu
            820                 825                 830

Gln Cys Leu Arg Arg Asp Ile Trp Gly Gly His Ile Arg Thr Pro Ser
            835                 840                 845

Ser Trp Trp Arg Gly Val Arg Trp Arg Pro Tyr Leu Ile Pro Arg Pro
    850                 855                 860

Leu Ser Leu Phe Pro Ser Thr Pro Leu Thr Pro Leu Pro Arg
865                 870                 875                 880

Pro Pro Pro Pro Leu Pro Gln Arg Leu Leu Ser Ser Cys Pro Arg Pro
                885                 890                 895

Gln Ala (2) INFORMATION FOR SEQ ID NO:13:

(i) SEQUENCE CHARACTERISTICS:
        (A) LENGTH: 1721 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 66..1274

(xi) SEQUENCE DESCRIPTION: SEQ ID NO:13:

AAGCTTGCGG CCGCATTGGG TACCGCGTGC CAGCAGGCAG TGGCCCTAGC CTTCCGCCTA        60

TGCCC TCC CTC CAA GAG GTG GAC TGC GGC TCC CCC AGC AGC TCC GAG           107
      Ser Leu Gln Glu Val Asp Cys Gly Ser Pro Ser Ser Ser Glu
          1               5                   10

GAG GAG GGG GTG CCA GGG TCC CGG GGG AGC CCA GCG ACC TCA CCC CAC         155
Glu Glu Gly Val Pro Gly Ser Arg Gly Ser Pro Ala Thr Ser Pro His
 15              20                  25                  30

CTG GGC CGC CGA CGA CCT CTG CTT CGG TCC ATG AGC GCC GCC TTC TGC         203
Leu Gly Arg Arg Arg Pro Leu Leu Arg Ser Met Ser Ala Ala Phe Cys
             35                  40                  45

TCC CTA CTG GCA CCG GAG CGG CAG GTG GGC CGG GCT GCG GCA GCA CTG         251
Ser Leu Leu Ala Pro Glu Arg Gln Val Gly Arg Ala Ala Ala Ala Leu
             50                  55                  60

ATG CAG GAC CGA CAC ACA GCC GCG GGC CAG CTG GTG CAG GAC CTA CTG         299
Met Gln Asp Arg His Thr Ala Ala Gly Gln Leu Val Gln Asp Leu Leu
             65                  70                  75

ACC CAG GTG CGG GAT GGG CAG AGG CCC CAG GAG CTC GAG GGC ATC CGT         347
Thr Gln Val Arg Asp Gly Gln Arg Pro Gln Glu Leu Glu Gly Ile Arg
     80                  85                  90

CAG GCG CTG AGC CGG GCC CGG GCC ATG CTG AGT GCG GAG CTG GGC CCT         395
Gln Ala Leu Ser Arg Ala Arg Ala Met Leu Ser Ala Glu Leu Gly Pro
 95                 100                 105                 110

GAG AAG CTC GTG TCG CCT AAG AGG CTG GAA CAT GTC CTG GAG AAG TCA         443
Glu Lys Leu Val Ser Pro Lys Arg Leu Glu His Val Leu Glu Lys Ser
                115                 120                 125

TTG CAT TGC TCT GTG CTC AAG CCT CTC CGG CCC ATC CTG GCA GCC CGC         491
Leu His Cys Ser Val Leu Lys Pro Leu Arg Pro Ile Leu Ala Ala Arg
            130                 135                 140

CTG CGG CGC CGG CTT GCC GCA GAC GGC TCC CTG GGC CGC CTA GCT GAG         539
Leu Arg Arg Arg Leu Ala Ala Asp Gly Ser Leu Gly Arg Leu Ala Glu
            145                 150                 155
```

```
GGC CTC CGC CTG GCC CGG GCC CAG GGC CCC GGA GCC TTC GGG TCC CAC        587
Gly Leu Arg Leu Ala Arg Ala Gln Gly Pro Gly Ala Phe Gly Ser His
    160                 165                 170

CTG AGC CTG CCC TCC CCA GTA GAG TTG GAG CAA GTG CGC CAG AAG CTG        635
Leu Ser Leu Pro Ser Pro Val Glu Leu Glu Gln Val Arg Gln Lys Leu
175                 180                 185                 190

CTG CAG CTC GTC CGC ACC TAC TCA CCC AGC GCC CAG GTC AAG CGG CTC        683
Leu Gln Leu Val Arg Thr Tyr Ser Pro Ser Ala Gln Val Lys Arg Leu
                195                 200                 205

CTG CAG GCC TGC AAG CTG CTC TAC ATG GCC CTG AGG ACC CAG GAA GGG        731
Leu Gln Ala Cys Lys Leu Leu Tyr Met Ala Leu Arg Thr Gln Glu Gly
            210                 215                 220

GAG GGC TCG GGT GCC GAC GGG TTC CTG CCT CTG CTG AGC CTC GTC TTG        779
Glu Gly Ser Gly Ala Asp Gly Phe Leu Pro Leu Leu Ser Leu Val Leu
        225                 230                 235

GCC CAC TGT GAC CTT CCT GAG CTG CTG CTG GAG GCC GAG TAC ATG TCG        827
Ala His Cys Asp Leu Pro Glu Leu Leu Leu Glu Ala Glu Tyr Met Ser
    240                 245                 250

GAG CTG CTG GAG CCC AGC CTG CTT ACT GGA GAG GGT GGC TAC TAC CTG        875
Glu Leu Leu Glu Pro Ser Leu Leu Thr Gly Glu Gly Gly Tyr Tyr Leu
255                 260                 265                 270

ACC AGC CTC TCT GCC AGC CTG GCC CTG CTG AGT GGC CTG GGT CAG GCC        923
Thr Ser Leu Ser Ala Ser Leu Ala Leu Leu Ser Gly Leu Gly Gln Ala
                275                 280                 285

CAC ACC CTC CCA CTG AGC CCC GTG CAG GAG CTA CGG CGC TCC CTC AGC        971
His Thr Leu Pro Leu Ser Pro Val Gln Glu Leu Arg Arg Ser Leu Ser
            290                 295                 300

CTC TGG GAG CAG CGC CGC CTG CCT GCC ACC CAC TGC TTC CAG CAC CTC       1019
Leu Trp Glu Gln Arg Arg Leu Pro Ala Thr His Cys Phe Gln His Leu
        305                 310                 315

CTC CGA GTA GCC TAT CAG GAT CCC AGC AGT GGC TGC ACC TCC AAG ACC       1067
Leu Arg Val Ala Tyr Gln Asp Pro Ser Ser Gly Cys Thr Ser Lys Thr
    320                 325                 330

CTG GCC GTG CCC CCA GAG GCC TCG ATT GCC ACC CTG AAC CAG CTC TGT       1115
Leu Ala Val Pro Pro Glu Ala Ser Ile Ala Thr Leu Asn Gln Leu Cys
335                 340                 345                 350

GCC ACC AAG TTC CGA GTG ACC CAG CCC AAC ACT TTT GGC CTC TTC CTG       1163
Ala Thr Lys Phe Arg Val Thr Gln Pro Asn Thr Phe Gly Leu Phe Leu
                355                 360                 365

TAC AAG GAG CAG GGC TAC CAC CGC CTG CCC CCT GGG CCC TGG CCC ACA       1211
Tyr Lys Glu Gln Gly Tyr His Arg Leu Pro Pro Gly Pro Trp Pro Thr
            370                 375                 380

GGC TGC CCA CCA CTG GCT ACC TCG TCT ACC GCC GGG CAG AGT GGC CTG       1259
Gly Cys Pro Pro Leu Ala Thr Ser Ser Thr Ala Gly Gln Ser Gly Leu
        385                 390                 395

AGA CCC AGG GGG CTG TGACAGAGGA GGAGGGCAGT GGGCAGTCAG AGGCAAGAAG       1314
Arg Pro Arg Gly Leu
    400

CAGAGGGGAG GAGCAAGGGT GCCAGGGAGA TGGGGATGCT GGGGTCAAAG CCAGCCCCAG     1374

GGACATTCGG GAACAGTCTG AGACAACTGC TGAAGGGGC CAGGGTCAAG CCCAGGAAGG      1434

CCCTGCTCAG CCAGGGGAAC CAGAGGCAGA GGGAAGCCGG GCAGCAGAGG AGTAGCTTGA     1494

AGTGGCCAGA AGGGTCATTC GGGGCGGGAG ACCCTGAGCC TGCTGAGAAA TCCTTTTAGC    1554

GCCAGCAAGC CCCACCCAGG GCCCTGTCCT GTGTCTGCCA CCACCTTTGT CTGATACTTG    1614

TTTCCAGGGA AGCTGGGGGA ACTGCCACAT CTGAGGAACT GGAATAAAGA TGAGGGGCCT    1674

TCGGGGGCCA ATGCGGCCGC CGCGGCCTTT TTGGCCAGCT CGAATTC                 1721
```

-continued (2) INFORMATION FOR SEQ ID NO:14:

(i) SEQUENCE CHARACTERISTICS:
        (A) LENGTH: 403 amino acids
        (B) TYPE: amino acid
        (D) TOPOLOGY: linear (ii) MOLECULE TYPE: protein (xi) SEQUENCE DESCRIPTION: SEQ ID NO:14:

```
Ser Leu Gln Glu Val Asp Cys Gly Ser Pro Ser Ser Glu Glu Glu
 1               5                  10                  15

Gly Val Pro Gly Ser Arg Gly Ser Pro Ala Thr Ser Pro His Leu Gly
                20                  25                  30

Arg Arg Arg Pro Leu Leu Arg Ser Met Ser Ala Ala Phe Cys Ser Leu
            35                  40                  45

Leu Ala Pro Glu Arg Gln Val Gly Arg Ala Ala Ala Leu Met Gln
        50                  55                  60

Asp Arg His Thr Ala Ala Gly Gln Leu Val Gln Asp Leu Leu Thr Gln
 65                  70                  75                  80

Val Arg Asp Gly Gln Arg Pro Gln Glu Leu Gly Ile Arg Gln Ala
                85                  90                  95

Leu Ser Arg Ala Arg Ala Met Leu Ser Ala Glu Leu Gly Pro Glu Lys
                100                 105                 110

Leu Val Ser Pro Lys Arg Leu Glu His Val Leu Glu Lys Ser Leu His
                115                 120                 125

Cys Ser Val Leu Lys Pro Leu Arg Pro Ile Leu Ala Ala Arg Leu Arg
            130                 135                 140

Arg Arg Leu Ala Ala Asp Gly Ser Leu Gly Arg Leu Ala Glu Gly Leu
145                 150                 155                 160

Arg Leu Ala Arg Ala Gln Gly Pro Gly Ala Phe Gly Ser His Leu Ser
                165                 170                 175

Leu Pro Ser Pro Val Glu Leu Glu Gln Val Arg Gln Lys Leu Leu Gln
                180                 185                 190

Leu Val Arg Thr Tyr Ser Pro Ser Ala Gln Val Lys Arg Leu Leu Gln
                195                 200                 205

Ala Cys Lys Leu Leu Tyr Met Ala Leu Arg Thr Gln Glu Gly Glu Gly
            210                 215                 220

Ser Gly Ala Asp Gly Phe Leu Pro Leu Ser Leu Val Leu Ala His
225                 230                 235                 240

Cys Asp Leu Pro Glu Leu Leu Leu Glu Ala Glu Tyr Met Ser Glu Leu
                245                 250                 255

Leu Glu Pro Ser Leu Leu Thr Gly Glu Gly Gly Tyr Tyr Leu Thr Ser
                260                 265                 270

Leu Ser Ala Ser Leu Ala Leu Leu Ser Gly Leu Gly Gln Ala His Thr
            275                 280                 285

Leu Pro Leu Ser Pro Val Gln Glu Leu Arg Arg Ser Leu Ser Leu Trp
        290                 295                 300

Glu Gln Arg Arg Leu Pro Ala Thr His Cys Phe Gln His Leu Leu Arg
305                 310                 315                 320

Val Ala Tyr Gln Asp Pro Ser Ser Gly Cys Thr Ser Lys Thr Leu Ala
                325                 330                 335

Val Pro Pro Glu Ala Ser Ile Ala Thr Leu Asn Gln Leu Cys Ala Thr
                340                 345                 350

Lys Phe Arg Val Thr Gln Pro Asn Thr Phe Gly Leu Phe Leu Tyr Lys
            355                 360                 365
```

-continued

```
Glu Gln Gly Tyr His Arg Leu Pro Pro Gly Pro Trp Pro Thr Gly Cys
    370                 375                 380

Pro Pro Leu Ala Thr Ser Ser Thr Ala Gly Gln Ser Gly Leu Arg Pro
385                 390                 395                 400

Arg Gly Leu
```

(2) INFORMATION FOR SEQ ID NO:15:

(i) SEQUENCE CHARACTERISTICS:
        (A) LENGTH: 1829 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 30..1421

(xi) SEQUENCE DESCRIPTION: SEQ ID NO:15:

```
GCGGCCGCGG CCGGCAGCGG CTGAGCGAC ATG AGC ATT TCT ACT TCC TCC TCC        53
                                Met Ser Ile Ser Thr Ser Ser Ser
                                 1               5

GAC TCG CTG GAG TTC GAC CGG AGC ATG CCT CTG TTT GGC TAC GAG GCG       101
Asp Ser Leu Glu Phe Asp Arg Ser Met Pro Leu Phe Gly Tyr Glu Ala
         10                  15                  20

GAC ACC AAC AGC AGC CTG GAG GAC TAC GAG GGG GAA AGT GAC CAA GAG       149
Asp Thr Asn Ser Ser Leu Glu Asp Tyr Glu Gly Glu Ser Asp Gln Glu
 25                  30                  35                  40

ACC ATG GCG CCC CCC ATC AAG TCC AAA AAG AAA AGG AGC AGC TCC TTC       197
Thr Met Ala Pro Pro Ile Lys Ser Lys Lys Lys Arg Ser Ser Ser Phe
                 45                  50                  55

GTG CTG CCC AAG CTC GTC AAG TCC CAG CTG CAG AAG GTG AGC GGG GTG       245
Val Leu Pro Lys Leu Val Lys Ser Gln Leu Gln Lys Val Ser Gly Val
             60                  65                  70

TTC AGC TCC TTC ATG ACC CCG GAG AAG CGG ATG GTC CGC AGG ATC GCC       293
Phe Ser Ser Phe Met Thr Pro Glu Lys Arg Met Val Arg Arg Ile Ala
         75                  80                  85

GAG CTT TCC CGG GAC AAA TGC ACC TAC TTC GGG TGC TTA GTG CAG GAC       341
Glu Leu Ser Arg Asp Lys Cys Thr Tyr Phe Gly Cys Leu Val Gln Asp
 90                  95                 100

TAC GTG AGC TTC CTG CAG GAG AAC AAG GAG TGC CAC GTG TCC AGC ACC       389
Tyr Val Ser Phe Leu Gln Glu Asn Lys Glu Cys His Val Ser Ser Thr
105                 110                 115                 120

GAC ATG CTG CAG ACC ATC CGG CAG TTC ATG ACC CAG GTC AAG AAC TAT       437
Asp Met Leu Gln Thr Ile Arg Gln Phe Met Thr Gln Val Lys Asn Tyr
                125                 130                 135

TTG TCT CAG AGC TCG GAG CTG GAC CCC CCC ATC GAG TCG CTG ATC CCT       485
Leu Ser Gln Ser Ser Glu Leu Asp Pro Pro Ile Glu Ser Leu Ile Pro
            140                 145                 150

GAA GAC CAA ATA GAT GTG GTG CTG GAA AAA GCC ATG CAC AAG TGC ATC       533
Glu Asp Gln Ile Asp Val Val Leu Glu Lys Ala Met His Lys Cys Ile
        155                 160                 165

TTG AAG CCC CTC AAG GGG CAC GTG GAG GCC ATG CTG AAG GAC TTT CAC       581
Leu Lys Pro Leu Lys Gly His Val Glu Ala Met Leu Lys Asp Phe His
        170                 175                 180

ATG GCC GAT GGC TCA TGG AAG CAA CTC AAG GAG AAC CTG CAG CTT GTG       629
Met Ala Asp Gly Ser Trp Lys Gln Leu Lys Glu Asn Leu Gln Leu Val
185                 190                 195                 200

CGG CAG AGG AAT CCG CAG GAG CTG GGG GTC TTC GCC CCG ACC CCT GAT       677
```

-continued

```
                    Arg Gln Arg Asn Pro Gln Glu Leu Gly Val Phe Ala Pro Thr Pro Asp
                                    205                 210                 215

TTT GTG GAT GTG GAG AAA ATC AAA GTC AAG TTC ATG ACC ATG CAG AAG                 725
Phe Val Asp Val Glu Lys Ile Lys Val Lys Phe Met Thr Met Gln Lys
            220                 225                 230

ATG TAT TCG CCG GAA AAG AAG GTC ATG CTG CTG CTG CGG GTC TGC AAG                 773
Met Tyr Ser Pro Glu Lys Lys Val Met Leu Leu Leu Arg Val Cys Lys
                235                 240                 245

CTC ATT TAC ACG GTC ATG GAG AAC AAC TCA GGG AGG ATG TAT GGC GCT                 821
Leu Ile Tyr Thr Val Met Glu Asn Asn Ser Gly Arg Met Tyr Gly Ala
            250                 255                 260

GAT GAC TTC TTG CCA GTC CTG ACC TAT GTC ATA GCC CAG TGT GAC ATG                 869
Asp Asp Phe Leu Pro Val Leu Thr Tyr Val Ile Ala Gln Cys Asp Met
265                 270                 275                 280

CTT GAA TTG GAC ACT GAA ATC GAG TAC ATG ATG GAG CTC CTA GAC CCA                 917
Leu Glu Leu Asp Thr Glu Ile Glu Tyr Met Met Glu Leu Leu Asp Pro
                285                 290                 295

TCG CTG TTA CAT GGA GAA GGA GGC TAT TAC TTG ACA AGC GCA TAT GGA                 965
Ser Leu Leu His Gly Glu Gly Gly Tyr Tyr Leu Thr Ser Ala Tyr Gly
            300                 305                 310

GCA CTT TCT CTG ATA AAG AAT TTC CAA GAA GAA CAA GCA GCG CGA CTG                1013
Ala Leu Ser Leu Ile Lys Asn Phe Gln Glu Glu Gln Ala Ala Arg Leu
                315                 320                 325

CTC AGC TCA GAA ACC AGA GAC ACC CTG AGG CAG TGG CAC AAA CGG AGA                1061
Leu Ser Ser Glu Thr Arg Asp Thr Leu Arg Gln Trp His Lys Arg Arg
330                 335                 340

ACC ACC AAC CGG ACC ATC CCC TCT GTG GAC GAC TTC CAG AAT TAC CTC                1109
Thr Thr Asn Arg Thr Ile Pro Ser Val Asp Asp Phe Gln Asn Tyr Leu
345                 350                 355                 360

CGA GTT GCA TTT CAG GAG GTC AAC AGT GGT TGC ACA GGA AAG ACC CTC                1157
Arg Val Ala Phe Gln Glu Val Asn Ser Gly Cys Thr Gly Lys Thr Leu
                365                 370                 375

CTT GTG AGA CCT TAC ATC ACC ACT GAG GAT GTG TGT CAG ATC TGC GCT                1205
Leu Val Arg Pro Tyr Ile Thr Thr Glu Asp Val Cys Gln Ile Cys Ala
            380                 385                 390

GAG AAG TTC AAG GTG GGG GAC CCT GAG GAG TAC AGC CTC TTT CTC TTC                1253
Glu Lys Phe Lys Val Gly Asp Pro Glu Glu Tyr Ser Leu Phe Leu Phe
                395                 400                 405

GTT GAC GAG ACA TGG CAG CAG CTG GCA GAG GAC ACT TAC CCT CAA AAA                1301
Val Asp Glu Thr Trp Gln Gln Leu Ala Glu Asp Thr Tyr Pro Gln Lys
410                 415                 420

ATC AAG GCG GAG CTG CAC AGC CGA CCA CAG CCC CAC ATC TTC CAC TTT                1349
Ile Lys Ala Glu Leu His Ser Arg Pro Gln Pro His Ile Phe His Phe
425                 430                 435                 440

GTC TAC AAA CGC ATC AAG AAC GAT CCT TAT GGC ATC ATT TTC CAG AAC                1397
Val Tyr Lys Arg Ile Lys Asn Asp Pro Tyr Gly Ile Ile Phe Gln Asn
                445                 450                 455

GGG GAA GAA GAC CTC ACC ACC TCC TAGAAGACAG GCGGGACTTC CCAGTGGTGC               1451
Gly Glu Glu Asp Leu Thr Thr Ser
                460

ATCCAAAGGG GAGCTGGAAG CCTTGCCTTC CCGCTTCTAC ATGCTTGAGC TTGAAAAGCA              1511

GTCACCTCCT CGGGGACCCC TCAGTGTAGT GACTAAGCCA TCCACAGGCC AACTCGGCCA              1571

AGGGCAACTT TAGCCACGCA AGGTAGCTGA GGTTTGTGAA ACAGTAGGAT TCTCTTTTGG              1631

CAATGGAGAA TTGCATCTGA TGGTTCAAGT GTCCTGAGAT TGTTTGCTAC CTACCCCCAG              1691

TCAGGTTCTA GGTTGGCTTA CAGGTATGTA TATGTGCAGA AGAAACACTT AAGATACAAG              1751

TTCTTTTGAA TTCAACAGCA GATGCTTGCG ATGCAGTGCG TCAGGTGATT CTCACTCCTG              1811
```

TGGATGGCTT CATCCCTG      1829

(2) INFORMATION FOR SEQ ID NO:16:

(i) SEQUENCE CHARACTERISTICS:
        (A) LENGTH: 464 amino acids
        (B) TYPE: amino acid
        (D) TOPOLOGY: linear (ii) MOLECULE TYPE: protein (xi) SEQUENCE DESCRIPTION: SEQ ID NO:16:

```
Met Ser Ile Ser Thr Ser Ser Asp Ser Leu Glu Phe Asp Arg Ser
 1               5                  10                  15

Met Pro Leu Phe Gly Tyr Glu Ala Asp Thr Asn Ser Ser Leu Glu Asp
            20                  25                  30

Tyr Glu Gly Glu Ser Asp Gln Glu Thr Met Ala Pro Pro Ile Lys Ser
            35                  40                  45

Lys Lys Lys Arg Ser Ser Phe Val Leu Pro Lys Leu Val Lys Ser
        50                  55                  60

Gln Leu Gln Lys Val Ser Gly Val Phe Ser Ser Phe Met Thr Pro Glu
65                  70                  75                  80

Lys Arg Met Val Arg Arg Ile Ala Glu Leu Ser Arg Asp Lys Cys Thr
                85                  90                  95

Tyr Phe Gly Cys Leu Val Gln Asp Tyr Val Ser Phe Leu Gln Glu Asn
                100                 105                 110

Lys Glu Cys His Val Ser Ser Thr Asp Met Leu Gln Thr Ile Arg Gln
            115                 120                 125

Phe Met Thr Gln Val Lys Asn Tyr Leu Ser Gln Ser Ser Glu Leu Asp
        130                 135                 140

Pro Pro Ile Glu Ser Leu Ile Pro Glu Asp Gln Ile Asp Val Val Leu
145                 150                 155                 160

Glu Lys Ala Met His Lys Cys Ile Leu Lys Pro Leu Lys Gly His Val
                165                 170                 175

Glu Ala Met Leu Lys Asp Phe His Met Ala Asp Gly Ser Trp Lys Gln
            180                 185                 190

Leu Lys Glu Asn Leu Gln Leu Val Arg Gln Arg Asn Pro Gln Glu Leu
        195                 200                 205

Gly Val Phe Ala Pro Thr Pro Asp Phe Val Asp Val Glu Lys Ile Lys
    210                 215                 220

Val Lys Phe Met Thr Met Gln Lys Met Tyr Ser Pro Glu Lys Lys Val
225                 230                 235                 240

Met Leu Leu Leu Arg Val Cys Lys Leu Ile Tyr Thr Val Met Glu Asn
                245                 250                 255

Asn Ser Gly Arg Met Tyr Gly Ala Asp Asp Phe Leu Pro Val Leu Thr
            260                 265                 270

Tyr Val Ile Ala Gln Cys Asp Met Leu Glu Leu Asp Thr Glu Ile Glu
        275                 280                 285

Tyr Met Met Glu Leu Leu Asp Pro Ser Leu Leu His Gly Glu Gly Gly
    290                 295                 300

Tyr Tyr Leu Thr Ser Ala Tyr Gly Ala Leu Ser Leu Ile Lys Asn Phe
305                 310                 315                 320

Gln Glu Glu Gln Ala Ala Arg Leu Leu Ser Ser Glu Thr Arg Asp Thr
                325                 330                 335

Leu Arg Gln Trp His Lys Arg Arg Thr Thr Asn Arg Thr Ile Pro Ser
            340                 345                 350
```

-continued

```
Val Asp Asp Phe Gln Asn Tyr Leu Arg Val Ala Phe Gln Glu Val Asn
    355                 360                 365

Ser Gly Cys Thr Gly Lys Thr Leu Leu Val Arg Pro Tyr Ile Thr Thr
    370                 375                 380

Glu Asp Val Cys Gln Ile Cys Ala Glu Lys Phe Lys Val Gly Asp Pro
385                 390                 395                 400

Glu Glu Tyr Ser Leu Phe Leu Phe Val Asp Glu Thr Trp Gln Gln Leu
                405                 410                 415

Ala Glu Asp Thr Tyr Pro Gln Lys Ile Lys Ala Glu Leu His Ser Arg
            420                 425                 430

Pro Gln Pro His Ile Phe His Phe Val Tyr Lys Arg Ile Lys Asn Asp
        435                 440                 445

Pro Tyr Gly Ile Ile Phe Gln Asn Gly Glu Glu Asp Leu Thr Thr Ser
    450                 455                 460
```

(2) INFORMATION FOR SEQ ID NO:17:

(i) SEQUENCE CHARACTERISTICS:
        (A) LENGTH: 1299 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1299

(xi) SEQUENCE DESCRIPTION: SEQ ID NO:17:

```
GGC CGC ATT GCC GAC CCG GCC CGT AGT GTG GAA GCA GCT TCA GCT CAA        48
Gly Arg Ile Ala Asp Pro Ala Arg Ser Val Glu Ala Ala Ser Ala Gln
 1               5                  10                  15

AGA TTA GAA CGA CTC CGA AAA GAG AGA CAA AAC CAG ATC AAA TGC AAA        96
Arg Leu Glu Arg Leu Arg Lys Glu Arg Gln Asn Gln Ile Lys Cys Lys
             20                  25                  30

AAT ATT CAG TGG AAA GAA AGA AAT TCT AAG CAA TCA GCC CAG GAG TTA       144
Asn Ile Gln Trp Lys Glu Arg Asn Ser Lys Gln Ser Ala Gln Glu Leu
         35                  40                  45

AAG TCA CTG TTT GAA AAA AAA TCT CTC AAA GAG AAG CCT CCA ATT TCT       192
Lys Ser Leu Phe Glu Lys Lys Ser Leu Lys Glu Lys Pro Pro Ile Ser
     50                  55                  60

GGG AAG CAG TCG ATA TTA TCT GTA CGC CTA GAA CAG TGC CCT CTG CAG       240
Gly Lys Gln Ser Ile Leu Ser Val Arg Leu Glu Gln Cys Pro Leu Gln
 65                  70                  75                  80

CTG AAT AAC CCT TTT AAC GAG TAT TCC AAA TTT GAT GGC AAG GGT CAT       288
Leu Asn Asn Pro Phe Asn Glu Tyr Ser Lys Phe Asp Gly Lys Gly His
                 85                  90                  95

GTA GGT ACA ACA GCA ACC AAG AAG ATC GAT GTC TAC CTC CCT CTG CAC       336
Val Gly Thr Thr Ala Thr Lys Lys Ile Asp Val Tyr Leu Pro Leu His
            100                 105                 110

TCG AGC CAG GAC AGA CTG CTG CCA ATG ACC GTG GTG ACA ATG GCC AGC       384
Ser Ser Gln Asp Arg Leu Leu Pro Met Thr Val Val Thr Met Ala Ser
        115                 120                 125

GCC AGG GTG CAG GAC CTG ATC GGG CTC ATC TGC TGG CAG TAT ACA AGC       432
Ala Arg Val Gln Asp Leu Ile Gly Leu Ile Cys Trp Gln Tyr Thr Ser
    130                 135                 140

GAA GGA CGG GAG CCG AAG CTC AAT GAC AAT GTC AGT GCC TAC TGC CTG       480
Glu Gly Arg Glu Pro Lys Leu Asn Asp Asn Val Ser Ala Tyr Cys Leu
145                 150                 155                 160
```

-continued

```
CAT ATT GCT GAG GAT GAT GGG GAG GTG GAC ACC GAT TTC CCC CCG CTG     528
His Ile Ala Glu Asp Asp Gly Glu Val Asp Thr Asp Phe Pro Pro Leu
            165                 170                 175

GAT TCC AAT GAG CCC ATT CAT AAG TTT GGC TTC AGT ACT TTG GCC CTG     576
Asp Ser Asn Glu Pro Ile His Lys Phe Gly Phe Ser Thr Leu Ala Leu
        180                 185                 190

GTT GAA AAG TAC TCA TCT CCT GGT CTG ACA TCC AAA GAG TCA CTC TTT     624
Val Glu Lys Tyr Ser Ser Pro Gly Leu Thr Ser Lys Glu Ser Leu Phe
    195                 200                 205

GTT CGA ATA AAT GCT GCT CAT GGA TTC TCC CTT ATT CAG GTG GAC AAC     672
Val Arg Ile Asn Ala Ala His Gly Phe Ser Leu Ile Gln Val Asp Asn
210                 215                 220

ACA AAG GTT ACC ATG AAG GAA ATC TTA CTG AAG GCA GTG AAG CGA AGA     720
Thr Lys Val Thr Met Lys Glu Ile Leu Leu Lys Ala Val Lys Arg Arg
225                 230                 235                 240

AAA GGA TCC CAG AAA GTT TCA GGC CCT CAG TAC CGC CTG GAG AAG CAG     768
Lys Gly Ser Gln Lys Val Ser Gly Pro Gln Tyr Arg Leu Glu Lys Gln
                245                 250                 255

AGC GAG CCC AAT GTC GCC GTT GAC CTG GAC AGC ACT TTG GAG AGC CAG     816
Ser Glu Pro Asn Val Ala Val Asp Leu Asp Ser Thr Leu Glu Ser Gln
            260                 265                 270

AGC GCA TGG GAG TTC TGC CTG GTC CGC GAG AAC AGT TCA AGG GCA GAC     864
Ser Ala Trp Glu Phe Cys Leu Val Arg Glu Asn Ser Ser Arg Ala Asp
        275                 280                 285

GGG GTT TTT GAG GAG GAT TCG CAA ATT GAC ATA GCC ACA GTA CAG GAT     912
Gly Val Phe Glu Glu Asp Ser Gln Ile Asp Ile Ala Thr Val Gln Asp
    290                 295                 300

ATG CTT AGC AGC CAC CAT TAC AAG TCA TTC AAA GTC AGC ATG ATC CAC     960
Met Leu Ser Ser His His Tyr Lys Ser Phe Lys Val Ser Met Ile His
305                 310                 315                 320

AGA CTG CGA TTC ACA ACC GAC GTA CAG CTA GGT ATC TCT GGA GAC AAA    1008
Arg Leu Arg Phe Thr Thr Asp Val Gln Leu Gly Ile Ser Gly Asp Lys
                325                 330                 335

GTA GAG ATA GAC CCT GTT ACG AAT CAG AAA GCC AGC ACT AAG TTT TGG    1056
Val Glu Ile Asp Pro Val Thr Asn Gln Lys Ala Ser Thr Lys Phe Trp
            340                 345                 350

ATT AAG CAG AAA CCC ATC TCA ATC GAT TCC GAC CTG CTC TGT GCC TGT    1104
Ile Lys Gln Lys Pro Ile Ser Ile Asp Ser Asp Leu Leu Cys Ala Cys
        355                 360                 365

GAC CTT GCT GAA GAG AAA AGC CCC AGT CAC GCA ATA TTT AAA CTC ACG    1152
Asp Leu Ala Glu Glu Lys Ser Pro Ser His Ala Ile Phe Lys Leu Thr
    370                 375                 380

TAT CTA AGC AAT CAC GAC TAT AAA CAC CTC TAC TTT GAA TCG GAC GCT    1200
Tyr Leu Ser Asn His Asp Tyr Lys His Leu Tyr Phe Glu Ser Asp Ala
385                 390                 395                 400

GCT ACC GTC AAT GAA ATT GTG CTC AAG GTT AAC TAC ATC CTG GAA TCG    1248
Ala Thr Val Asn Glu Ile Val Leu Lys Val Asn Tyr Ile Leu Glu Ser
                405                 410                 415

CGA GCT AGC ACT GCC CGG GCT GAC TAC TTT GCT CAA AAA AAA AGC GGC    1296
Arg Ala Ser Thr Ala Arg Ala Asp Tyr Phe Ala Gln Lys Lys Ser Gly
            420                 425                 430

CGC                                                                 1299
Arg
```

(2) INFORMATION FOR SEQ ID NO:18:

(i) SEQUENCE CHARACTERISTICS:
        (A) LENGTH: 433 amino acids
        (B) TYPE: amino acid
        (D) TOPOLOGY: linear (ii) MOLECULE TYPE: protein (xi) SEQUENCE DESCRIPTION: SEQ ID NO:18:

```
Gly Arg Ile Ala Asp Pro Ala Arg Ser Val Glu Ala Ala Ser Ala Gln
  1               5                  10                  15

Arg Leu Glu Arg Leu Arg Lys Glu Arg Gln Asn Gln Ile Lys Cys Lys
                 20                  25                  30

Asn Ile Gln Trp Lys Glu Arg Asn Ser Lys Gln Ser Ala Gln Glu Leu
             35                  40                  45

Lys Ser Leu Phe Glu Lys Lys Ser Leu Lys Glu Lys Pro Pro Ile Ser
         50                  55                  60

Gly Lys Gln Ser Ile Leu Ser Val Arg Leu Glu Gln Cys Pro Leu Gln
 65                  70                  75                  80

Leu Asn Asn Pro Phe Asn Glu Tyr Ser Lys Phe Asp Gly Lys Gly His
                 85                  90                  95

Val Gly Thr Thr Ala Thr Lys Lys Ile Asp Val Tyr Leu Pro Leu His
                100                 105                 110

Ser Ser Gln Asp Arg Leu Leu Pro Met Thr Val Thr Met Ala Ser
             115                 120                 125

Ala Arg Val Gln Asp Leu Ile Gly Leu Ile Cys Trp Gln Tyr Thr Ser
        130                 135                 140

Glu Gly Arg Glu Pro Lys Leu Asn Asp Asn Val Ser Ala Tyr Cys Leu
145                 150                 155                 160

His Ile Ala Glu Asp Asp Gly Glu Val Asp Thr Asp Phe Pro Pro Leu
                165                 170                 175

Asp Ser Asn Glu Pro Ile His Lys Phe Gly Phe Ser Thr Leu Ala Leu
            180                 185                 190

Val Glu Lys Tyr Ser Ser Pro Gly Leu Thr Ser Lys Glu Ser Leu Phe
        195                 200                 205

Val Arg Ile Asn Ala Ala His Gly Phe Ser Leu Ile Gln Val Asp Asn
        210                 215                 220

Thr Lys Val Thr Met Lys Glu Ile Leu Leu Lys Ala Val Lys Arg Arg
225                 230                 235                 240

Lys Gly Ser Gln Lys Val Ser Gly Pro Gln Tyr Arg Leu Glu Lys Gln
                245                 250                 255

Ser Glu Pro Asn Val Ala Val Asp Leu Asp Ser Thr Leu Glu Ser Gln
            260                 265                 270

Ser Ala Trp Glu Phe Cys Leu Val Arg Glu Asn Ser Ser Arg Ala Asp
        275                 280                 285

Gly Val Phe Glu Glu Asp Ser Gln Ile Asp Ile Ala Thr Val Gln Asp
290                 295                 300

Met Leu Ser Ser His His Tyr Lys Ser Phe Lys Val Ser Met Ile His
305                 310                 315                 320

Arg Leu Arg Phe Thr Thr Asp Val Gln Leu Gly Ile Ser Gly Asp Lys
                325                 330                 335

Val Glu Ile Asp Pro Val Thr Asn Gln Lys Ala Ser Thr Lys Phe Trp
            340                 345                 350

Ile Lys Gln Lys Pro Ile Ser Ile Asp Ser Asp Leu Leu Cys Ala Cys
        355                 360                 365

Asp Leu Ala Glu Glu Lys Ser Pro Ser His Ala Ile Phe Lys Leu Thr
        370                 375                 380

Tyr Leu Ser Asn His Asp Tyr Lys His Leu Tyr Phe Glu Ser Asp Ala
385                 390                 395                 400
```

```
Ala Thr Val Asn Glu Ile Val Leu Lys Val Asn Tyr Ile Leu Glu Ser
            405                 410                 415

Arg Ala Ser Thr Ala Arg Ala Asp Tyr Phe Ala Gln Lys Lys Ser Gly
            420                 425                 430

Arg (2) INFORMATION FOR SEQ ID NO:19:

(i) SEQUENCE CHARACTERISTICS:
        (A) LENGTH: 3987 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..1498

(xi) SEQUENCE DESCRIPTION: SEQ ID NO:19:
```

| | | | | | |
|---|---|---|---|---|---|
| GGCGGCCGCG | GCAGGGCGGG | CGCCGCGCGG | AGGCAGGGCG | GGCGTATTCA | ATGGAAGTGT | 60 |
| GTTACCAGCT | GCCGGTACTG | CCCCTGGACA | GGCCGGTCCC | CCAGCACGTC | CTCAGCCGCC | 120 |
| GAGGAGCCAT | CAGCTTCAGC | TCCAGCTCCG | CTCTCTTCGG | CTGCCCCAAT | CCCCGGCAGC | 180 |
| TCTCTCAGAG | GCGTGGAGCT | ATTTCCTATG | ACAGTTCTGA | TCAGACTGCA | TTATACATTC | 240 |
| GTATGCTAGG | AGATGTACGT | GTAAGGAGCC | GAGCAGGATT | TGAATCAGAA | AGAAGAGGTT | 300 |
| CTCACCCATA | TATTGATTTT | CGTATTTTCC | ACTCTCAATC | TGAAATTGAA | GTGTCTGTCT | 360 |
| CTGCAAGGAA | TATCAGAAGG | CTACTAAGTT | TCCAGCGATA | TCTTAGATCT | TCACGCTTTT | 420 |
| TTCGTGGTAC | TGCGGTTTCA | AATTCCCTAA | ACATTTTAGA | TGATGATTAT | AATGGACAAG | 480 |
| CCAAGTGTAT | GCTGGAAAAA | GTTGGAAATT | GGAATTTTGA | TATCTTTCTA | TTTGATAGAC | 540 |
| TAACAAATGG | AAATAGTCTA | GTAAGCTTAA | CCTTTCATTT | ATTTAGTCTT | CATGGATTAA | 600 |
| TTGAGTACTT | CCATTTAGAT | ATGATGAAAC | TTCGTAGATT | TTTAGTTATG | ATTCAAGAAG | 660 |
| ATTACCACAG | TCAAAATCCT | TACCATAACG | CAGTCCACGC | TGCGGATGTT | ACTCAGGCCA | 720 |
| TGCACTGTTA | CTTAAAGGAA | CCTAAGCTTG | CCAATTCTGT | AACTCCTTGG | GATATCTTGC | 780 |
| TGAGCTTAAT | TGCAGCTGCC | ACTCATGATC | TGGATCATCC | AGGTGTTAAT | CAACCTTTCC | 840 |
| TTATTAAAAC | TAACCATTAC | TTGGCAACTT | TATACAAGAA | TACCTCAGTA | CTGGAAAATC | 900 |
| ACCACTGGAG | ATCTGCAGTG | GGCTTATTGA | GAGAATCAGG | CTTATTCTCA | CATCTGCCAT | 960 |
| TAGAAAGCAG | GCAACAAATG | GAGACACAGA | TAGGTGCTCT | GATACTAGCC | ACAGACATCA | 1020 |
| GTCGCCAGAA | TGAGTATCTG | TCTTTGTTTA | GGTCCCATTT | GGATAGAGGT | GATTTATGCC | 1080 |
| TAGAAGACAC | CAGACACAGA | CATTTGGTTT | TACAGATGGC | TTTGAAATGT | GCTGATATTT | 1140 |
| GTAACCCATG | TCGGACGTGG | GAATTAAGCA | AGCAGTGGAG | TGAAAAAGTA | ACGGAGGAAT | 1200 |
| TCTTCCATCA | AGGAGATATA | GAAAAAAAAT | ATCATTTGGG | TGTGAGTCCA | CTTTGCGATC | 1260 |
| GTCACACTGA | ATCTATTGCC | AACATCCAGA | TTGGTTTTAT | GACTTACCTA | GTGGAGCCTT | 1320 |
| TATTTACAGA | ATGGGCCAGG | TTTTCCAATA | CAAGGCTATC | CCAGACAATG | CTTGGACACG | 1380 |
| TGGGGCTGAA | TAAAGCCAGC | TGGAAGGGAC | TGCAGAGAGA | ACAGTCGAGC | AGTGAGGACA | 1440 |
| CTGATGCTGC | ATTTGAGTTG | AACTCACAGT | TATTACCTCA | GGAAAATCGG | TTATCATAAC | 1500 |
| CCCCAGAACC | AGTGGGACAA | ACTGCCTCCT | GGAGGTTTTT | AGAAATGTGA | AATGGGTCTT | 1560 |
| TGAGGTGAGA | GAACTTAACT | CTTGACTGCC | AAGGTTTCCA | AGTGAGTGAT | GCCAGCCAGC | 1620 |

```
-continued

ATTATTTATT TCCAAGATTT CCTCTGTTGG ATCATTTGAA CCCACTTGTT AATTGCAAGA    1680

CCCGAACATA CAGCAATATG AATTTGGCTT TCATGTGAAA CCTTGAATAT NNAAAGCCCA    1740

GCAGGAGAGA ATCCGAAAGG AGTAACAAAG GAAGTTTTGA TATGTGCCAC GACTTTTTCA    1800

AAGCATCTAA TCTTCAAAAC GTCAAACTTG AATTGTTCAG CAACAATCTC TTGGAATTTA    1860

ACCAGTCTGA TGCAACAATG TGTATCTTGT ACCTTCCACT AAGTTCTCTC TGAGAAAATG    1920

GAAATGTGAA GTGCCCAGCC TCTGCNTGCC TCTGGCAAGA CAATGTTTAC AAATCAACTC    1980

TGAAAATATT GGTTCTAAAT TGCCTTGGAG CATGATTGTG AAGGAACCAC TCAAACAAAT    2040

TTAAAGATCA AACTTTAGAC TGCAGCTCTT TCCCCCTGGT TTGCCTTTTT CTTCTTTGGA    2100

TGCCACCAAA GCCTCCCATT TGCTATAGTT TTATTTCATG CACTGGAAAC TGAGCATTTA    2160

TCGTAGAGTA CCGCCAAGCT TTCACTCCAG TGCCGTTTGG CAATGCAATT TTTTTTAGCA    2220

ATTAGTTTTT AATTTGGGGT GGGAGGGGAA GAACACCAAT GTCCTAGCTG TATTATGATT    2280

CTGCACTCAA GACATTGCAT GTTGTTTTCA CTACTGTACA CTTGACCTGC ACATGCGAGA    2340

AAAAGGTGGA ATGTTTAAAA CACCATAATC AGCTCAGNGT ATTTGCCAAT CTGAAATAAA    2400

AGTGGGATGG GAGAGCGTGT CCTTCAGATC AAGGGTACTA AAGTCCCTTT CGCTGCAGTG    2460

AGTGAGAGGT ATGTTGTGTG TGAATGTACG GATGTGTGTT TGNGTGNATG TTTGTGCATG    2520

TGTGACNGTG CATGTTATGT TTCTCCATGT GGGCAAAGAT TTGAAANGTA AGCTTTTATT    2580

TATTATTTTA GAATGTGACA TAATGAGCAG CCACACTCGG GGGAGGGGAA GGTTGGTAGG    2640

TAAGCTGTAA CAGATTGCTC CAGTTGCCTT AAACTATGCA CATAGCTAAG TGACCAAACT    2700

TCTTGTTTTG ATTTGAAAAA AGTGCATTGT TTTCTTGTCC CTCCCTTTGA TGAAACGTTA    2760

CCCTTTGACG GGCCTTTTGA TGTGAACAGA TGTTTTCTAG GACAAACTAT AAGGACTAAT    2820

TTTAAACTTC AAACATTCCA CTTTTGTAAT TTGTTTTAAA TTGTTTTATG TATAGTAAGC    2880

ACAACTGTAA TCTAGTTTTA AGAGAAACCG GTGCTTTCTT TTAGTTCATT TGTATTTCCC    2940

TTGTTACTGT AAAAGACTGT TTATTAATTG TTTACAGTTT GTTGCAACAG CCATTTTCTT    3000

GGGAGAAAGC TTGAGTGTAA AGCCATTTGT AAAAGGCTTT GCCATACTCA TTTTAATATG    3060

TGCCTGTTGC TGTTAACTTT TGATGAATAA AAACCTATCT TTTCATGAAA CTTCTCTCTA    3120

TACAAATTGA AATACATAAT GCTTTCTGGT TCTTCTTCAA ACCAAAACTT GTCAAATTCA    3180

TAGACAAGAT AACAGTAAAA CTGATGAAAG TGTTCCATTG TTGGTATACC AGGAACAAGG    3240

TTATAGAGAT GAAACTTCAA AGCTTCACTC TTCAGTAAGC TATAAGCCAT CTCTGTAAGA    3300

TTGATTCCAA CTATTGCATA AGAATACCCT AATTTTGGAT GATTTGAACG GGAAAGAATC    3360

TGATGAGCTT CACTAGTGTA ATTTTCACTG AAATACACAA GATTGATTAA CCCAAGTATG    3420

CCCATGCCTC TGAAGTCTGT CTTGGGATCA TCACCCTGAA AACCAATTTC AGCCCACTGC    3480

TTGGAGATTC TAGCGTTTAA CTTCTTCGTG GGCATTAGAA GATTCCAAAG CTTCATGAGT    3540

AGCTCTTCAT GCTGTAGGTT ATCAGAATCA TATGGCCTTT TCCTCACACT TTCTACATCC    3600

AAATACAGCT GTTTATAACC AGTTATCTGC AGTAAGCACA TCTTCATGCA TATTTTAAAA    3660

CTGGCATCCT TCTCAGGGTT AATATTCTTT TCCTTCATAA TATCATCTAC ATATTTGTCC    3720

ACTTCACTCT GAACAACATG TGTCGCCTTC TGTAAAACCT TATTCTTGGA GTATGTCAAG    3780

GAATTTTCTA TCCTGTGTGT CCTTTGTGCA CCTACATAGG TATCAAATAT TCGCTGCAAT    3840

TCACACTTCC CAGTCATCTG TCGTAATAGC CATTTCATCC AAAATCGAAA AAGTGCCCA    3900

TAGAAGAACT CCCACAAAGA AATAAACATT TTTTTTTCCT CACAGGAGCG GAAGAACTAG    3960

GGGGAGCAGG AGCTGCAATG CGGCCGC                                       3987
```

(2) INFORMATION FOR SEQ ID NO:20:

(i) SEQUENCE CHARACTERISTICS:
        (A) LENGTH: 498 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

```
Arg Pro Arg Gln Gly Gly Arg Arg Ala Glu Ala Gly Arg Ala Tyr Ser
 1               5                  10                  15

Met Glu Val Cys Tyr Gln Leu Pro Val Leu Pro Leu Asp Arg Pro Val
            20                  25                  30

Pro Gln His Val Leu Ser Arg Arg Gly Ala Ile Ser Phe Ser Ser Ser
        35                  40                  45

Ser Ala Leu Phe Gly Cys Pro Asn Pro Arg Gln Leu Ser Gln Arg Arg
 50                  55                  60

Gly Ala Ile Ser Tyr Asp Ser Ser Asp Gln Thr Ala Leu Tyr Ile Arg
65                  70                  75                  80

Met Leu Gly Asp Val Arg Val Arg Ser Arg Ala Gly Phe Glu Ser Glu
            85                  90                  95

Arg Arg Gly Ser His Pro Tyr Ile Asp Phe Arg Ile Phe His Ser Gln
           100                 105                 110

Ser Glu Ile Glu Val Ser Val Ser Ala Arg Asn Ile Arg Arg Leu Leu
       115                 120                 125

Ser Phe Gln Arg Tyr Leu Arg Ser Ser Arg Phe Phe Arg Gly Thr Ala
   130                 135                 140

Val Ser Asn Ser Leu Asn Ile Leu Asp Asp Tyr Asn Gly Gln Ala
145                 150                 155                 160

Lys Cys Met Leu Glu Lys Val Gly Asn Trp Asn Phe Asp Ile Phe Leu
           165                 170                 175

Phe Asp Arg Leu Thr Asn Gly Asn Ser Leu Val Ser Leu Thr Phe His
       180                 185                 190

Leu Phe Ser Leu His Gly Leu Ile Glu Tyr Phe His Leu Asp Met Met
   195                 200                 205

Lys Leu Arg Arg Phe Leu Val Met Ile Gln Glu Asp Tyr His Ser Gln
   210                 215                 220

Asn Pro Tyr His Asn Ala Val His Ala Ala Asp Val Thr Gln Ala Met
225                 230                 235                 240

His Cys Tyr Leu Lys Glu Pro Lys Leu Ala Asn Ser Val Thr Pro Trp
           245                 250                 255

Asp Ile Leu Leu Ser Leu Ile Ala Ala Ala Thr His Asp Leu Asp His
       260                 265                 270

Pro Gly Val Asn Gln Pro Phe Leu Ile Lys Thr Asn His Tyr Leu Ala
   275                 280                 285

Thr Leu Tyr Lys Asn Thr Ser Val Leu Glu Asn His His Trp Arg Ser
290                 295                 300

Ala Val Gly Leu Leu Arg Glu Ser Gly Leu Phe Ser His Leu Pro Leu
305                 310                 315                 320

Glu Ser Arg Gln Gln Met Glu Thr Gln Ile Gly Ala Leu Ile Leu Ala
           325                 330                 335

Thr Asp Ile Ser Arg Gln Asn Glu Tyr Leu Ser Leu Phe Arg Ser His
       340                 345                 350
```

```
Leu Asp Arg Gly Asp Leu Cys Leu Glu Asp Thr Arg His Arg His Leu
        355                 360                 365

Val Leu Gln Met Ala Leu Lys Cys Ala Asp Ile Cys Asn Pro Cys Arg
        370                 375                 380

Thr Trp Glu Leu Ser Lys Gln Trp Ser Glu Lys Val Thr Glu Glu Phe
385                 390                 395                 400

Phe His Gln Gly Asp Ile Glu Lys Lys Tyr His Leu Gly Val Ser Pro
                405                 410                 415

Leu Cys Asp Arg His Thr Glu Ser Ile Ala Asn Ile Gln Ile Gly Phe
                420                 425                 430

Met Thr Tyr Leu Val Glu Pro Leu Phe Thr Glu Trp Ala Arg Phe Ser
        435                 440                 445

Asn Thr Arg Leu Ser Gln Thr Met Leu Gly His Val Gly Leu Asn Lys
        450                 455                 460

Ala Ser Trp Lys Gly Leu Gln Arg Glu Gln Ser Ser Ser Glu Asp Thr
465                 470                 475                 480

Asp Ala Ala Phe Glu Leu Asn Ser Gln Leu Leu Pro Gln Glu Asn Arg
                485                 490                 495

Leu Ser (2) INFORMATION FOR SEQ ID NO:21:

(i) SEQUENCE CHARACTERISTICS:
        (A) LENGTH: 3131 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (D) OTHER INFORMATION: /note= "Nucleotides 429-427 and
                        634-670 may represent introns; sequence
                        may have frame shifts at nucleotides
                        328, 592, 1590 and 1592."

(ix) FEATURE:
        (A) NAME/KEY: CDS
        (B) LOCATION: join(2..1648, 1651..2661)

(xi) SEQUENCE DESCRIPTION: SEQ ID NO:21:

G CGG CCG CGC GGC CTA GGC CGC ATC CCG GAG CTG CAA CTG GTG GCC           46
  Arg Pro Arg Gly Leu Gly Arg Ile Pro Glu Leu Gln Leu Val Ala
    1               5                   10                  15

TTC CCG GTG GCG GTG GCG GCT GAG GAC GAG GCG TTC CTG CCC GAG CCC         94
Phe Pro Val Ala Val Ala Ala Glu Asp Glu Ala Phe Leu Pro Glu Pro
                20                  25                  30

CTG GCC CCG CGC GCG CCC CGC CGC CCG CGT TCG CCG CCC TCC TCG CCC        142
Leu Ala Pro Arg Ala Pro Arg Arg Pro Arg Ser Pro Pro Ser Ser Pro
            35                  40                  45

GTC TTC TTC GCC AGC CCG TCC CCA ACT TTC CGC AGA CGC CTT CGG CTT        190
Val Phe Phe Ala Ser Pro Ser Pro Thr Phe Arg Arg Arg Leu Arg Leu
        50                  55                  60

CTC CGC AGC TGC CAG GAT TTG GGC CGC CAG GCT TGG GCT GGG GCT GGC        238
Leu Arg Ser Cys Gln Asp Leu Gly Arg Gln Ala Trp Ala Gly Ala Gly
    65                  70                  75

TTC GAG GCA GAG AAT GGG CCG ACA CCA TCT CCT GGC CGC AGC CCC CTG        286
Phe Glu Ala Glu Asn Gly Pro Thr Pro Ser Pro Gly Arg Ser Pro Leu
80                  85                  90                  95

GAC TCG CAG GCG AGC CCA GGA CTC GTG CTG CAC GCC GGG GCG CCA CCA        334
```

```
Asp Ser Gln Ala Ser Pro Gly Leu Val Leu His Ala Gly Ala Pro Pro
                100              105              110

GCC AGC GCC GGG AGT CCT TCC TGT ACC GCT CAG ACA GCG ACT ATG ACA        382
Ala Ser Ala Gly Ser Pro Ser Cys Thr Ala Gln Thr Ala Thr Met Thr
                115              120              125

TGT CAC CCA AGA CCA TGT CCC GGA ACT CAT CGG TCA CCA GCG AGG CAC        430
Cys His Pro Arg Pro Cys Pro Gly Thr His Arg Ser Pro Ala Arg His
                130              135              140

AGT TGC TTC TCT GCG GAC CCC TGA CCT GCC TCT GTC CTC AAT CAC AGG        478
Ser Cys Phe Ser Ala Asp Pro  *  Pro Ala Ser Val Leu Asn His Arg
            145              150              155

CAC GCT GAA GAC CTC ATC GTA ACA CCA TTT GCT CAG GTG CTG GCC AGC        526
His Ala Glu Asp Leu Ile Val Thr Pro Phe Ala Gln Val Leu Ala Ser
160              165              170              175

CTC CGG AGC GTC CGT AGC AAC TTC TCA CTC CTG ACC AAT GTG CCC GTT        574
Leu Arg Ser Val Arg Ser Asn Phe Ser Leu Leu Thr Asn Val Pro Val
                180              185              190

CCC AGT AAC AAG CGG TCC CGC TGG GCG GCC CCA CCC CTG TCT GCA AGG        622
Pro Ser Asn Lys Arg Ser Arg Trp Ala Ala Pro Pro Leu Ser Ala Arg
                195              200              205

CCA CGC TGT CAG ACC TTC TCA GTC ACT ACC CTG GCT GCC CCT TCC TTA        670
Pro Arg Cys Gln Thr Phe Ser Val Thr Thr Leu Ala Ala Pro Ser Leu
                210              215              220

GAA GAA ACG TGT CAG CAG TTG GCC CGG GAG ACT CTG GAG GAG CTG GAC        718
Glu Glu Thr Cys Gln Gln Leu Ala Arg Glu Thr Leu Glu Glu Leu Asp
                225              230              235

TGG TGT CTG GAG CAG CTG GAG ACC ATG CAG ACC TAT CGC TCT GTC AGC        766
Trp Cys Leu Glu Gln Leu Glu Thr Met Gln Thr Tyr Arg Ser Val Ser
240              245              250              255

GAG ATG GCC TCG CAC AAG TTC AAA AGG ATG TTG AAC CGT GAG CTC ACA        814
Glu Met Ala Ser His Lys Phe Lys Arg Met Leu Asn Arg Glu Leu Thr
                260              265              270

CAC CTG TCA GAA ATG AGC AGG TCC GGA AAC CAG GTC TCA GAG TAC ATT        862
His Leu Ser Glu Met Ser Arg Ser Gly Asn Gln Val Ser Glu Tyr Ile
                275              280              285

TCC ACA ACA TTC CTG GAC AAA CAG AAT GAA GTG GAG ATC CCA TCA CCC        910
Ser Thr Thr Phe Leu Asp Lys Gln Asn Glu Val Glu Ile Pro Ser Pro
                290              295              300

ACG ATG AAG GAA CGA GAA AAA CAG CAA GCG CCG CGA CCA AGA CCC TCC        958
Thr Met Lys Glu Arg Glu Lys Gln Gln Ala Pro Arg Pro Arg Pro Ser
305              310              315

CAG CCG CCC CCG CCC CCT GTA CCA CAC TTA CAG CCC ATG TCC CAA ATC       1006
Gln Pro Pro Pro Pro Pro Val Pro His Leu Gln Pro Met Ser Gln Ile
320              325              330              335

ACA GGG TTG AAA AAG TTG ATG CAT AGT AAC AGC CTG AAC AAC TCT AAC       1054
Thr Gly Leu Lys Lys Leu Met His Ser Asn Ser Leu Asn Asn Ser Asn
                340              345              350

ATT CCC CGA TTT GGG GTG AAG ACC GAT CAA GAA GAG CTC CTG GCC CAA       1102
Ile Pro Arg Phe Gly Val Lys Thr Asp Gln Glu Glu Leu Leu Ala Gln
                355              360              365

GAA CTG GAG AAC CTG AAC AAG TGG GGC CTG AAC ATC TTT TGC GTG TCG       1150
Glu Leu Glu Asn Leu Asn Lys Trp Gly Leu Asn Ile Phe Cys Val Ser
                370              375              380

GAT TAC GCT GGA GGC CGC TCA CTC ACC TGC ATC ATG TAC ATG ATA TTC       1198
Asp Tyr Ala Gly Gly Arg Ser Leu Thr Cys Ile Met Tyr Met Ile Phe
385              390              395

CAG GAG CGG GAC CTG CTG AAG AAA TTC CGC ATC CCT GTG GAC ACG ATG       1246
Gln Glu Arg Asp Leu Leu Lys Lys Phe Arg Ile Pro Val Asp Thr Met
400              405              410              415
```

```
GTG ACA TAC ATG CTG ACG CTG GAG GAT CAC TAC CAC GCT GAC GTG GCC         1294
Val Thr Tyr Met Leu Thr Leu Glu Asp His Tyr His Ala Asp Val Ala
            420                 425                 430

TAC CAT AAC AGC CTG CAC GCA GCT GAC GTG CTG CAG TCC ACC CAC GTA         1342
Tyr His Asn Ser Leu His Ala Ala Asp Val Leu Gln Ser Thr His Val
            435                 440                 445

CTG CTG GCC ACG CCT GCA CTA GAT GCA GTG TTC ACG GAC CTG GAG ATT         1390
Leu Leu Ala Thr Pro Ala Leu Asp Ala Val Phe Thr Asp Leu Glu Ile
            450                 455                 460

CTC GCC GCC CTC TTC GCG GCT GCC ATC CAC GAT GTG GAT CAC CCT GGG         1438
Leu Ala Ala Leu Phe Ala Ala Ala Ile His Asp Val Asp His Pro Gly
            465                 470                 475

GTC TCC AAC CAG TTC CTC ATC AAC ACC AAT TCG GAG CTG GCG CTC ATG         1486
Val Ser Asn Gln Phe Leu Ile Asn Thr Asn Ser Glu Leu Ala Leu Met
480                 485                 490                 495

TAC AAC GAT GAG TCG GTG CTC GAG AAT CAC CAC CTG GCC GTG GGC TTC         1534
Tyr Asn Asp Glu Ser Val Leu Glu Asn His His Leu Ala Val Gly Phe
                500                 505                 510

AAG CTG CTG CAG GAG GAC AAC TGC GAC ATC TTC CAG AAC CTC AGC AAG         1582
Lys Leu Leu Gln Glu Asp Asn Cys Asp Ile Phe Gln Asn Leu Ser Lys
            515                 520                 525

CGC CAG CGC AGA GCC TAC GCA AGA TGG TCA TCG ACA TGG TGC TGG CCA         1630
Arg Gln Arg Arg Ala Tyr Ala Arg Trp Ser Ser Thr Trp Cys Trp Pro
            530                 535                 540

CGG ACA TGT CCA AGC ACA TG ACC CTC CTG GCT GAC CTG AAG ACC ATG         1677
Arg Thr Cys Pro Ser Thr    Thr Leu Leu Ala Asp Leu Lys Thr Met
545                         550                 555

GTG GAG ACC AAG AAA GTG ACC AGC TCA GGG GTC CTC CTG CTA GAT AAC         1725
Val Glu Thr Lys Lys Val Thr Ser Ser Gly Val Leu Leu Leu Asp Asn
            560                 565                 570

TAC TCC GAC CGC ATC CAG GTC CTC CGG AAC ATG GTG CAC TGT GCC GAC         1773
Tyr Ser Asp Arg Ile Gln Val Leu Arg Asn Met Val His Cys Ala Asp
575                 580                 585                 590

CTC AGC AAC CCC ACC AAG CCG CTG GAG CTG TAC CGC CAG TGG ACA GAC         1821
Leu Ser Asn Pro Thr Lys Pro Leu Glu Leu Tyr Arg Gln Trp Thr Asp
                595                 600                 605

CGC ATC ATG GCC GAG TTC TTC CAG CAG GGT GAC CGA GAG CGC GAG CGT         1869
Arg Ile Met Ala Glu Phe Phe Gln Gln Gly Asp Arg Glu Arg Glu Arg
            610                 615                 620

GGC ATG GAA ATC AGC CCC ATG TGT GAC AAG CAC ACT GCC TCC GTG GAG         1917
Gly Met Glu Ile Ser Pro Met Cys Asp Lys His Thr Ala Ser Val Glu
            625                 630                 635

AAG TCT CAG GTG GGT TTT ATT GAC TAC ATT GTG CAC CCA TTG TGG GAG         1965
Lys Ser Gln Val Gly Phe Ile Asp Tyr Ile Val His Pro Leu Trp Glu
            640                 645                 650

ACC TGG GCG GAC CTT GTC CAC CCA GAT GCC CAG GAG ATC TTG GAC ACT         2013
Thr Trp Ala Asp Leu Val His Pro Asp Ala Gln Glu Ile Leu Asp Thr
655                 660                 665                 670

TTG GAG GAC AAC CGG GAC TGG TAC TAC AGC GCC ATC CGG CAG AGC CCA         2061
Leu Glu Asp Asn Arg Asp Trp Tyr Tyr Ser Ala Ile Arg Gln Ser Pro
                675                 680                 685

TCT CCG CCA CCC GAG GAG GAG TCA AGG GGG CCA GGC CAC CCA CCC CTG         2109
Ser Pro Pro Pro Glu Glu Glu Ser Arg Gly Pro Gly His Pro Pro Leu
            690                 695                 700

CCT GAC AAG TTC CAG TTT GAG CTG ACG CTG GAG GAG GAA GAG GAG GAA         2157
Pro Asp Lys Phe Gln Phe Glu Leu Thr Leu Glu Glu Glu Glu Glu Glu
            705                 710                 715

GAA ATA TCA ATG GCC CAG ATA CCG TGC ACA GCC CAA GAG GCA TTG ACT         2205
Glu Ile Ser Met Ala Gln Ile Pro Cys Thr Ala Gln Glu Ala Leu Thr
            720                 725                 730
```

```
GAG CAG GGA TTG TCA GGA GTC GAG GAA GCT CTG GAT GCA ACC ATA GCC      2253
Glu Gln Gly Leu Ser Gly Val Glu Glu Ala Leu Asp Ala Thr Ile Ala
735                 740                 745                 750

TGG GAG GCA TCC CCG GCC CAG GAG TCG TTG GAA GTT ATG GCA CAG GAA      2301
Trp Glu Ala Ser Pro Ala Gln Glu Ser Leu Glu Val Met Ala Gln Glu
                755                 760                 765

GCA TCC CTG GAG GCC GAG CTG GAG GCA GTG TAT TTG ACA CAG CAG GCA      2349
Ala Ser Leu Glu Ala Glu Leu Glu Ala Val Tyr Leu Thr Gln Gln Ala
            770                 775                 780

CAG TCC ACA GGC AGT GCA CCT GTG GCT CCG GAT GAG TTC TCG TCC CGG      2397
Gln Ser Thr Gly Ser Ala Pro Val Ala Pro Asp Glu Phe Ser Ser Arg
        785                 790                 795

GAG GAA TTC GTG GTT GCT GTA AGC CAC AGC AGC CCC TCT GCC CTG GCT      2445
Glu Glu Phe Val Val Ala Val Ser His Ser Ser Pro Ser Ala Leu Ala
    800                 805                 810

CTT CAA AGC CCC CTT CTC CCT GCT TGG AGG ACC CTG TCT GTT TCA GAG      2493
Leu Gln Ser Pro Leu Leu Pro Ala Trp Arg Thr Leu Ser Val Ser Glu
815                 820                 825                 830

CAT GCC CCG GGC CTC CCG GGC CTC CCC TCC ACG GCG GCC GAG GTG GAG      2541
His Ala Pro Gly Leu Pro Gly Leu Pro Ser Thr Ala Ala Glu Val Glu
                835                 840                 845

GCC CAA CGA GAG CAC CAG GCT GCC AAG AGG GCT TGC AGT GCC TGC GCA      2589
Ala Gln Arg Glu His Gln Ala Ala Lys Arg Ala Cys Ser Ala Cys Ala
            850                 855                 860

GGG ACA TTT GGG GAG GAC ACA TCC GCA CTC CCA GCT CCT GGT GGC GGG      2637
Gly Thr Phe Gly Glu Asp Thr Ser Ala Leu Pro Ala Pro Gly Gly Gly
        865                 870                 875

GGG TCA GGT GGA GAC CCT ACC TGATCCCCAG ACCTCTGTCC CTGTTCCCCT         2688
Gly Ser Gly Gly Asp Pro Thr
    880                 885

CCACTCCTCC CCTCACTCCC CTGCTCCCCC GACCACCTCC TCCTCTGCCT CAAAGACTCT    2748

TGTCCTCTTG TCCCTCCTGA GATTTTTTTT TTTTTTTTT TTTTTTTTTT TTTTACAACA     2808

CAAATGAATG GGCCATTTTA TTGATTTTTA CCTCCTAATA GTGGATACAG GTTGCTGTGG    2868

TTTCCAGCAG GATCTCAGAT GCAAAGGGAA GTGAAGAAAA CAGATGAATC CCTAGGGTAC    2928

CCCGCCATGG AACCAAACAC CACGTCAACT GGAACTCTTC TTGCAAACGA AGGCTGAAGA    2988

TCAAGAATGA CATTCTCACA CCACAGCACA GCTTAAATAC TTCTTTGACA AAAATAATAA    3048

TAAATTATAT TTGACTCAGA AAATAAATTC TGTTCAGCAG AGTGACAGGA GGTAAAAATC    3108

AAATGAATGG GCAATGCGGC CGC                                            3131

(2) INFORMATION FOR SEQ ID NO:22:

(i) SEQUENCE CHARACTERISTICS:
         (A) LENGTH: 150 amino acids
         (B) TYPE: amino acid
         (D) TOPOLOGY: linear (ii) MOLECULE TYPE: protein (xi) SEQUENCE DESCRIPTION: SEQ ID NO:22:

Arg Pro Arg Gly Leu Gly Arg Ile Pro Glu Leu Gln Leu Val Ala Phe
 1               5                  10                  15

Pro Val Ala Val Ala Ala Glu Asp Glu Ala Phe Leu Pro Glu Pro Leu
            20                  25                  30

Ala Pro Arg Ala Pro Arg Arg Pro Arg Ser Pro Pro Ser Ser Pro Val
        35                  40                  45

Phe Phe Ala Ser Pro Ser Pro Thr Phe Arg Arg Arg Leu Arg Leu Leu
```

```
            50                  55                  60
Arg Ser Cys Gln Asp Leu Gly Arg Gln Ala Trp Ala Gly Ala Gly Phe
 65                  70                  75                  80

Glu Ala Glu Asn Gly Pro Thr Pro Ser Pro Gly Arg Ser Pro Leu Asp
                 85                  90                  95

Ser Gln Ala Ser Pro Gly Leu Val Leu His Ala Gly Ala Pro Pro Ala
            100                 105                 110

Ser Ala Gly Ser Pro Ser Cys Thr Ala Gln Thr Ala Thr Met Thr Cys
            115                 120                 125

His Pro Arg Pro Cys Pro Gly Thr His Arg Ser Pro Ala Arg His Ser
            130                 135                 140

Cys Phe Ser Ala Asp Pro
145                 150
```

(2) INFORMATION FOR SEQ ID NO:23:

(i) SEQUENCE CHARACTERISTICS:
        (A) LENGTH: 3186 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 139..2348

(xi) SEQUENCE DESCRIPTION: SEQ ID NO:23:

```
GCGGCCGCGG CGGTGCAGCA GAGGCGCCTC GGGCAGGAGG AGGGCGGCTT CTGCGAGGGC      60

AGCCTGAGGT ATTAAAAAGT GTCAGCAAAC TGCATTGAAT AACAGACATC CTAAGAGGGG     120

ATATTTTCCA CCTCTATA ATG AAG AAA AGC AGG AGT GTG ATG ACG GTG ATG      171
                    Met Lys Lys Ser Arg Ser Val Met Thr Val Met
                     1               5                  10

GCT GAT GAT AAT GTT AAA GAT TAT TTT GAA TGT AGC TTG AGT AAA TCC      219
Ala Asp Asp Asn Val Lys Asp Tyr Phe Glu Cys Ser Leu Ser Lys Ser
                 15                  20                  25

TAC AGT TCT TCC AGT AAC ACA CTT GGG ATC GAC CTC TGG AGA GGG AGA      267
Tyr Ser Ser Ser Ser Asn Thr Leu Gly Ile Asp Leu Trp Arg Gly Arg
             30                  35                  40

AGG TGT TGC TCA GGA AAC TTA CAG TTA CCA CCA CTG TCT CAA AGA CAG      315
Arg Cys Cys Ser Gly Asn Leu Gln Leu Pro Pro Leu Ser Gln Arg Gln
         45                  50                  55

AGT GAA AGG GCA AGG ACT CCT GAG GGA GAT GGT ATT TCC AGG CCG ACC      363
Ser Glu Arg Ala Arg Thr Pro Glu Gly Asp Gly Ile Ser Arg Pro Thr
 60                  65                  70                  75

ACA CTG CCT TTG ACA ACG CTT CCA AGC ATT GCT ATT ACA ACT GTA AGC      411
Thr Leu Pro Leu Thr Thr Leu Pro Ser Ile Ala Ile Thr Thr Val Ser
                 80                  85                  90

CAG GAG TGC TTT GAT GTG GAA AAT GGC CCT TCC CCA GGT CGG AGT CCA      459
Gln Glu Cys Phe Asp Val Glu Asn Gly Pro Ser Pro Gly Arg Ser Pro
             95                 100                 105

CTG GAT CCC CAG GCC AGC TCT TCC GCT GGG CTG GTA CTT CAC GCC ACC      507
Leu Asp Pro Gln Ala Ser Ser Ser Ala Gly Leu Val Leu His Ala Thr
        110                 115                 120

TTT CCT GGG CAC AGC CAG CGC AGA GAG TCA TTT CTC TAC AGA TCA GAC      555
Phe Pro Gly His Ser Gln Arg Arg Glu Ser Phe Leu Tyr Arg Ser Asp
        125                 130                 135

AGC GAC TAT GAC TTG TCA CCA AAG GCG ATG TCG AGA AAC TCT TCT CTT      603
Ser Asp Tyr Asp Leu Ser Pro Lys Ala Met Ser Arg Asn Ser Ser Leu
```

```
                   140                    145                    150                    155
CCA AGC GAG CAA CAC GGC GAT GAC TTG ATT GTA ACT CCT TTT GCC CAG                      651
Pro Ser Glu Gln His Gly Asp Asp Leu Ile Val Thr Pro Phe Ala Gln
                    160                    165                    170

GTC CTT GCC AGC TTG CGA AGT GTG AGA AAC AAC TTC ACT ATA CTG ACA                      699
Val Leu Ala Ser Leu Arg Ser Val Arg Asn Asn Phe Thr Ile Leu Thr
                175                    180                    185

AAC CTT CAT GGT ACA TCT AAC AAG AGG TCC CCA GCT GCT AGT CAG CCT                      747
Asn Leu His Gly Thr Ser Asn Lys Arg Ser Pro Ala Ala Ser Gln Pro
            190                    195                    200

CCT GTC TCC AGA GTC AAC CCA CAA GAA GAA TCT TAT CAA AAA TTA GCA                      795
Pro Val Ser Arg Val Asn Pro Gln Glu Glu Ser Tyr Gln Lys Leu Ala
        205                    210                    215

ATG GAA ACG CTG GAG GAA TTA GAC TGG TGT TTA GAC CAG CTA GAG ACC                      843
Met Glu Thr Leu Glu Glu Leu Asp Trp Cys Leu Asp Gln Leu Glu Thr
220                    225                    230                    235

ATA CAG ACC TAC CGG TCT GTC AGT GAG ATG GCT TCT AAC AAG TTC AAA                      891
Ile Gln Thr Tyr Arg Ser Val Ser Glu Met Ala Ser Asn Lys Phe Lys
                240                    245                    250

AGA ATG CTG AAC CGG GAG CTG ACA CAC CTC TCA GAG ATG AGC CGA TCA                      939
Arg Met Leu Asn Arg Glu Leu Thr His Leu Ser Glu Met Ser Arg Ser
            255                    260                    265

GGG AAC CAG GTG TCT GAA TAC ATT TCA AAT ACT TTC TTA GAC AAG CAG                      987
Gly Asn Gln Val Ser Glu Tyr Ile Ser Asn Thr Phe Leu Asp Lys Gln
        270                    275                    280

AAT GAT GTG GAG ATC CCA TCT CCT ACC CAG AAA GAC AGG GAG AAA AAG                     1035
Asn Asp Val Glu Ile Pro Ser Pro Thr Gln Lys Asp Arg Glu Lys Lys
285                    290                    295

AAA AAG CAG CAG CTC ATG ACC CAG ATA AGT GGA GTG AAG AAA TTA ATG                     1083
Lys Lys Gln Gln Leu Met Thr Gln Ile Ser Gly Val Lys Lys Leu Met
300                    305                    310                    315

CAT AGT TCA AGC CTA AAC AAT ACA AGC ATC TCA CGC TTT GGA GTC AAC                     1131
His Ser Ser Ser Leu Asn Asn Thr Ser Ile Ser Arg Phe Gly Val Asn
                320                    325                    330

ACT GAA AAT GAA GAT CAC CTG GCC AAG GAG CTG GAA GAC CTG AAC AAA                     1179
Thr Glu Asn Glu Asp His Leu Ala Lys Glu Leu Glu Asp Leu Asn Lys
            335                    340                    345

TGG GGT CTT AAC ATC TTT AAT GTG GCT GGA TAT TCT CAC AAT AGA CCC                     1227
Trp Gly Leu Asn Ile Phe Asn Val Ala Gly Tyr Ser His Asn Arg Pro
        350                    355                    360

CTA ACA TGC ATC ATG TAT GCT ATA TTC CAG GAA AGA GAC CTC CTA AAG                     1275
Leu Thr Cys Ile Met Tyr Ala Ile Phe Gln Glu Arg Asp Leu Leu Lys
    365                    370                    375

ACA TTC AGA ATC TCA TCT GAC ACA TTT ATA ACC TAC ATG ATG ACT TTA                     1323
Thr Phe Arg Ile Ser Ser Asp Thr Phe Ile Thr Tyr Met Met Thr Leu
380                    385                    390                    395

GAA GAC CAT TAC CAT TCT GAC GTG GCA TAT CAC AAC AGC CTG CAC GCT                     1371
Glu Asp His Tyr His Ser Asp Val Ala Tyr His Asn Ser Leu His Ala
                400                    405                    410

GCT GAT GTA GCC CAG TCG ACC CAT GTT CTC CTT TCT ACA CCA GCA TTA                     1419
Ala Asp Val Ala Gln Ser Thr His Val Leu Leu Ser Thr Pro Ala Leu
            415                    420                    425

GAC GCT GTC TTC ACA GAT TTG GAG ATC CTG GCT GCC ATT TTT GCA GCT                     1467
Asp Ala Val Phe Thr Asp Leu Glu Ile Leu Ala Ala Ile Phe Ala Ala
        430                    435                    440

GCC ATC CAT GAC GTT GAT CAT CCT GGA GTC TCC AAT CAG TTT CTC ATC                     1515
Ala Ile His Asp Val Asp His Pro Gly Val Ser Asn Gln Phe Leu Ile
    445                    450                    455

AAC ACA AAT TCA GAA CTT GCT TTG ATG TAT AAT GAT GAA TCT GTG TTG                     1563
```

```
                Asn Thr Asn Ser Glu Leu Ala Leu Met Tyr Asn Asp Glu Ser Val Leu
                460                 465                 470                 475
GAA AAT CAT CAC CTT GCT GTG GGT TTC AAA CTG CTG CAA GAA GAA CAC                 1611
Glu Asn His His Leu Ala Val Gly Phe Lys Leu Leu Gln Glu Glu His
                    480                 485                 490

TGT GAC ATC TTC ATG AAT CTC ACC AAG AAG CAG CGT CAG ACA CTC AGG                 1659
Cys Asp Ile Phe Met Asn Leu Thr Lys Lys Gln Arg Gln Thr Leu Arg
                495                 500                 505

AAG ATG GTT ATT GAC ATG GTG TTA GCA ACT GAT ATG TCT AAA CAT ATG                 1707
Lys Met Val Ile Asp Met Val Leu Ala Thr Asp Met Ser Lys His Met
            510                 515                 520

AGC CTG CTG GCA GAC CTG AAG ACA ATG GTA GAA ACG AAG AAA GTT ACA                 1755
Ser Leu Leu Ala Asp Leu Lys Thr Met Val Glu Thr Lys Lys Val Thr
    525                 530                 535

AGT TCA GGC GTT CTT CTC CTA GAC AAC TAT ACC GAT CGC ATT CAG GTC                 1803
Ser Ser Gly Val Leu Leu Leu Asp Asn Tyr Thr Asp Arg Ile Gln Val
540                 545                 550                 555

CTT CGC AAC ATG GTA CAC TGT GCA GAC CTG AGC AAC CCC ACC AAG TCC                 1851
Leu Arg Asn Met Val His Cys Ala Asp Leu Ser Asn Pro Thr Lys Ser
                560                 565                 570

TTG GAA TTG TAT CGG CAA TGG ACA GAC CGC ATC ATG GAG GAA TTT TTC                 1899
Leu Glu Leu Tyr Arg Gln Trp Thr Asp Arg Ile Met Glu Glu Phe Phe
            575                 580                 585

CAG CAG GGA GAC AAA GAG CGG GAG AGG GGA ATG GAA ATT AGC CCA ATG                 1947
Gln Gln Gly Asp Lys Glu Arg Glu Arg Gly Met Glu Ile Ser Pro Met
        590                 595                 600

TGT GAT AAA CAC ACA GCT TCT GTG GAA AAA TCC CAG GTT GGT TTC ATC                 1995
Cys Asp Lys His Thr Ala Ser Val Glu Lys Ser Gln Val Gly Phe Ile
605                 610                 615

GAC TAC ATT GTC CAT CCA TTG TGG GAG ACA TGG GCA GAT TTG GTA CAG                 2043
Asp Tyr Ile Val His Pro Leu Trp Glu Thr Trp Ala Asp Leu Val Gln
620                 625                 630                 635

CCT GAT GCT CAG GAC ATT CTC GAT ACC TTA GAA GAT AAC AGG AAC TGG                 2091
Pro Asp Ala Gln Asp Ile Leu Asp Thr Leu Glu Asp Asn Arg Asn Trp
                640                 645                 650

TAT CAG AGC ATG ATA CCT CAA AGT CCC TCA CCA CCA CTG GAC GAG CAG                 2139
Tyr Gln Ser Met Ile Pro Gln Ser Pro Ser Pro Pro Leu Asp Glu Gln
            655                 660                 665

AAC AGG GAC TGC CAG GGT CTG ATG GAG AAG TTT CAG TTT GAA CTG ACT                 2187
Asn Arg Asp Cys Gln Gly Leu Met Glu Lys Phe Gln Phe Glu Leu Thr
        670                 675                 680

CTC GAT GAG GAA GAT TCT GAA GGA CCT GAG AAG GAG GGA GAG GGA CAC                 2235
Leu Asp Glu Glu Asp Ser Glu Gly Pro Glu Lys Glu Gly Glu Gly His
685                 690                 695

AGC TAT TTC AGC AGC ACA AAG ACG CTT TGT GTG ATT GAT CCA GAA AAC                 2283
er  Tyr Phe Ser Ser Thr Lys Thr Leu Cys Val Ile Asp Pro Glu Asn
700                 705                 710                 715

AGA GAT TCC CTG GGA GAG ACT GAC ATA GAC ATT GCA ACA GAA GAC AAG                 2331
Arg Asp Ser Leu Gly Glu Thr Asp Ile Asp Ile Ala Thr Glu Asp Lys
                720                 725                 730

TCC CCC GTG GAT ACA TA ATCCCCCTCT CCCTGTGGAG ATGAACATTC                         2378
Ser Pro Val Asp Thr
                735

TATCCTTGAT GAGCATGCCA GCTATGTGGT AGGGCCAGCC CACCATGGGG GCCAAGACCT              2438

GCACAGGACA AGGGCCACCT GGCCTTTCAG TTACTTGAGT TTGGAGTCAG AAAGCAAGAC              2498

CAGGAAGCAA ATAGCAGCTC AGGAAATCCC ACGGTTGACT TGCCTTGATG GCAAGCTTGG              2558

TGGAGAGGGC TGAAGCTGTT GCTGGGGGCC GATTCTGATC AAGACACATG GCTTGAAAAT              2618
```

| | |
|---|---|
| GGAAGACACA AAACTGAGAG ATCATTCTGC ACTAAGTTTC GGGAACTTAT CCCCGACAGT | 2678 |
| GACTGAACTC ACTGACTAAT AACTTCATTT ATGAATCTTC TCACTTGTCC CTTTGTCTGC | 2738 |
| CAACCTGTGT GCCTTTTTTG TAAAACATTT TCATGTCTTT AAAATGCCTG TTGAATACCT | 2798 |
| GGAGTTTAGT ATCAACTTCT ACACAGATAA GCTTTCAAAG TTGACAAACT TTTTTGACTC | 2858 |
| TTTCTGGAAA AGGGAAAGAA AATAGTCTTC CTTCTTTCTT GGGCAATATC CTTCACTTTA | 2918 |
| CTACAGTTAC TTTTGCAAAC AGACAGAAAG GATACACTTC TAACCACATT TTACTTCCTT | 2978 |
| CCCCTGTTGT CCAGTCCAAC TCCACAGTCA CTCTTAAAAC TTCTCTCTGT TTGCCTGCCT | 3038 |
| CCAACAGTAC TTTTAACTTT TTGCTGTAAA CAGAATAAAA TTGAACAAAT TAGGGGGTAG | 3098 |
| AAAGGAGCAG TGGTGTCGTT CACCGTGAGA GTCTGCATAG AACTCAGCAG TGTGCCCTGC | 3158 |
| TGTGTCTTGG ACCCTGCAAT GCGGCCGC | 3186 |

(2) INFORMATION FOR SEQ ID NO:24:

(i) SEQUENCE CHARACTERISTICS:
        (A) LENGTH: 736 amino acids
        (B) TYPE: amino acid
        (D) TOPOLOGY: linear (ii) MOLECULE TYPE: protein (xi) SEQUENCE DESCRIPTION: SEQ ID NO:24:

```
Met Lys Lys Ser Arg Ser Val Met Thr Val Met Ala Asp Asp Asn Val
 1               5                  10                  15

Lys Asp Tyr Phe Glu Cys Ser Leu Ser Lys Ser Tyr Ser Ser Ser Ser
                20                  25                  30

Asn Thr Leu Gly Ile Asp Leu Trp Arg Gly Arg Cys Cys Ser Gly
            35                  40                  45

Asn Leu Gln Leu Pro Pro Leu Ser Gln Arg Gln Ser Glu Arg Ala Arg
        50                  55                  60

Thr Pro Glu Gly Asp Gly Ile Ser Arg Pro Thr Thr Leu Pro Leu Thr
65                  70                  75                  80

Thr Leu Pro Ser Ile Ala Ile Thr Thr Val Ser Gln Glu Cys Phe Asp
                85                  90                  95

Val Glu Asn Gly Pro Ser Pro Gly Arg Ser Pro Leu Asp Pro Gln Ala
            100                 105                 110

Ser Ser Ser Ala Gly Leu Val Leu His Ala Thr Phe Pro Gly His Ser
        115                 120                 125

Gln Arg Arg Glu Ser Phe Leu Tyr Arg Ser Asp Ser Asp Tyr Asp Leu
    130                 135                 140

Ser Pro Lys Ala Met Ser Arg Asn Ser Ser Leu Pro Ser Glu Gln His
145                 150                 155                 160

Gly Asp Asp Leu Ile Val Thr Pro Phe Ala Gln Val Leu Ala Ser Leu
                165                 170                 175

Arg Ser Val Arg Asn Asn Phe Thr Ile Leu Thr Asn Leu His Gly Thr
            180                 185                 190

Ser Asn Lys Arg Ser Pro Ala Ala Ser Gln Pro Pro Val Ser Arg Val
        195                 200                 205

Asn Pro Gln Glu Glu Ser Tyr Gln Lys Leu Ala Met Glu Thr Leu Glu
    210                 215                 220

Glu Leu Asp Trp Cys Leu Asp Gln Leu Glu Thr Ile Gln Thr Tyr Arg
225                 230                 235                 240

Ser Val Ser Glu Met Ala Ser Asn Lys Phe Lys Arg Met Leu Asn Arg
                245                 250                 255
```

-continued

Glu Leu Thr His Leu Ser Glu Met Ser Arg Ser Gly Asn Gln Val Ser
            260                 265                 270

Glu Tyr Ile Ser Asn Thr Phe Leu Asp Lys Gln Asn Asp Val Glu Ile
        275                 280                 285

Pro Ser Pro Thr Gln Lys Asp Arg Glu Lys Lys Lys Gln Gln Leu
        290                 295                 300

Met Thr Gln Ile Ser Gly Val Lys Lys Leu Met His Ser Ser Ser Leu
305                 310                 315                 320

Asn Asn Thr Ser Ile Ser Arg Phe Gly Val Asn Thr Glu Asn Glu Asp
                325                 330                 335

His Leu Ala Lys Glu Leu Glu Asp Leu Asn Lys Trp Gly Leu Asn Ile
            340                 345                 350

Phe Asn Val Ala Gly Tyr Ser His Asn Arg Pro Leu Thr Cys Ile Met
        355                 360                 365

Tyr Ala Ile Phe Gln Glu Arg Asp Leu Leu Lys Thr Phe Arg Ile Ser
        370                 375                 380

Ser Asp Thr Phe Ile Thr Tyr Met Met Thr Leu Glu Asp His Tyr His
385                 390                 395                 400

Ser Asp Val Ala Tyr His Asn Ser Leu His Ala Ala Asp Val Ala Gln
                405                 410                 415

Ser Thr His Val Leu Leu Ser Thr Pro Ala Leu Asp Ala Val Phe Thr
            420                 425                 430

Asp Leu Glu Ile Leu Ala Ala Ile Phe Ala Ala Ala Ile His Asp Val
            435                 440                 445

Asp His Pro Gly Val Ser Asn Gln Phe Leu Ile Asn Thr Asn Ser Glu
        450                 455                 460

Leu Ala Leu Met Tyr Asn Asp Glu Ser Val Leu Glu Asn His His Leu
465                 470                 475                 480

Ala Val Gly Phe Lys Leu Leu Gln Glu Glu His Cys Asp Ile Phe Met
                485                 490                 495

Asn Leu Thr Lys Lys Gln Arg Gln Thr Leu Arg Lys Met Val Ile Asp
            500                 505                 510

Met Val Leu Ala Thr Asp Met Ser Lys His Met Ser Leu Leu Ala Asp
        515                 520                 525

Leu Lys Thr Met Val Glu Thr Lys Lys Val Thr Ser Ser Gly Val Leu
        530                 535                 540

Leu Leu Asp Asn Tyr Thr Asp Arg Ile Gln Val Leu Arg Asn Met Val
545                 550                 555                 560

His Cys Ala Asp Leu Ser Asn Pro Thr Lys Ser Leu Glu Leu Tyr Arg
                565                 570                 575

Gln Trp Thr Asp Arg Ile Met Glu Glu Phe Phe Gln Gln Gly Asp Lys
            580                 585                 590

Glu Arg Glu Arg Gly Met Glu Ile Ser Pro Met Cys Asp Lys His Thr
        595                 600                 605

Ala Ser Val Glu Lys Ser Gln Val Gly Phe Ile Asp Tyr Ile Val His
        610                 615                 620

Pro Leu Trp Glu Thr Trp Ala Asp Leu Val Gln Pro Asp Ala Gln Asp
625                 630                 635                 640

Ile Leu Asp Thr Leu Glu Asp Asn Arg Asn Trp Tyr Gln Ser Met Ile
                645                 650                 655

Pro Gln Ser Pro Ser Pro Leu Asp Glu Gln Asn Arg Asp Cys Gln
            660                 665                 670

```
Gly Leu Met Glu Lys Phe Gln Phe Glu Leu Thr Leu Asp Glu Glu Asp
            675                 680                 685

Ser Glu Gly Pro Glu Lys Glu Gly Gly His Ser Tyr Phe Ser Ser
    690                 695                 700

Thr Lys Thr Leu Cys Val Ile Asp Pro Glu Asn Arg Asp Ser Leu Gly
705                 710                 715                 720

Glu Thr Asp Ile Asp Ile Ala Thr Glu Asp Lys Ser Pro Val Asp Thr
                725                 730                 735

(2) INFORMATION FOR SEQ ID NO:25:

(i) SEQUENCE CHARACTERISTICS:
        (A) LENGTH: 1273 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 2..504

(xi) SEQUENCE DESCRIPTION: SEQ ID NO:25:
```

```
G CGG CCG CAT TGC GTG GTG GCG GCG GCC GAG CCT CGC TTT GAG AGA        46
  Arg Pro His Cys Val Val Ala Ala Ala Glu Pro Arg Phe Glu Arg
   1               5                  10                  15

CAG AAT GGA CAG CAA ATT ATG GAT GAA CCT ATG GGA GAG GAG GAG ATT     94
Gln Asn Gly Gln Gln Ile Met Asp Glu Pro Met Gly Glu Glu Glu Ile
                20                  25                  30

AAC CCA CAA ACT GAA GAA GTC AGT ATC AAA GAA ATT GCA ATC ACA CAT    142
Asn Pro Gln Thr Glu Glu Val Ser Ile Lys Glu Ile Ala Ile Thr His
            35                  40                  45

CAT GTA AAG GAA GGA CAT GAA AAG GCA GAT CCT TCC CAG TTT GAA CTT    190
His Val Lys Glu Gly His Glu Lys Ala Asp Pro Ser Gln Phe Glu Leu
        50                  55                  60

TTA AAA GTA TTA GGG CAG GGA TCA TTT GGA AAG GTT TTC TTA GTT AAA    238
Leu Lys Val Leu Gly Gln Gly Ser Phe Gly Lys Val Phe Leu Val Lys
    65                  70                  75

AAA ATC TCA GGC TCT GAT GCT AGG CAG CTT TAT GCC ATG AAG GTA TTG    286
Lys Ile Ser Gly Ser Asp Ala Arg Gln Leu Tyr Ala Met Lys Val Leu
80                  85                  90                  95

AAG AAG GCC ACA CTG AAA GTT CGA GAC CGA GTT CGG ACA AAA ATG GAA    334
Lys Lys Ala Thr Leu Lys Val Arg Asp Arg Val Arg Thr Lys Met Glu
                100                 105                 110

CGT GAT ATC TTG GTA GAG GTT AAT CAT CCT TTT ATT GTC AAG TTG CAT    382
Arg Asp Ile Leu Val Glu Val Asn His Pro Phe Ile Val Lys Leu His
            115                 120                 125

TAT CTT TTC AAA CTG AAG GGA AGT TGT ATC TTA TTT GGA TTT TCT CAG    430
Tyr Leu Phe Lys Leu Lys Gly Ser Cys Ile Leu Phe Gly Phe Ser Gln
        130                 135                 140

GGG AGG AGA TTT GTT TAC ACG CTT ATC CAA AGA GGT GAT GTT CAC AGA    478
Gly Arg Arg Phe Val Tyr Thr Leu Ile Gln Arg Gly Asp Val His Arg
    145                 150                 155

AGA AGA TGT CAA ATT CTA CCT GGC TG AACTTGCACT TGCTTTAGAC            524
Arg Arg Cys Gln Ile Leu Pro Gly
160                 165

CATCTACTAG CCTGGGAATA ATTTATAGAG ACTTAAAACC AGAAAATATC TTCTTGATGA   584

AGAAGGTCAC ATCAAGTTAA CAGATTTCGG CCTAAGTAAA GAGTCTATTG ACCATGAAAA   644

GAAGGCATAT CTTTTTGTGG AACTGTGGAG TATATGGCTC CAGAAGTAGT TAATCGTCGA   704
```

```
GGTCATACTC AGAGTGCTGA CTGGTGGTCT TTTGGTGTGT TAATGTTTGA AATGCTTACT    764

GGTACCACTC CCTTTCCAAG GAAAAGATCG AAAAGAAACA ATGACTATGA TTCTTAAAGC    824

CAAAACTTGG AATGCCACAG TTTTTGAGTC CTGAAGCGCA GAGTCTTTTA CGAATGCTTT    884

TAAGCGAAAT CCTGCAAACA GATTAGGTGC AGGACCAGAT GGAGTTGAAG AAATTAAAAG    944

ACATTCATTT TTCTCAACGA TAGACTGGAA TAAACTGTAT AGAGAGAAAT TCATCCGCCA   1004

TTTAAACCTG CAACGGGCAG GCCTGAAGAT ACATTCTATT TTGATCCTGA GTTTACTGCA   1064

AAAACTCCCA AAGATTCACC TGGCATTCCA CCTAGTGCTA ATGCACATCA GCTTTTTCGG   1124

GGGTTTAGTT TTGTTGCTAT TACCTCAGAT GATGAAAGCC AAGCTATGCA GACAGTTGGT   1184

GTACATTCAA TTGTTCAGCA GTTACACAGG AACAGTATCA GTTTACTGAT GGATATGAAG   1244

TAAAAGAAGA TATTGGAGTT GGCTCCTAC                                    1273
```

(2) INFORMATION FOR SEQ ID NO:26:

(i) SEQUENCE CHARACTERISTICS:
        (A) LENGTH: 167 amino acids
        (B) TYPE: amino acid
        (D) TOPOLOGY: linear (ii) MOLECULE TYPE: protein (xi) SEQUENCE DESCRIPTION: SEQ ID NO:26:

```
Arg Pro His Cys Val Ala Ala Ala Glu Pro Arg Phe Glu Arg Gln
 1               5                  10                  15

Asn Gly Gln Gln Ile Met Asp Glu Pro Met Gly Glu Glu Ile Asn
             20                  25                  30

Pro Gln Thr Glu Glu Val Ser Ile Lys Glu Ile Ala Ile Thr His His
         35                  40                  45

Val Lys Glu Gly His Glu Lys Ala Asp Pro Ser Gln Phe Glu Leu Leu
     50                  55                  60

Lys Val Leu Gly Gln Gly Ser Phe Gly Lys Val Phe Leu Val Lys Lys
 65                  70                  75                  80

Ile Ser Gly Ser Asp Ala Arg Gln Leu Tyr Ala Met Lys Val Leu Lys
                 85                  90                  95

Lys Ala Thr Leu Lys Val Arg Asp Arg Val Arg Thr Lys Met Glu Arg
                100                 105                 110

Asp Ile Leu Val Glu Val Asn His Pro Phe Ile Val Lys Leu His Tyr
            115                 120                 125

Leu Phe Lys Leu Lys Gly Ser Cys Ile Leu Phe Gly Phe Ser Gln Gly
        130                 135                 140

Arg Arg Phe Val Tyr Thr Leu Ile Gln Arg Gly Asp Val His Arg Arg
145                 150                 155                 160

Arg Cys Gln Ile Leu Pro Gly
                165
```

(2) INFORMATION FOR SEQ ID NO:27:

(i) SEQUENCE CHARACTERISTICS:
        (A) LENGTH: 2384 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: join(1..1539, 1859..2383)

(xi) SEQUENCE DESCRIPTION: SEQ ID NO:27:

| | | | | | | | | | | | | | | | | |
|---|---|---|---|---|---|---|---|---|---|---|---|---|---|---|---|---|
| GCG | GCC | GCA | TTC | GGG | GAC | AGC | GGC | GGG | CGG | CTG | GGA | CGG | CGG | GTG | CGG | 48 |
| Ala | Ala | Ala | Phe | Gly | Asp | Ser | Gly | Gly | Arg | Leu | Gly | Arg | Arg | Val | Arg | |
| 1 | | | | 5 | | | | | 10 | | | | | 15 | | |
| CGG | GGC | CGA | GCC | CGC | ACG | ATG | CCT | CAC | TTC | ACC | GTG | GTG | CCA | GTG | GAC | 96 |
| Arg | Gly | Arg | Ala | Arg | Thr | Met | Pro | His | Phe | Thr | Val | Val | Pro | Val | Asp | |
| | | | 20 | | | | | 25 | | | | | 30 | | | |
| GGG | CCG | AGG | CGC | GGC | GAC | TAT | GAC | AAC | CTC | GAG | GGG | CTC | AGT | TGG | GTG | 144 |
| Gly | Pro | Arg | Arg | Gly | Asp | Tyr | Asp | Asn | Leu | Glu | Gly | Leu | Ser | Trp | Val | |
| | | 35 | | | | | 40 | | | | | 45 | | | | |
| GAC | TAC | GGG | GAG | CGC | GCC | GAG | CTG | GAT | GAC | TCG | GAC | GGA | CAT | GGC | AAC | 192 |
| Asp | Tyr | Gly | Glu | Arg | Ala | Glu | Leu | Asp | Asp | Ser | Asp | Gly | His | Gly | Asn | |
| | 50 | | | | | 55 | | | | | 60 | | | | | |
| CAC | AGA | GAG | AGC | AGC | CCT | TTT | CTT | TCC | CCC | TTG | GAG | GCT | TCC | AGA | GGA | 240 |
| His | Arg | Glu | Ser | Ser | Pro | Phe | Leu | Ser | Pro | Leu | Glu | Ala | Ser | Arg | Gly | |
| 65 | | | | | 70 | | | | | 75 | | | | | 80 | |
| ATT | GAC | TAC | TAT | GAC | AGG | AAC | CTG | GCA | CTG | TTT | GAG | GAA | GAG | CTG | GAC | 288 |
| Ile | Asp | Tyr | Tyr | Asp | Arg | Asn | Leu | Ala | Leu | Phe | Glu | Glu | Glu | Leu | Asp | |
| | | | | 85 | | | | | 90 | | | | | 95 | | |
| ATC | CGC | CCA | AAG | GTA | TCG | TCT | CTT | CTG | GGA | AAG | CTC | GTC | AGC | TAC | ACC | 336 |
| Ile | Arg | Pro | Lys | Val | Ser | Ser | Leu | Leu | Gly | Lys | Leu | Val | Ser | Tyr | Thr | |
| | | | 100 | | | | | 105 | | | | | 110 | | | |
| AAC | CTC | ACC | CAG | GGC | GCC | AAA | GAG | CAT | GAG | GAG | GCC | GAG | AGT | GGG | GAG | 384 |
| Asn | Leu | Thr | Gln | Gly | Ala | Lys | Glu | His | Glu | Glu | Ala | Glu | Ser | Gly | Glu | |
| | | 115 | | | | | 120 | | | | | 125 | | | | |
| GGC | ACC | CGC | CGG | AGG | GCA | GCC | GAG | GCA | CCC | AGC | ATG | GGC | ACC | CTC | ATG | 432 |
| Gly | Thr | Arg | Arg | Arg | Ala | Ala | Glu | Ala | Pro | Ser | Met | Gly | Thr | Leu | Met | |
| | 130 | | | | | 135 | | | | | 140 | | | | | |
| GGG | GTG | TAC | CTG | CCC | TGC | CTG | CAG | AAT | ATC | TTT | GGG | GTT | ATC | CTC | TTC | 480 |
| Gly | Val | Tyr | Leu | Pro | Cys | Leu | Gln | Asn | Ile | Phe | Gly | Val | Ile | Leu | Phe | |
| 145 | | | | | 150 | | | | | 155 | | | | | 160 | |
| CTG | CGG | CTG | ACC | TGG | ATG | GTG | GGC | ACA | GCA | GGT | GTG | CTA | CAG | GCC | CTC | 528 |
| Leu | Arg | Leu | Thr | Trp | Met | Val | Gly | Thr | Ala | Gly | Val | Leu | Gln | Ala | Leu | |
| | | | | 165 | | | | | 170 | | | | | 175 | | |
| CTC | ATC | GTG | CTT | ATC | TGC | TGC | TGT | TGT | ACC | CTG | CTG | ACG | GCC | ATC | TCC | 576 |
| Leu | Ile | Val | Leu | Ile | Cys | Cys | Cys | Cys | Thr | Leu | Leu | Thr | Ala | Ile | Ser | |
| | | | 180 | | | | | 185 | | | | | 190 | | | |
| ATG | AGT | GCC | ATC | GCC | ACC | AAC | GGT | GTG | GTT | CCA | GCT | GGG | GGC | TCC | TAT | 624 |
| Met | Ser | Ala | Ile | Ala | Thr | Asn | Gly | Val | Val | Pro | Ala | Gly | Gly | Ser | Tyr | |
| | | 195 | | | | | 200 | | | | | 205 | | | | |
| TTC | ATG | ATC | TCT | CGT | TCA | CTG | GGG | CCA | GAA | TTT | GGA | GGT | GCT | GTG | GGC | 672 |
| Phe | Met | Ile | Ser | Arg | Ser | Leu | Gly | Pro | Glu | Phe | Gly | Gly | Ala | Val | Gly | |
| | 210 | | | | | 215 | | | | | 220 | | | | | |
| CTG | TGC | TTC | TAC | CTG | GGA | ACA | ACA | TTC | GCA | GCA | GCC | ATG | TAC | ATC | CTG | 720 |
| Leu | Cys | Phe | Tyr | Leu | Gly | Thr | Thr | Phe | Ala | Ala | Ala | Met | Tyr | Ile | Leu | |
| 225 | | | | | 230 | | | | | 235 | | | | | 240 | |
| GGG | GCC | ATC | GAG | ATC | TTG | CTG | ACC | TAC | ATT | GCC | CCA | CCA | GCT | GCC | ATT | 768 |
| Gly | Ala | Ile | Glu | Ile | Leu | Leu | Thr | Tyr | Ile | Ala | Pro | Pro | Ala | Ala | Ile | |
| | | | | 245 | | | | | 250 | | | | | 255 | | |
| TTT | TAC | CCA | TCG | GGT | GCT | CAT | GAC | ACG | TCG | AAT | GCC | ACT | TTG | AAC | AAT | 816 |
| Phe | Tyr | Pro | Ser | Gly | Ala | His | Asp | Thr | Ser | Asn | Ala | Thr | Leu | Asn | Asn | |
| | | | 260 | | | | | 265 | | | | | 270 | | | |
| ATG | CGT | GTG | TAT | GGG | ACC | ATT | TTC | CTG | GCC | TTC | ATG | ACC | CTG | GTG | GTG | 864 |
| Met | Arg | Val | Tyr | Gly | Thr | Ile | Phe | Leu | Ala | Phe | Met | Thr | Leu | Val | Val | |
| | | 275 | | | | | 280 | | | | | 285 | | | | |
| TTT | GTG | GGG | GTC | AAG | TAT | GTG | AAC | AAA | TTT | GCC | TCG | CTC | TTC | CTG | GCC | 912 |
| Phe | Val | Gly | Val | Lys | Tyr | Val | Asn | Lys | Phe | Ala | Ser | Leu | Phe | Leu | Ala | |
| | 290 | | | | | 295 | | | | | 300 | | | | | |

```
TGT GTG ATC ATC TCC ATC CTC TCC ATC TAT GCT GGG GGC ATA AAG TCT              960
Cys Val Ile Ile Ser Ile Leu Ser Ile Tyr Ala Gly Gly Ile Lys Ser
305                 310                 315                 320

ATA TTT GAC CCT CCC GTG TTT CCG GTA TGC ATG CTG GGC AAC AGG ACC             1008
Ile Phe Asp Pro Pro Val Phe Pro Val Cys Met Leu Gly Asn Arg Thr
                325                 330                 335

CTG TCC CGG GAC CAG TTT GAC ATC TGT GCC AAG ACA GCT GTA GTG GAC             1056
Leu Ser Arg Asp Gln Phe Asp Ile Cys Ala Lys Thr Ala Val Val Asp
            340                 345                 350

AAT GAG ACA GTG GCC ACC CAG CTA TGG AGT TTC TTC TGC CAC AGC CCC             1104
Asn Glu Thr Val Ala Thr Gln Leu Trp Ser Phe Phe Cys His Ser Pro
        355                 360                 365

AAC CTT ACG ACC GAC TCC TGT GAC CCC TAC TTC ATG CTC AAC AAT GTG             1152
Asn Leu Thr Thr Asp Ser Cys Asp Pro Tyr Phe Met Leu Asn Asn Val
    370                 375                 380

ACC GAG ATC CCT GGC ATC CCC GGG GCA GCT GCT GGT GTG CTC CAG GAA             1200
Thr Glu Ile Pro Gly Ile Pro Gly Ala Ala Ala Gly Val Leu Gln Glu
385                 390                 395                 400

AAC CTG TGG AGC GCC TAC CTG GAG AAG GGT GAC ATC GTG GAG AAG CAT             1248
Asn Leu Trp Ser Ala Tyr Leu Glu Lys Gly Asp Ile Val Glu Lys His
                405                 410                 415

GGG CTG CCC TCC GCA GAT GCC CCG AGC CTG AAG GAG AGC CTG CCT CTG             1296
Gly Leu Pro Ser Ala Asp Ala Pro Ser Leu Lys Glu Ser Leu Pro Leu
            420                 425                 430

TAC GTG GTC GCT GAC ATC GCC ACA TCC TTC ACC GTG CTG GTC GGC ATC             1344
Tyr Val Val Ala Asp Ile Ala Thr Ser Phe Thr Val Leu Val Gly Ile
        435                 440                 445

TTC TTC CCT TCT GTA ACA GGT ATG GCG ATG GTG TCA GCA GGA ACT TGG             1392
Phe Phe Pro Ser Val Thr Gly Met Ala Met Val Ser Ala Gly Thr Trp
    450                 455                 460

TGG TGG GCA CAC TGG CCT GGC CTT CAC CCT GGG TCA TCG TCA TCG GCT             1440
Trp Trp Ala His Trp Pro Gly Leu His Pro Gly Ser Ser Ser Ser Ala
465                 470                 475                 480

CCT TCT TTT CAA CGT GTG GCG CTG GCC TCC AGA GCC TCA CAG GGG CAC             1488
Pro Ser Phe Gln Arg Val Ala Leu Ala Ser Arg Ala Ser Gln Gly His
                485                 490                 495

CAC GCC TAT TGC AGG CCA TTG CCA AGG ACA ACA TCA TCC CCT TCC TCC             1536
His Ala Tyr Cys Arg Pro Leu Pro Arg Thr Thr Ser Ser Pro Ser Ser
            500                 505                 510

GGG TGAGCCCCTC TGCACTCCCC CATGGCCTGG CTGCTCCCAG GCCCTCGCCC                  1589
Gly

GGCTGGGGAG AGAGATAGGG AACACAGATG CAGCACGTCC TGCCCTTATT GCCCCCGGGC           1649

CAGGCGGCCA TCCATGAGGA GCTACTGAGA AGTGCCCTGG GCCTGGCACT CACCTGGGCC           1709

TGGAGCTGCC TGGACCCAGA ATCTTCATGG CCTGTTTAGG GCTCATCCAA AGGAGAGAGG           1769

CCTGGTGAGG TGGAATCAGG GAGACTGGTG ACACCCATAG GGATAGACAC AGGGGCGGCC           1829

TGAGCCCCCA AGGCGGGCCC TGGGGGTGA GGG AGG CCA GGC TGG GGT CTG GGG             1882
                                Gly Arg Pro Gly Trp Gly Leu Gly
                                    515                 520

CCC AAG GTG TGG AAT GGG GGT GAC AGG ACC CAG CTT CCT TCC TGG TGC             1930
Pro Lys Val Trp Asn Gly Gly Asp Arg Thr Gln Leu Pro Ser Trp Cys
                525                 530                 535

ACA CAG GTG TTT GGC CAC GGG AAG GTG AAT GGT GAA CCC ACA TGG GCA             1978
Thr Gln Val Phe Gly His Gly Lys Val Asn Gly Glu Pro Thr Trp Ala
            540                 545                 550

CTC CTC CTG ACG GCA CTC ATC GCC GAG CTG GGC ATC CTC ATC GCC TCC             2026
Leu Leu Leu Thr Ala Leu Ile Ala Glu Leu Gly Ile Leu Ile Ala Ser
        555                 560                 565
```

```
CTC GAC ATG GTG GCC CCC ATC TTA TCC ATG TTC TTT CTG ATG TGC TAC    2074
Leu Asp Met Val Ala Pro Ile Leu Ser Met Phe Phe Leu Met Cys Tyr
570                 575                 580                 585

CTG TTC GTG AAC CTC GCC TGT GCG GTG CAG ACA CTC CTG AGG ACC CCC    2122
Leu Phe Val Asn Leu Ala Cys Ala Val Gln Thr Leu Leu Arg Thr Pro
                590                 595                 600

AAC TGG CGG CCC CGG TTC AAG TAC TAT CAC TGG GCG CTG TCC TTC CTG    2170
Asn Trp Arg Pro Arg Phe Lys Tyr Tyr His Trp Ala Leu Ser Phe Leu
                605                 610                 615

GGC ATG AGT CTC TGC CTG GCC CTT ATG TTT GTC TCC TCC TGG TAC TAT    2218
Gly Met Ser Leu Cys Leu Ala Leu Met Phe Val Ser Ser Trp Tyr Tyr
                620                 625                 630

GCC CTG GTG GCC ATG CTC ATC GCC GGC ATG ATC TAC AAA TAC ATC GAG    2266
Ala Leu Val Ala Met Leu Ile Ala Gly Met Ile Tyr Lys Tyr Ile Glu
635                 640                 645

TAC CAA GGG GCT GAG AAG GAG TGG GGT GAC GGG ATC CGA GGC CTG TCC    2314
Tyr Gln Gly Ala Glu Lys Glu Trp Gly Asp Gly Ile Arg Gly Leu Ser
650                 655                 660                 665

CTG AGC GCT GCC CGC TAC GCG CTG TTG CGG CTG GAG GAG GGG CCT CCT    2362
Leu Ser Ala Ala Arg Tyr Ala Leu Leu Arg Leu Glu Glu Gly Pro Pro
                670                 675                 680

CAC ACC AAG AAC TGG CGG CCG C                                     2384
His Thr Lys Asn Trp Arg Pro
            685
```

(2) INFORMATION FOR SEQ ID NO:28:

(i) SEQUENCE CHARACTERISTICS:
(A) LENGTH: 688 amino acids
(B) TYPE: amino acid
(D) TOPOLOGY: linear (ii) MOLECULE TYPE: protein (xi) SEQUENCE DESCRIPTION: SEQ ID NO:28:

```
Ala Ala Ala Phe Gly Asp Ser Gly Gly Arg Leu Gly Arg Arg Val Arg
1               5                   10                  15

Arg Gly Arg Ala Arg Thr Met Pro His Phe Thr Val Val Pro Val Asp
                20                  25                  30

Gly Pro Arg Arg Gly Asp Tyr Asp Asn Leu Glu Gly Leu Ser Trp Val
            35                  40                  45

Asp Tyr Gly Glu Arg Ala Glu Leu Asp Asp Ser Asp Gly His Gly Asn
50                  55                  60

His Arg Glu Ser Ser Pro Phe Leu Ser Pro Leu Glu Ala Ser Arg Gly
65                  70                  75                  80

Ile Asp Tyr Tyr Asp Arg Asn Leu Ala Leu Phe Glu Glu Glu Leu Asp
                85                  90                  95

Ile Arg Pro Lys Val Ser Ser Leu Leu Gly Lys Leu Val Ser Tyr Thr
            100                 105                 110

Asn Leu Thr Gln Gly Ala Lys Glu His Glu Glu Ala Glu Ser Gly Glu
        115                 120                 125

Gly Thr Arg Arg Arg Ala Ala Glu Ala Pro Ser Met Gly Thr Leu Met
130                 135                 140

Gly Val Tyr Leu Pro Cys Leu Gln Asn Ile Phe Gly Val Ile Leu Phe
145                 150                 155                 160

Leu Arg Leu Thr Trp Met Val Gly Thr Ala Gly Val Leu Gln Ala Leu
                165                 170                 175

Leu Ile Val Leu Ile Cys Cys Cys Thr Leu Leu Thr Ala Ile Ser
            180                 185                 190
```

-continued

```
Met Ser Ala Ile Ala Thr Asn Gly Val Val Pro Ala Gly Gly Ser Tyr
            195                 200                 205

Phe Met Ile Ser Arg Ser Leu Gly Pro Glu Phe Gly Gly Ala Val Gly
            210                 215                 220

Leu Cys Phe Tyr Leu Gly Thr Thr Phe Ala Ala Ala Met Tyr Ile Leu
225                 230                 235                 240

Gly Ala Ile Glu Ile Leu Leu Thr Tyr Ile Ala Pro Pro Ala Ala Ile
                245                 250                 255

Phe Tyr Pro Ser Gly Ala His Asp Thr Ser Asn Ala Thr Leu Asn Asn
            260                 265                 270

Met Arg Val Tyr Gly Thr Ile Phe Leu Ala Phe Met Thr Leu Val Val
            275                 280                 285

Phe Val Gly Val Lys Tyr Val Asn Lys Phe Ala Ser Leu Phe Leu Ala
            290                 295                 300

Cys Val Ile Ile Ser Ile Leu Ser Ile Tyr Ala Gly Gly Ile Lys Ser
305                 310                 315                 320

Ile Phe Asp Pro Pro Val Phe Pro Val Cys Met Leu Gly Asn Arg Thr
                325                 330                 335

Leu Ser Arg Asp Gln Phe Asp Ile Cys Ala Lys Thr Ala Val Val Asp
            340                 345                 350

Asn Glu Thr Val Ala Thr Gln Leu Trp Ser Phe Phe Cys His Ser Pro
            355                 360                 365

Asn Leu Thr Thr Asp Ser Cys Asp Pro Tyr Phe Met Leu Asn Asn Val
            370                 375                 380

Thr Glu Ile Pro Gly Ile Pro Gly Ala Ala Gly Val Leu Gln Glu
385                 390                 395                 400

Asn Leu Trp Ser Ala Tyr Leu Glu Lys Gly Asp Ile Val Glu Lys His
                405                 410                 415

Gly Leu Pro Ser Ala Asp Ala Pro Ser Leu Lys Glu Ser Leu Pro Leu
            420                 425                 430

Tyr Val Val Ala Asp Ile Ala Thr Ser Phe Thr Val Leu Val Gly Ile
            435                 440                 445

Phe Phe Pro Ser Val Thr Gly Met Ala Met Val Ser Ala Gly Thr Trp
450                 455                 460

Trp Trp Ala His Trp Pro Gly Leu His Pro Gly Ser Ser Ser Ser Ala
465                 470                 475                 480

Pro Ser Phe Gln Arg Val Ala Leu Ala Ser Arg Ala Ser Gln Gly His
            485                 490                 495

His Ala Tyr Cys Arg Pro Leu Pro Arg Thr Thr Ser Ser Pro Ser Ser
            500                 505                 510

Gly Gly Arg Pro Gly Trp Gly Leu Gly Pro Lys Val Trp Asn Gly Gly
            515                 520                 525

Asp Arg Thr Gln Leu Pro Ser Trp Cys Thr Gln Val Phe Gly His Gly
            530                 535                 540

Lys Val Asn Gly Glu Pro Thr Trp Ala Leu Leu Leu Thr Ala Leu Ile
545                 550                 555                 560

Ala Glu Leu Gly Ile Leu Ile Ala Ser Leu Asp Met Val Ala Pro Ile
                565                 570                 575

Leu Ser Met Phe Phe Leu Met Cys Tyr Leu Phe Val Asn Leu Ala Cys
            580                 585                 590

Ala Val Gln Thr Leu Leu Arg Thr Pro Asn Trp Arg Pro Arg Phe Lys
            595                 600                 605
```

```
Tyr Tyr His Trp Ala Leu Ser Phe Leu Gly Met Ser Leu Cys Leu Ala
    610                 615                 620

Leu Met Phe Val Ser Ser Trp Tyr Tyr Ala Leu Val Ala Met Leu Ile
625                 630                 635                 640

Ala Gly Met Ile Tyr Lys Tyr Ile Glu Tyr Gln Gly Ala Glu Lys Glu
                    645                 650                 655

Trp Gly Asp Gly Ile Arg Gly Leu Ser Leu Ser Ala Ala Arg Tyr Ala
                660                 665                 670

Leu Leu Arg Leu Glu Glu Gly Pro Pro His Thr Lys Asn Trp Arg Pro
            675                 680                 685

(2) INFORMATION FOR SEQ ID NO:29:

(i) SEQUENCE CHARACTERISTICS:
        (A) LENGTH: 1675 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 492..1330

(xi) SEQUENCE DESCRIPTION: SEQ ID NO:29:

AAGCTTGCGG CCGCATTGCG AGAACGAGAA CGGGAGCGAG AGAGAGAGCG AGAGAGGGAA      60

CGGGAGCGAG AAAGAGAAAA AGACAAAAAA CGGGACCGAG AAGAAGATGA AGAAGATGCA     120

TACGAACGAA GAAAACTTGA AGAAAACTC CGAGAGAAAA AAGCTGCTTA TCAAGAGCGC      180

CTTAAGAATT GGGAAATCAG AGAACGAAAG AAAACCCGGG AATATGAGAA AGAAGCTGAA     240

AGAGAAGAAG AAAGAAGAAG AGAAATGGCC AAAGAAGCTA AACGACTAAA AGAATTCTTA     300

GAAGACTATG ATGATGATAG AGATGACCCC AAATATTACA GAGGAAGTGC TCTTCAGAAA     360

AGGTTGCGTG ATAGAGAAAA GGAAATGGAA GCAGATGAAC GAGATAGGAA GAGAGAGAAG     420

GAGGAGCTTG AGGAAATCAG GCAGCGCTTC TGGCAGAAGG GCATCCAGAT CCAGATGCAG     480

AGCTCCAGAG G ATG GAA CAA GAG GCT GAG AGG CGC AGG CAG CCA CAA ATA      530
             Met Glu Gln Glu Ala Glu Arg Arg Arg Gln Pro Gln Ile
               1               5                  10

AAG CAA GAG CCA GAA TCA GAA GAG GAG GAA GAA GAA AAG CAA GAA AAA       578
Lys Gln Glu Pro Glu Ser Glu Glu Glu Glu Glu Lys Gln Glu Lys
 15                  20                  25

GAA GAA AAA CGA GAA GAA CCC ATG GAA GAG GAA GAG GAG CCA GAG CAA       626
Glu Glu Lys Arg Glu Glu Pro Met Glu Glu Glu Glu Pro Glu Gln
 30                  35                  40                  45

AAG CCT TGT CTG AAA CCT ACT CTG AGG CCC ATC AGC TCT GCT CCA TCT       674
Lys Pro Cys Leu Lys Pro Thr Leu Arg Pro Ile Ser Ser Ala Pro Ser
                 50                  55                  60

GTT TCC TCT GCC AGT GGC AAT GCA ACA CCT AAC ACT CCT GGG GAT GAG       722
Val Ser Ser Ala Ser Gly Asn Ala Thr Pro Asn Thr Pro Gly Asp Glu
             65                  70                  75

TCT CCC TGT GGT ATT ATT ATT CCT CAT GAA AAC TCA CCA GAT CAA CAG       770
Ser Pro Cys Gly Ile Ile Ile Pro His Glu Asn Ser Pro Asp Gln Gln
         80                  85                  90

CAA CCT GAG GAG CAT AGG CCA AAA ATA GGA CTA AGT CTT AAA CTG GGT       818
Gln Pro Glu Glu His Arg Pro Lys Ile Gly Leu Ser Leu Lys Leu Gly
     95                 100                 105

GCT TCC AAT AGT CCT GGT CAG CCT AAT TCT GTG AAG AGA AAG AAA CTA       866
Ala Ser Asn Ser Pro Gly Gln Pro Asn Ser Val Lys Arg Lys Lys Leu
110                 115                 120                 125
```

```
CCT GTA GAT AGT GTC TTT AAC AAA TTT GAG GAT GAA GAC AGT GAT GAC    914
Pro Val Asp Ser Val Phe Asn Lys Phe Glu Asp Glu Asp Ser Asp Asp
            130                 135                 140

GTA CCC CGA AAA AGG AAA CTG GTT CCC TTG GAT TAT GGT GAA GAT GAT    962
Val Pro Arg Lys Arg Lys Leu Val Pro Leu Asp Tyr Gly Glu Asp Asp
            145                 150                 155

AAA AAT GCA ACC AAA GGC ACT GTA AAC ACT GAA GAA AAG CGT AAA CAC   1010
Lys Asn Ala Thr Lys Gly Thr Val Asn Thr Glu Glu Lys Arg Lys His
            160                 165                 170

ATT AAG AGT CTC ATT GAG AAA ATC CCT ACA GCC AAA CCT GAG CTC TTC   1058
Ile Lys Ser Leu Ile Glu Lys Ile Pro Thr Ala Lys Pro Glu Leu Phe
            175                 180                 185

GCT TAT CCC CTG GAT TGG TCT ATT GTG GAT TCT ATA CTG ATG GAA CGT   1106
Ala Tyr Pro Leu Asp Trp Ser Ile Val Asp Ser Ile Leu Met Glu Arg
190                 195                 200                 205

CGA ATT AGA CCA TGG ATT AAT AAG AAA ATC ATA GAA TAT ATA GGT GAA   1154
Arg Ile Arg Pro Trp Ile Asn Lys Lys Ile Ile Glu Tyr Ile Gly Glu
            210                 215                 220

GAA GAA GCT ACA TTA GTT GAT TTT GTT TGT TCT AAG GTT ATG GCT CAT   1202
Glu Glu Ala Thr Leu Val Asp Phe Val Cys Ser Lys Val Met Ala His
            225                 230                 235

AGT TCA CCC CAG AGC ATT TTA GAT GAT GTT GCC ATG GTA CTT GAT GAA   1250
Ser Ser Pro Gln Ser Ile Leu Asp Asp Val Ala Met Val Leu Asp Glu
            240                 245                 250

GAA GCA GAA GTT TTT ATA GTC AAA ATG TGG AGA TTA TTG ATA TAT GAA   1298
Glu Ala Glu Val Phe Ile Val Lys Met Trp Arg Leu Leu Ile Tyr Glu
            255                 260                 265

ACA GAA GCC AAG AAA ATT GGT CTT GTG AAG TA AAACTTTTTA TATTTAGAGT  1350
Thr Glu Ala Lys Lys Ile Gly Leu Val Lys
270                 275

TCCATTTCAG ATTTCTTCTT TGCCACCCTT TTAAGGACTT TGAATTTTTC TTTGTCTTTG 1410

AAGACATTGT GAGATCTGTA ATTTTTTTTT TTTGTAGAAA ATGTGAATTT TTTGGTCCTC 1470

TAATTTGTTG TTGCCCTGTG TACTCCCTTG GTTGTAAAGT CATCTGAATC CTTGGTTCTC 1530

TTTATACTCA CCAGGTACAA ATTACTGGTA TGTTTTATAA GCCGCAGCTA CTGTACACAG 1590

CCTATCTGAT ATAATCTTGT TCTGCTGATT TGTTTCTTGT AAATATTAAA ACGACTCCCC 1650

AATTAAAAAA AAAAAATGCG GCCGC                                      1675
```

(2) INFORMATION FOR SEQ ID NO:30:

(i) SEQUENCE CHARACTERISTICS:
        (A) LENGTH: 279 amino acids
        (B) TYPE: amino acid
        (D) TOPOLOGY: linear (ii) MOLECULE TYPE: protein (xi) SEQUENCE DESCRIPTION: SEQ ID NO:30:

```
Met Glu Gln Glu Ala Glu Arg Arg Gln Pro Gln Ile Lys Gln Glu
1               5                   10                  15

Pro Glu Ser Glu Glu Glu Glu Lys Gln Glu Lys Glu Glu Lys
            20                  25                  30

Arg Glu Glu Pro Met Glu Glu Glu Glu Pro Glu Gln Lys Pro Cys
            35                  40                  45

Leu Lys Pro Thr Leu Arg Pro Ile Ser Ser Ala Pro Ser Val Ser Ser
        50                  55                  60

Ala Ser Gly Asn Ala Thr Pro Asn Thr Pro Gly Asp Glu Ser Pro Cys
65                  70                  75                  80
```

```
Gly Ile Ile Ile Pro His Glu Asn Ser Pro Asp Gln Gln Pro Glu
                85                  90                  95

Glu His Arg Pro Lys Ile Gly Leu Ser Leu Lys Leu Gly Ala Ser Asn
            100                 105                 110

Ser Pro Gly Gln Pro Asn Ser Val Lys Arg Lys Lys Leu Pro Val Asp
        115                 120                 125

Ser Val Phe Asn Lys Phe Glu Asp Glu Asp Ser Asp Asp Val Pro Arg
    130                 135                 140

Lys Arg Lys Leu Val Pro Leu Asp Tyr Gly Glu Asp Asp Lys Asn Ala
145                 150                 155                 160

Thr Lys Gly Thr Val Asn Thr Glu Glu Lys Arg Lys His Ile Lys Ser
                165                 170                 175

Leu Ile Glu Lys Ile Pro Thr Ala Lys Pro Glu Leu Phe Ala Tyr Pro
            180                 185                 190

Leu Asp Trp Ser Ile Val Asp Ser Ile Leu Met Glu Arg Arg Ile Arg
        195                 200                 205

Pro Trp Ile Asn Lys Lys Ile Ile Glu Tyr Ile Gly Glu Glu Glu Ala
    210                 215                 220

Thr Leu Val Asp Phe Val Cys Ser Lys Val Met Ala His Ser Ser Pro
225                 230                 235                 240

Gln Ser Ile Leu Asp Asp Val Ala Met Val Leu Asp Glu Glu Ala Glu
                245                 250                 255

Val Phe Ile Val Lys Met Trp Arg Leu Leu Ile Tyr Glu Thr Glu Ala
            260                 265                 270

Lys Lys Ile Gly Leu Val Lys
        275

(2) INFORMATION FOR SEQ ID NO:31:

(i) SEQUENCE CHARACTERISTICS:
        (A) LENGTH: 3073 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..1111

(xi) SEQUENCE DESCRIPTION: SEQ ID NO:31:

GC GGC CGC GCG CCG CAT TCG GAG AGC GGA CCC CAG AGA GCC CTG AGC           47
   Gly Arg Ala Pro His Ser Glu Ser Gly Pro Gln Arg Ala Leu Ser
    1               5                   10                  15

AGC CCC ACC GCC GCC GCC GGC CTA GTT ACC ATC ACA CCC CGG GAG GAG         95
Ser Pro Thr Ala Ala Ala Gly Leu Val Thr Ile Thr Pro Arg Glu Glu
                20                  25                  30

CCG CAG CTG CCG CAG CCG GCC CCA GTC ACC ATC ACC GCA ACC ATG AGC         143
Pro Gln Leu Pro Gln Pro Ala Pro Val Thr Ile Thr Ala Thr Met Ser
            35                  40                  45

AGC GAG GCC GAG ACC CAG CAG CCG CCC GCC GCC CCC CCC GCC GCC CCC         191
Ser Glu Ala Glu Thr Gln Gln Pro Pro Ala Ala Pro Pro Ala Ala Pro
        50                  55                  60

GCC CTC AGC GCC GCC GAC ACC AAG CCC GGC ACT ACG GGC AGC GGC GCA         239
Ala Leu Ser Ala Ala Asp Thr Lys Pro Gly Thr Thr Gly Ser Gly Ala
    65                  70                  75

GGG AGC GGT GGC CCG GGC GGC CTC ACA TCG GCG GCG CCT GCC GGC GGG         287
Gly Ser Gly Gly Pro Gly Gly Leu Thr Ser Ala Ala Pro Ala Gly Gly
```

```
           80                  85                    90                    95
GAC AAG AAG GTC ATC GCA ACG AAG GTT TTG GGA ACA GTA AAA TGG TTC              335
Asp Lys Lys Val Ile Ala Thr Lys Val Leu Gly Thr Val Lys Trp Phe
                        100                 105                 110

AAT GTA AGG AAC GGA TAT GGT TTC ATC AAC AGG AAT GAC ACC AAG GAA              383
Asn Val Arg Asn Gly Tyr Gly Phe Ile Asn Arg Asn Asp Thr Lys Glu
                115                 120                 125

GAT GTA TTT GTA CAC CAG ACT GCC ATA AAG AAG AAT AAC CCC AGG AAG              431
Asp Val Phe Val His Gln Thr Ala Ile Lys Lys Asn Asn Pro Arg Lys
        130                 135                 140

TAC CTT CGC AGT GTA GGA GAT GGA GAG ACT GTG GAG TTT GAT GTT GTT              479
Tyr Leu Arg Ser Val Gly Asp Gly Glu Thr Val Glu Phe Asp Val Val
    145                 150                 155

GAA GGA GAA AAG GGT GCG GAG GCA GCA AAT GTT ACA GGT CCT GGT GGT              527
Glu Gly Glu Lys Gly Ala Glu Ala Ala Asn Val Thr Gly Pro Gly Gly
160                 165                 170                 175

GTT CCA GTT CAA GGC AGT AAA TAT GCA GCA GAC CGT AAC CAT TAT AGA              575
Val Pro Val Gln Gly Ser Lys Tyr Ala Ala Asp Arg Asn His Tyr Arg
                180                 185                 190

CGC TAT CCA CGT CGT AGG GGT CCT CCA CGC AAT TAC CAG CAA AAT TAC              623
Arg Tyr Pro Arg Arg Gly Pro Pro Arg Asn Tyr Gln Gln Asn Tyr
            195                 200                 205

CAG AAT AGT GAG AGT GGG GAA AAG AAC GAG GGA TCG GAG AGT GCT CCC              671
Gln Asn Ser Glu Ser Gly Glu Lys Asn Glu Gly Ser Glu Ser Ala Pro
        210                 215                 220

GAA GGC CAG GCC CAA CAA CGC CGG CCC TAC CGC AGG CGA AGG TTC CCA              719
Glu Gly Gln Ala Gln Gln Arg Arg Pro Tyr Arg Arg Arg Phe Pro
    225                 230                 235

CCT TAC TAC ATG CGG AGA CCC TAT GGG CGT CGA CCA CAG TAT TCC AAC              767
Pro Tyr Tyr Met Arg Arg Pro Tyr Gly Arg Arg Pro Gln Tyr Ser Asn
240                 245                 250                 255

CCT CCT GTG CAG GGA GAA GTG ATG GAG GGT GCT GAC AAC CAG GGT GCA              815
Pro Pro Val Gln Gly Glu Val Met Glu Gly Ala Asp Asn Gln Gly Ala
                260                 265                 270

GGA GAA CAA GGT AGA CCA GTG AGG CAG AAT ATG TAT CGG GGA TAT AGA              863
Gly Glu Gln Gly Arg Pro Val Arg Gln Asn Met Tyr Arg Gly Tyr Arg
            275                 280                 285

CCA CGA TTC CGC AGG GGC CCT CCT CGC CAA AGA CAG CCT AGA GAG GAC              911
Pro Arg Phe Arg Arg Gly Pro Pro Arg Gln Arg Gln Pro Arg Glu Asp
        290                 295                 300

GGC AAT GAA GAA GAT AAA GAA AAT CAA GGA GAT GAG ACC CAA GGT CAG              959
Gly Asn Glu Glu Asp Lys Glu Asn Gln Gly Asp Glu Thr Gln Gly Gln
    305                 310                 315

CAG CCA CCT CAA CGT CGG TAC CGC CGC AAC TTC AAT TAC CGA CGC AGA              1007
Gln Pro Pro Gln Arg Arg Tyr Arg Arg Asn Phe Asn Tyr Arg Arg Arg
320                 325                 330                 335

CGC CCA GAA AAC CCT AAA CCA CAA GAT GGC AAA GAG ACA AAA GCA GCC              1055
Arg Pro Glu Asn Pro Lys Pro Gln Asp Gly Lys Glu Thr Lys Ala Ala
                340                 345                 350

GAT CCA CCA GCT GAG AAT TCG TCC GCT CCC GAG GCT GAG CAG GGC GGG              1103
Asp Pro Pro Ala Glu Asn Ser Ser Ala Pro Glu Ala Glu Gln Gly Gly
            355                 360                 365

GCT GAG TA AATGCCGGCT TACCATCTCT ACCATCATCC GGTTTAGTCA TCCAACAAGA           1161
Ala Glu

AGAAATATGA AATTCCAGCA ATAAGAAATG AACAAAGAT TGGAGCTGAA GACCTAAAGT            1221

GCTTGCTTTT TGCCCGTTGA CCAGATAAAT AGAACTATCT GCATTATCTA TGCAGCATGG           1281

GGTTTTTATT ATTTTTACCT AAAGACGTCT CTTTTTGGTA ATAACAAACG TGTTTTTTAA           1341
```

```
AAAAGCCTGG TTTTTCTCAA TACGCCTTTA AAGGTTTTTA AATTGTTTCA TATCTGGTCA    1401

AGTTGAGATT TTTAAGAACT TCATTTTTAA TTTGTAATAA AAGTTTACAA CTTGATTTTT    1461

TCAAAAAAGT CAACAAACTG CAAGCACCTG TTAATAAAGG TCTTAAATAA TTGTCTTTGT    1521

GTAAAAAAAA AAAAAAAAAA AAAAAAAAAA AAAAAAAAAG CTTGGTATTC ATTACTTCAT    1581

GTATATCAAG CACAGCAGTA AAACAAAAAC CCATGTATTT AACTTTTTTT TAGGATTTTT    1641

GCTTTTGTGA TTTTTTTTTT TTTTTTTTTG ATACTTGCCT AACATGCATG TGCTGTAAAA    1701

ATAGTTAACA GGGAAATAAC TTGAGATGAT GGCTAGCTTT GTTTAATGTC TTATGAAATT    1761

TTCATGAACA ATCCAAGCAT AATTGTTAAG AACACGTGTA TTAAATTCAT GTAAGTGGAA    1821

TAAAAGTTTT ATGAATGGAC TTTTCAACTA CTTTCTCTAC AGCTTTTCAT GTAAATTAGT    1881

CTTGGTTCTG AAACTTCTCT AAAGGAAATT GTACATTTTT TGAAATTTAT TCCTTATTCC    1941

CTCTTGGCAG CTAATGGGCT CTTACCAAGT TTAAACACAA AATTTATCAT AACAAAAATA    2001

CTACTAATAT AACTACTGTT TCCATGTCCC ATGATCCCCT CTCTTCCTCC CCACCCTGAA    2061

AAAAATGAGT TCCTATTTTT TCTGGGAGAG GGGGGGATTG ATTAGAAAAA AATGTAGTGT    2121

GTTCCATTTA AAATTTTGGC ATATGGCATT TTCTAACTTA GGAAGCCACA ATGTTCTTGG    2181

CCCATCATGA CATTGGGTAG CATTAACTGT AAGTTTTGTG CTTCCAAATC ACTTTTTGGT    2241

TTTTAAGAAT TTCTTGATAC TCTTATAGCC TGCCTTCAAT TTTGATCCTT TATTCTTTCT    2301

ATTTGTCAGG TGCACAAGAT TACCTTCCTG TTTTAGCCTT CTGTCTTGTC ACCAACCATT    2361

CTTACTTGGT GGCCATGTAC TTGGAAAAAG GCCGCATGAT CTTTCTGGCT CCACTCAGTG    2421

TCTAAGGCAC CCTGCTTCCT TTGCTTGCAT CCCACAGACT ATTTCCCTCA TCCTATTTAC    2481

TGCAGCAAAT CTCTCCTTAG TTGATGAGAC TGTGTTTATC TCCCTTTAAA ACCCTACCTA    2541

TCCTGAATGG TCTGTCATTG TCTGCCTTTA AAATCCTTCC TCTTTCTTCC TCCTCTATTC    2601

TCTAAATAAT GATGGGCTA  AGTTATACCC AAAGCTCACT TTACAAAATA TTTCCTCAGT    2661

ACTTTGCAGA AAACACCAAA CAAAAATGCC ATTTTAAAAA AGGTGTATTT TTTCTTTTAG    2721

AATGTAAGCT CCTCAAGAGC AGGGACAATG TTTTCTGTAT GTTCTATTGT GCCTAGTACA    2781

CTGTAAATGC TCAATGAATA TTATCCCTAA TACCTGCCAC CCCACTCTTA ATCAGTGGTG    2841

GAAGAACGGT CTCAGAACTG TTTGTTTCAA TTGGCCATTT AAGTTTAGTA GTAAAAGACT    2901

GGTTAATGAT AACAATGCAT CGTAAAACCT TCAGAAGGAA AGGAGAATGT TTTGTGGACC    2961

ACTTTGGTTT TCTTTTTTGC GTGTGGCAGT TTTAAGTTAT TAGTTTTTAA AATCAGTACT    3021

TTTTAATGGA AACAACTTGA CCAAAAATTT GTCACAGAAT TTTGGCGGCC GC           3073
```

(2) INFORMATION FOR SEQ ID NO:32:

(i) SEQUENCE CHARACTERISTICS:
        (A) LENGTH: 369 amino acids
        (B) TYPE: amino acid
        (D) TOPOLOGY: linear (ii) MOLECULE TYPE: protein (xi) SEQUENCE DESCRIPTION: SEQ ID NO:32:

```
Gly Arg Ala Pro His Ser Glu Ser Gly Pro Gln Arg Ala Leu Ser Ser
 1               5                  10                  15

Pro Thr Ala Ala Ala Gly Leu Val Thr Ile Thr Pro Arg Glu Glu Pro
             20                  25                  30

Gln Leu Pro Gln Pro Ala Pro Val Thr Ile Thr Ala Thr Met Ser Ser
         35                  40                  45
```

-continued

```
Glu Ala Glu Thr Gln Gln Pro Pro Ala Pro Pro Ala Ala Pro Ala
 50                  55                  60

Leu Ser Ala Ala Asp Thr Lys Pro Gly Thr Thr Gly Ser Gly Ala Gly
 65                  70                  75                  80

Ser Gly Gly Pro Gly Gly Leu Thr Ser Ala Ala Pro Ala Gly Gly Asp
                 85                  90                  95

Lys Lys Val Ile Ala Thr Lys Val Leu Gly Thr Val Lys Trp Phe Asn
                100                 105                 110

Val Arg Asn Gly Tyr Gly Phe Ile Asn Arg Asn Asp Thr Lys Glu Asp
                115                 120                 125

Val Phe Val His Gln Thr Ala Ile Lys Lys Asn Asn Pro Arg Lys Tyr
             130                 135                 140

Leu Arg Ser Val Gly Asp Gly Glu Thr Val Glu Phe Asp Val Val Glu
145                 150                 155                 160

Gly Glu Lys Gly Ala Glu Ala Ala Asn Val Thr Gly Pro Gly Gly Val
                165                 170                 175

Pro Val Gln Gly Ser Lys Tyr Ala Ala Asp Arg Asn His Tyr Arg Arg
                180                 185                 190

Tyr Pro Arg Arg Arg Gly Pro Pro Arg Asn Tyr Gln Gln Asn Tyr Gln
                195                 200                 205

Asn Ser Glu Ser Gly Glu Lys Asn Glu Gly Ser Glu Ser Ala Pro Glu
210                 215                 220

Gly Gln Ala Gln Gln Arg Arg Pro Tyr Arg Arg Arg Phe Pro Pro
225                 230                 235                 240

Tyr Tyr Met Arg Arg Pro Tyr Gly Arg Arg Pro Gln Tyr Ser Asn Pro
                245                 250                 255

Pro Val Gln Gly Glu Val Met Glu Gly Ala Asp Asn Gln Gly Ala Gly
                260                 265                 270

Glu Gln Gly Arg Pro Val Arg Gln Asn Met Tyr Arg Gly Tyr Arg Pro
                275                 280                 285

Arg Phe Arg Arg Gly Pro Pro Arg Gln Arg Gln Pro Arg Glu Asp Gly
                290                 295                 300

Asn Glu Glu Asp Lys Glu Asn Gln Gly Asp Glu Thr Gln Gly Gln Gln
305                 310                 315                 320

Pro Pro Gln Arg Arg Tyr Arg Arg Asn Phe Asn Tyr Arg Arg Arg Arg
                325                 330                 335

Pro Glu Asn Pro Lys Pro Gln Asp Gly Lys Glu Thr Lys Ala Ala Asp
                340                 345                 350

Pro Pro Ala Glu Asn Ser Ser Ala Pro Glu Ala Glu Gln Gly Gly Ala
                355                 360                 365

Glu
```

(2) INFORMATION FOR SEQ ID NO:33:

(i) SEQUENCE CHARACTERISTICS:
        (A) LENGTH: 1811 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

```
GAATTCCTGG TAGGGCCAGC CCACCATGGG GGCCAAGACC TGCACAGGAC AAGGGCCACC     60

TGGCCTTTCA GTTACTTGAG TTTGGAGTCA GAAAGCAAGA CCAGGAAGCA AATAGCAGCT    120
```

-continued

```
CAGGAAATCC CACGGTTGAC TTGCCTTGAT GGCAAGCTTG GTGGAGAGGG CTGAAGCTGT      180

TGCTGGGGGC CGATTCTGAT CAAGACACAT GGCTTGAAAA TGGAAGACAC AAAACTGAGA      240

GATCATTCTG CACTAAGTTT CGGGAACTTA TCCCCGACAG TGACTGAACT CACTGACTAA      300

TAACTTCATT TATGAATCTT CTCCCTTGTC CCTTTGTCTG CCAACCTGTG TGCCTTTTTT      360

GTAAAACATT TTCATGTCTT TAAAATGCCT GTTGAATACC TGGAGTTTAG TATCAACTTC      420

TACACAGATA AGCTTTCAAA GTTGACAAAC TTTTTTGACT CTTTCTGGAA AAGGGAAAGA      480

AAATAGTCTT CCTTCTTTCT TGGGCAATAT CCTTCACTTT ACTACAGTTA CTTTTGCAAA      540

CAGACAGAAA GGATACACTT CTAACCACAT TTTACTTCCT TCCCCTGTTG TCCAGTCCAA      600

CTCCACAGTC ACTCTTAAAA CTTCTCTCTG TTTGCCTGCC TCCAACAGTA CTTTTAACTT      660

TTTGCTGTAA ACAGAATAAA ATTGAACAAA TTAGGGGGTA GAAAGGAGCA GTGGTGTCGT      720

TCACCGTGAG AGTCTGCATA GAACTCAGCA GTGTGCCCTG CTGTGTCTTG ACCCTGCCC      780

CCCACAGGAG TTGTACAGTC CCTGGCCCTG TTCCCTACCT CCTCTCTTCA CCCCGTTAGG      840

CTGTTTTCAA TGTAATGCTG CCGTCCTTCT CTTGCACTGC CTTCTGCGCT AACACCTCCA      900

TTCCTGTTTA TAACCGTGTA TTTATTACTT AATGTATATA ATGTAATGTT TTGTAAGTTA      960

TTAATTTATA TATCTAACAT TGCCTGCCAA TGGTGGTGTT AAATTTGTGT AGAAAACTCT      1020

GCCTAAGAGT TACGACTTTT TCTTGTAATG TTTTGTATTG TGTATTATAT AACCCAAACG      1080

TCACTTAGTA GAGACATATG GCCCCCTTGG CAGAGAGGAC AGGGGTGGGC TTTTGTTCAA      1140

AGGGTCTGCC CTTTCCCTGC CTGAGTTGCT ACTTCTGCAC AACCCCTTTA TGAACCAGTT      1200

TTGGAAACAA TATTCTCACA TTAGATACTA AATGGTTTAT ACTGAGCTTT TACTTTTGTA      1260

TAGCTTGATA GGGGCAGGGG GCAATGGGAT GTAGTTTTTA CCCAGGTTCT ATCCAAATCT      1320

ATGTGGGCAT GAGTTGGGTT ATAACTGGAT CCTACTATCA TTGTGGCTTT GGTTCAAAAG      1380

GAAACACTAC ATTTGCTCAC AGATGATTCT TCTGAATGCT CCCGAACTAC TGACTTTGAA      1440

GAGGTAGCCT CCTGCCTGCC ATTAAGCAGG AATGTCATGT TCCAGTTCAT TACAAAAGAA      1500

AACAATAAAA CAATGTGAAT TTTTATAATA AAATGTGAAC TGATGTAGCA AATTACGCAA      1560

ATGTGAAGCC TCTTCTGATA ACACTTGTTA GGCCTCTTAC TGATGTCAGT TTCAGTTTGT      1620

AAAATATGTT TCATGCTTTC AGTTCAGCAT TGTGACTCAG TAATTACAGA AAATGGCACA      1680

AATGTGCATG ACCAATGGGT TTGTATGTCT ATGAACACTG CATTGTTTCA GGTGGACATT      1740

TTATCATTTT CAAATGTTTC TCACAATGTA TGTTATAGTA TTATTATTAT ATATTGTGTT      1800

CAAATGCATT C                                                          1811
```

(2) INFORMATION FOR SEQ ID NO:34:

(i) SEQUENCE CHARACTERISTICS:
        (A) LENGTH: 1672 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

```
GAATTCCCCA CCATGGGGGC CAAGACCTGC ACAGGACAAG GCCACCTGGC CTTTCAGTTA       60

CTTGAGTTTG GAGTCAGAAA GCAAGACCAG GAAGCAAATA GCAGCTCAGG AAATCCCACG      120

GTTGACTTGC CTTGATGGCA AGCTTGGTGG AGAGGGCTGA AGCTGTTGCT GGGGGCCGTT      180

CTGATCAAGA CACATGGCTT GAAAATGGAA GACACAAAAC TGAGAGATCA TTCTGCACTA      240
```

-continued

```
AGTTTCGGGA ACTTATCCCC GACAGTGACT GAACTCACTG ACTAATAACT TCATTTATGA      300

ATCTTCTCCC TTGTCCCTTT GTCTGCCAAC CTGTGTGCCT TTTTTGTAAA ACATTTCAGT      360

CTTTAAAATG CCTGTTGAAT ACCTGGAGTT AGATCAACTT CTACACAGAT AAGCTTTCAA      420

AGTTGACAAA CTTTTTTGAC TCTTCTGGAA AAGGGAAAGA AAATAGTCTT CCTTCTTTCT      480

TGGGCAATAT CCTTCACTTT ACTACAGTTA CTTTTGCAAA CAGACAGAAA GGATACACTT      540

CTAACCACAT TTTACTTCCT TCCCCTGTTG TCCAGTCCAA CTCCACAGTC ACTCTTAAAA      600

CTTCTCTCTG TTTGCCTGCC TCCAACAGTA CTTTTAACTT TTAACTTTTT GCTGTAAACA      660

GAATAAAATT GAACAAATTA GGGGGTAGAA AGGAGCAGTG GTGTCGTTCA CCGTGAGAGT      720

CTGCATAGAA CTCAGCAGTG TGCCCTGCTG TGTCTTGGAC CCTGCCCCCC ACAGGAGTTG      780

TACAGTCCCT GGCCCTGTTC CCTACCTCCT CTCTTCACCC CGTTAGGCTG TTTTCAATGT      840

AATGCTGCCG TCCTTCTCTT GCACTGCCTT CTGCGCTAAC ACCTCCATTC CTGTTTATAA      900

CCGTGTATTT ATTACTTAAT GTATATAATG TAATGTTTTG TAAGTTATTA ATTTATATAT      960

CTAACATTGC CTGCCAATGG TGGTGTTAAA TTTGTGTAGA AAACTCTGCC TAAGAGTTAC     1020

GACTTTTTCT TGTAATGTTT TGTATTGTGT ATTATATAAC CCAAACGTCA CTTAGTAGAG     1080

ACATATGGCC CCCTTGGCAG AGAGGACAGG GGTGGGCTTT TGTTCAAAGG GTCTGCCCTT     1140

TCCCTGCCTG AGTTGCTACT TCTGCACAAC CCCTTTATGA ACCAGTTTTG GAAACAATAT     1200

TCTCACATTA GATACTAAAT GGTTTATACT GAGCTTTTAC TTTTGTATAG CTTGATAGGG     1260

GCAGGGGCA ATGGGATGTA GTTTTTACCC AGGTTCTATC CAAATCTATG TGGGCATGAG      1320

TTGGGTTATA ACTGGATCCT ACTATCATTG TGGCTTTGGT TCAAAAGGAA ACACTACATT     1380

TGCTCACAGA TGATTCTTCT GAATGCTCCC GAACTACTGA CTTTGAAGAG GTAGCCTCCT     1440

GCCTGCCATT AAGCAGGAAT GTCATGTTCC AGTTCATTAC AAAAGAAAAC AATAAAACAA     1500

TGTGAATTTT TATAATAAAA TGTGAACTGA TGTAGCAAAT TACGCAAATG TGAAGCCTCT     1560

TCTGATAACA CTTGTTAGGC CTCTTACTGA TGTCAGTTTC AGTTTGTAAA ATATGTTTCA     1620

TGCTTTCAGT TCAGCATTGT GACTCAGTAA TTACAGAAAA AAAAAGAAT TC              1672
```

(2) INFORMATION FOR SEQ ID NO:35:

(i) SEQUENCE CHARACTERISTICS:
        (A) LENGTH: 1649 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 9..1018

(xi) SEQUENCE DESCRIPTION: SEQ ID NO:35:

```
GAATTCCT TCT GAC GTG GCA TAT CAC AAC AGC CTG CAC GCT GCT GAT GTA       50
         Ser Asp Val Ala Tyr His Asn Ser Leu His Ala Ala Asp Val
          1               5                  10

GCC CAG TCG ACC CAT GTT CTC CTT TCT ACA CCA GCA TTA GAC GCT GTC         98
Ala Gln Ser Thr His Val Leu Leu Ser Thr Pro Ala Leu Asp Ala Val
 15              20                  25                  30

TTC ACA GAT TTG GAA ATC CTG GCT GCC ATT TTT GCA GCT GCC ATC CAT        146
Phe Thr Asp Leu Glu Ile Leu Ala Ala Ile Phe Ala Ala Ala Ile His
             35                  40                  45

GAC GTT GAT CAT CCT GGA GTC TCC AAT CAG TTT CTC ATC AAC ACA AAT        194
Asp Val Asp His Pro Gly Val Ser Asn Gln Phe Leu Ile Asn Thr Asn
```

-continued

```
                50                      55                      60
TCA GAA CTT GCT TTG ATG TAT AAT GAT GAA TCT GTG TTG GAA AAT CAT      242
Ser Glu Leu Ala Leu Met Tyr Asn Asp Glu Ser Val Leu Glu Asn His
            65                      70                      75

CAC CTT GCT GTG GGT TTC AAA CTG CTG CAA GAA GAA CAC TGT GAC ATC      290
His Leu Ala Val Gly Phe Lys Leu Leu Gln Glu Glu His Cys Asp Ile
        80                      85                      90

TTC ATG AAT CTC ACC AAG AAG CAG CGT CAG ACA CTC AGG AAG ATG GTT      338
Phe Met Asn Leu Thr Lys Lys Gln Arg Gln Thr Leu Arg Lys Met Val
 95                     100                     105                     110

ATT GAC ATG GTG TTA GCA ACT GAT ATG TCT AAA CAT ATG AGC CTG CTG      386
Ile Asp Met Val Leu Ala Thr Asp Met Ser Lys His Met Ser Leu Leu
                115                     120                     125

GCA GAC CTG AAG ACA ATG GTA GAA ACG AAG AAA GTT ACA AGT TCA GGC      434
Ala Asp Leu Lys Thr Met Val Glu Thr Lys Lys Val Thr Ser Ser Gly
            130                     135                     140

GTT CTT CTC CTA GAC AAC TAT ACC GAT CGC ATT CAG GTC CTT CGC AAC      482
Val Leu Leu Leu Asp Asn Tyr Thr Asp Arg Ile Gln Val Leu Arg Asn
        145                     150                     155

ATG GTA CAC TGT GCA GAC CTG AGC AAC CCC ACC AAG TCC TTG GAA TTG      530
Met Val His Cys Ala Asp Leu Ser Asn Pro Thr Lys Ser Leu Glu Leu
    160                     165                     170

TAT CGG CAA TGG ACA GAC CGC ATC ATG GAG GAA TTT TTC CAG CAG GGA      578
Tyr Arg Gln Trp Thr Asp Arg Ile Met Glu Glu Phe Phe Gln Gln Gly
175                     180                     185                     190

GAC AAA GAG CGG GAG AGG GGA ATG GAA ATT AGC CCA ATG TGT GAT AAA      626
Asp Lys Glu Arg Glu Arg Gly Met Glu Ile Ser Pro Met Cys Asp Lys
                195                     200                     205

CAC ACA GCT TCT GTG GAA AAA TCC CAG GTT GGT TTC ATC GAC TAC ATT      674
His Thr Ala Ser Val Glu Lys Ser Gln Val Gly Phe Ile Asp Tyr Ile
            210                     215                     220

GTC CAT CCA TTG TGG GAG ACA TGG GCA GAT TTG GTA CAG CCT GAT GCT      722
Val His Pro Leu Trp Glu Thr Trp Ala Asp Leu Val Gln Pro Asp Ala
        225                     230                     235

CAG GAC ATT CTC GAT ACC TTA GAA GAT AAC AGG AAC TGG TAT CAG AGC      770
Gln Asp Ile Leu Asp Thr Leu Glu Asp Asn Arg Asn Trp Tyr Gln Ser
    240                     245                     250

ATG ATA CCT CAA AGT CCC TCA CCA CCA CTG GAC GAG CAG AAC AGG GAC      818
Met Ile Pro Gln Ser Pro Ser Pro Pro Leu Asp Glu Gln Asn Arg Asp
255                     260                     265                     270

TGC CAG GGT CTG ATG GAG AAG TTT CAG TTT GAA CTG ACT CTC GAT GAG      866
Cys Gln Gly Leu Met Glu Lys Phe Gln Phe Glu Leu Thr Leu Asp Glu
                275                     280                     285

GAA GAT TCT GAA GGA CCT GAG AAG GAG GGA GAG GGA CAC AGC TAT TTC      914
Glu Asp Ser Glu Gly Pro Glu Lys Glu Gly Glu Gly His Ser Tyr Phe
            290                     295                     300

AGC AGC ACA AAG ACG CTT TGT GTG ATT GAT CCA GAA AAC AGA GAT TCC      962
Ser Ser Thr Lys Thr Leu Cys Val Ile Asp Pro Glu Asn Arg Asp Ser
        305                     310                     315

CTG GGA GAG ACT GAC ATA GAC ATT GCA ACA GAA GAC AAG TCC CCC GTG     1010
Leu Gly Glu Thr Asp Ile Asp Ile Ala Thr Glu Asp Lys Ser Pro Val
    320                     325                     330

GAT ACA TA ATCCCCCTCT CCCTGTGGAG ATGAACATTC TATCCTTGAT GAGCATGCCA   1068
Asp Thr
335

GCTATGTGGT AGGGCCAGCC CACCATGGGG CCAAGACCT GCACAGGACA AGGGCCACCT   1128

GGCCTTTCAG TTACTTGAGT TTGGAGTCAG AAAGCAAGAC CAGGAAGCAA ATAGCAGCTC  1188

AGGAAATCCC ACGGTTGACT TGCCTTGATG GCAAGCTTGG TGGAGAGGGC TGAAGCTGTT  1248
```

```
GCTGGGGGCC GATTCTGATC AAGACACATG GCTTGAAAAT GGAAGACACA AAACCGAGAG    1308

ATCATTCTGC ACTAAGTTTC GGGAACTTAT CCCCGACAGT GACTGAACTC ACTGACTAAT    1368

AACTTCATTT ATGAATCTTC TCCCTTGTCC CTTTGTCTGC CAACCTGTGT GCCTTTTTG     1428

TAAAACATTT TCATGTCTTT AAAATGCCTG TTGAATACCT GGAGTTTAGT ATCAACTTCT    1488

ACACAGATAA GCTTTCAAAG TTGACAAACT TTTTTGACTC TTTCTGGAAA AGGGAAAGAA    1548

AATAGTCTTC CTTCTTTCTT GGGCAATATC CTTCACTTTA CTACAGTTAC TTTTGCAAAC    1608

AGACAGAAAG GATACACTTC TAACCACATT TTACGGAATT C                        1649
```

(2) INFORMATION FOR SEQ ID NO:36:

(i) SEQUENCE CHARACTERISTICS:
        (A) LENGTH: 336 amino acids
        (B) TYPE: amino acid
        (D) TOPOLOGY: linear (ii) MOLECULE TYPE: protein (xi) SEQUENCE DESCRIPTION: SEQ ID NO:36:

```
Ser Asp Val Ala Tyr His Asn Ser Leu His Ala Ala Asp Val Ala Gln
  1               5                  10                  15

Ser Thr His Val Leu Leu Ser Thr Pro Ala Leu Asp Ala Val Phe Thr
                 20                  25                  30

Asp Leu Glu Ile Leu Ala Ala Ile Phe Ala Ala Ile His Asp Val
             35                  40                  45

Asp His Pro Gly Val Ser Asn Gln Phe Leu Ile Asn Thr Asn Ser Glu
         50                  55                  60

Leu Ala Leu Met Tyr Asn Asp Glu Ser Val Leu Glu Asn His His Leu
 65                  70                  75                  80

Ala Val Gly Phe Lys Leu Leu Gln Glu Glu His Cys Asp Ile Phe Met
                 85                  90                  95

Asn Leu Thr Lys Lys Gln Arg Gln Thr Leu Arg Lys Met Val Ile Asp
                100                 105                 110

Met Val Leu Ala Thr Asp Met Ser Lys His Met Ser Leu Leu Ala Asp
            115                 120                 125

Leu Lys Thr Met Val Glu Thr Lys Lys Val Thr Ser Ser Gly Val Leu
        130                 135                 140

Leu Leu Asp Asn Tyr Thr Asp Arg Ile Gln Val Leu Arg Asn Met Val
145                 150                 155                 160

His Cys Ala Asp Leu Ser Asn Pro Thr Lys Ser Leu Glu Leu Tyr Arg
                165                 170                 175

Gln Trp Thr Asp Arg Ile Met Glu Glu Phe Phe Gln Gln Gly Asp Lys
            180                 185                 190

Glu Arg Glu Arg Gly Met Glu Ile Ser Pro Met Cys Asp Lys His Thr
        195                 200                 205

Ala Ser Val Glu Lys Ser Gln Val Gly Phe Ile Asp Tyr Ile Val His
    210                 215                 220

Pro Leu Trp Glu Thr Trp Ala Asp Leu Val Gln Pro Asp Ala Gln Asp
225                 230                 235                 240

Ile Leu Asp Thr Leu Glu Asp Asn Arg Asn Trp Tyr Gln Ser Met Ile
                245                 250                 255

Pro Gln Ser Pro Ser Pro Pro Leu Asp Glu Gln Asn Arg Asp Cys Gln
            260                 265                 270

Gly Leu Met Glu Lys Phe Gln Phe Glu Leu Thr Leu Asp Glu Glu Asp
```

```
                   275                 280                 285
Ser Glu Gly Pro Glu Lys Glu Gly Gly His Ser Tyr Phe Ser Ser
                   290                 295                 300

Thr Lys Thr Leu Cys Val Ile Asp Pro Glu Asn Arg Asp Ser Leu Gly
305                 310                 315                 320

Glu Thr Asp Ile Asp Ile Ala Thr Glu Asp Lys Ser Pro Val Asp Thr
                        325                 330                 335
```

(2) INFORMATION FOR SEQ ID NO:37:

(i) SEQUENCE CHARACTERISTICS:
        (A) LENGTH: 609 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 8..606

(xi) SEQUENCE DESCRIPTION: SEQ ID NO:37:

```
GAATTCC AAC ATT CCC CGA TTT GGG GTG AAG ACC GAT CAA GAA GAG CTC         49
        Asn Ile Pro Arg Phe Gly Val Lys Thr Asp Gln Glu Glu Leu
         1               5                  10

CTG GCC CAA GAA CTG GAG AAC CTG AAC AAG TGG GGC CTG AAC ATC TTT         97
Leu Ala Gln Glu Leu Glu Asn Leu Asn Lys Trp Gly Leu Asn Ile Phe
15                  20                  25                  30

TGC GTG TCG GAT TAC GCT GGA GGC CGC TCA CTC ACC TGC ATC ATG TAC        145
Cys Val Ser Asp Tyr Ala Gly Gly Arg Ser Leu Thr Cys Ile Met Tyr
                35                  40                  45

ATG ATA TTC CAG GAG CGG GAC CTG CTG AAG AAA TTC CGC ATC CCT GTG        193
Met Ile Phe Gln Glu Arg Asp Leu Leu Lys Lys Phe Arg Ile Pro Val
                    50                  55                  60

GAC ACG ATG GTG ACA TAC ATG CTG ACG CTG GAG GAT CAC TAC CAC GCT        241
Asp Thr Met Val Thr Tyr Met Leu Thr Leu Glu Asp His Tyr His Ala
                65                  70                  75

GAC GTG GCC TAC CAT AAC AGC CTG CAC GCA GCT GAC GTG CTG CAG TCC        289
Asp Val Ala Tyr His Asn Ser Leu His Ala Ala Asp Val Leu Gln Ser
80                  85                  90

ACC CAC GTA CTG CTG GCC ACG CCT GCA CTA GAT GCA GTG TTC ACG GAC        337
Thr His Val Leu Leu Ala Thr Pro Ala Leu Asp Ala Val Phe Thr Asp
95                  100                 105                 110

CTG GAG ATT CTC GCC GCC CTC TTC GCG GCT GCC ATC CAC GAT GTG GAT        385
Leu Glu Ile Leu Ala Ala Leu Phe Ala Ala Ala Ile His Asp Val Asp
                    115                 120                 125

CAC CCT GGG GTC TCC AAC CAG TTC CTC ATC AAC ACC AAT TCG GAG CTG        433
His Pro Gly Val Ser Asn Gln Phe Leu Ile Asn Thr Asn Ser Glu Leu
                130                 135                 140

GCG CTC ATG TAC AAC GAT GAG TCG GTG CTC GAG AAT CAC CAC CTG GCC        481
Ala Leu Met Tyr Asn Asp Glu Ser Val Leu Glu Asn His His Leu Ala
                145                 150                 155

GTG GGC TTC AAG CTG CTG CAG GAG GAC AAC TGC GAC ATC TTC CAG AAC        529
Val Gly Phe Lys Leu Leu Gln Glu Asp Asn Cys Asp Ile Phe Gln Asn
160                 165                 170

CTC AGC AAG CGC CAG CGG CAG AGC TAC GCA AGA TGG TCA TCG ACA TGG        577
Leu Ser Lys Arg Gln Arg Gln Ser Tyr Ala Arg Trp Ser Ser Thr Trp
175                 180                 185                 190

TGC TGG CCA CGG ACA TGT CCA AGC ACA TG ACC                             609
Cys Trp Pro Arg Thr Cys Pro Ser Thr
                195
```

(2) INFORMATION FOR SEQ ID NO:38:

(i) SEQUENCE CHARACTERISTICS:
        (A) LENGTH: 199 amino acids
        (B) TYPE: amino acid
        (D) TOPOLOGY: linear (ii) MOLECULE TYPE: protein (xi) SEQUENCE DESCRIPTION: SEQ ID NO:38:

```
Asn Ile Pro Arg Phe Gly Val Lys Thr Asp Gln Glu Glu Leu Leu Ala
 1               5                  10                  15

Gln Glu Leu Glu Asn Leu Asn Lys Trp Gly Leu Asn Ile Phe Cys Val
             20                  25                  30

Ser Asp Tyr Ala Gly Gly Arg Ser Leu Thr Cys Ile Met Tyr Met Ile
         35                  40                  45

Phe Gln Glu Arg Asp Leu Leu Lys Lys Phe Arg Ile Pro Val Asp Thr
     50                  55                  60

Met Val Thr Tyr Met Leu Thr Leu Glu Asp His Tyr His Ala Asp Val
 65                  70                  75                  80

Ala Tyr His Asn Ser Leu His Ala Ala Asp Val Leu Gln Ser Thr His
                 85                  90                  95

Val Leu Leu Ala Thr Pro Ala Leu Asp Ala Val Phe Thr Asp Leu Glu
            100                 105                 110

Ile Leu Ala Ala Leu Phe Ala Ala Ala Ile His Asp Val Asp His Pro
        115                 120                 125

Gly Val Ser Asn Gln Phe Leu Ile Asn Thr Asn Ser Glu Leu Ala Leu
    130                 135                 140

Met Tyr Asn Asp Glu Ser Val Leu Glu Asn His His Leu Ala Val Gly
145                 150                 155                 160

Phe Lys Leu Leu Gln Glu Asp Asn Cys Asp Ile Phe Gln Asn Leu Ser
                165                 170                 175

Lys Arg Gln Arg Gln Ser Tyr Ala Arg Trp Ser Ser Thr Trp Cys Trp
            180                 185                 190

Pro Arg Thr Cys Pro Ser Thr
        195
```

(2) INFORMATION FOR SEQ ID NO:39:

(i) SEQUENCE CHARACTERISTICS:
        (A) LENGTH: 1230 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..1156

(xi) SEQUENCE DESCRIPTION: SEQ ID NO:39:

```
AC ATG GTG CAC TGT GCC GAC CTC AGC AAC CCC ACC AAG CCG CTG GAG        47
   Met Val His Cys Ala Asp Leu Ser Asn Pro Thr Lys Pro Leu Glu
    1               5                  10                  15

CTG TAC CGC CAG TGG ACA GAC CGC ATC ATG GCC GAG TTC TTC CAG CAG       95
Leu Tyr Arg Gln Trp Thr Asp Arg Ile Met Ala Glu Phe Phe Gln Gln
             20                  25                  30

GGT GAC CGA GAG CGC GAG CGT GGC ATG GAA ATC AGC CCC ATG TGT GAC      143
Gly Asp Arg Glu Arg Glu Arg Gly Met Glu Ile Ser Pro Met Cys Asp
```

```
            35                    40                     45
AAG CAC ACT GCC TCC GTG GAG AAG TCT CAG GTG GGT TTT ATT GAC TAC      191
Lys His Thr Ala Ser Val Glu Lys Ser Gln Val Gly Phe Ile Asp Tyr
            50                    55                    60

ATT GTG CAC CCA TTG TGG GAG ACC TGG GCG GAC CTT GTC CAC CCA GAT      239
Ile Val His Pro Leu Trp Glu Thr Trp Ala Asp Leu Val His Pro Asp
     65                    70                    75

GCC CAG GAG ATC TTG GAC ACT TTG GAG GAC AAC CGG GAC TGG TAC TAC      287
Ala Gln Glu Ile Leu Asp Thr Leu Glu Asp Asn Arg Asp Trp Tyr Tyr
 80                    85                    90                95

AGC GCC ATC CGG CAG AGC CCA TCT CCG CCA CCC GAG GAG GAG TCA AGG      335
Ser Ala Ile Arg Gln Ser Pro Ser Pro Pro Pro Glu Glu Glu Ser Arg
                100                   105                   110

GGG CCA GGC CAC CCA CCC CTG CCT GAC AAG TTC CAG TTT GAC GTG ACG      383
Gly Pro Gly His Pro Pro Leu Pro Asp Lys Phe Gln Phe Asp Val Thr
                    115                   120                   125

CTG GAG GAG GAA GAG GAG GAA GAA ATA TCA ATG GCC CAG ATA CCG TGC      431
Leu Glu Glu Glu Glu Glu Glu Glu Ile Ser Met Ala Gln Ile Pro Cys
            130                   135                   140

ACA GCC CAA GAG GCA TTG ACT GCG CAG GGA TTG TCA GGA GTC GAG GAA      479
Thr Ala Gln Glu Ala Leu Thr Ala Gln Gly Leu Ser Gly Val Glu Glu
        145                   150                   155

GCT CTG GAT GCA ACC ATA GCC TGG GAG GCA TCC CCG GCC CAG GAG TCG      527
Ala Leu Asp Ala Thr Ile Ala Trp Glu Ala Ser Pro Ala Gln Glu Ser
160                   165                   170                   175

TTG GAA GTT ATG GCA CAG GAA GCA TCC CTG GAG GCC GAG CTG GAG GCA      575
Leu Glu Val Met Ala Gln Glu Ala Ser Leu Glu Ala Glu Leu Glu Ala
                180                   185                   190

GNG TAT TTG ACA CAG CAG GCA CAG TCC ACA GGC AGT GCA CCT GTG GCT      623
Val Tyr Leu Thr Gln Gln Ala Gln Ser Thr Gly Ser Ala Pro Val Ala
                    195                   200                   205

CCG GAT GAG TTC TCG TCC CGG GAG GAA TTC GTG GTT GCT GTA AGC CAC      671
Pro Asp Glu Phe Ser Ser Arg Glu Glu Phe Val Val Ala Val Ser His
            210                   215                   220

AGC AGC CCC TCT GCC CTG GCT CTT CAA AGC CCC CTT CTC CCT GCT TGG      719
Ser Ser Pro Ser Ala Leu Ala Leu Gln Ser Pro Leu Leu Pro Ala Trp
        225                   230                   235

AGG ACC CTG TCT GTT TCA GAG CAT GCC CCG GGC CTC CCG GCC TCC CCT      767
Arg Thr Leu Ser Val Ser Glu His Ala Pro Gly Leu Pro Ala Ser Pro
240                   245                   250                   255

CCA CGG CGG CCT AGG TGG AAC GAG AGC ACC AGG CTG CCA AGA GGG CTT      815
Pro Arg Arg Pro Arg Trp Asn Glu Ser Thr Arg Leu Pro Arg Gly Leu
                260                   265                   270

GCA GTG CCT GCG CAG GGA CAT TTG GGG AGG ACA CAT CCG CAC TCC CAG      863
Ala Val Pro Ala Gln Gly His Leu Gly Arg Thr His Pro His Ser Gln
                    275                   280                   285

CTC CTG GTG GCG GGG GGT CAG GTG GAG ACC CTA CCT GAT CCC CAG ACC      911
Leu Leu Val Ala Gly Gly Gln Val Glu Thr Leu Pro Asp Pro Gln Thr
            290                   295                   300

TCT GTC CCT GTT CCC CTC CAC TCC TCC CCT CAC TCC CCT GCT CCC CCG      959
Ser Val Pro Val Pro Leu His Ser Ser Pro His Ser Pro Ala Pro Pro
        305                   310                   315

ACC ACC TCC TCC TCT GCC TCA AAG ACT CTT GTC CTC TTG TCC CTC CTG      1007
Thr Thr Ser Ser Ser Ala Ser Lys Thr Leu Val Leu Leu Ser Leu Leu
320                   325                   330                   335

AGA AAA AAG AAA ACG AAA AGT GGG GTT TTT TTC TGT TTT CTT TTT TTC      1055
Arg Lys Lys Lys Thr Lys Ser Gly Val Phe Phe Cys Phe Leu Phe Phe
                340                   345                   350

CCC TTT CCC CCT GCC CCC ACC CAC GGG GCC TTT TTT TGG AGG TGG GGG      1103
```

```
Pro Phe Pro Pro Ala Pro Thr His Gly Ala Phe Phe Trp Arg Trp Gly
            355                 360                 365

CTG GGG AAT GAG GGG CTG AGG TCC CGG AAG GGA TTT TAT TTT TTT GAA        1151
Leu Gly Asn Glu Gly Leu Arg Ser Arg Lys Gly Phe Tyr Phe Phe Glu
            370                 375                 380

TTT TA ATTGTAACAT TTTTAGAAAA AGAACAAAAA AAGAAAAAAA AAAGAAAGAA          1206
Phe

ACACAAAAAA AAAAAAAGGA ATTC                                             1230

(2) INFORMATION FOR SEQ ID NO:40:

(i) SEQUENCE CHARACTERISTICS:
        (A) LENGTH: 384 amino acids
        (B) TYPE: amino acid
        (D) TOPOLOGY: linear (ii) MOLECULE TYPE: protein (xi) SEQUENCE DESCRIPTION: SEQ ID NO:40:

Met Val His Cys Ala Asp Leu Ser Asn Pro Thr Lys Pro Leu Glu Leu
 1               5                  10                  15

Tyr Arg Gln Trp Thr Asp Arg Ile Met Ala Glu Phe Gln Gln Gly
             20                  25                  30

Asp Arg Glu Arg Glu Arg Gly Met Glu Ile Ser Pro Met Cys Asp Lys
             35                  40                  45

His Thr Ala Ser Val Glu Lys Ser Gln Val Gly Phe Ile Asp Tyr Ile
         50                  55                  60

Val His Pro Leu Trp Glu Thr Trp Ala Asp Leu Val His Pro Asp Ala
 65                  70                  75                  80

Gln Glu Ile Leu Asp Thr Leu Glu Asp Asn Arg Asp Trp Tyr Tyr Ser
                 85                  90                  95

Ala Ile Arg Gln Ser Pro Ser Pro Pro Glu Glu Ser Arg Gly
             100                 105                 110

Pro Gly His Pro Pro Leu Pro Asp Lys Phe Gln Phe Asp Val Thr Leu
             115                 120                 125

Glu Glu Glu Glu Glu Glu Ile Ser Met Ala Gln Ile Pro Cys Thr
         130                 135                 140

Ala Gln Glu Ala Leu Thr Ala Gln Gly Leu Ser Gly Val Glu Glu Ala
145                 150                 155                 160

Leu Asp Ala Thr Ile Ala Trp Glu Ala Ser Pro Ala Gln Glu Ser Leu
                 165                 170                 175

Glu Val Met Ala Gln Glu Ala Ser Leu Glu Ala Glu Leu Glu Ala Val
             180                 185                 190

Tyr Leu Thr Gln Gln Ala Gln Ser Thr Gly Ser Ala Pro Val Ala Pro
             195                 200                 205

Asp Glu Phe Ser Ser Arg Glu Glu Phe Val Val Ala Val Ser His Ser
         210                 215                 220

Ser Pro Ser Ala Leu Ala Leu Gln Ser Pro Leu Leu Pro Ala Trp Arg
225                 230                 235                 240

Thr Leu Ser Val Ser Glu His Ala Pro Gly Leu Pro Ala Ser Pro Pro
                 245                 250                 255

Arg Arg Pro Arg Trp Asn Glu Ser Thr Arg Leu Pro Arg Gly Leu Ala
             260                 265                 270

Val Pro Ala Gln Gly His Leu Gly Arg Thr His Pro His Ser Gln Leu
         275                 280                 285

Leu Val Ala Gly Gly Gln Val Glu Thr Leu Pro Asp Pro Gln Thr Ser
```

```
              290                 295                 300
Val Pro Val Pro Leu His Ser Ser Pro His Ser Pro Ala Pro Pro Thr
305                 310                 315                 320

Thr Ser Ser Ser Ala Ser Lys Thr Leu Val Leu Leu Ser Leu Leu Arg
                325                 330                 335

Lys Lys Lys Thr Lys Ser Gly Val Phe Phe Cys Phe Leu Phe Phe Pro
                340                 345                 350

Phe Pro Pro Ala Pro Thr His Gly Ala Phe Phe Trp Arg Trp Gly Leu
                355                 360                 365

Gly Asn Glu Gly Leu Arg Ser Arg Lys Gly Phe Tyr Phe Phe Glu Phe
                370                 375                 380
```

(2) INFORMATION FOR SEQ ID NO:41:

(i) SEQUENCE CHARACTERISTICS:
        (A) LENGTH: 798 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 9..798

(xi) SEQUENCE DESCRIPTION: SEQ ID NO:41:

```
GAATTCCT CTG ACT AAT TCA AGT ATC CCA AGG TTT GGA GTT AAA ACT GAA         50
         Leu Thr Asn Ser Ser Ile Pro Arg Phe Gly Val Lys Thr Glu
           1               5                  10

CAA GAA GAT GTC CTT GCC AAG GAA CTA GAA GAT GTG AAC AAA TGG GGT          98
Gln Glu Asp Val Leu Ala Lys Glu Leu Glu Asp Val Asn Lys Trp Gly
 15              20                  25                  30

CTT CAT GTT TTC AGA ATA GCA GAG TTG TCT GGT AAC CGG CCC TTG ACT         146
Leu His Val Phe Arg Ile Ala Glu Leu Ser Gly Asn Arg Pro Leu Thr
                 35                  40                  45

GTT ATC ATG CAC ACC ATT TTT CAG GAA CGG GAT TTA TTA AAA ACA TTT         194
Val Ile Met His Thr Ile Phe Gln Glu Arg Asp Leu Leu Lys Thr Phe
             50                  55                  60

AAA ATT CCA GTA GAT ACT TTA ATT ACA TAT CTT ATG ACT CTC GAA GAC         242
Lys Ile Pro Val Asp Thr Leu Ile Thr Tyr Leu Met Thr Leu Glu Asp
         65                  70                  75

CAT TAC CAT GCT GAT GTG GCC TAT CAC AAC AAT ATC CAT GCT GCA GAT         290
His Tyr His Ala Asp Val Ala Tyr His Asn Asn Ile His Ala Ala Asp
     80                  85                  90

GTT GTC CAG TCT ACT CAT GTG CTA TTA TCT ACA CCT GCT TTG GAG GCT         338
Val Val Gln Ser Thr His Val Leu Leu Ser Thr Pro Ala Leu Glu Ala
 95                 100                 105                 110

GTG TTT ACA GAT TTG GAG ATT CTT GCA GCA ATT TTT GCC AGT GCA ATA         386
Val Phe Thr Asp Leu Glu Ile Leu Ala Ala Ile Phe Ala Ser Ala Ile
                115                 120                 125

CAT GAT GTA GAT CAT CCT GGT GTG TCC AAT CAA TTT CTG ATC AAT ACA         434
His Asp Val Asp His Pro Gly Val Ser Asn Gln Phe Leu Ile Asn Thr
            130                 135                 140

AAC TCT GAA CTT GCC TTG ATG TAC AAT GAT TCC TCA GTC TTA GAG AAC         482
Asn Ser Glu Leu Ala Leu Met Tyr Asn Asp Ser Ser Val Leu Glu Asn
        145                 150                 155

CAT CAT TTG GCT GTG GGC TTT AAA TTG CTT CAG GAA GAA AAC TGT GAC         530
His His Leu Ala Val Gly Phe Lys Leu Leu Gln Glu Glu Asn Cys Asp
    160                 165                 170

ATT TTC CAG AAT TTG ACC AAA AAA CAA AGA CAA TCT TTA AGG AAA ATG         578
```

```
Ile Phe Gln Asn Leu Thr Lys Lys Gln Arg Gln Ser Leu Arg Lys Met
175                 180                 185                 190

GTC ATT GAC ATC GTA CTT GCA ACA GAT ATG TCA AAA CAC ATG AAT CTA     626
Val Ile Asp Ile Val Leu Ala Thr Asp Met Ser Lys His Met Asn Leu
                195                 200                 205

CTG GCT GAT TTG AAG ACT ATG GTT GAA ACT AAG AAA GTG ACA AGC TCT     674
Leu Ala Asp Leu Lys Thr Met Val Glu Thr Lys Lys Val Thr Ser Ser
                210                 215                 220

GGA GTT CTT CTT CTT GAT AAT TAT TCC GAT AGG ATT CAG GTT CTT CAG     722
Gly Val Leu Leu Leu Asp Asn Tyr Ser Asp Arg Ile Gln Val Leu Gln
                225                 230                 235

AAT ATG GTG CAC TGT GCA GAT CTG AGC AAC CCA ACA AAG CCT CTC CAG     770
Asn Met Val His Cys Ala Asp Leu Ser Asn Pro Thr Lys Pro Leu Gln
    240                 245                 250

CTG TAC CGC CAG TGG ACG GAC GGA ATT C                                798
Leu Tyr Arg Gln Trp Thr Asp Gly Ile
255                 260
```

(2) INFORMATION FOR SEQ ID NO:42:

(i) SEQUENCE CHARACTERISTICS:
       (A) LENGTH: 263 amino acids
       (B) TYPE: amino acid
       (D) TOPOLOGY: linear (ii) MOLECULE TYPE: protein (xi) SEQUENCE DESCRIPTION: SEQ ID NO:42:

```
Leu Thr Asn Ser Ser Ile Pro Arg Phe Gly Val Lys Thr Glu Gln Glu
  1               5                  10                  15

Asp Val Leu Ala Lys Glu Leu Glu Asp Val Asn Lys Trp Gly Leu His
             20                  25                  30

Val Phe Arg Ile Ala Glu Leu Ser Gly Asn Arg Pro Leu Thr Val Ile
         35                  40                  45

Met His Thr Ile Phe Gln Glu Arg Asp Leu Leu Lys Thr Phe Lys Ile
     50                  55                  60

Pro Val Asp Thr Leu Ile Thr Tyr Leu Met Thr Leu Glu Asp His Tyr
 65                  70                  75                  80

His Ala Asp Val Ala Tyr His Asn Asn Ile His Ala Ala Asp Val Val
                 85                  90                  95

Gln Ser Thr His Val Leu Leu Ser Thr Pro Ala Leu Glu Ala Val Phe
            100                 105                 110

Thr Asp Leu Glu Ile Leu Ala Ala Ile Phe Ala Ser Ala Ile His Asp
        115                 120                 125

Val Asp His Pro Gly Val Ser Asn Gln Phe Leu Ile Asn Thr Asn Ser
    130                 135                 140

Glu Leu Ala Leu Met Tyr Asn Asp Ser Ser Val Leu Glu Asn His His
145                 150                 155                 160

Leu Ala Val Gly Phe Lys Leu Leu Gln Glu Glu Asn Cys Asp Ile Phe
                165                 170                 175

Gln Asn Leu Thr Lys Lys Gln Arg Gln Ser Leu Arg Lys Met Val Ile
            180                 185                 190

Asp Ile Val Leu Ala Thr Asp Met Ser Lys His Met Asn Leu Leu Ala
        195                 200                 205

Asp Leu Lys Thr Met Val Glu Thr Lys Lys Val Thr Ser Ser Gly Val
    210                 215                 220

Leu Leu Leu Asp Asn Tyr Ser Asp Arg Ile Gln Val Leu Gln Asn Met
225                 230                 235                 240
```

```
                    Val His Cys Ala Asp Leu Ser Asn Pro Thr Lys Pro Leu Gln Leu Tyr
                                245                 250                 255

Arg Gln Trp Thr Asp Gly Ile
                                260

(2) INFORMATION FOR SEQ ID NO:43:

(i) SEQUENCE CHARACTERISTICS:
          (A) LENGTH: 1902 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: CDS
          (B) LOCATION: 43..1254

(xi) SEQUENCE DESCRIPTION: SEQ ID NO:43:

GAATTCCTTT GTTCACATCT TCTAGTTCCT TGGCAAGGAC AT CTT CAT GTT TTC           54
                                               Leu His Val Phe
                                                 1

AGA ATA GCA GAG TTG TCT GGT AAC CGG CCC TTG ACT GTT ATC ATG CAC        102
Arg Ile Ala Glu Leu Ser Gly Asn Arg Pro Leu Thr Val Ile Met His
  5                  10                  15                  20

ACC ATT TTT CAG GAA CGG GAT TTA TTA AAA ACA TTT AAA ATT CCA GTA        150
Thr Ile Phe Gln Glu Arg Asp Leu Leu Lys Thr Phe Lys Ile Pro Val
                 25                  30                  35

GAT ACT TTA ATT ACA TAT CTT ATG ACT CTC GAA GAC CAT TAC CAT GCT        198
Asp Thr Leu Ile Thr Tyr Leu Met Thr Leu Glu Asp His Tyr His Ala
             40                  45                  50

GAT GTG GCC TAT CAC AAC AAT ATC CAT GCT GCA GAT GTT GTC CAG TCT        246
Asp Val Ala Tyr His Asn Asn Ile His Ala Ala Asp Val Val Gln Ser
         55                  60                  65

ACT CAT GTG CTA TTA TCT ACA CCT GCT TTG GAG GCT GTG TTT ACA GAT        294
Thr His Val Leu Leu Ser Thr Pro Ala Leu Glu Ala Val Phe Thr Asp
     70                  75                  80

TTG GAG ATT CTT GCA GCA ATT TTT GCC AGT GCA ATA CAT GAT GTA GAT        342
Leu Glu Ile Leu Ala Ala Ile Phe Ala Ser Ala Ile His Asp Val Asp
 85                  90                  95                 100

CAT CCT GGT GTG TCC AAT CAA TTT CTG ATC AAT ACA AAC TCT GAA CTT        390
His Pro Gly Val Ser Asn Gln Phe Leu Ile Asn Thr Asn Ser Glu Leu
                105                 110                 115

GCC TTG ATG TAC AAT GAT TCC TCA GTC TTA GAG AAC CAT CAT TTG GCT        438
Ala Leu Met Tyr Asn Asp Ser Ser Val Leu Glu Asn His His Leu Ala
            120                 125                 130

GTG GGC TTT AAA TTG CTT CAG GAA GAA AAC TGT GAC ATT TTC CAG AAT        486
Val Gly Phe Lys Leu Leu Gln Glu Glu Asn Cys Asp Ile Phe Gln Asn
        135                 140                 145

TTG ACC AAA AAA CAA AGA CAA TCT TTA AGG AAA ATG GTC ATT GAC ATC        534
Leu Thr Lys Lys Gln Arg Gln Ser Leu Arg Lys Met Val Ile Asp Ile
    150                 155                 160

GTA CTT GCA ACA GAT ATG TCA AAA CAC ATG AAT CTA CTG GCT GAT TTG        582
Val Leu Ala Thr Asp Met Ser Lys His Met Asn Leu Leu Ala Asp Leu
165                 170                 175                 180

AAG ACT ATG GTT GAA ACT AAG AAA GTG ACA AGC TCT GGA GTT CTT CTT        630
Lys Thr Met Val Glu Thr Lys Lys Val Thr Ser Ser Gly Val Leu Leu
                185                 190                 195

CTT GAT AAT TAT TCC GAT AGG ATT CAG GTT CTT CAG AAT ATG GTG CAC        678
Leu Asp Asn Tyr Ser Asp Arg Ile Gln Val Leu Gln Asn Met Val His
            200                 205                 210
```

-continued

| | | |
|---|---|---|
| TGT GCA GAT CTG AGC AAC CCA ACA AAG CCT CTC CAG CTG TAC CGC CAG<br>Cys Ala Asp Leu Ser Asn Pro Thr Lys Pro Leu Gln Leu Tyr Arg Gln<br>215                    220                  225 | 726 |
| TGG ACG GAC CGG ATA ATG GAG GAG TTC TTC CGC CAA GGA GAC CGA GAG<br>Trp Thr Asp Arg Ile Met Glu Glu Phe Phe Arg Gln Gly Asp Arg Glu<br>230                    235                  240 | 774 |
| AGG GAA CGT GGC ATG GAG ATA AGC CCC ATG TGT GAC AAG CAC AAT GCT<br>Arg Glu Arg Gly Met Glu Ile Ser Pro Met Cys Asp Lys His Asn Ala<br>245                    250                  255                  260 | 822 |
| TCC GTG GAA AAA TCA CAG GTG GGC TTC ATA GAC TAT ATT GTT CAT CCC<br>Ser Val Glu Lys Ser Gln Val Gly Phe Ile Asp Tyr Ile Val His Pro<br>265                    270                  275 | 870 |
| CTC TGG GAG ACA TGG GCA GAC CTC GTC CAC CCT GAC GCC CAG GAT ATT<br>Leu Trp Glu Thr Trp Ala Asp Leu Val His Pro Asp Ala Gln Asp Ile<br>280                    285                  290 | 918 |
| TTG GAC ACT TTG GAG GAC AAT CGT GAA TGG TAC CAG AGC ACA ATC CCT<br>Leu Asp Thr Leu Glu Asp Asn Arg Glu Trp Tyr Gln Ser Thr Ile Pro<br>295                    300                  305 | 966 |
| CAG AGC CCC TCT CCT GCA CCT GAT GAC CCA GAG GAG GGC CGG CAG GGT<br>Gln Ser Pro Ser Pro Ala Pro Asp Asp Pro Glu Glu Gly Arg Gln Gly<br>310                    315                  320 | 1014 |
| CAA ACT GAG AAA TTC CAG TTT GAA CTA ACT TTA GAG GAA GAT GGT GAG<br>Gln Thr Glu Lys Phe Gln Phe Glu Leu Thr Leu Glu Glu Asp Gly Glu<br>325                    330                  335                  340 | 1062 |
| TCA GAC ACG GAA AAG GAC AGT GGC AGT CAA GTG GAA GAA GAC ACT AGC<br>Ser Asp Thr Glu Lys Asp Ser Gly Ser Gln Val Glu Glu Asp Thr Ser<br>345                    350                  355 | 1110 |
| TGC AGT GAC TCC AAG ACT CTT TGT ACT CAA GAC TCA GAG TCT ACT GAA<br>Cys Ser Asp Ser Lys Thr Leu Cys Thr Gln Asp Ser Glu Ser Thr Glu<br>360                    365                  370 | 1158 |
| ATT CCC CTT GAT GAA CAG GTT GAA GAG GAG GCA GTA GGG GAA GAA GAG<br>Ile Pro Leu Asp Glu Gln Val Glu Glu Glu Ala Val Gly Glu Glu Glu<br>375                    380                  385 | 1206 |
| GAA AGC CAG CCT GAA GCC TGT GTC ATA GAT GAT CGT TCT CCT GAC ACG<br>Glu Ser Gln Pro Glu Ala Cys Val Ile Asp Asp Arg Ser Pro Asp Thr<br>390                    395                  400 | 1254 |
| TAACAGTGCA AAAACTTTCA TGCCTTTTTT TTTTTTAAGT AGAAAAATTG TTTCCAAAGT | 1314 |
| GCATGTCACA TGCCACAACC ACGGTCACAC CTCACTGTCA TCTGCCAGGA CGTTTGTTGA | 1374 |
| ACAAAACTGA CCTTGACTAC TCAGTCCAGC GCTCAGGAAT ATCGTAACCA GTTTTTTCAC | 1434 |
| CTCCATGTCA TCCGAGCAAG GTGGACATCT TCACGAACAG CGTTTTTAAC AAGATTTCAG | 1494 |
| CTTGGTAGAG CTGACAAAGC AGATAAAATC TACTCCAAAT TATTTTCAAG AGAGTGTGAC | 1554 |
| TCATCAGGCA GCCCAAAAGT TTATTGGACT TGGGGTTTCT ATTCCTTTTT ATTTGTTTGC | 1614 |
| AATATTTTCA GAAGAAAGGC ATTGCACAGA GTGAACTTAA TGGACGAAGC AACAAATATG | 1674 |
| TCAAGAACAG GACATAGCAC GAATCTGTTA CCAGTAGGAG GAGGATGAGC CACAGAAATT | 1734 |
| GCATAATTTT CTAATTTCAA GTCTTCCTGA TACATGACTG AATAGTGTGG TTCAGTGAGC | 1794 |
| TGCACTGACC TCTACATTTT GTATGATATG TAAAACAGAT TTTTTGTAGA GCTTACTTTT | 1854 |
| ATTATTAAAT GTATTGAGGT ATTATATTTA AAAAAAAAAA AGGAATTC | 1902 |

(2) INFORMATION FOR SEQ ID NO:44:

(i) SEQUENCE CHARACTERISTICS:
        (A) LENGTH: 404 amino acids
        (B) TYPE: amino acid
        (D) TOPOLOGY: linear (ii) MOLECULE TYPE: protein (xi) SEQUENCE DESCRIPTION: SEQ ID NO:44:

```
Leu His Val Phe Arg Ile Ala Glu Leu Ser Gly Asn Arg Pro Leu Thr
 1               5                  10                  15

Val Ile Met His Thr Ile Phe Gln Glu Arg Asp Leu Leu Lys Thr Phe
             20                  25                  30

Lys Ile Pro Val Asp Thr Leu Ile Thr Tyr Leu Met Thr Leu Glu Asp
         35                  40                  45

His Tyr His Ala Asp Val Ala Tyr His Asn Asn Ile His Ala Ala Asp
     50                  55                  60

Val Val Gln Ser Thr His Val Leu Leu Ser Thr Pro Ala Leu Glu Ala
 65                  70                  75                  80

Val Phe Thr Asp Leu Glu Ile Leu Ala Ala Ile Phe Ala Ser Ala Ile
             85                  90                  95

His Asp Val Asp His Pro Gly Val Ser Asn Gln Phe Leu Ile Asn Thr
        100                 105                 110

Asn Ser Glu Leu Ala Leu Met Tyr Asn Asp Ser Ser Val Leu Glu Asn
    115                 120                 125

His His Leu Ala Val Gly Phe Lys Leu Leu Gln Glu Glu Asn Cys Asp
130                 135                 140

Ile Phe Gln Asn Leu Thr Lys Lys Gln Arg Gln Ser Leu Arg Lys Met
145                 150                 155                 160

Val Ile Asp Ile Val Leu Ala Thr Asp Met Ser Lys His Met Asn Leu
                165                 170                 175

Leu Ala Asp Leu Lys Thr Met Val Glu Thr Lys Lys Val Thr Ser Ser
            180                 185                 190

Gly Val Leu Leu Leu Asp Asn Tyr Ser Asp Arg Ile Gln Val Leu Gln
        195                 200                 205

Asn Met Val His Cys Ala Asp Leu Ser Asn Pro Thr Lys Pro Leu Gln
    210                 215                 220

Leu Tyr Arg Gln Trp Thr Asp Arg Ile Met Glu Glu Phe Phe Arg Gln
225                 230                 235                 240

Gly Asp Arg Glu Arg Glu Arg Gly Met Glu Ile Ser Pro Met Cys Asp
                245                 250                 255

Lys His Asn Ala Ser Val Glu Lys Ser Gln Val Gly Phe Ile Asp Tyr
            260                 265                 270

Ile Val His Pro Leu Trp Glu Thr Trp Ala Asp Leu Val His Pro Asp
        275                 280                 285

Ala Gln Asp Ile Leu Asp Thr Leu Glu Asp Asn Arg Glu Trp Tyr Gln
    290                 295                 300

Ser Thr Ile Pro Gln Ser Pro Ser Pro Ala Pro Asp Asp Pro Glu Glu
305                 310                 315                 320

Gly Arg Gln Gly Gln Thr Glu Lys Phe Gln Phe Glu Leu Thr Leu Glu
                325                 330                 335

Glu Asp Gly Glu Ser Asp Thr Glu Lys Asp Ser Gly Ser Gln Val Glu
            340                 345                 350

Glu Asp Thr Ser Cys Ser Asp Ser Lys Thr Leu Cys Thr Gln Asp Ser
        355                 360                 365

Glu Ser Thr Glu Ile Pro Leu Asp Glu Gln Val Glu Glu Ala Val
    370                 375                 380

Gly Glu Glu Glu Glu Ser Gln Pro Glu Ala Cys Val Ile Asp Asp Arg
385                 390                 395                 400
```

Ser Pro Asp Thr (2) INFORMATION FOR SEQ ID NO:45:

(i) SEQUENCE CHARACTERISTICS:
        (A) LENGTH: 1155 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..760

(xi) SEQUENCE DESCRIPTION: SEQ ID NO:45:

```
G AAT TCC CTG GCT GTG GGC TTC AAG CTG CTG CAG GCA GAG AAC TGC         46
  Asn Ser Leu Ala Val Gly Phe Lys Leu Leu Gln Ala Glu Asn Cys
   1               5                  10                  15

GAT ATC TTC CAG AAC CTC AGC GCC AAG CAG CGA CTG AGT CTG CGC AGG       94
Asp Ile Phe Gln Asn Leu Ser Ala Lys Gln Arg Leu Ser Leu Arg Arg
                 20                  25                  30

ATG GTC ATT GAC ATG GTG CTG GCC ACA GAC ATG TCC AAA CAC ATG AAC      142
Met Val Ile Asp Met Val Leu Ala Thr Asp Met Ser Lys His Met Asn
             35                  40                  45

CTC CTG GCC GAC CTC AAG ACC ATG GTG GAG ACC AAG AAG GTG ACA AGC      190
Leu Leu Ala Asp Leu Lys Thr Met Val Glu Thr Lys Lys Val Thr Ser
         50                  55                  60

CTC GGT GTC CTC CTC CTG GAC AAC TAT TCC GAC CGA ATC CAG GTC TTG      238
Leu Gly Val Leu Leu Leu Asp Asn Tyr Ser Asp Arg Ile Gln Val Leu
     65                  70                  75

CAG AAC CTG GTG CAC TGT GCT GAT CTG AGC AAC CCC ACC AAG CCG CTG      286
Gln Asn Leu Val His Cys Ala Asp Leu Ser Asn Pro Thr Lys Pro Leu
 80                  85                  90                  95

CCC CTG TAC CGC CAG TGG ACG GAC CGC ATC ATG GCC GAG TTC TTC CAG      334
Pro Leu Tyr Arg Gln Trp Thr Asp Arg Ile Met Ala Glu Phe Phe Gln
                100                 105                 110

CAG GGA GAC CGC GAG CGT GAG TCG GGC CTG GAC ATC AGT CCC ATG TGT      382
Gln Gly Asp Arg Glu Arg Glu Ser Gly Leu Asp Ile Ser Pro Met Cys
            115                 120                 125

GAC AAG CAT ACG GCC TCA GTG GAG AAG TCC CAG GTG GGT TTC ATT GAC      430
Asp Lys His Thr Ala Ser Val Glu Lys Ser Gln Val Gly Phe Ile Asp
        130                 135                 140

TAC ATT GCT CAC CCA CTG TGG GAG ACT TGG GCT GAC CTG GTC CAC CCA      478
Tyr Ile Ala His Pro Leu Trp Glu Thr Trp Ala Asp Leu Val His Pro
    145                 150                 155

GAT GCA CAG GAC CTG CTG GAC ACG CTG GAG GAC AAT CGA GAG TGG TAC      526
Asp Ala Gln Asp Leu Leu Asp Thr Leu Glu Asp Asn Arg Glu Trp Tyr
160                 165                 170                 175

CAG AGC AAG ATC CCC CGA AGT CCC TCA GAC CTC ACC AAC CCC GAG CGG      574
Gln Ser Lys Ile Pro Arg Ser Pro Ser Asp Leu Thr Asn Pro Glu Arg
                180                 185                 190

GAC GGG CCT GAC AGA TTC CAG TTT GAA CTG ACT CTG GAG GAG GCA GAG      622
Asp Gly Pro Asp Arg Phe Gln Phe Glu Leu Thr Leu Glu Glu Ala Glu
            195                 200                 205

GAA GAG GAT GAG GAG GAA GAA GAG GAG GGA GAA GAG ACA GCT TTA GCC      670
Glu Glu Asp Glu Glu Glu Glu Glu Glu Gly Glu Glu Thr Ala Leu Ala
        210                 215                 220

AAA GAG GCC TTG GAG TTG CCT GAC ACT GAA CTC CTG TCC CCT GAA GCC      718
Lys Glu Ala Leu Glu Leu Pro Asp Thr Glu Leu Leu Ser Pro Glu Ala
    225                 230                 235
```

```
GGC CCA GAC CCT GGG GAC TTA CCC CTC GAC AAC CAG AGG ACT         760
Gly Pro Asp Pro Gly Asp Leu Pro Leu Asp Asn Gln Arg Thr
240                 245                 250

TAGGGCCAGC CCTGCGTGAA CTGCAGGGGC AATGGATGGT AAAGCCCTTT GGCTCTTGGC    820

AGGCAGACTT TCCAGGAAGA GGCTCCATGT GGCTCCTGCT TCACTTTCCC ACCCATTTAG    880

GGAGACAATC AAGCTCTTAG TTATAGGTGG CTCCCAGGGT CTAATTGGAG CACCTGGCT     940

GGGGTCCACT CTGACCCTAG ACTTGCCTAA AAGAGCTCTC TAAGGGGCAG CCTCTTACGA    1000

TGCCCTGGTG TCTTTCTCCT GGGCTTCTAT CCCTGTGAGG AGAGGTGCTG TCTGCTGGAG    1060

CCTCTAGTCC ACCCTCTCCA GTGGTCACTC TTGAGTCACA TCTGTCACTT AATTATTTCC    1120

TTCTTTATCA AATATTTATT GCTCATCTGG AATTC                              1155
```

(2) INFORMATION FOR SEQ ID NO:46:

(i) SEQUENCE CHARACTERISTICS:
        (A) LENGTH: 253 amino acids
        (B) TYPE: amino acid
        (D) TOPOLOGY: linear (ii) MOLECULE TYPE: protein (xi) SEQUENCE DESCRIPTION: SEQ ID NO:46:

```
Asn Ser Leu Ala Val Gly Phe Lys Leu Leu Gln Ala Glu Asn Cys Asp
 1               5                  10                  15

Ile Phe Gln Asn Leu Ser Ala Lys Gln Arg Leu Ser Leu Arg Arg Met
                20                  25                  30

Val Ile Asp Met Val Leu Ala Thr Asp Met Ser Lys His Met Asn Leu
            35                  40                  45

Leu Ala Asp Leu Lys Thr Met Val Glu Thr Lys Lys Val Thr Ser Leu
        50                  55                  60

Gly Val Leu Leu Leu Asp Asn Tyr Ser Asp Arg Ile Gln Val Leu Gln
65                  70                  75                  80

Asn Leu Val His Cys Ala Asp Leu Ser Asn Pro Thr Lys Pro Leu Pro
                85                  90                  95

Leu Tyr Arg Gln Trp Thr Asp Arg Ile Met Ala Glu Phe Phe Gln Gln
                100                 105                 110

Gly Asp Arg Glu Arg Glu Ser Gly Leu Asp Ile Ser Pro Met Cys Asp
            115                 120                 125

Lys His Thr Ala Ser Val Glu Lys Ser Gln Val Gly Phe Ile Asp Tyr
        130                 135                 140

Ile Ala His Pro Leu Trp Glu Thr Trp Ala Asp Leu Val His Pro Asp
145                 150                 155                 160

Ala Gln Asp Leu Leu Asp Thr Leu Glu Asp Asn Arg Glu Trp Tyr Gln
                165                 170                 175

Ser Lys Ile Pro Arg Ser Pro Ser Asp Leu Thr Asn Pro Glu Arg Asp
                180                 185                 190

Gly Pro Asp Arg Phe Gln Phe Glu Leu Thr Leu Glu Glu Ala Glu Glu
            195                 200                 205

Glu Asp Glu Glu Glu Glu Glu Gly Glu Glu Thr Ala Leu Ala Lys
        210                 215                 220

Glu Ala Leu Glu Leu Pro Asp Thr Glu Leu Leu Ser Pro Glu Ala Gly
225                 230                 235                 240

Pro Asp Pro Gly Asp Leu Pro Leu Asp Asn Gln Arg Thr
                245                 250
```

(2) INFORMATION FOR SEQ ID NO:47:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:47:

TACGAAGCTT TGATGGGGTC TACTGCTAC                                      29

(2) INFORMATION FOR SEQ ID NO:48:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:48:

TACGAAGCTT TGATGGTTGG CTTGGCATAT C                                31

(2) INFORMATION FOR SEQ ID NO:49:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (iv) ANTI-SENSE:

(xi) SEQUENCE DESCRIPTION: SEQ ID NO:49:

ATTAACCCTC ATAAAG                                                        16

(2) INFORMATION FOR SEQ ID NO:50:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:50:

TACGAAGCTT TGATGCGCCG ACAGCCTGC                                      29

(2) INFORMATION FOR SEQ ID NO:51:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:51:

GGTCTCCTGT TGCAGATATT G                                          21

(2) INFORMATION FOR SEQ ID NO:52:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:52:

TTYAARTCTN YTNCARGRNG A                                          21

(2) INFORMATION FOR SEQ ID NO:53:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:53:

ACNATRTCTR ATNACCATYT T                          21

(2) INFORMATION FOR SEQ ID NO:54:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:54:

Phe Lys Leu Leu Gln Glu Glu Asn
1          5

(2) INFORMATION FOR SEQ ID NO:55:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:55:

Phe Lys Leu Leu Gln Gly Glu Asn
1          5

(2) INFORMATION FOR SEQ ID NO:56:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:56:

Asp Met Val Ile Asp Met Val
1          5

(2) INFORMATION FOR SEQ ID NO:57:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:57:

Asp Met Val Ile Asp Ile Val
1          5

(2) INFORMATION FOR SEQ ID NO:58:

(i) SEQUENCE CHARACTERISTICS:
        (A) LENGTH: 4068 base pairs
        (B) TYPE: nucleic acid -continued (C) STRANDEDNESS: single
        (D) TOPOLOGY: linear (ii) MOLECULE TYPE: cDNA (ix) FEATURE:
        (A) NAME/KEY: CDS
        (B) LOCATION: 766..2458

(xi) SEQUENCE DESCRIPTION: SEQ ID NO:58:

```
GAATTCCTCC TCTCTTCACC CCGTTAGCTG TTTTCAATGT AATGCTGCCG TCCTTCTCTT      60

GCACTGCCTT CTGCGCTAAC ACCTCCATTC CTGTTTATAA CCGTGTATTT ATTACTTAAT     120

GTATATAATG TAATGTTTTG TAAGTTATTA ATTTATATAT CTAACATTGC CTGCCAATGG     180

TGGTGTTAAA TTTGTGTAGA AAACTCTGCC TAAGAGTTAC GACTTTTTCT TGTAATGTTT     240

TGTATTGTGT ATTATATAAC CCAAACGTCA CTTAGTAGAG ACATATGGCC CCCTTGGCAG     300

AGAGGACAGG GGTGGGCTTT TGTTCAAAGG GTCTGCCCTT TCCCTGCCTG AGTTGCTACT     360

TCTGCACAAC CCCTTTATGA ACCAGTTTTC ACCCGAATTT TGACTGTTTC ATTTAGAAGA     420

AAAGCAAAAT GAGAAAAAGC TTTCCTCATT TCTCCTTGAG ATGGCAAAGC ACTCAGAAAT     480

GACATCACAT ACCCTAAAGA ACCCTGGGAT GACTAAGGCA GAGAGAGTCT GAGAAAACTC     540

TTTGGTGCTT CTGCCTTTAG TTTTAGGACA CATTTATGCA GATGAGCTTA TAAGAGACCG     600

TTCCCTCCGC CTTCTTCCTC AGAGGAAGTT TCTTGGTAGA TCACCGACAC CTCATCCAGG     660

CGGGGGGTTG GGGGGAAACT TGGCACCAGC CATCCCAGGC AGAGCACCAC TGTGATTTGT     720

TCTCCTGGTG GAGAGAGCTG GAAGGAAGGA GCCAGCGTGC AAATA ATG AAG GAG         774
                                                  Met Lys Glu
                                                   1

CAC GGG GGC ACC TTC AGT AGC ACC GGA ATC AGC GGT GGT AGC GGT GAC       822
His Gly Gly Thr Phe Ser Ser Thr Gly Ile Ser Gly Gly Ser Gly Asp
     5                  10                  15

TCT GCT ATG GAC AGC CTG CAG CCG CTC CAG CCT AAC TAC ATG CCT GTG       870
Ser Ala Met Asp Ser Leu Gln Pro Leu Gln Pro Asn Tyr Met Pro Val
 20                  25                  30                  35

TGT TTG TTT GCA GAA GAA TCT TAT CAA AAA TTA GCA ATG GAA ACG CTG       918
Cys Leu Phe Ala Glu Glu Ser Tyr Gln Lys Leu Ala Met Glu Thr Leu
                 40                  45                  50

GAG GAA TTA GAC TGG TGT TTA GAC CAG CTA GAG ACC ATA CAG ACC TAC       966
Glu Glu Leu Asp Trp Cys Leu Asp Gln Leu Glu Thr Ile Gln Thr Tyr
             55                  60                  65

CGG TCT GTC AGT GAG ATG GCT TCT AAC AAG TTC AAA AGA ATG CTG AAC      1014
Arg Ser Val Ser Glu Met Ala Ser Asn Lys Phe Lys Arg Met Leu Asn
         70                  75                  80

CGG GAG CTG ACA CAC CTC TCA GAG ATG AGC CGA TCA GGG AAC CAG GTG      1062
Arg Glu Leu Thr His Leu Ser Glu Met Ser Arg Ser Gly Asn Gln Val
 85                  90                  95

TCT GAA TAC ATT TCA AAT ACT TTC TTA GAC AAG CAG AAT GAT GTG GAG      1110
Ser Glu Tyr Ile Ser Asn Thr Phe Leu Asp Lys Gln Asn Asp Val Glu
100                 105                 110                 115

ATC CCA TCT CCT ACC CAG AAA GAC AGG GAG AAA AAG AAA AAG CAG CAG      1158
Ile Pro Ser Pro Thr Gln Lys Asp Arg Glu Lys Lys Lys Lys Gln Gln
                120                 125                 130

CTC ATG ACC CAG ATA AGT GGA GTG AAG AAA TTA ATG CAT AGT TCA AGC      1206
Leu Met Thr Gln Ile Ser Gly Val Lys Lys Leu Met His Ser Ser Ser
            135                 140                 145

CTA AAC AAT ACA AGC ATC TCA CGC TTT GGA GTC AAC ACT GAA AAT GAA      1254
Leu Asn Asn Thr Ser Ile Ser Arg Phe Gly Val Asn Thr Glu Asn Glu
        150                 155                 160
```

```
GAT CAC CTG GCC AAG GAG CTG GAA GAC CTG AAC AAA TGG GGT CTT AAC     1302
Asp His Leu Ala Lys Glu Leu Glu Asp Leu Asn Lys Trp Gly Leu Asn
    165                 170                 175

ATC TTT AAT GTG GCT GGA TAT TCT CAC AAT AGA CCC CTA ACA TGC ATC     1350
Ile Phe Asn Val Ala Gly Tyr Ser His Asn Arg Pro Leu Thr Cys Ile
180                 185                 190                 195

ATG TAT GCT ATA TTC CAG GAA AGA GAC CTC CTA AAG ACA TTC AGA ATC     1398
Met Tyr Ala Ile Phe Gln Glu Arg Asp Leu Leu Lys Thr Phe Arg Ile
                200                 205                 210

TCA TCT GAC ACA TTT ATA ACC TAC ATG ATG ACT TTA GAA GAC CAT TAC     1446
Ser Ser Asp Thr Phe Ile Thr Tyr Met Met Thr Leu Glu Asp His Tyr
            215                 220                 225

CAT TCT GAC GTG GCA TAT CAC AAC AGC CTG CAC GCT GCT GAT GTA GCC     1494
His Ser Asp Val Ala Tyr His Asn Ser Leu His Ala Ala Asp Val Ala
        230                 235                 240

CAG TCG ACC CAT GTT CTC CTT TCT ACA CCA GCA TTA GAC GCT GTC TTC     1542
Gln Ser Thr His Val Leu Leu Ser Thr Pro Ala Leu Asp Ala Val Phe
    245                 250                 255

ACA GAT TTG GAG ATC CTG GCT GCC ATT TTT GCA GCT GCC ATC CAT GAC     1590
Thr Asp Leu Glu Ile Leu Ala Ala Ile Phe Ala Ala Ala Ile His Asp
260                 265                 270                 275

GTT GAT CAT CCT GGA GTC TCC AAT CAG TTT CTC ATC AAC ACA AAT TCA     1638
Val Asp His Pro Gly Val Ser Asn Gln Phe Leu Ile Asn Thr Asn Ser
                280                 285                 290

GAA CTT GCT TTG ATG TAT AAT GAT GAA TCT GTG TTG GAA AAT CAT CAC     1686
Glu Leu Ala Leu Met Tyr Asn Asp Glu Ser Val Leu Glu Asn His His
            295                 300                 305

CTT GCT GTG GGT TTC AAA CTG CTG CAA GAA GAA CAC TGT GAC ATC TTC     1734
Leu Ala Val Gly Phe Lys Leu Leu Gln Glu Glu His Cys Asp Ile Phe
        310                 315                 320

ATG AAT CTC ACC AAG AAG CAG CGT CAG ACA CTC AGG AAG ATG GTT ATT     1782
Met Asn Leu Thr Lys Lys Gln Arg Gln Thr Leu Arg Lys Met Val Ile
    325                 330                 335

GAC ATG GTG TTA GCA ACT GAT ATG TCT AAA CAT ATG AGC CTG CTG GCA     1830
Asp Met Val Leu Ala Thr Asp Met Ser Lys His Met Ser Leu Leu Ala
340                 345                 350                 355

GAC CTG AAG ACA ATG GTA GAA ACG AAG AAA GTT ACA AGT TCA GGC GTT     1878
Asp Leu Lys Thr Met Val Glu Thr Lys Lys Val Thr Ser Ser Gly Val
                360                 365                 370

CTT CTC CTA GAC AAC TAT ACC GAT CGC ATT CAG GTC CTT CGC AAC ATG     1926
Leu Leu Leu Asp Asn Tyr Thr Asp Arg Ile Gln Val Leu Arg Asn Met
            375                 380                 385

GTA CAC TGT GCA GAC CTG AGC AAC CCC ACC AAG TCC TTG GAA TTG TAT     1974
Val His Cys Ala Asp Leu Ser Asn Pro Thr Lys Ser Leu Glu Leu Tyr
        390                 395                 400

CGG CAA TGG ACA GAC CGC ATC ATG GAG GAA TTT TTC CAG CAG GGA GAC     2022
Arg Gln Trp Thr Asp Arg Ile Met Glu Glu Phe Phe Gln Gln Gly Asp
    405                 410                 415

AAA GAG CGG GAG AGG GGA ATG GAA ATT AGC CCA ATG TGT GAT AAA CAC     2070
Lys Glu Arg Glu Arg Gly Met Glu Ile Ser Pro Met Cys Asp Lys His
420                 425                 430                 435

ACA GCT TCT GTG GAA AAA TCC CAG GTT GGT TTC ATC GAC TAC ATT GTC     2118
Thr Ala Ser Val Glu Lys Ser Gln Val Gly Phe Ile Asp Tyr Ile Val
                440                 445                 450

CAT CCA TTG TGG GAG ACA TGG GCA GAT TTG GTA CAG CCT GAT GCT CAG     2166
His Pro Leu Trp Glu Thr Trp Ala Asp Leu Val Gln Pro Asp Ala Gln
            455                 460                 465

GAC ATT CTC GAT ACC TTA GAA GAT AAC AGG AAC TGG TAT CAG AGC ATG     2214
Asp Ile Leu Asp Thr Leu Glu Asp Asn Arg Asn Trp Tyr Gln Ser Met
        470                 475                 480
```

| | | |
|---|---|---|
| ATA CCT CAA AGT CCC TCA CCA CCA CTG GAC GAG CAG AAC AGG GAC TGC<br>Ile Pro Gln Ser Pro Ser Pro Pro Leu Asp Glu Gln Asn Arg Asp Cys<br>485 490 495 | | 2262 |
| CAG GGT CTG ATG GAG AAG TTT CAG TTT GAA CTG ACT CTC GAT GAG GAA<br>Gln Gly Leu Met Glu Lys Phe Gln Phe Glu Leu Thr Leu Asp Glu Glu<br>500 505 510 515 | | 2310 |
| GAT TCT GAA GGA CCT GAG AAG GAG GGA GAG GGA CAC AGC TAT TTC AGC<br>Asp Ser Glu Gly Pro Glu Lys Glu Gly Glu Gly His Ser Tyr Phe Ser<br>520 525 530 | | 2358 |
| AGC ACA AAG ACG CTT TGT GTG ATT GAT CCA GAA AAC AGA GAT TCC CTG<br>Ser Thr Lys Thr Leu Cys Val Ile Asp Pro Glu Asn Arg Asp Ser Leu<br>535 540 545 | | 2406 |
| GGA GAG ACT GAC ATA GAC ATT GCA ACA GAA GAC AAG TCC CCC GTG GAT<br>Gly Glu Thr Asp Ile Asp Ile Ala Thr Glu Asp Lys Ser Pro Val Asp<br>550 555 560 | | 2454 |
| ACA T AATCCCCCTC TCCCTGTGGA GATGAACATT CTATCCTTGA TGAGCATGCC<br>Thr | | 2508 |
| AGCTATGTGG TAGGGCCAGC CCACCATGGG GGCCAAGACC TGCACAGGAC AAGGGCCACC | | 2568 |
| TGGCCTTTCA GTTACTTGAG TTTGGAGTCA GAAAGCAAGA CCAGGAAGCA AATAGCAGCT | | 2628 |
| CAGGAAATCC CACGGTTGAC TTGCCTTGAT GGCAAGCTTG GTGGAGAGGG CTGAAGCTGT | | 2688 |
| TGCTGGGGGC CGATTCTGAT CAAGACACAT GGCTTGAAAA TGGAAGACAC AAAACTGAGA | | 2748 |
| GATCATTCTG CACTAAGTTT CGGGAACTTA TCCCCGACAG TGACTGAACT CACTGACTAA | | 2808 |
| TAACTTCATT TATGAATCTT CTCACTTGTC CCTTTGTCTG CCAACCTGTG TGCCTTTTTT | | 2868 |
| GTAAAACATT TTCATGTCTT TAAAATGCCT GTTGAATACC TGGAGTTTAG TATCAACTTC | | 2928 |
| TACACAGATA AGCTTTCAAA GTTGACAAAC TTTTTTGACT CTTTCTGGAA AAGGGAAAGA | | 2988 |
| AAATAGTCTT CCTTCTTTCT TGGGCAATAT CCTTCACTTT ACTACAGTTA CTTTTGCAAA | | 3048 |
| CAGACAGAAA GGATACACTT CTAACCACAT TTTACTTCCT TCCCCTGTTG TCCAGTCCAA | | 3108 |
| CTCCACAGTC ACTCTTAAAA CTTCTCTCTG TTTGCCTGCC TCCAACAGTA CTTTTAACTT | | 3168 |
| TTTGCTGTAA ACAGAATAAA ATTGAACAAA TTAGGGGGTA GAAAGGAGCA GTGGTGTCGT | | 3228 |
| TCACCGTGAG AGTCTGCATA GAACTCAGCA GTGTGCCCTG CTGTGTCTTG ACCCTGCCC | | 3288 |
| CCCACAGGAG TTGCTACAGT CCCTGGCCCT GCTTCCCATC CTCCTCTCTT CACCCCGTTA | | 3348 |
| GCTGTTTTCA ATGTAATGCT GCCGTCCTTC TCTTGCACTG CCTTCTGCGC TAACACCTCC | | 3408 |
| ATTCCTGTTT ATAACCGTGT ATTTATTACT TAATGTATAT AATGTAATGT TTTGTAAGTT | | 3468 |
| ATTAATTTAT ATATCTAACA TTGCCTGCCA ATGGTGGTGT TAAATTTGTG TAGAAAACTC | | 3528 |
| TGCCTAAGAG TTACGACTTT TTCTTGTAAT GTTTTGTATT GTGTATTATA TAACCCAAAC | | 3588 |
| GTCACTTAGT AGAGACATAT GGCCCCCTTG GCAGAGAGGA CAGGGGTGGG CTTTTGTTCA | | 3648 |
| AAGGGTCTGC CCTTTCCCTG CCTGAGTTGC TACTTCTGCA CAACCCCTTT ATGAACCAGT | | 3708 |
| TTTGGAAACA ATATTCTCAC ATTAGATACT AAATGGTTTA TACTGAGTCT TTTACTTTTG | | 3768 |
| TATAGCTTGA TAGGGGCAGG GGCAATGGGA TGTAGTTTTT ACCCAGGTTC TATCCAAATC | | 3828 |
| TATGTGGGCA TGAGTTGGGT TATAACTGGA TCCTACTATC ATTGTGGCTT TGGTTCAAAA | | 3888 |
| GGAAACACTA CATTTGCTCA CAGATGATTC TTCTGATTCT TCTGAATGCT CCCGAACTAC | | 3948 |
| TGACTTTGAA GAGGTAGCCT CCTGCCTGCC ATTAAGCAGG AATGTCATGT TCCAGTTCAT | | 4008 |
| TACAAAGAA AACAATAAAA CAATGTGAAT TTTTATAATA AAAAAAAAAA AAAGGAATTC | | 4068 |

(2) INFORMATION FOR SEQ ID NO:59:

(i) SEQUENCE CHARACTERISTICS:
    (A) LENGTH: 564 amino acids
    (B) TYPE: amino acid
    (D) TOPOLOGY: linear (ii) MOLECULE TYPE: protein (xi) SEQUENCE DESCRIPTION: SEQ ID NO:59:

```
Met Lys Glu His Gly Gly Thr Phe Ser Ser Thr Gly Ile Ser Gly Gly
 1               5                  10                  15

Ser Gly Asp Ser Ala Met Asp Ser Leu Gln Pro Leu Gln Pro Asn Tyr
             20                  25                  30

Met Pro Val Cys Leu Phe Ala Glu Glu Ser Tyr Gln Lys Leu Ala Met
         35                  40                  45

Glu Thr Leu Glu Glu Leu Asp Trp Cys Leu Asp Gln Leu Glu Thr Ile
     50                  55                  60

Gln Thr Tyr Arg Ser Val Ser Glu Met Ala Ser Asn Lys Phe Lys Arg
 65                  70                  75                  80

Met Leu Asn Arg Glu Leu Thr His Leu Ser Glu Met Ser Arg Ser Gly
                 85                  90                  95

Asn Gln Val Ser Glu Tyr Ile Ser Asn Thr Phe Leu Asp Lys Gln Asn
            100                 105                 110

Asp Val Glu Ile Pro Ser Pro Thr Gln Lys Asp Arg Glu Lys Lys Lys
            115                 120                 125

Lys Gln Gln Leu Met Thr Gln Ile Ser Gly Val Lys Lys Leu Met His
        130                 135                 140

Ser Ser Ser Leu Asn Asn Thr Ser Ile Ser Arg Phe Gly Val Asn Thr
145                 150                 155                 160

Glu Asn Glu Asp His Leu Ala Lys Glu Leu Glu Asp Leu Asn Lys Trp
                165                 170                 175

Gly Leu Asn Ile Phe Asn Val Ala Gly Tyr Ser His Asn Arg Pro Leu
            180                 185                 190

Thr Cys Ile Met Tyr Ala Ile Phe Gln Glu Arg Asp Leu Leu Lys Thr
        195                 200                 205

Phe Arg Ile Ser Ser Asp Thr Phe Ile Thr Tyr Met Met Thr Leu Glu
    210                 215                 220

Asp His Tyr His Ser Asp Val Ala Tyr His Asn Ser Leu His Ala Ala
225                 230                 235                 240

Asp Val Ala Gln Ser Thr His Val Leu Leu Ser Thr Pro Ala Leu Asp
                245                 250                 255

Ala Val Phe Thr Asp Leu Glu Ile Leu Ala Ala Ile Phe Ala Ala Ala
            260                 265                 270

Ile His Asp Val Asp His Pro Gly Val Ser Asn Gln Phe Leu Ile Asn
        275                 280                 285

Thr Asn Ser Glu Leu Ala Leu Met Tyr Asn Asp Glu Ser Val Leu Glu
    290                 295                 300

Asn His His Leu Ala Val Gly Phe Lys Leu Leu Gln Glu Glu His Cys
305                 310                 315                 320

Asp Ile Phe Met Asn Leu Thr Lys Lys Gln Arg Gln Thr Leu Arg Lys
                325                 330                 335

Met Val Ile Asp Met Val Leu Ala Thr Asp Met Ser Lys His Met Ser
            340                 345                 350

Leu Leu Ala Asp Leu Lys Thr Met Val Glu Thr Lys Lys Val Thr Ser
        355                 360                 365

Ser Gly Val Leu Leu Leu Asp Asn Tyr Thr Asp Arg Ile Gln Val Leu
```

```
            370                375                380
Arg Asn Met Val His Cys Ala Asp Leu Ser Asn Pro Thr Lys Ser Leu
385                390                395                400

Glu Leu Tyr Arg Gln Trp Thr Asp Arg Ile Met Glu Glu Phe Phe Gln
                405                410                415

Gln Gly Asp Lys Glu Arg Glu Arg Gly Met Glu Ile Ser Pro Met Cys
            420                425                430

Asp Lys His Thr Ala Ser Val Glu Lys Ser Gln Val Gly Phe Ile Asp
        435                440                445

Tyr Ile Val His Pro Leu Trp Glu Thr Trp Ala Asp Leu Val Gln Pro
    450                455                460

Asp Ala Gln Asp Ile Leu Asp Thr Leu Glu Asp Asn Arg Asn Trp Tyr
465                470                475                480

Gln Ser Met Ile Pro Gln Ser Pro Ser Pro Pro Leu Asp Glu Gln Asn
                485                490                495

Arg Asp Cys Gln Gly Leu Met Glu Lys Phe Gln Phe Glu Leu Thr Leu
            500                505                510

Asp Glu Glu Asp Ser Glu Gly Pro Glu Lys Glu Gly Glu Gly His Ser
        515                520                525

Tyr Phe Ser Ser Thr Lys Thr Leu Cys Val Ile Asp Pro Glu Asn Arg
    530                535                540

Asp Ser Leu Gly Glu Thr Asp Ile Asp Ile Ala Thr Glu Asp Lys Ser
545                550                555                560

Pro Val Asp Thr (2) INFORMATION FOR SEQ ID NO:60:

(i) SEQUENCE CHARACTERISTICS:
        (A) LENGTH: 2115 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 762..2115

(xi) SEQUENCE DESCRIPTION: SEQ ID NO:60:

GAATTCCCTG GGATTACAGG CCTTTTTATG ACTTTTACTT CCTTTATAGT CAAATTCCAA      60

CGTCTTCTCA GTGCTCCACC AGGCTGGCAA CCTGGGCCCA ACCAGGCTCA CTAAACCATC     120

CAATCAGTAG GAGCCATAGA CTACTTTATT TAGCCAAAGG CAAAAATGAG TCAACTGAAT     180

TCTGTTTTTC CATTTACTTC TGTCTGTTTT TCCTTCCTCT TGCCACCCTC AGTGCCACAA     240

GAGGGGACCC CTCTCGGTAG CCCTGAGGCT CTGGCGCCTT CAAGTGAGAA GCTAAGCACC     300

AGCCTCTGCT GGCTGCAGAA GCGGCGGCGG CGGCAGCAGC AGCAGCAGCA TCAGGAAGGC     360

TCTCGGGCCA GCGCGGTGAA CCCGGGCTGG CAGCAGGTCG CGGACGCGCG AGCCAGGATG     420

GAGGCAGAGG GCAGCAGCGC GCCGGCCCGG CGGGCGAGCG GAGAGGGCAG CGACGGCGGC     480

ACGCTCAAAG CCCCCAAGCA TCTCTGGAGG CACGAGCAGC ACCACCAGTA CCCGCTCCGG     540

CAGCCCCAGT TCCGCCTCCT GCATCCCCAT CACCACCTGC CCCCGCCGCC GCCACCCTCG     600

CCCCAGCCCC AGCCCCAGTG TCAGCCGCCG CCGCCGCCCC CCTGCCGCC GCCCCCGCCG      660

CCGCCCGGGG CTGCCCGCGG CCGCTACGCC TCGAGCGGGG CCACCGGCGC GTCCGGCATC     720

GCGGCTACTC GGACACCGAG CGCTACCTGT ACTGTCGCGC C ATG GAC CGC ACC         773
```

-continued

```
                        Met Asp Arg Thr
                         1

TCC TAC GCG GTG GAG ACC GGC CAC CGG CCC GGC CTG AAG AAA TCC AGG      821
Ser Tyr Ala Val Glu Thr Gly His Arg Pro Gly Leu Lys Lys Ser Arg
 5               10                  15                  20

ATG TCC TGG CCC TCC TCG TTC CAG GGA CTC AGG CGT TTT GAT GTG GAC      869
Met Ser Trp Pro Ser Ser Phe Gln Gly Leu Arg Arg Phe Asp Val Asp
             25                  30                  35

AAT GGC ACA TCT GCG GGA CGG AGT CCC TTG GAT CCC ATG ACC AGC CCA      917
Asn Gly Thr Ser Ala Gly Arg Ser Pro Leu Asp Pro Met Thr Ser Pro
                 40                  45                  50

GGA TCC GGG CTA ATT CTC CAA GCA AAT TTT GTC CAC AGT CAA CGA CGG      965
Gly Ser Gly Leu Ile Leu Gln Ala Asn Phe Val His Ser Gln Arg Arg
             55                  60                  65

GAG TCC TTC CTG TAT CGA TCC GAC AGC GAT TAT GAC CTC TCT CCA AAG     1013
Glu Ser Phe Leu Tyr Arg Ser Asp Ser Asp Tyr Asp Leu Ser Pro Lys
 70                  75                  80

TCT ATG TCC CGG AAC TCC TCC ATT GCC AGT GAT ATA CAC GGA GAT GAC     1061
Ser Met Ser Arg Asn Ser Ser Ile Ala Ser Asp Ile His Gly Asp Asp
 85                  90                  95                 100

TTG ATT GTG ACT CCA TTT GCT CAG GTC TTG GCC AGT CTG CGA ACT GTA     1109
Leu Ile Val Thr Pro Phe Ala Gln Val Leu Ala Ser Leu Arg Thr Val
                105                 110                 115

CGA AAC AAC TTT GCT GCA TTA ACT AAT TTG CAA GAT CGA GCA CCT AGC     1157
Arg Asn Asn Phe Ala Ala Leu Thr Asn Leu Gln Asp Arg Ala Pro Ser
             120                 125                 130

AAA AGA TCA CCC ATG TGC AAC CAA CCA TCC ATC AAC AAA GCC ACC ATA     1205
Lys Arg Ser Pro Met Cys Asn Gln Pro Ser Ile Asn Lys Ala Thr Ile
         135                 140                 145

ACA GAG GAG GCC TAC CAG AAA CTG GCC AGC GAG ACC CTG GAG GAG CTG     1253
Thr Glu Glu Ala Tyr Gln Lys Leu Ala Ser Glu Thr Leu Glu Glu Leu
    150                 155                 160

GAC TGG TGT CTG GAC CAG CTA GAG ACC CTA CAG ACC AGG CAC TCC GTC     1301
Asp Trp Cys Leu Asp Gln Leu Glu Thr Leu Gln Thr Arg His Ser Val
165                 170                 175                 180

AGT GAG ATG GCC TCC AAC AAG TTT AAA AGG ATG CTT AAT CGG GAG CTC     1349
Ser Glu Met Ala Ser Asn Lys Phe Lys Arg Met Leu Asn Arg Glu Leu
                185                 190                 195

ACC CAT CTC TCT GAA ATG AGT CGG TCT GGA AAT CAA GTG TCA GAG TTT     1397
Thr His Leu Ser Glu Met Ser Arg Ser Gly Asn Gln Val Ser Glu Phe
            200                 205                 210

ATA TCA AAC ACA TTC TTA GAT AAG CAA CAT GAA GTG GAA ATT CCT TCT     1445
Ile Ser Asn Thr Phe Leu Asp Lys Gln His Glu Val Glu Ile Pro Ser
        215                 220                 225

CCA ACT CAG AAG GAA AAG GAG AAA AAG AAA AGA CCA ATG TCT CAG ATC     1493
Pro Thr Gln Lys Glu Lys Glu Lys Lys Lys Arg Pro Met Ser Gln Ile
    230                 235                 240

AGT GGA GTC AAG AAA TTG ATG CAC AGC TCT AGT CTG ACT AAT TCA AGT     1541
Ser Gly Val Lys Lys Leu Met His Ser Ser Ser Leu Thr Asn Ser Ser
245                 250                 255                 260

ATC CCA AGG TTT GGA GTT AAA ACT GAA CAA GAA GAT GTC CTT GCC AAG     1589
Ile Pro Arg Phe Gly Val Lys Thr Glu Gln Glu Asp Val Leu Ala Lys
                265                 270                 275

GAA CTA GAA GAT GTG AAC AAA TGG GGT CTT CAT GTT TTC AGA ATA GCA     1637
Glu Leu Glu Asp Val Asn Lys Trp Gly Leu His Val Phe Arg Ile Ala
            280                 285                 290

GAG TTG TCT GGT AAC CGG CCC TTG ACT GTT ATC ATG CAC ACC ATT TTT     1685
Glu Leu Ser Gly Asn Arg Pro Leu Thr Val Ile Met His Thr Ile Phe
        295                 300                 305
```

```
CAG GAA CGG GAT TTA TTA AAA ACA TTT AAA ATT CCA GTA GAT ACT TTA        1733
Gln Glu Arg Asp Leu Leu Lys Thr Phe Lys Ile Pro Val Asp Thr Leu
        310                 315                 320

ATT ACA TAT CTT ATG ACT CTC GAA GAC CAT TAC CAT GCT GAT GTG GCC        1781
Ile Thr Tyr Leu Met Thr Leu Glu Asp His Tyr His Ala Asp Val Ala
325                 330                 335                 340

TAT CAC AAC AAT ATC CAT GCT GCA GAT GTT GTC CAG TCT ACT CAT GTG        1829
Tyr His Asn Asn Ile His Ala Ala Asp Val Val Gln Ser Thr His Val
                345                 350                 355

CTA TTA TCT ACA CCT GCT TTG GAG GCT GTG TTT ACA GAT TTG GAG ATT        1877
Leu Leu Ser Thr Pro Ala Leu Glu Ala Val Phe Thr Asp Leu Glu Ile
            360                 365                 370

CTT GCA GCA ATT TTT GCC AGT GCA ATA CAT GAT GTA GAT CAT CCT GGT        1925
Leu Ala Ala Ile Phe Ala Ser Ala Ile His Asp Val Asp His Pro Gly
        375                 380                 385

GTG TCC AAT CAA TTT CTG ATC AAT ACA AAC TCT GAA CTT GCC TTG ATG        1973
Val Ser Asn Gln Phe Leu Ile Asn Thr Asn Ser Glu Leu Ala Leu Met
390                 395                 400

TAC AAT GAT TCC TCA GTC TTA GAG AAC CAT CAT TTG GCT GTG GGC TTT        2021
Tyr Asn Asp Ser Ser Val Leu Glu Asn His His Leu Ala Val Gly Phe
405                 410                 415                 420

AAA TTG CTT CAG GAA GAA AAC TGT GAC ATT TTC CAG AAT TTG ACC AAA        2069
Lys Leu Leu Gln Glu Glu Asn Cys Asp Ile Phe Gln Asn Leu Thr Lys
                425                 430                 435

AAA CAA AGA CAA TCT TTA AGG AAA ATG GTC ATT GAC ATC GTA CTT G          2115
Lys Gln Arg Gln Ser Leu Arg Lys Met Val Ile Asp Ile Val Leu
            440                 445                 450
```

(2) INFORMATION FOR SEQ ID NO:61:

(i) SEQUENCE CHARACTERISTICS:
        (A) LENGTH: 451 amino acids
        (B) TYPE: amino acid
        (D) TOPOLOGY: linear (ii) MOLECULE TYPE: protein (xi) SEQUENCE DESCRIPTION: SEQ ID NO:61:

```
Met Asp Arg Thr Ser Tyr Ala Val Glu Thr Gly His Arg Pro Gly Leu
 1               5                  10                  15

Lys Lys Ser Arg Met Ser Trp Pro Ser Ser Phe Gln Gly Leu Arg Arg
             20                  25                  30

Phe Asp Val Asp Asn Gly Thr Ser Ala Gly Arg Ser Pro Leu Asp Pro
         35                  40                  45

Met Thr Ser Pro Gly Ser Gly Leu Ile Leu Gln Ala Asn Phe Val His
     50                  55                  60

Ser Gln Arg Arg Glu Ser Phe Leu Tyr Arg Ser Asp Ser Asp Tyr Asp
65                  70                  75                  80

Leu Ser Pro Lys Ser Met Ser Arg Asn Ser Ser Ile Ala Ser Asp Ile
                 85                  90                  95

His Gly Asp Asp Leu Ile Val Thr Pro Phe Ala Gln Val Leu Ala Ser
            100                 105                 110

Leu Arg Thr Val Arg Asn Asn Phe Ala Ala Leu Thr Asn Leu Gln Asp
        115                 120                 125

Arg Ala Pro Ser Lys Arg Ser Pro Met Cys Asn Gln Pro Ser Ile Asn
    130                 135                 140

Lys Ala Thr Ile Thr Glu Glu Ala Tyr Gln Lys Leu Ala Ser Glu Thr
145                 150                 155                 160

Leu Glu Glu Leu Asp Trp Cys Leu Asp Gln Leu Glu Thr Leu Gln Thr
```

```
                   165                 170                 175
Arg His Ser Val Ser Glu Met Ala Ser Asn Lys Phe Lys Arg Met Leu
                180                 185                 190

Asn Arg Glu Leu Thr His Leu Ser Glu Met Ser Arg Ser Gly Asn Gln
            195                 200                 205

Val Ser Glu Phe Ile Ser Asn Thr Phe Leu Asp Lys Gln His Glu Val
    210                 215                 220

Glu Ile Pro Ser Pro Thr Gln Lys Glu Lys Lys Lys Arg Pro
225                 230                 235                 240

Met Ser Gln Ile Ser Gly Val Lys Lys Leu Met His Ser Ser Ser Leu
                245                 250                 255

Thr Asn Ser Ser Ile Pro Arg Phe Gly Val Lys Thr Glu Gln Glu Asp
            260                 265                 270

Val Leu Ala Lys Glu Leu Glu Asp Val Asn Lys Trp Gly Leu His Val
    275                 280                 285

Phe Arg Ile Ala Glu Leu Ser Gly Asn Arg Pro Leu Thr Val Ile Met
290                 295                 300

His Thr Ile Phe Gln Glu Arg Asp Leu Leu Lys Thr Phe Lys Ile Pro
305                 310                 315                 320

Val Asp Thr Leu Ile Thr Tyr Leu Met Thr Leu Glu Asp His Tyr His
                325                 330                 335

Ala Asp Val Ala Tyr His Asn Asn Ile His Ala Ala Asp Val Val Gln
            340                 345                 350

Ser Thr His Val Leu Leu Ser Thr Pro Ala Leu Glu Ala Val Phe Thr
    355                 360                 365

Asp Leu Glu Ile Leu Ala Ala Ile Phe Ala Ser Ala Ile His Asp Val
370                 375                 380

Asp His Pro Gly Val Ser Asn Gln Phe Leu Ile Asn Thr Asn Ser Glu
385                 390                 395                 400

Leu Ala Leu Met Tyr Asn Asp Ser Ser Val Leu Glu Asn His His Leu
                405                 410                 415

Ala Val Gly Phe Lys Leu Leu Gln Glu Glu Asn Cys Asp Ile Phe Gln
            420                 425                 430

Asn Leu Thr Lys Lys Gln Arg Gln Ser Leu Arg Lys Met Val Ile Asp
    435                 440                 445

Ile Val Leu
450

(2) INFORMATION FOR SEQ ID NO:62:

(i) SEQUENCE CHARACTERISTICS:
        (A) LENGTH: 3130 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 132..2151

(xi) SEQUENCE DESCRIPTION: SEQ ID NO:62:

GAATTCCCAA TACTTGTTGC AATAATTGCC CACGATAGCT GCTCAAACAA GAGAGTTGGA      60

ATTCATCTGT AAAAATCACT ACATGTAACG TAGGAGACAA GAAAAATATT AATGACAGAA     120

GATCTGCGAA C ATG ATG CAC GTG AAT AAT TTT CCC TTT AGA AGG CAT TCC     170
             Met Met His Val Asn Asn Phe Pro Phe Arg Arg His Ser
```

```
                  1              5                  10
TGG ATA TGT TTT GAT GTG GAC AAT GGC ACA TCT GCG GGA CGG AGT CCC        218
Trp Ile Cys Phe Asp Val Asp Asn Gly Thr Ser Ala Gly Arg Ser Pro
        15                  20                  25

TTG GAT CCC ATG ACC AGC CCA GGA TCC GGG CTA ATT CTC CAA GCA AAT        266
Leu Asp Pro Met Thr Ser Pro Gly Ser Gly Leu Ile Leu Gln Ala Asn
30                  35                  40                  45

TTT GTC CAC AGT CAA CGA CGG GAG TCC TTC CTG TAT CGA TCC GAC AGC        314
Phe Val His Ser Gln Arg Arg Glu Ser Phe Leu Tyr Arg Ser Asp Ser
                50                  55                  60

GAT TAT GAC CTC TCT CCA AAG TCT ATG TCC CGG AAC TCC TCC ATT GCC        362
Asp Tyr Asp Leu Ser Pro Lys Ser Met Ser Arg Asn Ser Ser Ile Ala
            65                  70                  75

AGT GAT ATA CAC GGA GAT GAC TTG ATT GTG ACT CCA TTT GCT CAG GTC        410
Ser Asp Ile His Gly Asp Asp Leu Ile Val Thr Pro Phe Ala Gln Val
        80                  85                  90

TTG GCC AGT CTG CGA ACT GTA CGA AAC AAC TTT GCT GCA TTA ACT AAT        458
Leu Ala Ser Leu Arg Thr Val Arg Asn Asn Phe Ala Ala Leu Thr Asn
95                  100                 105

TTG CAA GAT CGA GCA CCT AGC AAA AGA TCA CCC ATG TGC AAC CAA CCA        506
Leu Gln Asp Arg Ala Pro Ser Lys Arg Ser Pro Met Cys Asn Gln Pro
110             115                 120                 125

TCC ATC AAC AAA GCC ACC ATA ACA GAG GAG GCC TAC CAG AAA CTG GCC        554
Ser Ile Asn Lys Ala Thr Ile Thr Glu Glu Ala Tyr Gln Lys Leu Ala
                130                 135                 140

AGC GAG ACC CTG GAG GAG CTG GAC TGG TGT CTG GAC CAG CTA GAG ACC        602
Ser Glu Thr Leu Glu Glu Leu Asp Trp Cys Leu Asp Gln Leu Glu Thr
            145                 150                 155

CTA CAG ACC AGG CAC TCC GTC AGT GAG ATG GCC TCC AAC AAG TTT AAA        650
Leu Gln Thr Arg His Ser Val Ser Glu Met Ala Ser Asn Lys Phe Lys
        160                 165                 170

AGG ATG CTT AAT CGG GAG CTC ACC CAT CTC TCT GAA ATG AGT CGG TCT        698
Arg Met Leu Asn Arg Glu Leu Thr His Leu Ser Glu Met Ser Arg Ser
    175                 180                 185

GGA AAT CAA GTG TCA GAG TTT ATA TCA AAC ACA TTC TTA GAT AAG CAA        746
Gly Asn Gln Val Ser Glu Phe Ile Ser Asn Thr Phe Leu Asp Lys Gln
190                 195                 200                 205

CAT GAA GTG GAA ATT CCT TCT CCA ACT CAG AAG GAA AAG GAG AAA AAG        794
His Glu Val Glu Ile Pro Ser Pro Thr Gln Lys Glu Lys Glu Lys Lys
                210                 215                 220

AAA AGA CCA ATG TCT CAG ATC AGT GGA GTC AAG AAA TTG ATG CAC AGC        842
Lys Arg Pro Met Ser Gln Ile Ser Gly Val Lys Lys Leu Met His Ser
            225                 230                 235

TCT AGT CTG ACT AAT TCA AGT ATC CCA AGG TTT GGA GTT AAA ACT GAA        890
Ser Ser Leu Thr Asn Ser Ser Ile Pro Arg Phe Gly Val Lys Thr Glu
        240                 245                 250

CAA GAA GAT GTC CTT GCC AAG GAA CTA GAA GAT GTG AAC AAA TGG GGT        938
Gln Glu Asp Val Leu Ala Lys Glu Leu Glu Asp Val Asn Lys Trp Gly
    255                 260                 265

CTT CAT GTT TTC AGA ATA GCA GAG TTG TCT GGT AAC CGG CCC TTG ACT        986
Leu His Val Phe Arg Ile Ala Glu Leu Ser Gly Asn Arg Pro Leu Thr
270                 275                 280                 285

GTT ATC ATG CAC ACC ATT TTT CAG GAA CGG GAT TTA TTA AAA ACA TTT        1034
Val Ile Met His Thr Ile Phe Gln Glu Arg Asp Leu Leu Lys Thr Phe
                290                 295                 300

AAA ATT CCA GTA GAT ACT TTA ATT ACA TAT CTT ATG ACT CTC GAA GAC        1082
Lys Ile Pro Val Asp Thr Leu Ile Thr Tyr Leu Met Thr Leu Glu Asp
            305                 310                 315

CAT TAC CAT GCT GAT GTG GCC TAT CAC AAC AAT ATC CAT GCT GCA GAT        1130
```

```
                His Tyr His Ala Asp Val Ala Tyr His Asn Asn Ile His Ala Ala Asp
                        320                 325                 330

GTT GTC CAG TCT ACT CAT GTG CTA TTA TCT ACA CCT GCT TTG GAG GCT        1178
Val Val Gln Ser Thr His Val Leu Leu Ser Thr Pro Ala Leu Glu Ala
335                 340                 345

GTG TTT ACA GAT TTG GAG ATT CTT GCA GCA ATT TTT GCC AGT GCA ATA        1226
Val Phe Thr Asp Leu Glu Ile Leu Ala Ala Ile Phe Ala Ser Ala Ile
350                 355                 360                 365

CAT GAT GTA GAT CAT CCT GGT GTG TCC AAT CAA TTT CTG ATC AAT ACA        1274
His Asp Val Asp His Pro Gly Val Ser Asn Gln Phe Leu Ile Asn Thr
                370                 375                 380

AAC TCT GAA CTT GCC TTG ATG TAC AAT GAT TCA GTC TTA GAG AAC            1322
Asn Ser Glu Leu Ala Leu Met Tyr Asn Asp Ser Ser Val Leu Glu Asn
            385                 390                 395

CAT CAT TTG GCT GTG GGC TTT AAA TTG CTT CAG GAA GAA AAC TGT GAC        1370
His His Leu Ala Val Gly Phe Lys Leu Leu Gln Glu Glu Asn Cys Asp
            400                 405                 410

ATT TTC CAG AAT TTG ACC AAA AAA CAA AGA CAA TCT TTA AGG AAA ATG        1418
Ile Phe Gln Asn Leu Thr Lys Lys Gln Arg Gln Ser Leu Arg Lys Met
            415                 420                 425

GTC ATT GAC ATC GTA CTT GCA ACA GAT ATG TCA AAA CAC ATG AAT CTA        1466
Val Ile Asp Ile Val Leu Ala Thr Asp Met Ser Lys His Met Asn Leu
430                 435                 440                 445

CTG GCT GAT TTG AAG ACT ATG GTT GAA ACT AAG AAA GTG ACA AGC TCT        1514
Leu Ala Asp Leu Lys Thr Met Val Glu Thr Lys Lys Val Thr Ser Ser
                450                 455                 460

GGA GTT CTT CTT CTT GAT AAT TAT TCC GAT AGG ATT CAG GTT CTT CAG        1562
Gly Val Leu Leu Leu Asp Asn Tyr Ser Asp Arg Ile Gln Val Leu Gln
                465                 470                 475

AAT ATG GTG CAC TGT GCA GAT CTG AGC AAC CCA ACA AAG CCT CTC CAG        1610
Asn Met Val His Cys Ala Asp Leu Ser Asn Pro Thr Lys Pro Leu Gln
            480                 485                 490

CTG TAC CGC CAG TGG ACG GAC CGG ATA ATG GAG GAG TTC TTC CGC CAA        1658
Leu Tyr Arg Gln Trp Thr Asp Arg Ile Met Glu Glu Phe Phe Arg Gln
    495                 500                 505

GGA GAC CGA GAG AGG GAA CGT GGC ATG GAG ATA AGC CCC ATG TGT GAC        1706
Gly Asp Arg Glu Arg Glu Arg Gly Met Glu Ile Ser Pro Met Cys Asp
510                 515                 520                 525

AAG CAC AAT GCT TCC GTG GAA AAA TCA CAG GTG GGC TTC ATA GAC TAT        1754
Lys His Asn Ala Ser Val Glu Lys Ser Gln Val Gly Phe Ile Asp Tyr
                530                 535                 540

ATT GTT CAT CCC CTC TGG GAG ACA TGG GCA GAC CTC GTC CAC CCT GAC        1802
Ile Val His Pro Leu Trp Glu Thr Trp Ala Asp Leu Val His Pro Asp
                545                 550                 555

GCC CAG GAT ATT TTG GAC ACT TTG GAG GAC AAT CGT GAA TGG TAC CAG        1850
Ala Gln Asp Ile Leu Asp Thr Leu Glu Asp Asn Arg Glu Trp Tyr Gln
            560                 565                 570

AGC ACA ATC CCT CAG AGC CCC TCT CCT GCA CCT GAT GAC CCA GAG GAG        1898
Ser Thr Ile Pro Gln Ser Pro Ser Pro Ala Pro Asp Asp Pro Glu Glu
    575                 580                 585

GGC CGG CAG GGT CAA ACT GAG AAA TTC CAG TTT GAA CTA ACT TTA GAG        1946
Gly Arg Gln Gly Gln Thr Glu Lys Phe Gln Phe Glu Leu Thr Leu Glu
590                 595                 600                 605

GAA GAT GGT GAG TCA GAC ACG GAA AAG GAC AGT GGC AGT CAA GTG GAA        1994
Glu Asp Gly Glu Ser Asp Thr Glu Lys Asp Ser Gly Ser Gln Val Glu
                610                 615                 620

GAA GAC ACT AGC TGC AGT GAC TCC AAG ACT CTT TGT ACT CAA GAC TCA        2042
Glu Asp Thr Ser Cys Ser Asp Ser Lys Thr Leu Cys Thr Gln Asp Ser
            625                 630                 635
```

```
GAG TCT ACT GAA ATT CCC CTT GAT GAA CAG GTT GAA GAG GAG GCA GTA      2090
Glu Ser Thr Glu Ile Pro Leu Asp Glu Gln Val Glu Glu Glu Ala Val
        640                 645                 650

GGG GAA GAA GAG GAA AGC CAG CCT GAA GCC TGT GTC ATA GAT GAT CGT      2138
Gly Glu Glu Glu Glu Ser Gln Pro Glu Ala Cys Val Ile Asp Asp Arg
        655                 660                 665

TCT CCT GAC ACG T AACAGTGCAA AAACTTTCAT GCCTTTTTTT TTTTTAAGTA        2191
Ser Pro Asp Thr
670

GAAAAATTGT TTCCAAAGTG CATGTCACAT GCCACAACCA CGGTCACACC TCACTGTCAT    2251

CTGCCAGGAC GTTTGTTGAA CAAAACTGAC CTTGACTACT CAGTCCAGCG CTCAGGAATA    2311

TCGTAACCAG TTTTTTCACC TCCATGTTCA TCCGAGCAAG GTGGACATCT TCACGAACAG    2371

CGTTTTTAAC AAGATTTCAG CTTGGTAGAG CTGACAAAGC AGATAAAATC TACTCCAAAT    2431

TATTTTCAAG AGAGTGTGAC TCATCAGGCA GCCCAAAAGT TTATTGGACT TGGGGTTTCT    2491

ATTCCTTTTT ATTTGTTTGC AATATTTTCA GAAGAAAGGC ATTGCACAGA GTGAACTTAA    2551

TGGACGAAGC AACAAATATG TCAAGAACAG GACATAGCAC GAATCTGTTA CCAGTAGGAG    2611

GAGGATGAGC CACAGAAATT GCATAATTTT CTAATTTCAA GTCTTCCTGA TACATGACTG    2671

AATAGTGTGG TTCAGTGAGC TGCACTGACC TCTACATTTT GTATGATATG TAAAACAGAT    2731

TTTTTGTAGA GCTTACTTTT ATTATTAAAT GTATTGAGGT ATTATATTTA AAAAAAACTA    2791

TGTTCAGAAC TTCATCTGCC ACTGGTTATT TTTTTCTAAG GAGTAACTTG CAAGTTTTCA    2851

GTACAAATCT GTGCTACACT GGATAAAAAT CTAATTTATG AATTTTACTT GCACCTTATA    2911

GTTCATAGCA ATAACTGAT TTGTAGTGAT TCATTGTTTG TTTTATATAC CAATGACTTC     2971

CATATTTTAA AAGAGAAAAA CAACTTTATG TTGCAGGAAA CCCTTTTTGT AAGTCTTTAT    3031

TATTTACTTT GCATTTTGTT TCACTCTTTC CAGATAAGCA GAGTTGCTCT TCACCAGTGT    3091

TTTTCTTCAT GTGCAAAGTG ACTATTTGTT CTATAATAC                           3130
```

(2) INFORMATION FOR SEQ ID NO:63:

(i) SEQUENCE CHARACTERISTICS:
        (A) LENGTH: 673 amino acids
        (B) TYPE: amino acid
        (D) TOPOLOGY: linear (ii) MOLECULE TYPE: protein (xi) SEQUENCE DESCRIPTION: SEQ ID NO:63:

```
Met Met His Val Asn Asn Phe Pro Phe Arg Arg His Ser Trp Ile Cys
 1               5                  10                  15

Phe Asp Val Asp Asn Gly Thr Ser Ala Gly Arg Ser Pro Leu Asp Pro
                20                  25                  30

Met Thr Ser Pro Gly Ser Gly Leu Ile Leu Gln Ala Asn Phe Val His
            35                  40                  45

Ser Gln Arg Arg Glu Ser Phe Leu Tyr Arg Ser Asp Ser Asp Tyr Asp
        50                  55                  60

Leu Ser Pro Lys Ser Met Ser Arg Asn Ser Ile Ala Ser Asp Ile
65                  70                  75                  80

His Gly Asp Asp Leu Ile Val Thr Pro Phe Ala Gln Val Leu Ala Ser
                85                  90                  95

Leu Arg Thr Val Arg Asn Asn Phe Ala Ala Leu Thr Asn Leu Gln Asp
                100                 105                 110

Arg Ala Pro Ser Lys Arg Ser Pro Met Cys Asn Gln Pro Ser Ile Asn
            115                 120                 125
```

-continued

```
Lys Ala Thr Ile Thr Glu Glu Ala Tyr Gln Lys Leu Ala Ser Glu Thr
    130                 135                 140
Leu Glu Glu Leu Asp Trp Cys Leu Asp Gln Leu Glu Thr Leu Gln Thr
145                 150                 155                 160
Arg His Ser Val Ser Glu Met Ala Ser Asn Lys Phe Lys Arg Met Leu
                165                 170                 175
Asn Arg Glu Leu Thr His Leu Ser Glu Met Ser Arg Ser Gly Asn Gln
            180                 185                 190
Val Ser Glu Phe Ile Ser Asn Thr Phe Leu Asp Lys Gln His Glu Val
        195                 200                 205
Glu Ile Pro Ser Pro Thr Gln Lys Glu Lys Lys Lys Arg Pro
    210                 215                 220
Met Ser Gln Ile Ser Gly Val Lys Lys Leu Met His Ser Ser Ser Leu
225                 230                 235                 240
Thr Asn Ser Ser Ile Pro Arg Phe Gly Val Lys Thr Glu Gln Glu Asp
                245                 250                 255
Val Leu Ala Lys Glu Leu Glu Asp Val Asn Lys Trp Gly Leu His Val
            260                 265                 270
Phe Arg Ile Ala Glu Leu Ser Gly Asn Arg Pro Leu Thr Val Ile Met
        275                 280                 285
His Thr Ile Phe Gln Glu Arg Asp Leu Leu Lys Thr Phe Lys Ile Pro
    290                 295                 300
Val Asp Thr Leu Ile Thr Tyr Leu Met Thr Leu Glu Asp His Tyr His
305                 310                 315                 320
Ala Asp Val Ala Tyr His Asn Asn Ile His Ala Ala Asp Val Val Gln
                325                 330                 335
Ser Thr His Val Leu Leu Ser Thr Pro Ala Leu Glu Ala Val Phe Thr
            340                 345                 350
Asp Leu Glu Ile Leu Ala Ala Ile Phe Ala Ser Ala Ile His Asp Val
        355                 360                 365
Asp His Pro Gly Val Ser Asn Gln Phe Leu Ile Asn Thr Asn Ser Glu
    370                 375                 380
Leu Ala Leu Met Tyr Asn Asp Ser Ser Val Leu Glu Asn His His Leu
385                 390                 395                 400
Ala Val Gly Phe Lys Leu Leu Gln Glu Glu Asn Cys Asp Ile Phe Gln
                405                 410                 415
Asn Leu Thr Lys Lys Gln Arg Gln Ser Leu Arg Lys Met Val Ile Asp
            420                 425                 430
Ile Val Leu Ala Thr Asp Met Ser Lys His Met Asn Leu Leu Ala Asp
        435                 440                 445
Leu Lys Thr Met Val Glu Thr Lys Lys Val Thr Ser Ser Gly Val Leu
    450                 455                 460
Leu Leu Asp Asn Tyr Ser Asp Arg Ile Gln Val Leu Gln Asn Met Val
465                 470                 475                 480
His Cys Ala Asp Leu Ser Asn Pro Thr Lys Pro Leu Gln Leu Tyr Arg
                485                 490                 495
Gln Trp Thr Asp Arg Ile Met Glu Glu Phe Phe Arg Gln Gly Asp Arg
            500                 505                 510
Glu Arg Glu Arg Gly Met Glu Ile Ser Pro Met Cys Asp Lys His Asn
        515                 520                 525
Ala Ser Val Glu Lys Ser Gln Val Gly Phe Ile Asp Tyr Ile Val His
    530                 535                 540
```

```
Pro Leu Trp Glu Thr Trp Ala Asp Leu Val His Pro Asp Ala Gln Asp
545                 550                 555                 560

Ile Leu Asp Thr Leu Glu Asp Asn Arg Glu Trp Tyr Gln Ser Thr Ile
                565                 570                 575

Pro Gln Ser Pro Ser Pro Ala Pro Asp Asp Pro Glu Gly Arg Gln
            580                 585                 590

Gly Gln Thr Glu Lys Phe Gln Phe Glu Leu Thr Leu Glu Glu Asp Gly
            595                 600                 605

Glu Ser Asp Thr Glu Lys Asp Ser Gly Ser Gln Val Glu Glu Asp Thr
610                 615                 620

Ser Cys Ser Asp Ser Lys Thr Leu Cys Thr Gln Asp Ser Glu Ser Thr
625                 630                 635                 640

Glu Ile Pro Leu Asp Glu Gln Val Glu Glu Ala Val Gly Glu Glu
                645                 650                 655

Glu Glu Ser Gln Pro Glu Ala Cys Val Ile Asp Asp Arg Ser Pro Asp
            660                 665                 670

Thr
```

(2) INFORMATION FOR SEQ ID NO:64:

(i) SEQUENCE CHARACTERISTICS:
        (A) LENGTH: 3705 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 116..2774

(xi) SEQUENCE DESCRIPTION: SEQ ID NO:64:

```
GGAATTCCCG GCCGGGCGCA CCCGCGGGGC CCTGGGCTCG CTGGCTTGCG CGCAGCTGAG      60

CGGGGTGTAG GTTGGAAGGG CCAGGGCCCC TGGGGCGCAA GTGGGGGCCG GCGCC ATG      118
                                                              Met
                                                                1

GAA CCC CCG ACC GTC CCC TCG GAA AGG AGC CTG TCT CTG TCA CTG CCC      166
Glu Pro Pro Thr Val Pro Ser Glu Arg Ser Leu Ser Leu Ser Leu Pro
          5                  10                  15

GGG CCC CGG GAG GGC CAG GCC ACC CTG AAG CCT CCC CCG CAG CAC CTG      214
Gly Pro Arg Glu Gly Gln Ala Thr Leu Lys Pro Pro Pro Gln His Leu
         20                  25                  30

TGG CGG CAG CCT CGG ACC CCC ATC CGT ATC CAG CAG CGC GGC TAC TCC      262
Trp Arg Gln Pro Arg Thr Pro Ile Arg Ile Gln Gln Arg Gly Tyr Ser
 35                  40                  45

GAC AGC GCG GAG CGC GCC GAG CGG GAG CGG CAG CCG CAC CGG CCC ATA      310
Asp Ser Ala Glu Arg Ala Glu Arg Glu Arg Gln Pro His Arg Pro Ile
 50                  55                  60                  65

GAG CGC GCC GAT GCC ATG GAC ACC AGC GAC CGG CCC GGC CTG CGC ACG      358
Glu Arg Ala Asp Ala Met Asp Thr Ser Asp Arg Pro Gly Leu Arg Thr
                 70                  75                  80

ACC CGC ATG TCC TGG CCC TCG TCC TTC CAT GGC ACT GGC ACC GGC AGC      406
Thr Arg Met Ser Trp Pro Ser Ser Phe His Gly Thr Gly Thr Gly Ser
             85                  90                  95

GGC GGC GCG GGC GGA GGC AGC AGC AGG CGC TTC GAG GCA GAG AAT GGG      454
Gly Gly Ala Gly Gly Gly Ser Ser Arg Arg Phe Glu Ala Glu Asn Gly
        100                 105                 110

CCG ACA CCA TCT CCT GGC CGC AGC CCC CTG GAC TCG CAG GCG AGC CCA      502
Pro Thr Pro Ser Pro Gly Arg Ser Pro Leu Asp Ser Gln Ala Ser Pro
```

```
                -continued
    115                 120                 125
GGA CTC GTG CTG CAC GCC GGG GCG GCC ACC AGC CAG CGC CGG GAG TCC     550
Gly Leu Val Leu His Ala Gly Ala Ala Thr Ser Gln Arg Arg Glu Ser
130                 135                 140                 145

TTC CTG TAC CGC TCA GAC AGC GAC TAT GAC ATG TCA CCC AAG ACC ATG     598
Phe Leu Tyr Arg Ser Asp Ser Asp Tyr Asp Met Ser Pro Lys Thr Met
                150                 155                 160

TCC CGG AAC TCA TCG GTC ACC AGC GAG GCG CAC GCT GAA GAC CTC ATC     646
Ser Arg Asn Ser Ser Val Thr Ser Glu Ala His Ala Glu Asp Leu Ile
            165                 170                 175

GTA ACA CCA TTT GCT CAG GTG CTG GCC AGC CTC CGG AGC GTC CGT AGC     694
Val Thr Pro Phe Ala Gln Val Leu Ala Ser Leu Arg Ser Val Arg Ser
        180                 185                 190

AAC TTC TCA CTC CTG ACC AAT GTG CCC GTT CCC AGT AAC AAG CGG TCC     742
Asn Phe Ser Leu Leu Thr Asn Val Pro Val Pro Ser Asn Lys Arg Ser
195                 200                 205

CCG CTG GGC GGC CCC ACC CCT GTC TGC AAG GCC ACG CTG TCA GAA GAA     790
Pro Leu Gly Gly Pro Thr Pro Val Cys Lys Ala Thr Leu Ser Glu Glu
210                 215                 220                 225

ACG TGT CAG CAG TTG GCC CGG GAG ACT CTG GAG GAG CTG GAC TGG TGT     838
Thr Cys Gln Gln Leu Ala Arg Glu Thr Leu Glu Glu Leu Asp Trp Cys
                230                 235                 240

CTG GAG CAG CTG GAG ACC ATG CAG ACC TAT CGC TCT GTC AGC GAG ATG     886
Leu Glu Gln Leu Glu Thr Met Gln Thr Tyr Arg Ser Val Ser Glu Met
            245                 250                 255

GCC TCG CAC AAG TTC AAA AGG ATG TTG AAC CGT GAG CTC ACA CAC CTG     934
Ala Ser His Lys Phe Lys Arg Met Leu Asn Arg Glu Leu Thr His Leu
        260                 265                 270

TCA GAA ATG AGC AGG TCC GGA AAC CAG GTC TCA GAG TAC ATT TCC ACA     982
Ser Glu Met Ser Arg Ser Gly Asn Gln Val Ser Glu Tyr Ile Ser Thr
275                 280                 285

ACA TTC CTG GAC AAA CAG AAT GAA GTG GAG ATC CCA TCA CCC ACG ATG    1030
Thr Phe Leu Asp Lys Gln Asn Glu Val Glu Ile Pro Ser Pro Thr Met
290                 295                 300                 305

AAG GAA CGA GAA AAA CAG CAA GCG CCG CGA CCA AGA CCC TCC CAG CCG    1078
Lys Glu Arg Glu Lys Gln Gln Ala Pro Arg Pro Arg Pro Ser Gln Pro
                310                 315                 320

CCC CCG CCC CCT GTA CCA CAC TTA CAG CCC ATG TCC CAA ATC ACA GGG    1126
Pro Pro Pro Pro Val Pro His Leu Gln Pro Met Ser Gln Ile Thr Gly
            325                 330                 335

TTG AAA AAG TTG ATG CAT AGT AAC AGC CTG AAC AAC TCT AAC ATT CCC    1174
Leu Lys Lys Leu Met His Ser Asn Ser Leu Asn Asn Ser Asn Ile Pro
        340                 345                 350

CGA TTT GGG GTG AAG ACC GAT CAA GAA GAG CTC CTG GCC CAA GAA CTG    1222
Arg Phe Gly Val Lys Thr Asp Gln Glu Glu Leu Leu Ala Gln Glu Leu
355                 360                 365

GAG AAC CTG AAC AAG TGG GGC CTG AAC ATC TTT TGC GTG TCG GAT TAC    1270
Glu Asn Leu Asn Lys Trp Gly Leu Asn Ile Phe Cys Val Ser Asp Tyr
370                 375                 380                 385

GCT GGA GGC CGC TCA CTC ACC TGC ATC ATG TAC ATG ATA TTC CAG GAG    1318
Ala Gly Gly Arg Ser Leu Thr Cys Ile Met Tyr Met Ile Phe Gln Glu
                390                 395                 400

CGG GAC CTG CTG AAG AAA TTC CGC ATC CCG GTG GAC ACG ATG GTG ACA    1366
Arg Asp Leu Leu Lys Lys Phe Arg Ile Pro Val Asp Thr Met Val Thr
            405                 410                 415

TAC ATG CTG ACG CTG GAG GAT CAC TAC CAC GCT GAC GTG GCC TAC CAT    1414
Tyr Met Leu Thr Leu Glu Asp His Tyr His Ala Asp Val Ala Tyr His
        420                 425                 430

AAC AGC CTG CAC GCA GCT GAC GTG CTG CAG TCC ACC CAC GTA CTG CTG    1462
```

```
Asn Ser Leu His Ala Ala Asp Val Leu Gln Ser Thr His Val Leu Leu
    435                 440                 445

GCC ACG CCT GCA CTA GAT GCA GTG TTC ACG GAC CTG GAG ATT CTC GCC    1510
Ala Thr Pro Ala Leu Asp Ala Val Phe Thr Asp Leu Glu Ile Leu Ala
450                 455                 460                 465

GCC CTC TTC GCG GCT GCC ATC CAC GAT GTG GAT CAC CCT GGG GTC TCC    1558
Ala Leu Phe Ala Ala Ala Ile His Asp Val Asp His Pro Gly Val Ser
                470                 475                 480

AAC CAG TTC CTC ATC AAC ACC AAT TCG GAG CTG GCG CTC ATG TAC AAC    1606
Asn Gln Phe Leu Ile Asn Thr Asn Ser Glu Leu Ala Leu Met Tyr Asn
            485                 490                 495

GAT GAG TCG GTG CTC GAG AAT CAC CAC CTG GCC GTG GGC TTC AAG CTG    1654
Asp Glu Ser Val Leu Glu Asn His His Leu Ala Val Gly Phe Lys Leu
        500                 505                 510

CTG CAG GAG GAC AAC TGC GAC ATC TTC CAG AAC CTC AGC AAG CGC CAG    1702
Leu Gln Glu Asp Asn Cys Asp Ile Phe Gln Asn Leu Ser Lys Arg Gln
    515                 520                 525

CGG CAG AGC CTA CGC AAG ATG GTC ATC GAC ATG GTG CTG GCC ACG GAC    1750
Arg Gln Ser Leu Arg Lys Met Val Ile Asp Met Val Leu Ala Thr Asp
530                 535                 540                 545

ATG TCC AAG CAC ATG ACC CTC CTG GCT GAC CTG AAG ACC ATG GTG GAG    1798
Met Ser Lys His Met Thr Leu Leu Ala Asp Leu Lys Thr Met Val Glu
                550                 555                 560

ACC AAG AAA GTG ACC AGC TCA GGG GTC CTC CTG CTA GAT AAC TAC TCC    1846
Thr Lys Lys Val Thr Ser Ser Gly Val Leu Leu Leu Asp Asn Tyr Ser
            565                 570                 575

GAC CGC ATC CAG GTC CTC CGG AAC ATG GTG CAC TGT GCC GAC CTC AGC    1894
Asp Arg Ile Gln Val Leu Arg Asn Met Val His Cys Ala Asp Leu Ser
        580                 585                 590

AAC CCC ACC AAG CCG CTG GAG CTG TAC CGC CAG TGG ACA GAC CGC ATC    1942
Asn Pro Thr Lys Pro Leu Glu Leu Tyr Arg Gln Trp Thr Asp Arg Ile
    595                 600                 605

ATG GCC GAG TTC TTC CAG CAG GGT GAC CGA GAG CGC GAG CGT GGC ATG    1990
Met Ala Glu Phe Phe Gln Gln Gly Asp Arg Glu Arg Glu Arg Gly Met
610                 615                 620                 625

GAA ATC AGC CCC ATG TGT GAC AAG CAC ACT GCC TCC GTG GAG AAG TCT    2038
Glu Ile Ser Pro Met Cys Asp Lys His Thr Ala Ser Val Glu Lys Ser
                630                 635                 640

CAG GTG GGT TTT ATT GAC TAC ATT GTG CAC CCA TTG TGG GAG ACC TGG    2086
Gln Val Gly Phe Ile Asp Tyr Ile Val His Pro Leu Trp Glu Thr Trp
            645                 650                 655

GCG GAC CTT GTC CAC CCA GAT GCC CAG GAG ATC TTG GAC ACT TTG GAG    2134
Ala Asp Leu Val His Pro Asp Ala Gln Glu Ile Leu Asp Thr Leu Glu
        660                 665                 670

GAC AAC CGG GAC TGG TAC TAC AGC GCC ATC CGG CAG AGC CCA TCT CCG    2182
Asp Asn Arg Asp Trp Tyr Tyr Ser Ala Ile Arg Gln Ser Pro Ser Pro
    675                 680                 685

CCA CCC GAG GAG GAG TCA AGG GGG CCA GGC CAC CCA CCC CTG CCT GAC    2230
Pro Pro Glu Glu Glu Ser Arg Gly Pro Gly His Pro Pro Leu Pro Asp
690                 695                 700                 705

AAG TTC CAG TTT GAG CTG ACG CTG GAG GAG GAA GAG GAG GAA GAA ATA    2278
Lys Phe Gln Phe Glu Leu Thr Leu Glu Glu Glu Glu Glu Glu Glu Ile
                710                 715                 720

TCA ATG GCC CAG ATA CCG TGC ACA GCC CAA GAG GCA TTG ACT GCG CAG    2326
Ser Met Ala Gln Ile Pro Cys Thr Ala Gln Glu Ala Leu Thr Ala Gln
            725                 730                 735

GGA TTG TCA GGA GTC GAG GAA GCT CTG GAT GCA ACC ATA GCC TGG GAG    2374
Gly Leu Ser Gly Val Glu Glu Ala Leu Asp Ala Thr Ile Ala Trp Glu
        740                 745                 750
```

```
GCA TCC CCG GCC CAG GAG TCG TTG GAA GTT ATG GCA CAG GAA GCA TCC       2422
Ala Ser Pro Ala Gln Glu Ser Leu Glu Val Met Ala Gln Glu Ala Ser
    755                 760                 765

CTG GAG GCC GAG CTG GAG GCA GTG TAT TTG ACA CAG CAG GCA CAG TCC       2470
Leu Glu Ala Glu Leu Glu Ala Val Tyr Leu Thr Gln Gln Ala Gln Ser
770                 775                 780                 785

ACA GGC AGT GCA CCT GTG GCT CCG GAT GAG TTC TCG TCC CGG GAG GAA       2518
Thr Gly Ser Ala Pro Val Ala Pro Asp Glu Phe Ser Ser Arg Glu Glu
                790                 795                 800

TTC GTG GTT GCT GTA AGC CAC AGC AGC CCC TCT GCC CTG GCT CTT CAA       2566
Phe Val Val Ala Val Ser His Ser Ser Pro Ser Ala Leu Ala Leu Gln
                    805                 810                 815

AGC CCC CTT CTC CCT GCT TGG AGG ACC CTG TCT GTT TCA GAG CAT GCC       2614
Ser Pro Leu Leu Pro Ala Trp Arg Thr Leu Ser Val Ser Glu His Ala
        820                 825                 830

CCG GGC CTC CCG GGC CTC CCC TCC ACG GCG GCC GAG GTG GAG GCC CAA       2662
Pro Gly Leu Pro Gly Leu Pro Ser Thr Ala Ala Glu Val Glu Ala Gln
            835                 840                 845

CGA GAG CAC CAG GCT GCC AAG AGG GCT TGC AGT GCC TGC GCA GGG ACA       2710
Arg Glu His Gln Ala Ala Lys Arg Ala Cys Ser Ala Cys Ala Gly Thr
850                 855                 860                 865

TTT GGG GAG GAC ACA TCC GCA CTC CCA GCT CCT GGT GGC GGG GGG TCA       2758
Phe Gly Glu Asp Thr Ser Ala Leu Pro Ala Pro Gly Gly Gly Gly Ser
                870                 875                 880

GGT GGA GAC CCT ACC T GATCCCCAGA CCTCTGTCCC TGTTCCCCTC CACTCCTCCC     2814
Gly Gly Asp Pro Thr
                885

CTCACTCCCC TGCTCCCCCG ACCACCTCCT CCTCTGCCTC AAAGACTCTT GTCCTCTTGT     2874

CCCTCCTGAG AAAAAAGAAA ACGAAAAGTG GGGTTTTTTT CTGTTTTCTT TTTTTCCCCT     2934

TTCCCCCTGC CCCCACCCAC GGGGCCTTTT TTTGGAGGTG GGGGCTGGGG AATGAGGGGC     2994

TGAGGTCCCG GAAGGATTTT ATTTTTTTGA ATTTTAATTG TAACATTTTT AGAAAAAGAA     3054

CAAAAAAAGA AAAAAAAAG AAAGAAACAC AGCAACTGTA GATGCTCCTG TTCCTGGTTC      3114

CCGCTTTCCA CTTCCAAATC CCTCCCCTCA CCTTCCCCCA CTGCCCCCCA AGTTCCAGGC    3174

TCAGTCTTCC AGCCGCCTGG GGAGTCTCTA CCTGGGCCCA AGCAGGTGTG GGGCCTCCTT    3234

CTGGGCTTTT CTTCTGAATT TAGAGGATTT CTAGAACGTG GTCAGGAATA GCCATTCTAG    3294

GCGGGGCTGG GGCCAGGGTG GGGGGCAGTC ACTGTGGGAG GTCCCAGCTC CAGCCCCCCT    3354

CTGGTTTGCT GCCTCCTCTC CCCTCTAAAA AAGTCTTCCG CTTGATTTTG CACAATCCCG    3414

GCGATACTCC TGGCGATACT GACTAGAAGT CAGGGAGCTG GGGGAGCTGT TCACTTTAGG    3474

ATACGGGGGG ATGGAAGGGA GCGTTCACAC CGCCAGCCTC GGGCCTGGGA TTTGAGGAGG    3534

GCCCTAGACC TCCTCCACTC TCCATCCCCT TTCCCTTCCA CTTTGGGTTC ACTTTGAATT    3594

TTCTCCGTTT TTTGGGGCAG TGGCTCTGAT CCACTCACCC CCCCGCCCCG TAAGTTATAG    3654

CCACTGTGGA AAGTAGTATG AAAGTTCCTC AAGAAACTAA AAATGGAATT C             3705

(2) INFORMATION FOR SEQ ID NO:65:

(i) SEQUENCE CHARACTERISTICS:
        (A) LENGTH: 886 amino acids
        (B) TYPE: amino acid
        (D) TOPOLOGY: linear (ii) MOLECULE TYPE: protein (xi) SEQUENCE DESCRIPTION: SEQ ID NO:65:

Met Glu Pro Pro Thr Val Pro Ser Glu Arg Ser Leu Ser Leu Ser Leu
```

-continued

```
  1               5                  10                 15
Pro Gly Pro Arg Glu Gly Gln Ala Thr Leu Lys Pro Pro Gln His
                20                  25                 30
Leu Trp Arg Gln Pro Arg Thr Pro Ile Arg Ile Gln Arg Gly Tyr
                35                  40                 45
Ser Asp Ser Ala Glu Arg Ala Glu Arg Glu Arg Gln Pro His Arg Pro
 50                      55                      60
Ile Glu Arg Ala Asp Ala Met Asp Thr Ser Asp Arg Pro Gly Leu Arg
 65                      70                      75                 80
Thr Thr Arg Met Ser Trp Pro Ser Ser Phe His Gly Thr Gly Thr Gly
                85                  90                 95
Ser Gly Gly Ala Gly Gly Ser Ser Arg Arg Phe Glu Ala Glu Asn
                100                 105                110
Gly Pro Thr Pro Ser Pro Gly Arg Ser Pro Leu Asp Ser Gln Ala Ser
                115                 120                125
Pro Gly Leu Val Leu His Ala Gly Ala Thr Ser Gln Arg Arg Glu
                130                 135                140
Ser Phe Leu Tyr Arg Ser Asp Ser Asp Tyr Asp Met Ser Pro Lys Thr
145                     150                 155                160
Met Ser Arg Asn Ser Ser Val Thr Ser Glu Ala His Ala Glu Asp Leu
                165                 170                175
Ile Val Thr Pro Phe Ala Gln Val Leu Ala Ser Leu Arg Ser Val Arg
                180                 185                190
Ser Asn Phe Ser Leu Leu Thr Asn Val Pro Val Pro Ser Asn Lys Arg
                195                 200                 205
Ser Pro Leu Gly Gly Pro Thr Pro Val Cys Lys Ala Thr Leu Ser Glu
                210                 215                 220
Glu Thr Cys Gln Gln Leu Ala Arg Glu Thr Leu Glu Glu Leu Asp Trp
225                     230                 235                240
Cys Leu Glu Gln Leu Glu Thr Met Gln Thr Tyr Arg Ser Val Ser Glu
                245                 250                255
Met Ala Ser His Lys Phe Lys Arg Met Leu Asn Arg Glu Leu Thr His
                260                 265                270
Leu Ser Glu Met Ser Arg Ser Gly Asn Gln Val Ser Glu Tyr Ile Ser
                275                 280                285
Thr Thr Phe Leu Asp Lys Gln Asn Glu Val Glu Ile Pro Ser Pro Thr
                290                 295                300
Met Lys Glu Arg Glu Lys Gln Gln Ala Pro Arg Pro Arg Pro Ser Gln
305                     310                 315                320
Pro Pro Pro Pro Pro Val Pro His Leu Gln Pro Met Ser Gln Ile Thr
                325                 330                335
Gly Leu Lys Lys Leu Met His Ser Asn Ser Leu Asn Asn Ser Asn Ile
                340                 345                350
Pro Arg Phe Gly Val Lys Thr Asp Gln Glu Glu Leu Leu Ala Gln Glu
                355                 360                365
Leu Glu Asn Leu Asn Lys Trp Gly Leu Asn Ile Phe Cys Val Ser Asp
                370                 375                380
Tyr Ala Gly Gly Arg Ser Leu Thr Cys Ile Met Tyr Met Ile Phe Gln
385                     390                 395                400
Glu Arg Asp Leu Leu Lys Lys Phe Arg Ile Pro Val Asp Thr Met Val
                405                 410                415
Thr Tyr Met Leu Thr Leu Glu Asp His Tyr His Ala Asp Val Ala Tyr
                420                 425                430
```

-continued

```
His Asn Ser Leu His Ala Ala Asp Val Leu Gln Ser Thr His Val Leu
        435                 440                 445
Leu Ala Thr Pro Ala Leu Asp Ala Val Phe Thr Asp Leu Glu Ile Leu
450                 455                 460
Ala Ala Leu Phe Ala Ala Ile His Asp Val Asp His Pro Gly Val
465                 470                 475                 480
Ser Asn Gln Phe Leu Ile Asn Thr Asn Ser Glu Leu Ala Leu Met Tyr
                485                 490                 495
Asn Asp Glu Ser Val Leu Glu Asn His His Leu Ala Val Gly Phe Lys
                500                 505                 510
Leu Leu Gln Glu Asp Asn Cys Asp Ile Phe Gln Asn Leu Ser Lys Arg
        515                 520                 525
Gln Arg Gln Ser Leu Arg Lys Met Val Ile Asp Met Val Leu Ala Thr
530                 535                 540
Asp Met Ser Lys His Met Thr Leu Leu Ala Asp Leu Lys Thr Met Val
545                 550                 555                 560
Glu Thr Lys Lys Val Thr Ser Ser Gly Val Leu Leu Leu Asp Asn Tyr
                565                 570                 575
Ser Asp Arg Ile Gln Val Leu Arg Asn Met Val His Cys Ala Asp Leu
                580                 585                 590
Ser Asn Pro Thr Lys Pro Leu Glu Leu Tyr Arg Gln Trp Thr Asp Arg
        595                 600                 605
Ile Met Ala Glu Phe Phe Gln Gln Gly Asp Arg Glu Arg Glu Arg Gly
610                 615                 620
Met Glu Ile Ser Pro Met Cys Asp Lys His Thr Ala Ser Val Glu Lys
625                 630                 635                 640
Ser Gln Val Gly Phe Ile Asp Tyr Ile Val His Pro Leu Trp Glu Thr
                645                 650                 655
Trp Ala Asp Leu Val His Pro Asp Ala Gln Glu Ile Leu Asp Thr Leu
                660                 665                 670
Glu Asp Asn Arg Asp Trp Tyr Tyr Ser Ala Ile Arg Gln Ser Pro Ser
        675                 680                 685
Pro Pro Pro Glu Glu Glu Ser Arg Gly Pro Gly His Pro Pro Leu Pro
690                 695                 700
Asp Lys Phe Gln Phe Glu Leu Thr Leu Glu Glu Glu Glu Glu Glu Glu
705                 710                 715                 720
Ile Ser Met Ala Gln Ile Pro Cys Thr Ala Gln Glu Ala Leu Thr Ala
                725                 730                 735
Gln Gly Leu Ser Gly Val Glu Glu Ala Leu Asp Ala Thr Ile Ala Trp
        740                 745                 750
Glu Ala Ser Pro Ala Gln Glu Ser Leu Glu Val Met Ala Gln Glu Ala
                755                 760                 765
Ser Leu Glu Ala Glu Leu Glu Ala Val Tyr Leu Thr Gln Gln Ala Gln
        770                 775                 780
Ser Thr Gly Ser Ala Pro Val Ala Pro Asp Glu Phe Ser Ser Arg Glu
785                 790                 795                 800
Glu Phe Val Val Ala Val Ser His Ser Ser Pro Ser Ala Leu Ala Leu
                805                 810                 815
Gln Ser Pro Leu Leu Pro Ala Trp Arg Thr Leu Ser Val Ser Glu His
        820                 825                 830
Ala Pro Gly Leu Pro Gly Leu Pro Ser Thr Ala Ala Glu Val Glu Ala
        835                 840                 845
```

```
Gln Arg Glu His Gln Ala Ala Lys Arg Ala Cys Ser Ala Cys Ala Gly
    850                 855                 860

Thr Phe Gly Glu Asp Thr Ser Ala Leu Pro Ala Pro Gly Gly Gly Gly
865                 870                 875                 880

Ser Gly Gly Asp Pro Thr
            885
```

(2) INFORMATION FOR SEQ ID NO:66:

(i) SEQUENCE CHARACTERISTICS:
    (A) LENGTH: 288 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:66:

```
GAATTCCTCT GACTAATTCA AGTATCCCAA GGTTTGGAGT TAAAACTGAA CAAGAAGATG      60

TCCTTGCCAA GGAACTAGAA GATGTGAACA AATGGGGTCT TCATGTTTTC AGAATAGCAG     120

AGTTGTCTGG TAACCGGCCC TTGACTGTTA TCATGCACAC CATTTTTCAG GAACGGGATT    180

TATTAAAAAC ATTTAAAATT CCAGTAGATA CTTTAATTAC ATATCTTATG ACTCTCGAAG    240

ACCATTACCA TGCTGATGTG GCCTATCACA ACAATATCCA TGCTGCAG                 288
```

(2) INFORMATION FOR SEQ ID NO:68:

(i) SEQUENCE CHARACTERISTICS:
    (A) LENGTH: 604 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:68:

```
AAGCTTGCGG CCGCGCGGCC TAGGCCGCAT CCCGGAGCTG CAACTGGTGG CCTTCCCGGT      60

GGCGGTGGCG GCTGAGGACG AGGCGTTCCT GCCCGAGCCC CTGGCCCCGC GCGCGCCCCG    120

CCGCCGCGTT CGCCGCCCTC CTCGCCCGTC TTCTTCGCCA GCCCGTCCCC AACTTTCCGC    180

AGACGCCTTC GGCTTCTCCG CAGCTGCCAG GATTTGGGCC GCCAGGCTTG GGCTGGGGCT    240

GGCTTCGAGG CAGAGAATGG GCCGACACCA TCTCCTGGCC GCAGCCCCTG GACTGCAGGC    300

GAGCCCAGGA CTCGTGCTGC ACGCCGGGGC GGCCACCAGC CAGCGCCGGG AGTCCTTCCT    360

GTACCGCTCA GACAGCGACT ATGACATGTC ACCCAAGACC ATGTCCCGGA ACTCATCGGT    420

CACCAGCGAG GCGCACGCTG AAGACCTCAT CGTAACACCA TTTGCTCAGG TGCTGGCCAG    480

CCTCCGGAGC GTCCGTAGCA ACTTCTCACT CCTGACCAAT GTGCCCGTTC CCAGTAACAA    540

GCGGTCCCCG CTGGGCGGCC CCACCCCTGT CTGCAAGGCC ACGCTGTCAG AAGAAACGTG    600

TCAG                                                                  604
```

(2) INFORMATION FOR SEQ ID NO:69:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:69:

```
GAGGTACCAC YTTYTTNGTY TCNACCAT                                              28

(2) INFORMATION FOR SEQ ID NO:70:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:70:

CTAGCAGTGC GGTACCGCCC ANGTYTCCCA NARNGG                                     36

(2) INFORMATION FOR SEQ ID NO:71:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:71:

GAATTCATHC AYGTNGAYCA YCC                                                   23

(2) INFORMATION FOR SEQ ID NO:72:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:72:

CGATGCTACG GAATTCGAYA TGWSNAARCA YATG                                       34

(2) INFORMATION FOR SEQ ID NO:73:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:73:

CGATGCTACG GAATTCAARA TGGTNATHGA YATNGT                                     36

(2) INFORMATION FOR SEQ ID NO:74:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:74:

CTAGCAGTGC GTTACCACNA TRTCDATNAC CATYTT                                     36
```

-continued (2) INFORMATION FOR SEQ ID NO:75:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:75:

```
CGATGCTACG GAATTCTTYA ARYTNYTNCA RGRNGA                           36
```

(2) INFORMATION FOR SEQ ID NO:76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:76:

```
AACAGCTATG ACCATGATTA                                            20
```

(2) INFORMATION FOR SEQ ID NO:77:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:77:

```
AGGGTTTTCC CAGTCACGAC                                            20
```

(2) INFORMATION FOR SEQ ID NO:78:

(i) SEQUENCE CHARACTERISTICS:
        (A) LENGTH: 760 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:78:

```
CATGGGGGCC AAGACCTGCA CAGGACAAGG GCCACCTGGC CTTTCAGTTA CTTGAGTTTG    60

GAGTCAGAAA GCAAGACCAG GAAGCAAATA GCAGCTCAGG AAATCCCACG GTTGACTTGC   120

CTTGATGGCA AGCTTGGTGG AGAGGGCTGA AGCTGTTGCT GGGGGCCGAT TCTGATCAAG   180

ACACATGGCT TGAAAATGGA AGACACAAAA CTGAGAGATC ATTCTGCACT AAGTTTCGGG   240

AACTTATCCC CGACAGTGAC TGAACTCACT GACTAATAAC TTCATTTATG AATCTTCTCA   300

CTTGTCCCTT TGTCTGCCAA CCTGTGTGCC TTTTTTGTAA ACATTTTCA TGTCTTTAAA    360

ATGCCTGTTG AATACCTGGA GTTTAGTATC AACTTCTACA CAGATAAGCT TTCAAAGTTG   420

ACAAACTTTT TTGACTCTTT CTGGAAAAGG GAAAGAAAAT AGTCTTCCTT CTTTCTTGGG   480

CAATATCCTT CACTTTACTA CAGTTACTTT TGCAAACAGA CAGAAAGGAT ACACTTCTAA   540

CCACATTTTA CTTCCTTCCC CTGTTGTCCA GTCAACTCC ACAGTCACTC TTAAAACTTC    600

TCTCTGTTTG CCTGCCTCCA ACAGTACTTT TAACTTTTTG CTGTAAACAG AATAAAATTG   660
```

| AACAAATTAG GGGGTAGAAA GGAGCAGTGG TGTCGTTCAC CGTGAGAGTC TGCATAGAAC | 720 |
| TCAGCAGTGT GCCCTGCTGT GTCTTGGACC CTGCAATGCG | 760 |

(2) INFORMATION FOR SEQ ID NO:79:

(i) SEQUENCE CHARACTERISTICS:
        (A) LENGTH: 2041 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:79:

| GCAACTTCTC ACTCCTGACC AATGTGCCCG TTCCCAGTAA CAAGCGGTCC CCGCTGGGCG | 60 |
| GCCCCACCCC TGTCTGCAAG GCCACGCTGT CAGAAGAAAC GTGTCAGCAG TTGGCCCGGG | 120 |
| AGACTCTGGA GGAGCTGGAC TGGTGTCTGG AGCAGCTGGA GACCATGCAG ACCTATCGCT | 180 |
| CTGTCAGCGA GATGGCCTCG CACAAGTTCA AAGGATGTT GAACCGTGAG CTCACACACC | 240 |
| TGTCAGAAAT GAGCAGGTCC GGAAACCAGG TCTCAGAGTA CATTTCCACA ACATTCCTGG | 300 |
| ACAAACAGAA TGAAGTGGAG ATCCCATCAC CCACGATGAA GGAACGAGAA AAACAGCAAG | 360 |
| CGCCGCGACC AAGACCCTCC CAGCCGCCCC CGCCCCCTGT ACCACACTTA CAGCCCATGT | 420 |
| CCCAAATCAC AGGGTTGAAA AAGTTGATGC ATAGTAACAG CCTGAACAAC TCTAACATTC | 480 |
| CCCGATTTGG GGTGAAGACC GATCAAGAAG AGCTCCTGGC CCAAGAACTG GAGAACCTGA | 540 |
| ACAAGTGGGG CCTGAACATC TTTTGCGTGT CGGATTACGC TGGAGGCCGC TCACTCACCT | 600 |
| GCATCATGTA CATGATATTC CAGGAGCGGG ACCTGCTGAA GAAATTCCGC ATCCCGGTGG | 660 |
| ACACGATGGT GACATACATG CTGACGCTGG AGGATCACTA CCACGCTGAC GTGGCCTACC | 720 |
| ATAACAGCCT GCACGCAGCT GACGTGCTGC AGTCCACCCA CGTACTGCTG GCCACGCCTG | 780 |
| CACTAGATGC AGTGTTCACG GACCTGGAGA TTCTCGCCGC CCTCTTCGCG GCTGCCATCC | 840 |
| ACGATGTGGA TCACCCTGGG GTCTCCAACC AGTTCCTCAT CAACACCAAT TCGGAGCTGG | 900 |
| CGCTCATGTA CAACGATGAG TCGGTGCTCG AGAATCACCA CCTGGCCGTG GGCTTCAAGC | 960 |
| TGCTGCAGGA GGACAACTGC GACATCTTCC AGAACCTCAG CAAGCGCCAG CGGCAGAGCC | 1020 |
| TACGCAAGAT GGTCATCGAC ATGGTGCTGG CCACGGACAT GTCCAAGCAC ATGACCCTCC | 1080 |
| TGGCTGACCT GAAGACCATG GTGGAGACCA AGAAAGTGAC CAGCTCAGGG GTCCTCCTGC | 1140 |
| TAGATAACTA CTCCGACCGC ATCCAGGTCC TCCGGAACAT GGTGCACTGT GCCGACCTCA | 1200 |
| GCAACCCCAC CAAGCCGCTG GAGCTGTACC GCCAGTGGAC AGACCGCATC ATGGCCGAGT | 1260 |
| TCTTCCAGCA GGGTGACCGA GAGCGCGAGC GTGGCATGGA AATCAGCCCC ATGTGTGACA | 1320 |
| AGCACACTGC CTCCGTGGAG AAGTCTCAGG TGGGTTTTAT TGACTACATT GTGCACCCAT | 1380 |
| TGTGGGAGAC CTGGGCGGAC CTTGTCCACC CAGATGCCCA GGAGATCTTG GACACTTTGG | 1440 |
| AGGACAACCG GGACTGGTAC TACAGCGCCA TCCGGCAGAG CCCATCTCCG CCACCCGAGG | 1500 |
| AGGAGTCAAG GGGGCCAGGC CACCCACCCC TGCCTGACAA GTTCCAGTTT GAGCTGACGC | 1560 |
| TGGAGGAGGA AGAGGAGGAA GAAATATCAA TGGCCCAGAT ACCGTGCACA GCCCAAGAGG | 1620 |
| CATTGACTGC GCAGGGATTG TCAGGAGTCG AGGAAGCTCT GGATGCAACC ATAGCCTGGG | 1680 |
| AGGCATCCCC GGCCCAGGAG TCGTTGGAAG TTATGGCACA GGAAGCATCC CTGGAGGCCG | 1740 |
| AGCTGGAGGC AGTGTATTTG ACACAGCAGG CACAGTCCAC AGGCAGTGCA CCTGTGGCTC | 1800 |
| CGGATGAGTT CTCGTCCCGG GAGGAATTCG TGGTTGCTGT AAGCCACAGC AGCCCCTCTG | 1860 |

-continued

| | |
|---|---|
| CCCTGGCTCT TCAAAGCCCC CTTCTCCCTG CTTGGAGGAC CCTGTCTGTT TCAGAGCATG | 1920 |
| CCCCGGGCCT CCCGGGCCTC CCCTCCACGG CGGCCGAGGT GGAGGCCCAA CGAGAGCACC | 1980 |
| AGGCTGCCAA GAGGGCTTGC AGTGCCTGCG CAGGGACATT TGGGGAGGAC ACATCCGCAC | 2040 |
| T | 2041 |

(2) INFORMATION FOR SEQ ID NO:80:

(i) SEQUENCE CHARACTERISTICS:
        (A) LENGTH: 2178 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:80:

| | |
|---|---|
| CAGGCACTCC GTCAGTGAGA TGGCCTCCAA CAAGTTTAAA AGGATGCTTA ATCGGGAGCT | 60 |
| CACCCATCTC TCTGAAATGA GTCGGTCTGG AAATCAAGTG TCAGAGTTTA TATCAAACAC | 120 |
| ATTCTTAGAT AAGCAACATG AAGTGGAAAT TCCTTCTCCA ACTCAGAAGG AAAAGGAGAA | 180 |
| AAAGAAAAGA CCAATGTCTC AGATCAGTGG AGTCAAGAAA TTGATGCACA GCTCTAGTCT | 240 |
| GACTAATTCA AGTATCCCAA GGTTTGGAGT TAAAACTGAA CAAGAAGATG TCCTTGCCAA | 300 |
| GGAACTAGAA GATGTGAACA AATGGGGTCT TCATGTTTTC AGAATAGCAG AGTTGTCTGG | 360 |
| TAACCGGCCC TTGACTGTTA TCATGCACAC CATTTTTCAG GAACGGGATT TATTAAAAAC | 420 |
| ATTTAAAATT CCAGTAGATA CTTTAATTAC ATATCTTATG ACTCTCGAAG ACCATTACCA | 480 |
| TGCTGATGTG GCCTATCACA ACAATATCCA TGCTGCAGAT GTTGTCCAGT CTACTCATGT | 540 |
| GCTATTATCT ACACCTGCTT TGGAGGCTGT GTTTACAGAT TTGGAGATTC TTGCAGCAAT | 600 |
| TTTTGCCAGT GCAATACATG ATGTAGATCA TCCTGGTGTG TCCAATCAAT TTCTGATCAA | 660 |
| TACAAACTCT GAACTTGCCT TGATGTACAA TGATTCCTCA GTCTTAGAGA ACCATCATTT | 720 |
| GGCTGTGGGC TTTAAATTGC TTCAGGAAGA AAACTGTGAC ATTTTCCAGA ATTTGACCAA | 780 |
| AAAACAAAGA CAATCTTTAA GGAAAATGGT CATTGACATC GTACTTGCAA CAGATATGTC | 840 |
| AAAACACATG AATCTACTGG CTGATTTGAA GACTATGGTT GAAACTAAGA AAGTGACAAG | 900 |
| CTCTGGAGTT CTTCTTCTTG ATAATTATTC CGATAGGATT CAGGTTCTTC AGAATATGGT | 960 |
| GCACTGTGCA GATCTGAGCA ACCCAACAAA GCCTCTCCAG CTGTACCGCC AGTGGACGGA | 1020 |
| CCGGATAATG GAGGAGTTCT TCCGCCAAGG AGACCGAGAG AGGGAACGTG GCATGGAGAT | 1080 |
| AAGCCCCATG TGTGACAAGC ACAATGCTTC CGTGGAAAAA TCACAGGTGG GCTTCATAGA | 1140 |
| CTATATTGTT CATCCCCTCT GGGAGACATG GGCAGACCTC GTCCACCCTG ACGCCCAGGA | 1200 |
| TATTTTGGAC ACTTTGGAGG ACAATCGTGA ATGGTACCAG AGCACAATCC CTCAGAGCCC | 1260 |
| CTCTCCTGCA CCTGATGACC CAGAGGAGGG CCGGCAGGGT CAAACTGAGA AATTCCAGTT | 1320 |
| TGAACTAACT TTAGAGGAAG ATGGTGAGTC AGACACGGAA AAGGACAGTG CAGTCAAGT | 1380 |
| GGAAGAAGAC ACTAGCTGCA GTGACTCCAA GACTCTTTGT ACTCAAGACT CAGAGTCTAC | 1440 |
| TGAAATTCCC CTTGATGAAC AGGTTGAAGA GGAGGCAGTA GGGGAAGAAG AGGAAAGCCA | 1500 |
| GCCTGAAGCC TGTGTCATAG ATGATCGTTC TCCTGACACG TAACAGTGCA AAACTTTCA | 1560 |
| TGCCTTTTTT TTTTTAAGT AGAAAAATTG TTTCCAAAGT GCATGTCACA TGCCACAACC | 1620 |
| ACGGTCACAC CTCACTGTCA TCTGCCAGGA CGTTTGTTGA ACAAAACTGA CCTTGACTAC | 1680 |
| TCAGTCCAGC GCTCAGGAAT ATCGTAACCA GTTTTTTCAC CTCCATGTTC ATCCGAGCAA | 1740 |

```
GGTGGACATC TTCACGAACA GCGTTTTTAA CAAGATTTCA GCTTGGTAGA GCTGACAAAG      1800

CAGATAAAAT CTACTCCAAA TTATTTTCAA GAGAGTGTGA CTCATCAGGC AGCCCAAAAG      1860

TTTATTGGAC TTGGGGTTTC TATTCCTTTT TATTTGTTTG CAATATTTTC AGAAGAAAGG      1920

CATTGCACAG AGTGAACTTA ATGGACGAAG CAACAAATAT GTCAAGAACA GGACATAGCA      1980

CGAATCTGTT ACCAGTAGGA GGAGGATGAG CCACAGAAAT TGCATAATTT TCTAATTTCA      2040

AGTCTTCCTG ATACATGACT GAATAGTGTG GTTCAGTGAG CTGCACTGAC CTCTACATTT      2100

TGTATGATAT GTAAAACAGA TTTTTTGTAG AGCTTACTTT TATTATTAAA TGTATTGAGG      2160

TATTATATTT AAAAAAAA                                                    2178

(2) INFORMATION FOR SEQ ID NO:81:

(i) SEQUENCE CHARACTERISTICS:
        (A) LENGTH: 934 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:81:

ACCGAATCCA GGTCTTGCAG AACCTGGTGC ACTGTGCTGA TCTGAGCAAC CCCACCAAGC        60

CGCTGCCCCT GTACCGCCAG TGGACGGACC GCATCATGGC CGAGTTCTTC CAGCAGGGAG       120

ACCGCGAGCG TGAGTCGGGC CTGGACATCA GTCCCATGTG TGACAAGCAT ACGGCCTCAG       180

TGGAGAAGTC CCAGGTGGGT TTCATTGACT ACATTGCTCA CCCACTGTGG GAGACTTGGG       240

CTGACCTGGT CCACCCAGAT GCACAGGACC TGCTGGACAC GCTGGAGGAC AATCGAGAGT       300

GGTACCAGAG CAAGATCCCC CGAAGTCCCT CAGACCTCAC CAACCCCGAG CGGGACGGGC       360

CTGACAGATT CCAGTTTGAA CTGACTCTGG AGGAGGCAGA GGAAGAGGAT GAGGAGGAAG       420

AAGAGGAGGG GGAAGAGACA GCTTTAGCCA AAGAGGCCTT GGAGTTGCCT GACACTGAAC       480

TCCTGTCCCC TGAAGCCGGC CCAGACCCTG GGGACTTACC CCTCGACAAC CAGAGGACTT       540

AGGGCCAGCC CTGCGTGAAC TGCAGGGGCA ATGGATGGTA AAGCCCTTTG GCTCTTGGCA       600

GGCAGACTTT CCAGGAAGAG GCTCCATGTG GCTCCTGCTT CACTTTCCCA CCCATTTAGG       660

GAGACAATCA AGCTCTTAGT TATAGGTGGC TCCCAGGGTC TAATTGGAGG CACCTGGCTG       720

GGGTCCACTC TGACCCTAGA CTTGCCTAAA AGAGCTCTCT AAGGGGCAGC CTCTTACGAT       780

GCCCTGGTGT CTTTCTCCTG GGCTTCTATC CCTGTGAGGA GAGGTGCTGT CTGCTGGAGC       840

CTCTAGTCCA CCCTCTCCAG TGGTCACTCT TGAGTCACAT CTGTCACTTA ATTATTTCCT       900

TCTTTATCAA ATATTTATTG CTCATCTGGA ATTC                                  934

(2) INFORMATION FOR SEQ ID NO:82:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:82:

AGCTTTCAAA GTTGACAAAC TTTTTTGACT CTTTCTGGAA AAGGGAAAGA AAATAGTCTT        60

CCTTCTTTCT TGGGCAATAT CCTTCACTTT ACTACAGTTA CTTTTGCAAA CAGACAGAAA       120

GGATACACTT CTAACCACAT TTTACTTCCT TCCCCTGTTG TCCAGTCCAA CTCCACAGTC       180
```

ACTCTTAAAA CTTCTCTCTG TTTGCCTGCC TCCAACAGTA CTTTTAACTT TTTGCTGTAA          240

ACAGAATAAA ATTGAACAAA TTAGGGGGTA GAAAGGAGCA GTGGTGTCGT TCACCGTGAG          300

AGTCTGCATA GAACTCAGCA GTGTGCCCTG CTGTGTCTTG GACCCTGCAA TGCG               354

(2) INFORMATION FOR SEQ ID NO:83:

(i) SEQUENCE CHARACTERISTICS:
        (A) LENGTH: 161 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:83:

AATTGCATAA TTTTCTAATT TCAAGTCTTC CTGATACATG ACTGAATAGT GTGGTTCAGT          60

GAGCTGCACT GACCTCTACA TTTTGTATGA TATGTAAAAC AGATTTTTTG TAGAGCTTAC         120

TTTTATTATT AAATGTATTG AGGTATTATA TTTAAAAAAA A                            161

(2) INFORMATION FOR SEQ ID NO:84:

(i) SEQUENCE CHARACTERISTICS:
        (A) LENGTH: 370 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:84:

GGGGCAATGG ATGGTAAAGC CCTTTGGCTC TTGGCAGGCA GACTTTCCAG GAAGAGGCTC          60

CATGTGGCTC CTGCTTCACT TTCCCACCCA TTTAGGGAGA CAATCAAGCT CTTAGTTATA         120

GGTGGCTCCC AGGGTCTAAT TGGAGGCACC TGGCTGGGGT CCACTCTGAC CCTAGACTTG         180

CCTAAAAGAG CTCTCTAAGG GGCAGCCTCT TACGATGCCC TGGTGTCTTT CTCCTGGGCT         240

TCTATCCCTG TGAGGAGAGG TGCTGTCTGC TGGAGCCTCT AGTCCACCCT CTCCAGTGGT         300

CACTCTTGAG TCACATCTGT CACTTAATTA TTTCCTTCTT TATCAAATAT TTATTGCTCA         360

TCTGGAATTC                                                               370

(2) INFORMATION FOR SEQ ID NO:85:

(i) SEQUENCE CHARACTERISTICS:
        (A) LENGTH: 734 amino acids
        (B) TYPE: amino acid
        (D) TOPOLOGY: linear (ii) MOLECULE TYPE: protein (ix) FEATURE:
        (A) NAME/KEY: misc_feature
        (D) OTHER INFORMATION: /note="Sequence coresponds to amino
                acids 152-885 of SEQ ID NO:22 which
                begins inediately after the stop codon.
                Stop codon may be in an intron."

(xi) SEQUENCE DESCRIPTION: SEQ ID NO:85:

Pro Ala Ser Val Leu Asn His Arg His Ala Glu Asp Leu Ile Val Thr
 1               5                  10                  15

Pro Phe Ala Gln Val Leu Ala Ser Leu Arg Ser Val Arg Ser Asn Phe
                20                  25                  30

Ser Leu Leu Thr Asn Val Pro Val Pro Ser Asn Lys Arg Ser Arg Trp

```
              35                  40                  45
Ala Ala Pro Pro Leu Ser Ala Arg Pro Arg Cys Gln Thr Phe Ser Val
             50                  55                  60
Thr Thr Leu Ala Ala Pro Ser Leu Glu Glu Thr Cys Gln Gln Leu Ala
 65                  70                  75                  80
Arg Glu Thr Leu Glu Glu Leu Asp Trp Cys Leu Glu Gln Leu Glu Thr
                 85                  90                  95
Met Gln Thr Tyr Arg Ser Val Ser Glu Met Ala Ser His Lys Phe Lys
                100                 105                 110
Arg Met Leu Asn Arg Glu Leu Thr His Leu Ser Glu Met Ser Arg Ser
                115                 120                 125
Gly Asn Gln Val Ser Glu Tyr Ile Ser Thr Thr Phe Leu Asp Lys Gln
130                 135                 140
Asn Glu Val Glu Ile Pro Ser Pro Thr Met Lys Glu Arg Glu Lys Gln
145                 150                 155                 160
Gln Ala Pro Arg Pro Arg Pro Ser Gln Pro Pro Pro Pro Val Pro
                165                 170                 175
His Leu Gln Pro Met Ser Gln Ile Thr Gly Leu Lys Lys Leu Met His
                180                 185                 190
Ser Asn Ser Leu Asn Asn Ser Asn Ile Pro Arg Phe Gly Val Lys Thr
                195                 200                 205
Asp Gln Glu Glu Leu Leu Ala Gln Glu Leu Glu Asn Leu Asn Lys Trp
210                 215                 220
Gly Leu Asn Ile Phe Cys Val Ser Asp Tyr Ala Gly Gly Arg Ser Leu
225                 230                 235                 240
Thr Cys Ile Met Tyr Met Ile Phe Gln Glu Arg Asp Leu Leu Lys Lys
                245                 250                 255
Phe Arg Ile Pro Val Asp Thr Met Val Thr Tyr Met Leu Thr Leu Glu
                260                 265                 270
Asp His Tyr His Ala Asp Val Ala Tyr His Asn Ser Leu His Ala Ala
                275                 280                 285
Asp Val Leu Gln Ser Thr His Val Leu Leu Ala Thr Pro Ala Leu Asp
                290                 295                 300
Ala Val Phe Thr Asp Leu Glu Ile Leu Ala Ala Leu Phe Ala Ala Ala
305                 310                 315                 320
Ile His Asp Val Asp His Pro Gly Val Ser Asn Gln Phe Leu Ile Asn
                325                 330                 335
Thr Asn Ser Glu Leu Ala Leu Met Tyr Asn Asp Glu Ser Val Leu Glu
                340                 345                 350
Asn His His Leu Ala Val Gly Phe Lys Leu Leu Gln Glu Asp Asn Cys
                355                 360                 365
Asp Ile Phe Gln Asn Leu Ser Lys Arg Gln Arg Arg Ala Tyr Ala Arg
                370                 375                 380
Trp Ser Ser Thr Trp Cys Trp Pro Arg Thr Cys Pro Ser Thr Thr Leu
385                 390                 395                 400
Leu Ala Asp Leu Lys Thr Met Val Glu Thr Lys Lys Val Thr Ser Ser
                405                 410                 415
Gly Val Leu Leu Leu Asp Asn Tyr Ser Asp Arg Ile Gln Val Leu Arg
                420                 425                 430
Asn Met Val His Cys Ala Asp Leu Ser Asn Pro Thr Lys Pro Leu Glu
                435                 440                 445
Leu Tyr Arg Gln Trp Thr Asp Arg Ile Met Ala Glu Phe Phe Gln Gln
450                 455                 460
```

```
Gly Asp Arg Glu Arg Glu Arg Gly Met Glu Ile Ser Pro Met Cys Asp
465                 470                 475                 480

Lys His Thr Ala Ser Val Glu Lys Ser Gln Val Gly Phe Ile Asp Tyr
            485                 490                 495

Ile Val His Pro Leu Trp Glu Thr Trp Ala Asp Leu Val His Pro Asp
            500                 505                 510

Ala Gln Glu Ile Leu Asp Thr Leu Glu Asp Asn Arg Asp Trp Tyr Tyr
        515                 520                 525

Ser Ala Ile Arg Gln Ser Pro Ser Pro Pro Glu Glu Glu Ser Arg
        530                 535             540

Gly Pro Gly His Pro Pro Leu Pro Asp Lys Phe Gln Phe Glu Leu Thr
545                 550                 555                 560

Leu Glu Glu Glu Glu Glu Glu Ile Ser Met Ala Gln Ile Pro Cys
                565                 570             575

Thr Ala Gln Glu Ala Leu Thr Glu Gln Gly Leu Ser Gly Val Glu Glu
            580                 585                 590

Ala Leu Asp Ala Thr Ile Ala Trp Glu Ala Ser Pro Ala Gln Glu Ser
        595                 600             605

Leu Glu Val Met Ala Gln Glu Ala Ser Leu Glu Ala Glu Leu Glu Ala
        610                 615                 620

Val Tyr Leu Thr Gln Gln Ala Gln Ser Thr Gly Ser Ala Pro Val Ala
625             630                 635                 640

Pro Asp Glu Phe Ser Ser Arg Glu Glu Phe Val Val Ala Val Ser His
                645                 650                 655

Ser Ser Pro Ser Ala Leu Ala Leu Gln Ser Pro Leu Leu Pro Ala Trp
            660                 665                 670

Arg Thr Leu Ser Val Ser Glu His Ala Pro Gly Leu Pro Gly Leu Pro
        675                 680                 685

Ser Thr Ala Ala Glu Val Glu Ala Gln Arg Glu His Gln Ala Ala Lys
        690                 695                 700

Arg Ala Cys Ser Ala Cys Ala Gly Thr Phe Gly Glu Asp Thr Ser Ala
705             710                 715                 720

Leu Pro Ala Pro Gly Gly Gly Ser Gly Gly Asp Pro Thr
                725                 730
```